US009995734B2

(12) United States Patent
Smith et al.

(10) Patent No.: US 9,995,734 B2
(45) Date of Patent: Jun. 12, 2018

(54) HUMAN T CELL LINE ASSAY FOR EVALUATING THE IMMUNOLOGIC IDENTITY OF GLATIRAMER ACETATE PREPARATIONS

(71) Applicant: Mylan Inc., Canonsburg, PA (US)

(72) Inventors: Jeffrey P. Smith, Morgantown, WV (US); Peter E. Lipsky, Charlottesville, VA (US); Anne Lodge, Everett, WA (US)

(73) Assignee: MYLAN INC., Canonsburg, PA (US)

( * ) Notice: Subject to any disclaimer, the term of this patent is extended or adjusted under 35 U.S.C. 154(b) by 0 days. days.

(21) Appl. No.: 14/522,521

(22) Filed: Oct. 23, 2014

(65) Prior Publication Data

US 2015/0141284 A1 May 21, 2015

Related U.S. Application Data

(60) Provisional application No. 61/895,370, filed on Oct. 24, 2013.

(51) Int. Cl.

*G01N 33/50* (2006.01)
*G01N 33/68* (2006.01)
*C12N 5/0783* (2010.01)

(52) U.S. Cl.

CPC ......... *G01N 33/505* (2013.01); *C12N 5/0636* (2013.01); *G01N 33/5023* (2013.01); *G01N 33/6863* (2013.01); *C12N 2503/02* (2013.01); *G01N 2500/10* (2013.01)

(58) Field of Classification Search

CPC ............. G01N 33/505; G01N 33/5023; G01N 33/6863

See application file for complete search history.

(56) References Cited

U.S. PATENT DOCUMENTS

| | | | |
|---|---|---|---|
| 3,849,550 | A | 11/1974 | Teitelbaum et al. |
| 5,800,808 | A | 9/1998 | Konfino et al. |
| 5,958,707 | A | 9/1999 | De Vries et al. |
| 5,981,589 | A | 11/1999 | Konfino et al. |
| 6,733,746 | B2 | 5/2004 | Daley et al. |
| 7,429,374 | B2 | 9/2008 | Klinger |
| 7,923,215 | B2 | 4/2011 | Klinger |
| 8,389,228 | B2 | 3/2013 | Klinger |
| 8,481,315 | B2 | 7/2013 | Fong et al. |
| 8,709,433 | B2 | 4/2014 | Kasper et al. |
| 8,759,302 | B2 | 6/2014 | Dhib-Jalbut |
| 2003/0170729 | A1 | 9/2003 | Klinger |
| 2009/0005419 | A1 | 1/2009 | Auer et al. |
| 2011/0053203 | A1 | 3/2011 | D'Alessandro et al. |
| 2011/0189706 | A1 | 8/2011 | Klinger |
| 2011/0295782 | A1 | 12/2011 | Stojadinovic et al. |
| 2013/0210054 | A1 | 8/2013 | D'Alessandro |
| 2014/0107208 | A1 | 4/2014 | Comabella et al. |
| 2014/0193827 | A1 | 7/2014 | Schwartz et al. |
| 2014/0272987 | A1 | 9/2014 | Smith et al. |

FOREIGN PATENT DOCUMENTS

| | | | |
|---|---|---|---|
| AR | 098194 | A1 | 5/2016 |
| CN | 1308683 | C | 4/2007 |
| CN | 105377308 | A | 3/2016 |
| EP | 1261361 | A1 | 12/2002 |
| EP | 2971173 | A2 | 1/2016 |
| EP | 3060684 | A2 | 8/2016 |
| JP | 2016512432 | A | 4/2016 |
| TW | 201447297 | A | 12/2014 |
| TW | 201606305 | A | 2/2016 |
| WO | WO 1999/014360 | A1 | 3/1999 |
| WO | WO-03048735 | A2 | 6/2003 |
| WO | WO-2006029411 | A2 | 3/2006 |
| WO | WO 2008/157697 | A2 | 12/2008 |
| WO | WO 2013/120106 | A2 | 8/2013 |
| WO | WO 2013/139728 | A1 | 9/2013 |
| WO | WO 2014/107533 | A2 | 7/2014 |
| WO | WO 2014/159685 | A2 | 10/2014 |
| WO | WO 2014/159685 | A3 | 10/2014 |
| WO | WO 2015/061610 | | 4/2015 |

OTHER PUBLICATIONS

Qin et al., J Neuroimmunol. Aug. 1, 2000;108(1-2):201-206.*

Anderson, et al. Demonstration of Equivalence between a Generic (M356) and Brand Comaxone (glatiramer acetate injection) (Apr. 20, 2015).

Anderson, et al. Demonstration of Equivalence between a Generic (M356) and Brand Copaxone (glatiramer acetate injection). Momenta Pharmaceuticals Poster P1.145 (Apr. 20, 2015).

D'Alessandro et al. Comparative Gene Expression Profiling between a Generic (Glatopa) and Brand Copaxone (glatiramer acetate injection). Momenta Pharmaceuticals (Apr. 20, 2015).

D'Alessandro et al. Comparative Gene Expression Profiling Between a Generic (Glatopa) and Brand Copaxone (glatiramer acetate injection). Momenta Pharmaceuticals Poster P1.144 (Apr. 20, 2015).

Kolitz et al. Gene expression studies of a human monocyte cell line identify dissimilarities between differently manufactured glatiramoids. Scientific Reports 5:1-14 (May 22, 2015).

PCT/US2014/024748 International Preliminary Report on Patentability dated Sep. 24, 2015.

U.S. Appl. No. 14/206,681 Restriction Requirement dated Feb. 1, 2016.

Bakshi, et al., "Gene expression analysis reveals functional pathways of glatiramer acetate activation," Expert Opin Ther Targets. Apr. 2013;17(4):351-362.

Biolegend.com web reference, "Mouse alloantigens." URL: http://www.biolegend.com/media_assets/support_resource/BioLegend_Mouse_Alloantigens.pdf ; file downloaded Mar. 5, 2014.

Bustin, et al., 2005, "Quantitative real-time RT-PCR—a perspective," Journal of Molecular Endocrinology, 34:597-601.

(Continued)

*Primary Examiner* — Daniel C Gamett

(74) *Attorney, Agent, or Firm* — Wilson Sonsini Goodrich & Rosati

(57) ABSTRACT

The invention relates to the field of medicine. The invention provides methods for generating glatiramer-acetate-specific human T-cell lines, and assays that use these T-cell lines for demonstrating immunological identity between glatiramer acetate preparations. These assays allow sensitive and accurate comparison of glatiramer acetate preparations, and find utility as lot-release assays.

40 Claims, 25 Drawing Sheets

(56) References Cited

OTHER PUBLICATIONS

Choi, et al., Nov. 1989, "Interaction of *Staphylococcus aureus* toxin 'superantigens' with human T cells," Proc Natl Acad Sci USA 86(22):8941-8945.
Duda, et al, "Human and murine CD4 T cell reactivity to a complex antigen: recognition of the synthetic random polypeptide glatiramer acetate." J Immunol. Dec. 15, 2000;165(12):7300-7307.
Eppig JT and Strivens M, 1999, "Finding a mouse: the International Mouse Strain Resource (IMSR)." Trends in Genetics 15:81-82.
Friberg, et al. "In vitro cytokine production by normal human peripheral blood mononuclear cells as a measure of immunocompetence or the state of activation." Clin Diagn Lab Immunol. May 1994;1(3):261-268.
Good, et al. "Human T clones reactive to the sexual stages of Plasmodium falciparum malaria. High frequency of gamete-reactive T cells in peripheral blood from nonexposed donors." J Immunol. Jan. 1, 1987;138(1):306-311.
Gorski, et al., May 15, 1994 "Circulating T cell repertoire complexity in normal individuals and bone marrow recipients analyzed by CDR3 size spectratyping. Correlation with immune status," J Immunol. 152(10):5109-5119.
Imitola, et al, "Cytokines in multiple sclerosis: from bench to bedside." Pharmacol Ther. May 2005;106(2):163-177.
Kersh, et al., "Structural basis for T cell recognition of altered peptide ligands: a single T cell receptor can productively recognize a large continuum of related ligands." J Exp Med. Oct. 1, 1996;184(4):1259-1268.
Krensky, et al., 1982, "Long-term human cytolytic T-cell lines allospecific for HLA-DR6 antigen are OKT4+." Proc Natl Acad Sci. Apr. 1982;79(7):2365-2369.
Lee, et al, "A novel strategy for rapid and efficient isolation of human tumor-specific CD4(+) and CD8(+) T-cell clones." J Immunol Methods. Feb. 29, 2008;331(1-2):13-26.
Li, et al., "RNA-Seq gene expression estimation with read mapping uncertainty." Bioinformatics. Feb. 15, 2010;26(4):493-500.
Mariotti, et al., "Generation of human T cell clones." Methods Mol Biol. 2009;514:65-93.
Miller, et al., "Treatment of multiple sclerosis with copolymer-1 (Copaxone): implicating mechanisms of Th1 to Th2/Th3 immune-deviation." J Neuroimmunol. Dec. 1, 1998;92(12):113-121.
Nagalakshmi, et al., Jan. 2010, "RNA-Seq: A Method for Comprehensive Transcriptome Analysis," Current Protocols in Molecular Biology, Wiley Interscience, Unit 4.11, Supplement 89, Copyright 2010 John Wiley & Sons, Inc.
Nie, et al., "Correlation between mRNA and protein abundance in Desulfovibrio vulgaris: a multiple regression to identify sources of variations." Biochem Biophys Res Commun. Jan. 13, 2006;339(2):603-610.
Oftung F., et al., 1994, "Mapping of multiple HLA class II restricted T-cell epitopes of the mycobacterial 70-kilodalton heat shock protein," Infect. Immun. 62:5411-5418.
Ota, et al. T-cell recognition of an immunodominant myelin basic protein epitope in multiple sclerosis. Nature 346:183-187 (1990).
Overbergh, et al., 1999, "Quantification of murine cytokine mRNAs using real time quantitative reverse transcriptase PCR," Cytokine 11(4):305-312.
PCT/US14/24748 International Search Report and Written Opinion dated Oct. 24, 2014.
Quah, et al., 2007, "Monitoring lymphocyte proliferation in vitro and in vivo with the intracellular fluorescent dye carboxyfluorescein diacetate succinimidyl ester," Nature Protocols 2(9):2049-2056.
Stern et al., "Peptide 15-mers of defined sequence that substitute for random amino acid copolymers in amelioration of experimental autoimmune encephalomyelitis." Proc Natl Acad Sci U S A. Feb. 1, 2005;102(5):1620-1625.
"Techniques for Immune Function Analysis: Application Handbook 1st Edition." 2006, Becton, Dickinson and Company.
Towfic, et al., "Comparing the biological impact of glatiramer acetate with the biological impact of a generic." PLoS One. Jan. 8, 2014;9(1):e83757.
Ucker, et al., "Activation-driven T cell death. II. Quantitative differences alone distinguish stimuli triggering nontransformed T cell proliferation or death." J Immunol. Sep. 1, 1992;149(5):1583-1592.
Udvardi, et al., "Eleven golden rules of quantitative RT-PCR." Plant Cell. Jul. 2008;20(7):1736-1737.
VanGuilder, et al., "Twenty-five years of quantitative PCR for gene expression analysis," Biotechniques. 2008; 44:619-626.
Wiesemann, et al., "Glatiramer acetate (GA) induces IL-13/IL-5 secretion in naive T cells." J Neuroimmunol. Sep. 3, 2001;119(1):137-144.
Wong and Medrano, 2005, "Real-Time PCR for mRNA quantitation," Biotechniques 39:75-85.
Wucherpfennig, et al., 1994, "Structural requirements for binding of an immunodominant myelin basic protein peptide to DR2 isotypes and for its recognition by human T cell clones." J Exp Med. Jan. 1, 1994;179(1):279-290.
Yang, J. "Peripheral immune response in chronic relapsing experimental autoimmune encephalomyelitis in SJL mice," Academic Dissertation, Nov. 14, 2003; available at URL: <http://ethesis.helsinki.fi/julkaisut/laa/haart/vk/yang/peripher.pdf>; accessed Nov. 6, 2014.
Dabbert, et al. Glatiramer Acetate (Copolymer-1)-Specific, Human T Cell Lines: Cytokine Profile and Suppression of T Cell Lines Reactive Against Myelin Basic Protein. Neuroscience Letters. 289:205-208 (2000).
Henri et al. The Dendritic Cell Populations of Mouse Lymph Nodes. The Journal of Immunology. 167:741-748 (2001).
Neuhaus et al. Multiple Sclerosis: Comparison of Copolymer-1-Reactive T Cell Lines from Treated and Untreated Subjects Reveals Cytokine Shift from T Helper 1 to Helper 2 Cells. PNAS. 97(13):7452-7457 (2000).
PCT/US14/62039 International Search Report and Written Opinion dated Apr. 20, 2015.
Seo et al. Activation of murine epidermal V gamma 5/V delta 1-TCR(+) T cell lines by Glu-Tyr polypeptides. Jour of Invest Derm. 116:880-885 (2001).
Ziemssen et al. Glatiramer Acetate-Specific T-Helper 1-And 2-Type Cell Lines Produce BDNF: Implications for multiple sclerosis therapy. Brain 125:2381-2391 (2002).
Albershardt et al. Evaluation of reference genes for quantitative PCR analysis of mouse lymphocytes. J Immunol Meth 384:196-199 (2012).
D'Alessandro et al. Equivalent Gene Expression Profiles between Glatopa™ and Copaxone®. PLos One 10:e140299 (19 pgs) (2015).
PCT/US2014/062039 International Preliminary Report on Patentability dated May 6, 2016.
Schrock. Cell-based potency assays: expectations and realities. BioProcessing J 11:4/12 (2012).
Vandesompele et al. Accurate normalization of real-time quantitative RT-PCR data by geometric averaging of multiple internal control genes. Genome Biol. 3(7):1-12 (2002).
Achiron et al., Molecular profiling of glatiramer aacetate early treatment effects in multiple sclerosis. Disease Markers, 27:63-73, 2009.
Albershardt et al., Evaluation of reference genes for quantitative PCR analysis of mouse lymphocytes. Journal of Immunological Methods, 384:196-199, 2012.
D'Alessandro et al., Equivalent gene expression profiles between Glatopa and Copaxone. PLOS/One, 10:e0140299, p. 1-19, 2015.
European Patent Application No. 14773936.1 Extended European Search Report dated Oct. 26, 2016.
Schrock, R., Cell-based potency assays: Expectations and realities. Bioprocessing Journal: Trends and Developments in Bioprocess Technology, 11:4-12, 2012.
U.S. Appl. No. 14/206,681 Office Action dated Jun. 24, 2016.
Vandesompele et al., Accurate normalization of real-time quantitative RT-PCR data by geometric averaging of miltiple internal control genes. Genome Biology, 3(7):1-12, 2002.

(56) References Cited

OTHER PUBLICATIONS

Yong. Differential mechanisms of action of interferon-beta and glatiramer acetate in MS. Neurology, 59:802-808, 2002.
Chinese Patent Application No. 2014800284162 First Office Action dated Jun. 26, 2017.
Duda et al., Glatiramer acetate (Copaxone) induxces degenerate Th2-polarized immune responses in patients with multiple sclerosis. J.Clinical Investigation, 105:967-976, 2000.
European Patent Application No. 14856438.8 extended European search report dated May 10, 2017.
Johnson. Glatiramer acetate and the glatiramoid class of immunomodulator drugs in multiple sclerosis: an update. Expert Opinion on Drug Metabolism & Toxicology. 6:5, 643-660, 2010.
Johnson K.P., Copolymer 1 reduces relapse rate and improves disability in relapsing-remitting multiple sclerosis: Results of a phase III multicenter, double-blind, placebo-controlled trial. Neurology, 45:1268-1276, 1995. Abstract.
Nicholas et al., Multiple sclerosis. Neurology Clinical Practice, 3(5):404-412, 2013.
Racke et al., The mechanism of action of glatiramer acetate treatment in multiple sclerosis. Neurology, 74(Suppl 1):S25-S30, 2010.
Taiwan Patent Application No. 103109072 Official Letter with a Search Report dated Oct. 23, 2017.
U.S. Appl. No. 14/206,681 Office Action dated Jan. 19, 2017.
U.S. Appl. No. 14/206,681 Office Action dated Oct. 31, 2017.
Teva Pharmaceuticals, Citizen Petition Requesting That FDA Refrain From Approving Any Abbreviated New Drug Application Referencing Copaxone® (glatiramer acetate injection) Until Certain Conditions Are Met, Jun. 4, 2012, pp. 1-35; downloaded from: www.fdanews.com/ext/resources/files/archives/0/06/06-20-12-briefs.pdf (Year: 2012).

* cited by examiner

FIGURE 2
2A
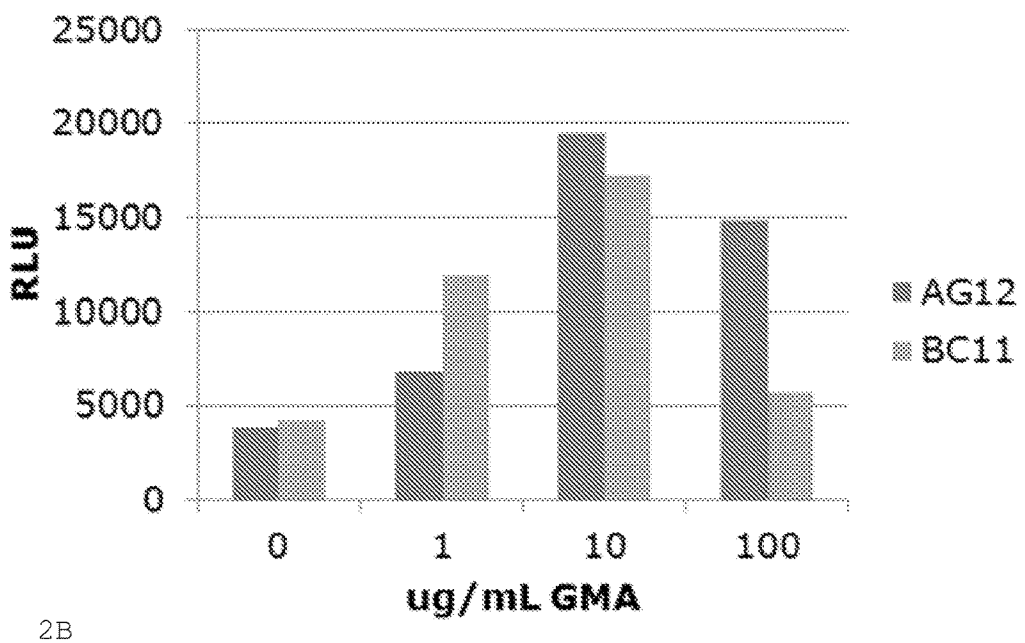
2B
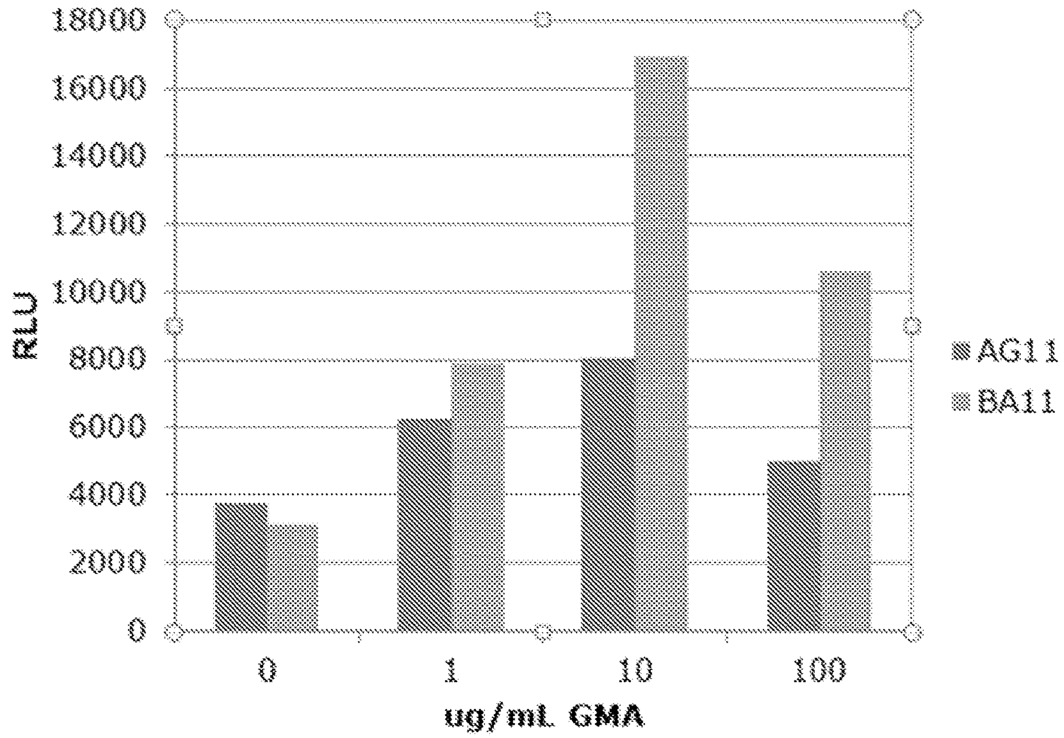

FIGURE 3A-B
A.
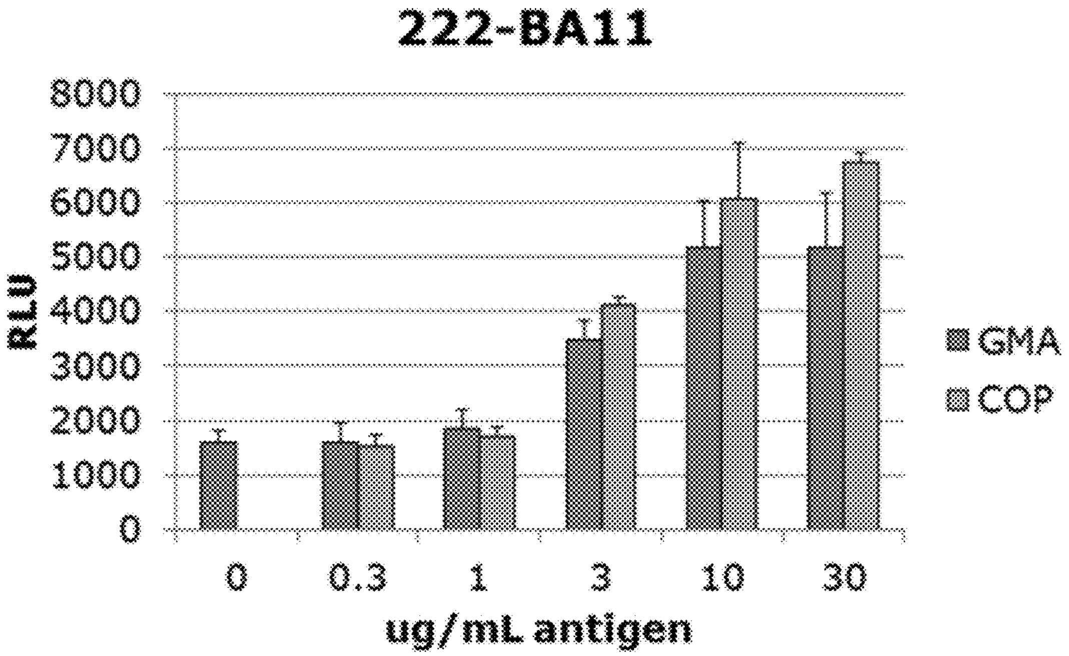
B.
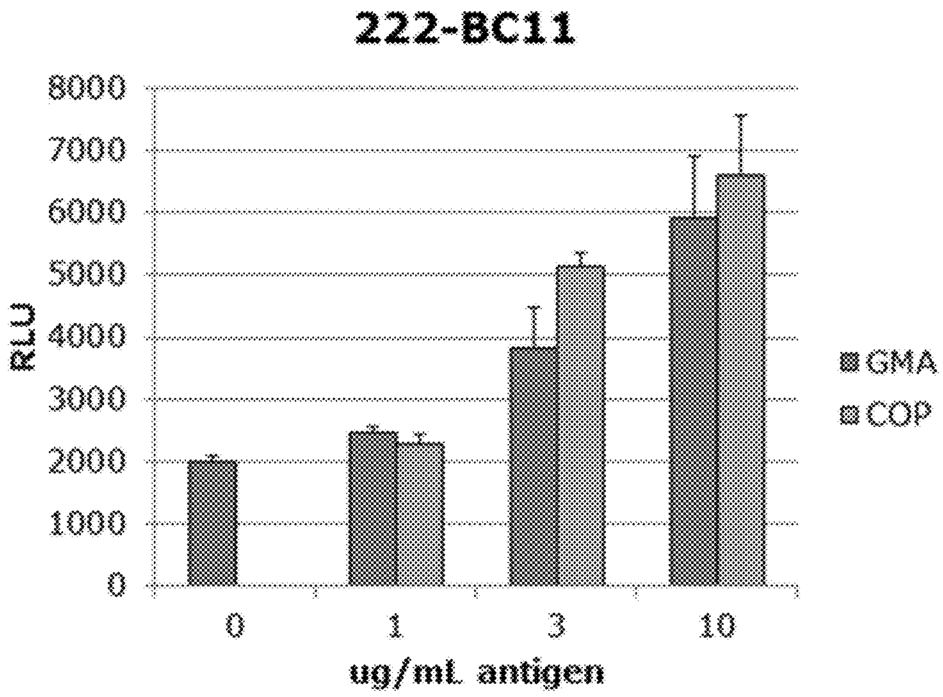

C.

FIGURE 4
4A
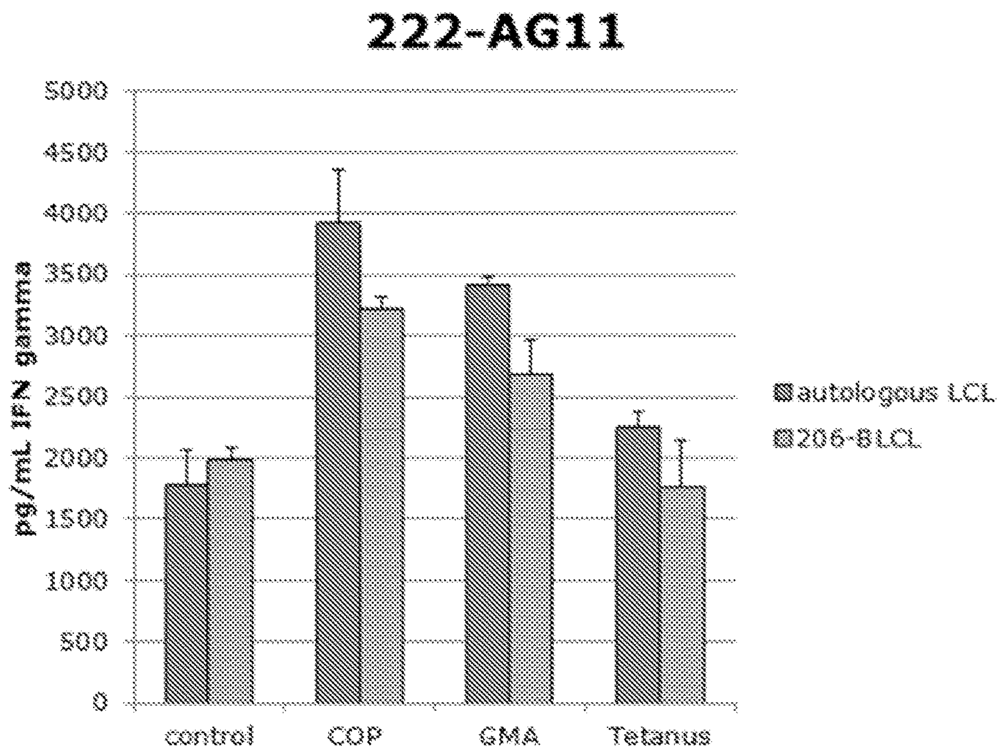
4B
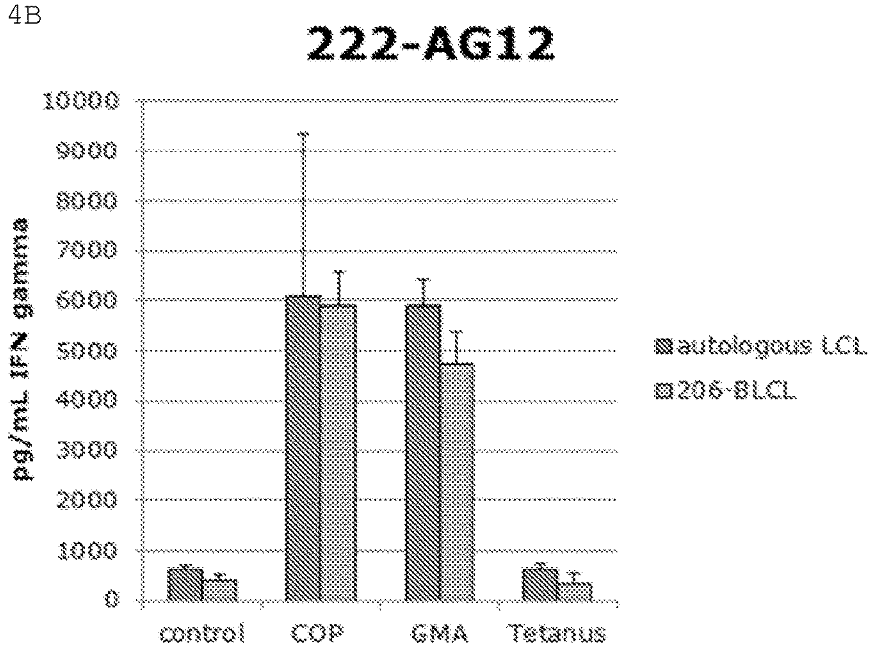

FIGURE 5A-B
A.
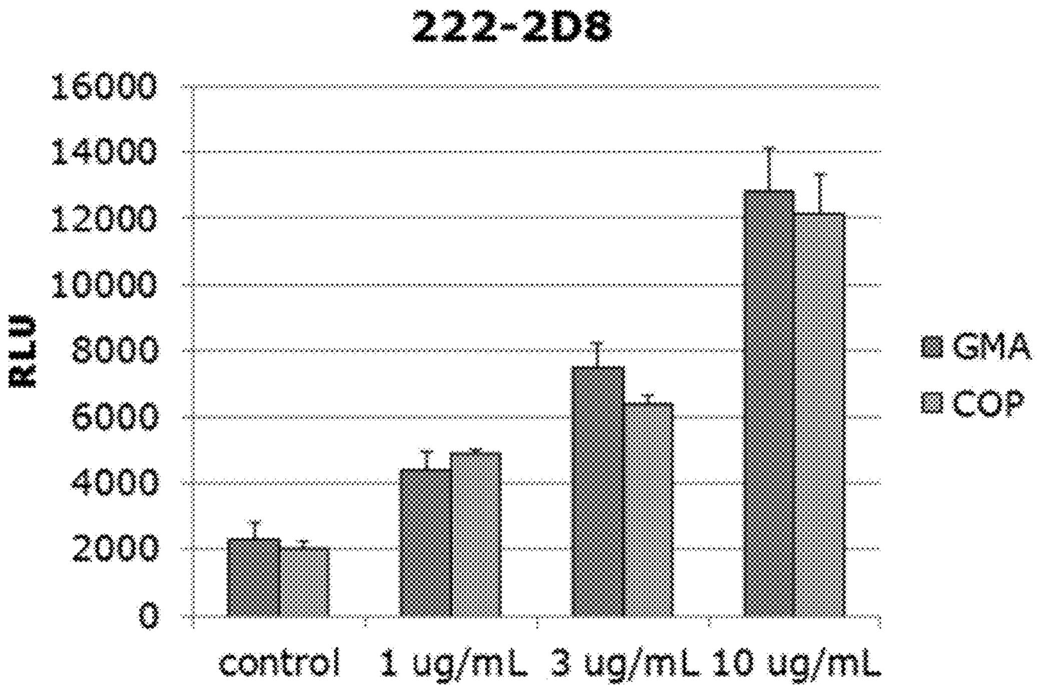
B.
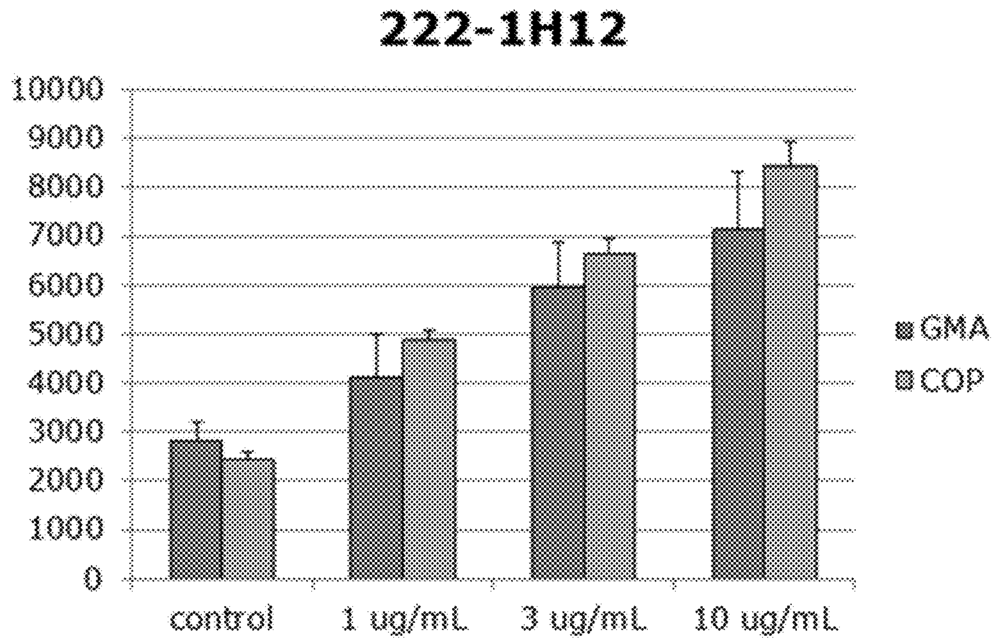

FIGURE 5C-D
C.
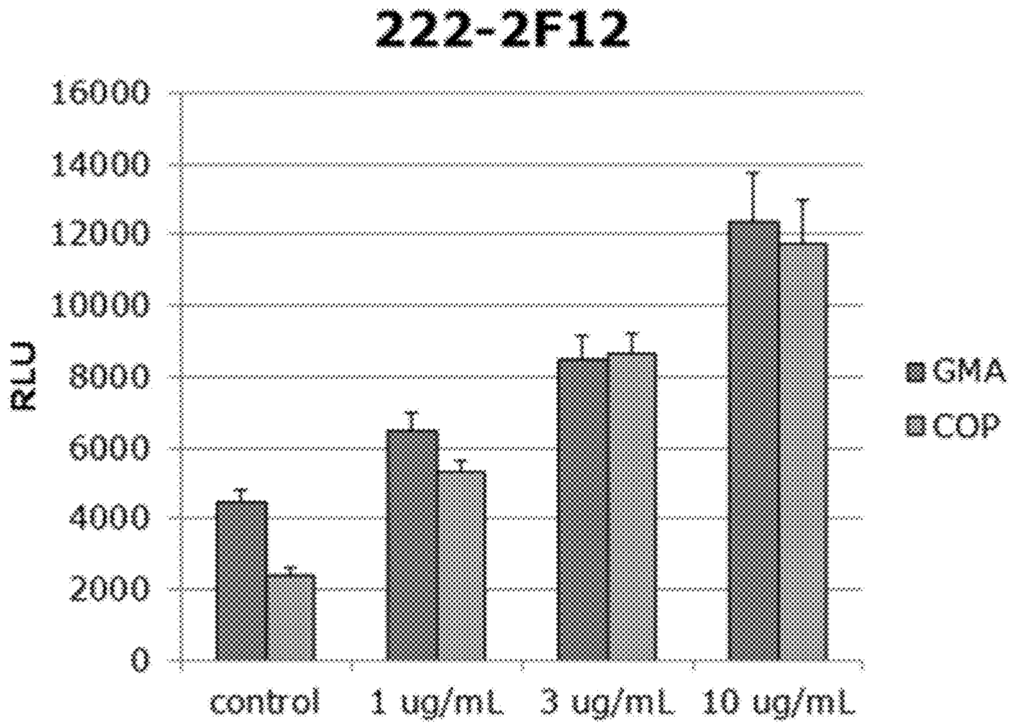
D.
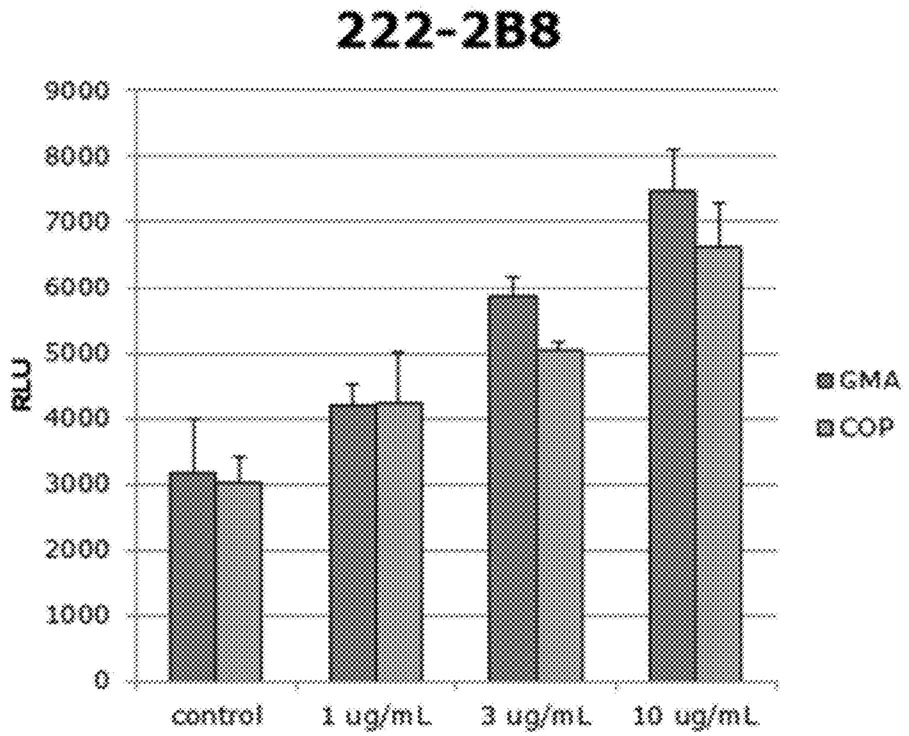

FIGURE 5E-F
E.
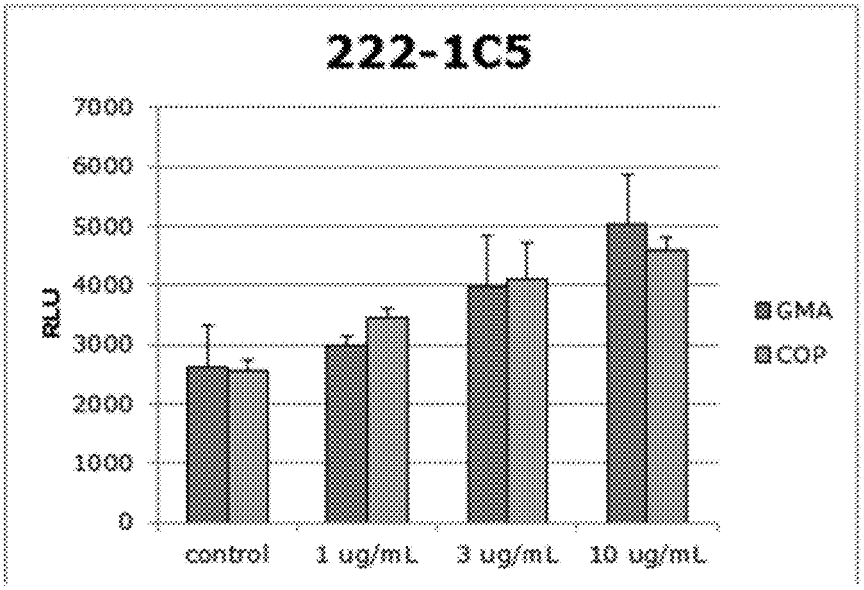
F.
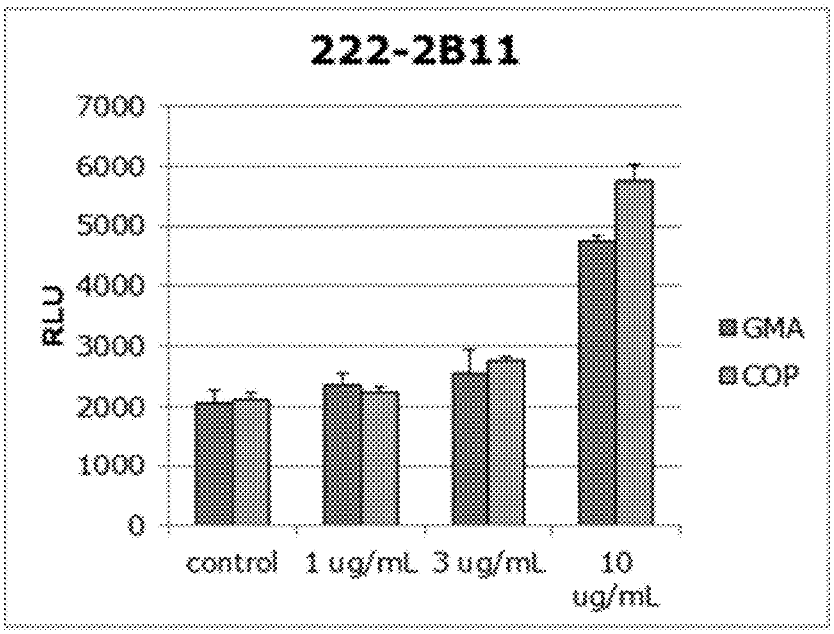

G.

FIGURE 6A-B
A.
B.
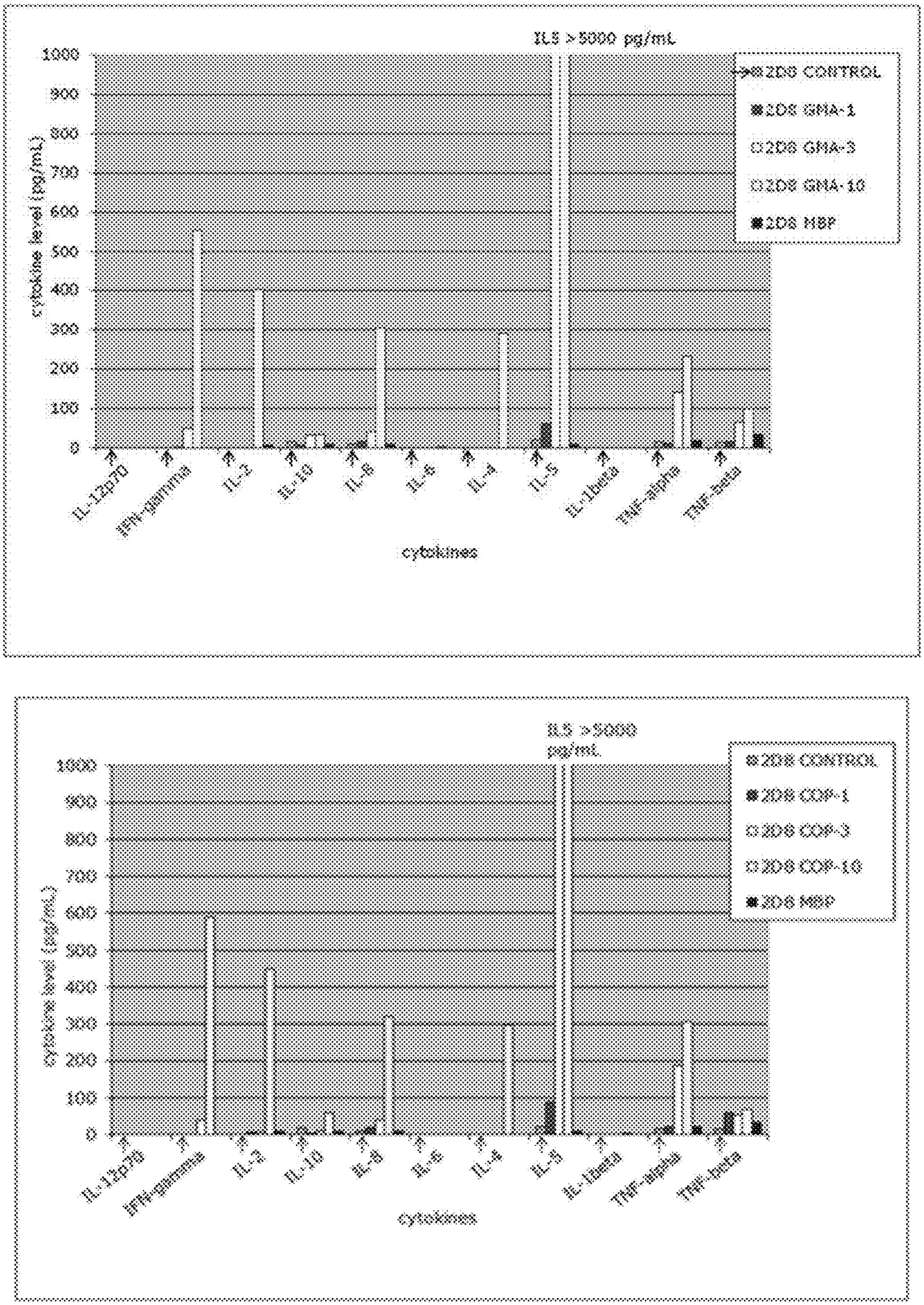

FIGURE 6C-D
C.
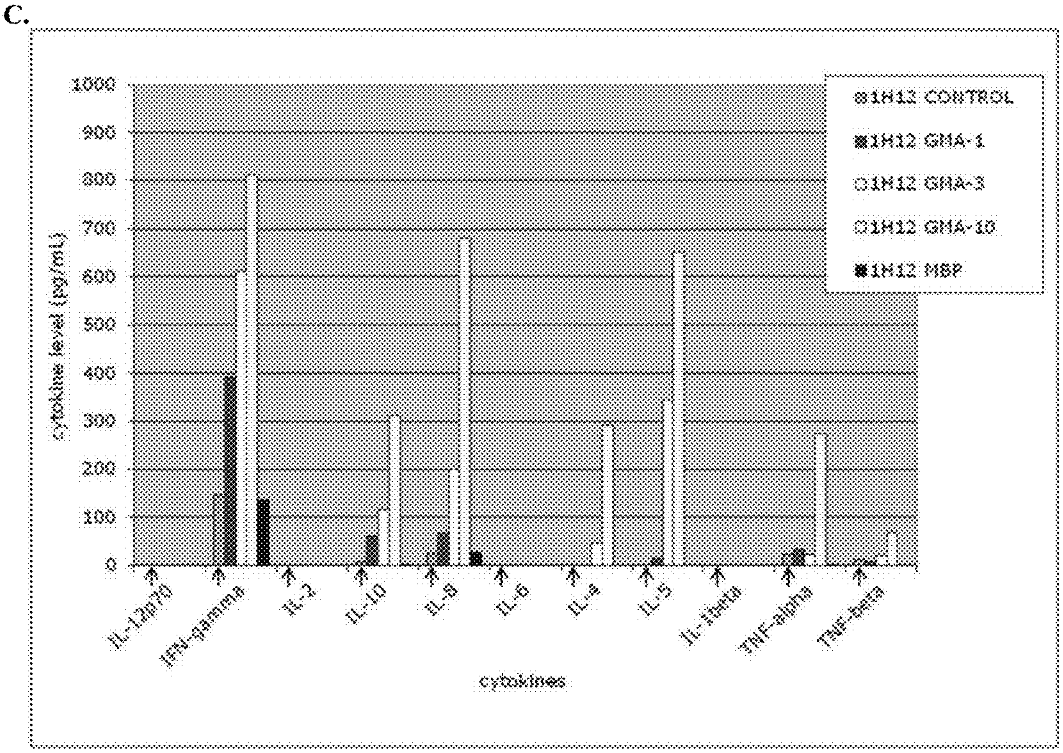
D.
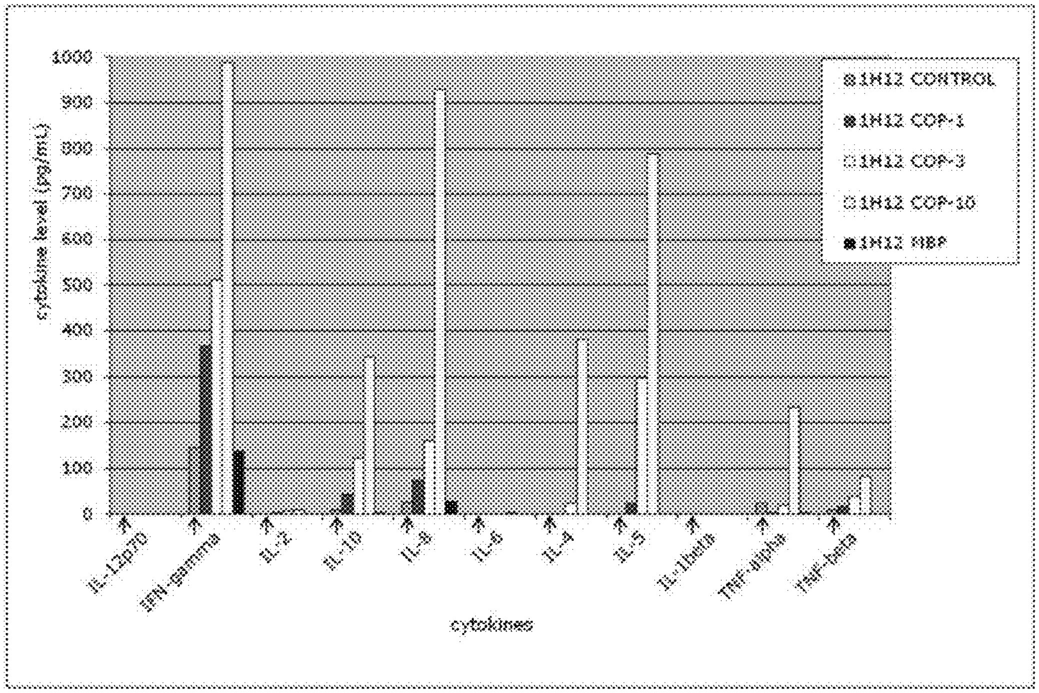

FIGURE 6E-F
E.
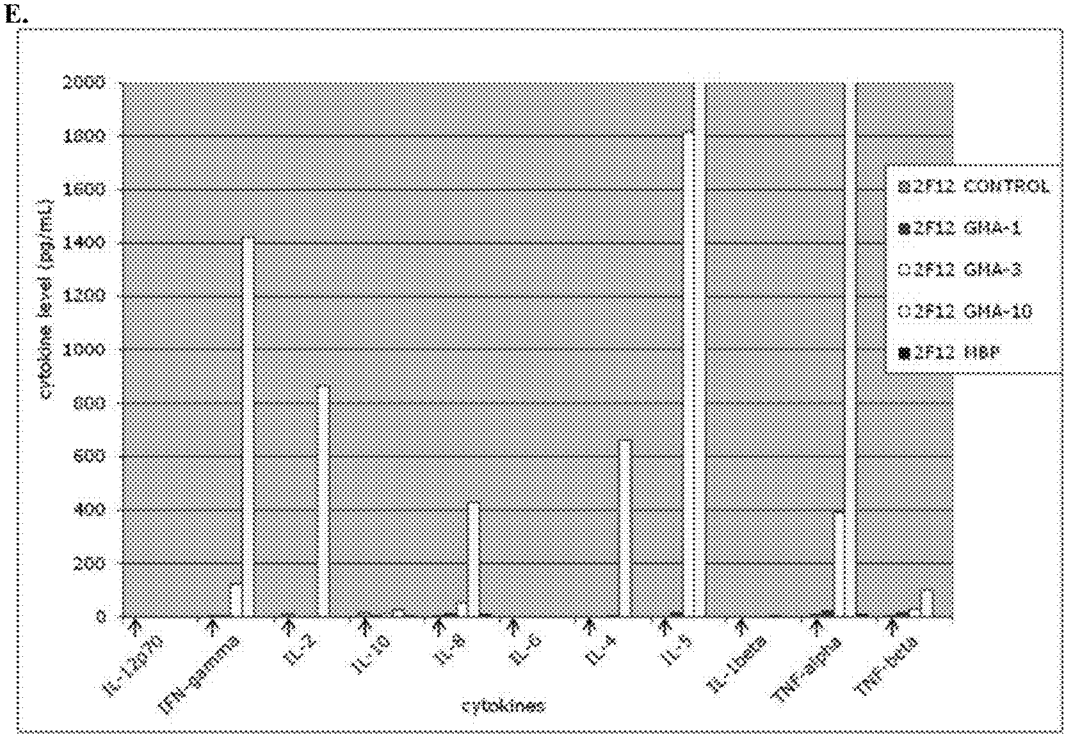
F.
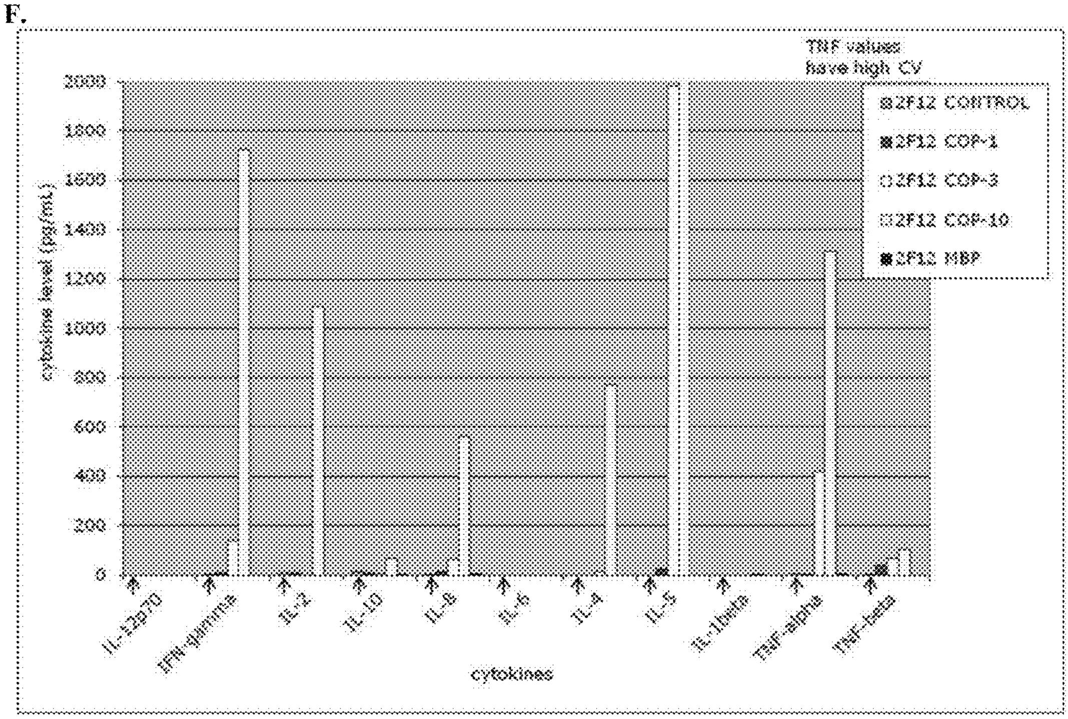

FIGURE 7
7A
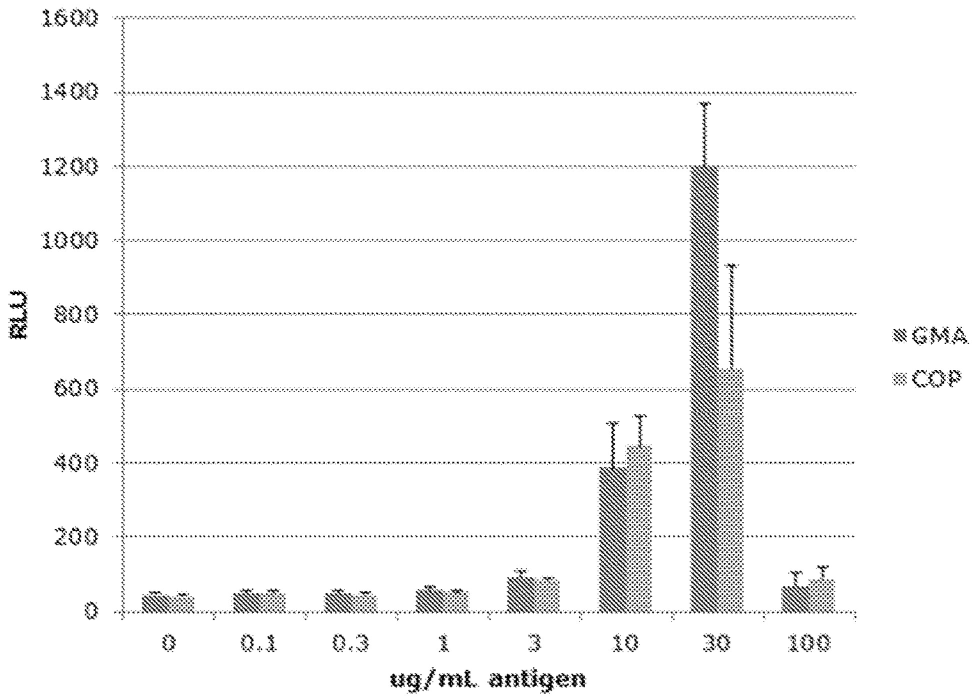
7B
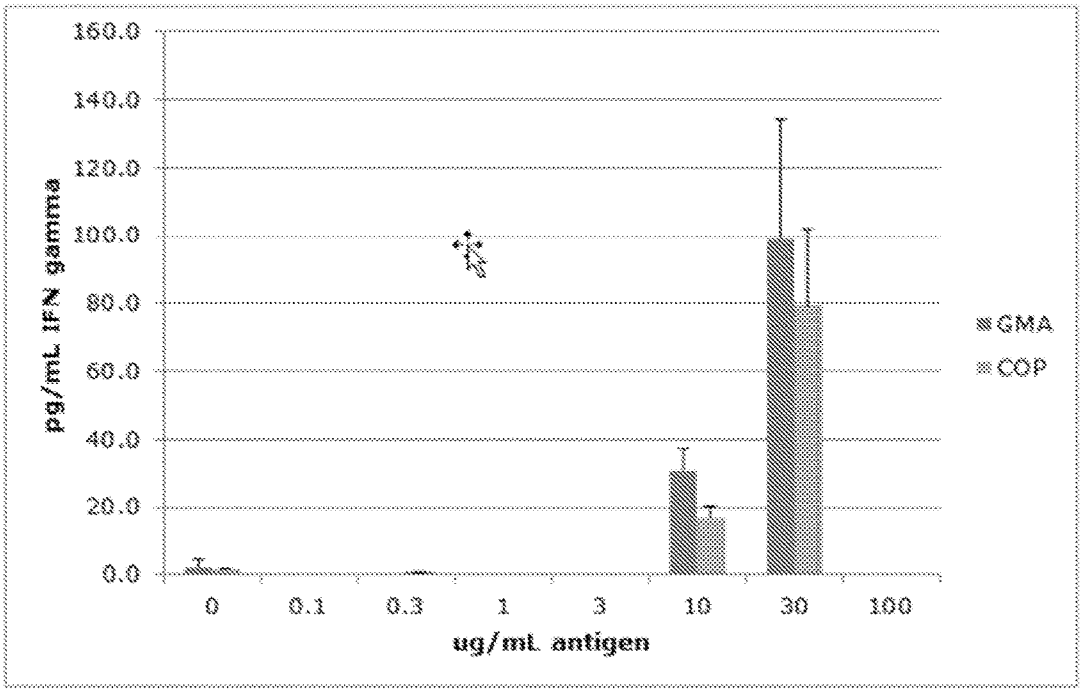

FIGURE 9
9A
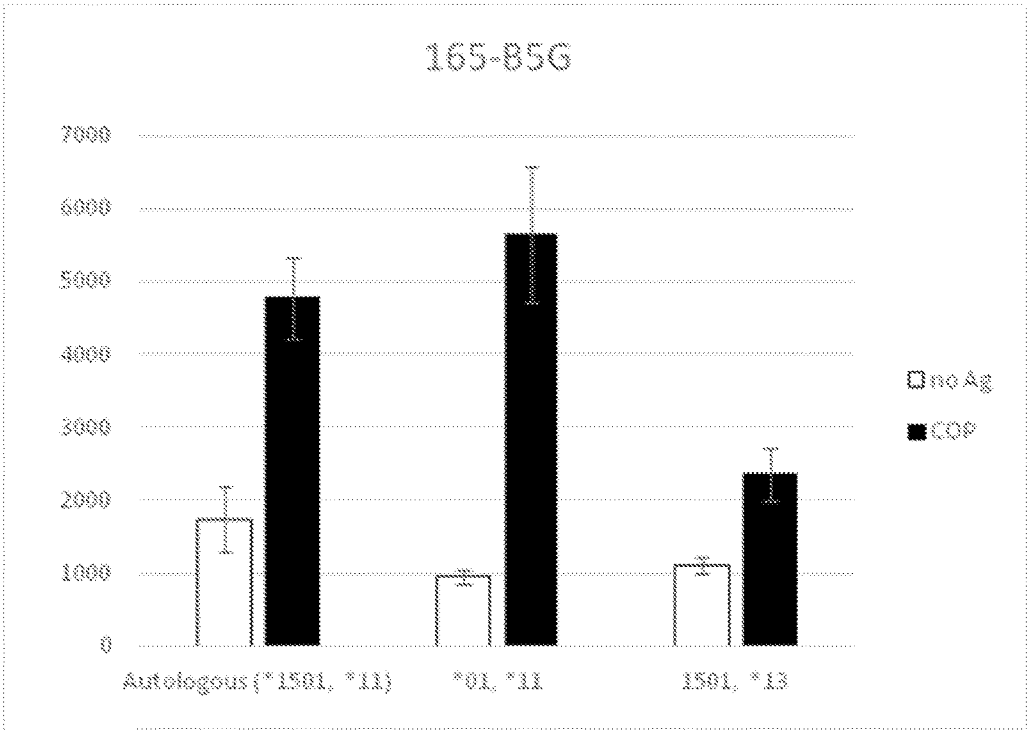
9B
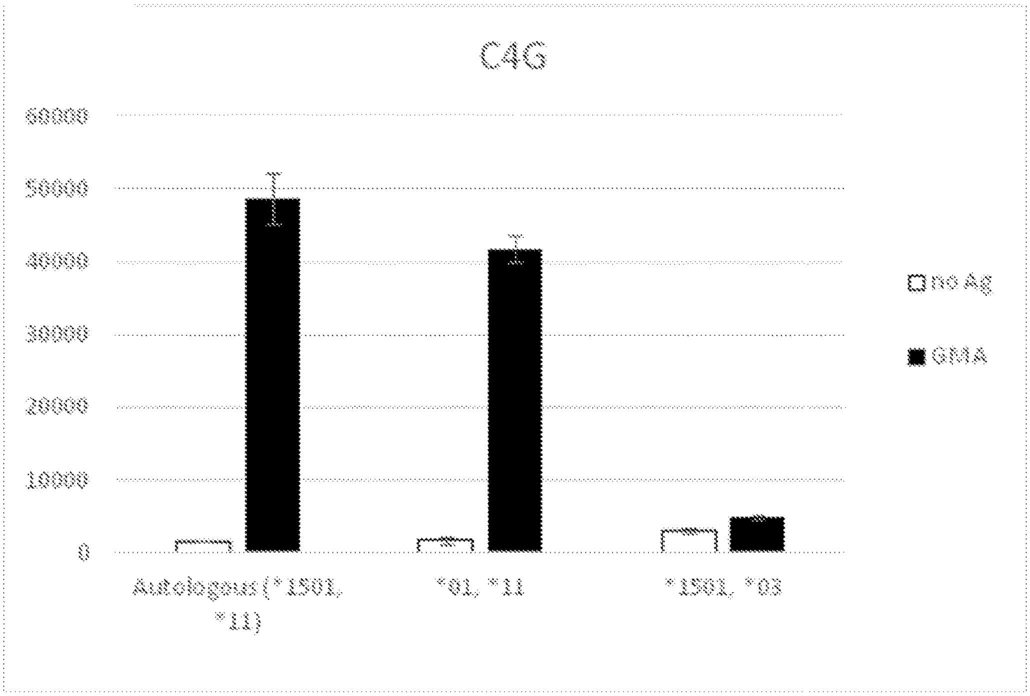

FIGURE 10
10A
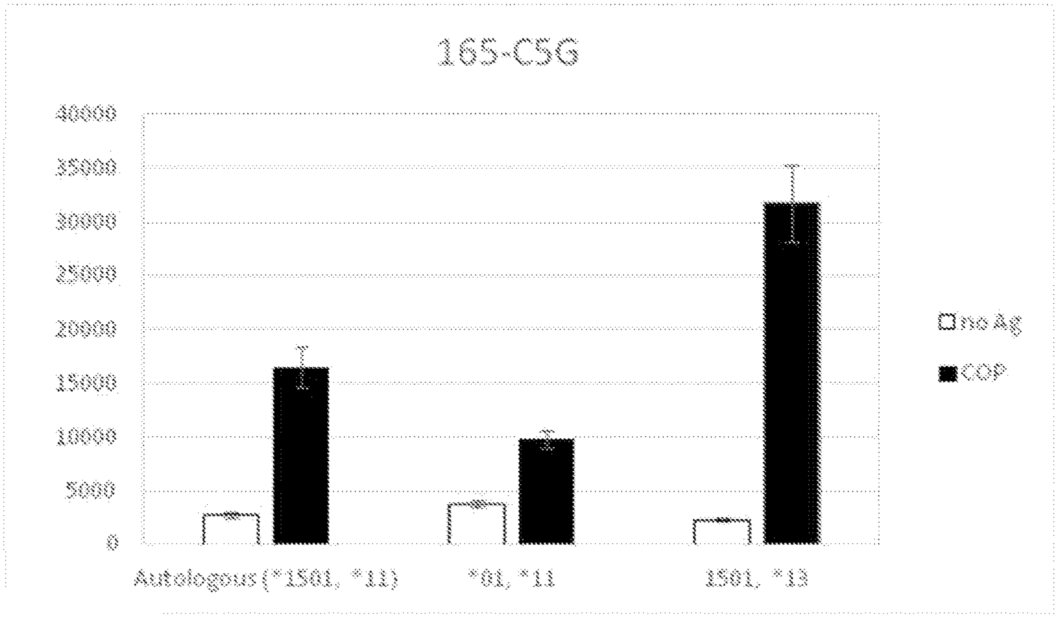
10B
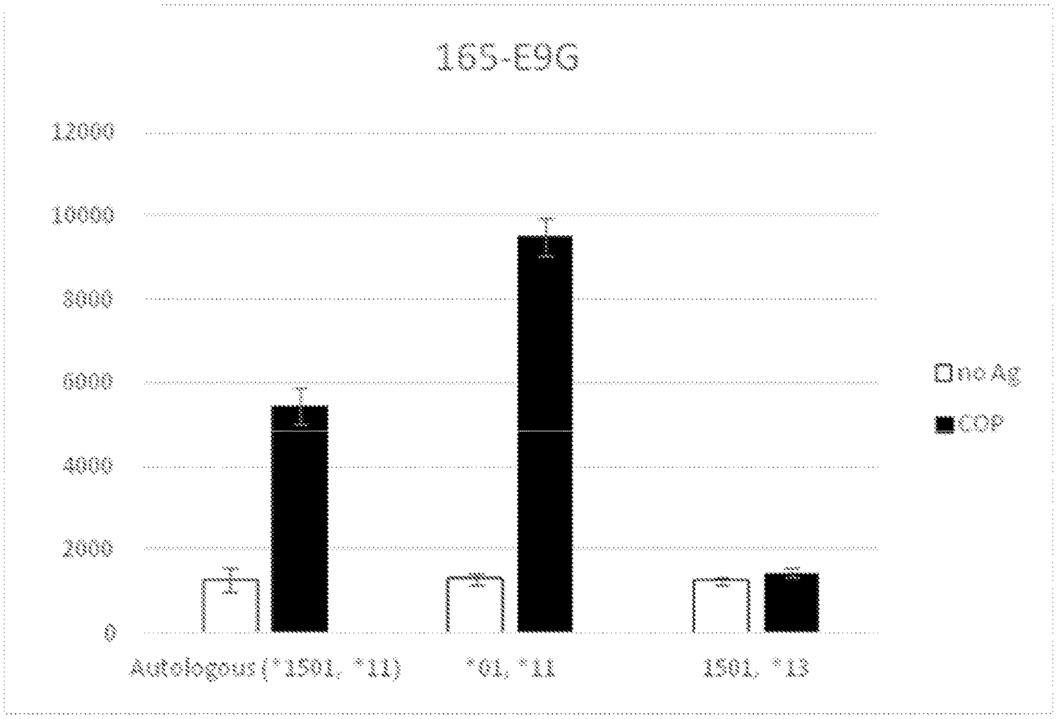

FIGURE 11
11A
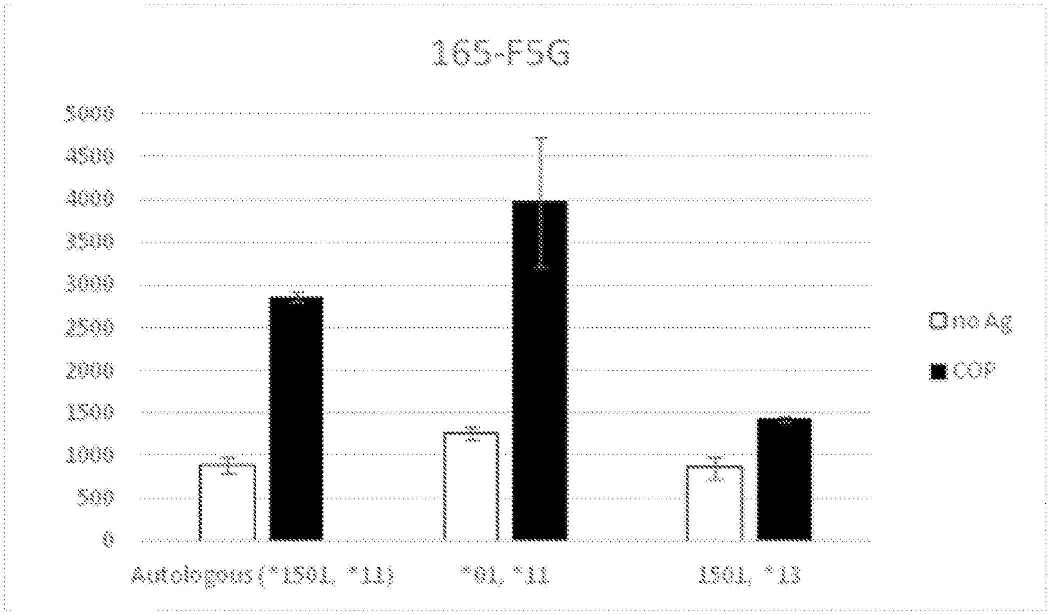
11B
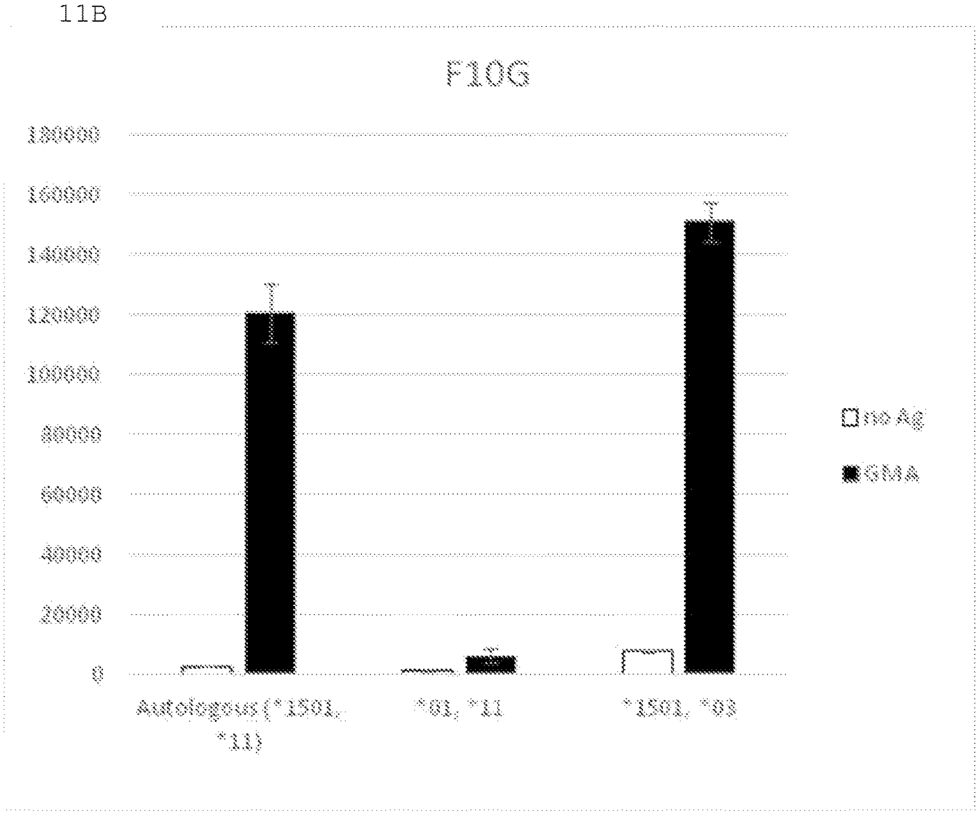

FIGURE 12
12A
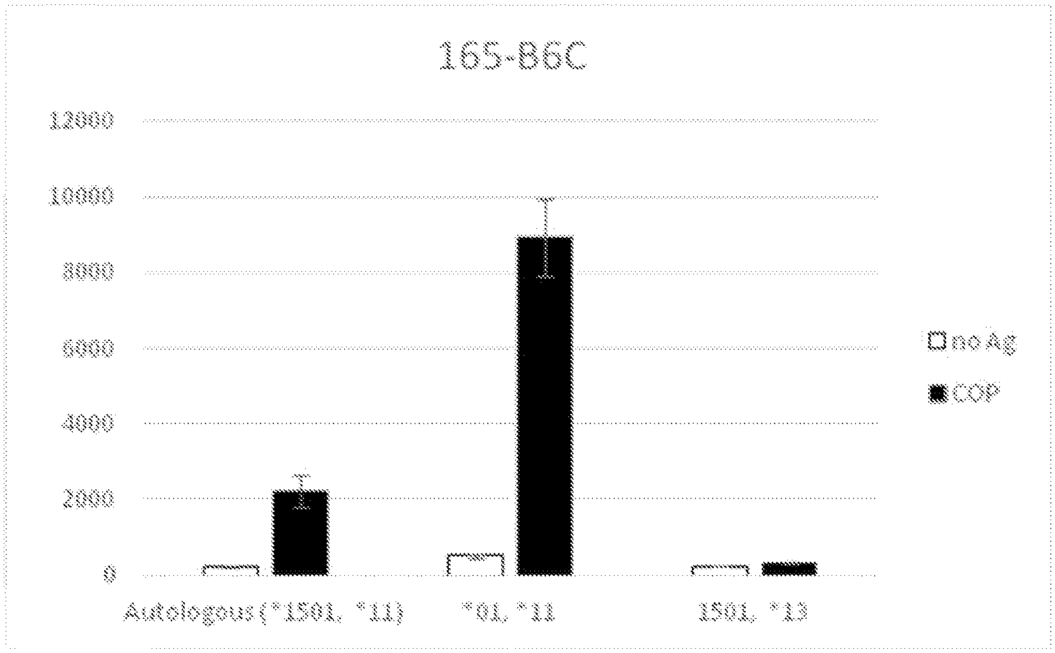
12B
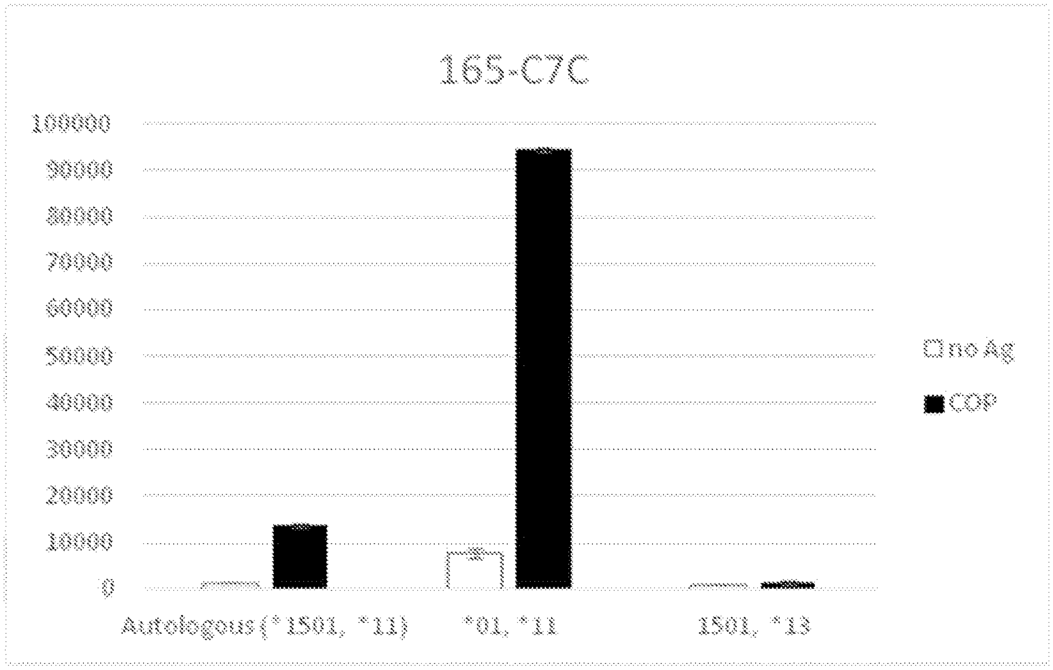

FIGURE 13
13A
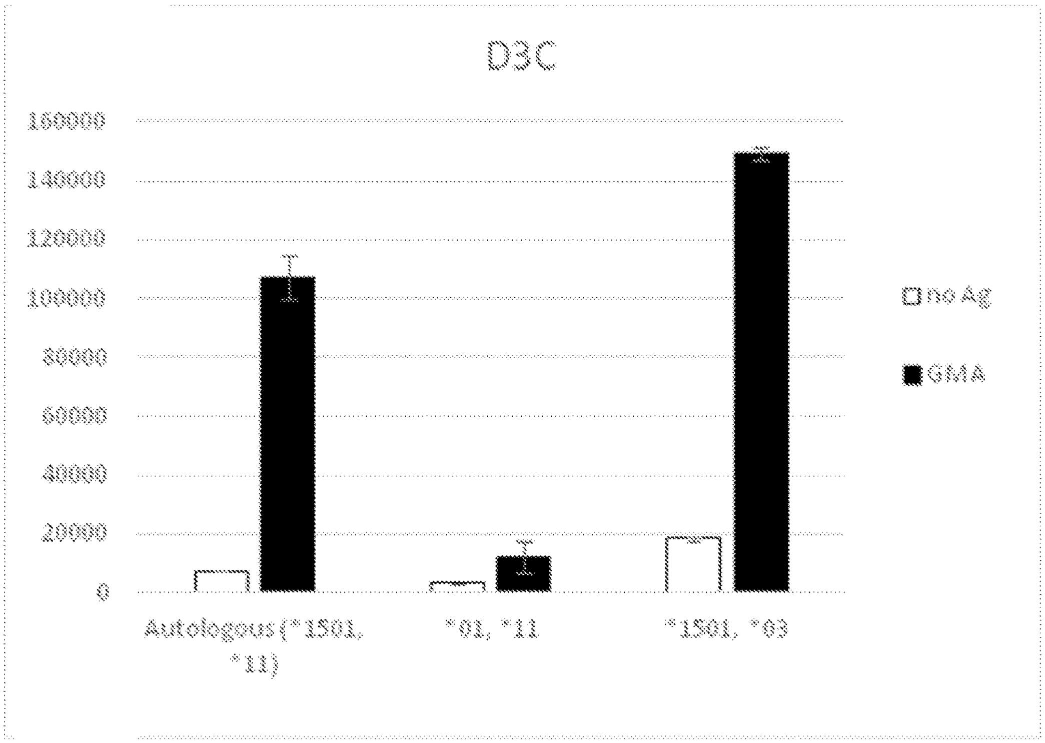
13B
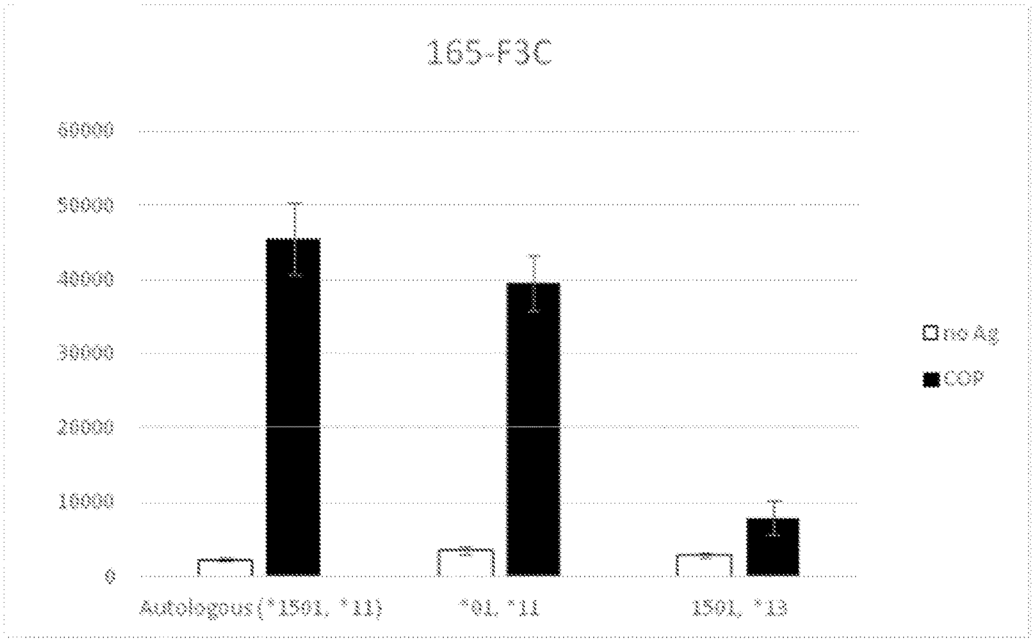

FIGURE 14
14A
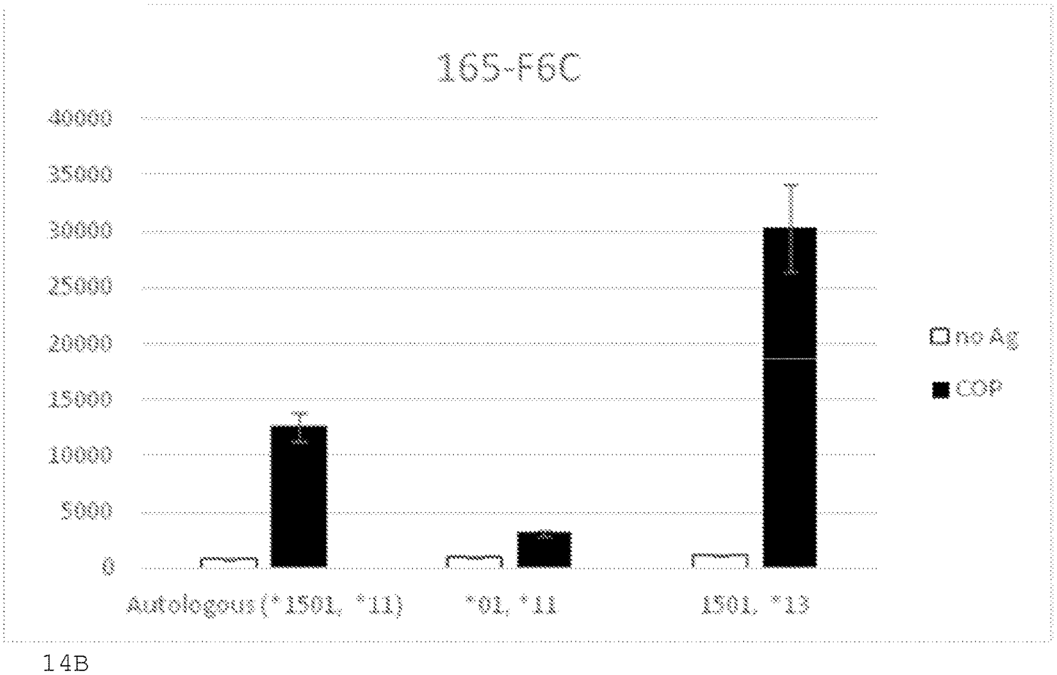
14B
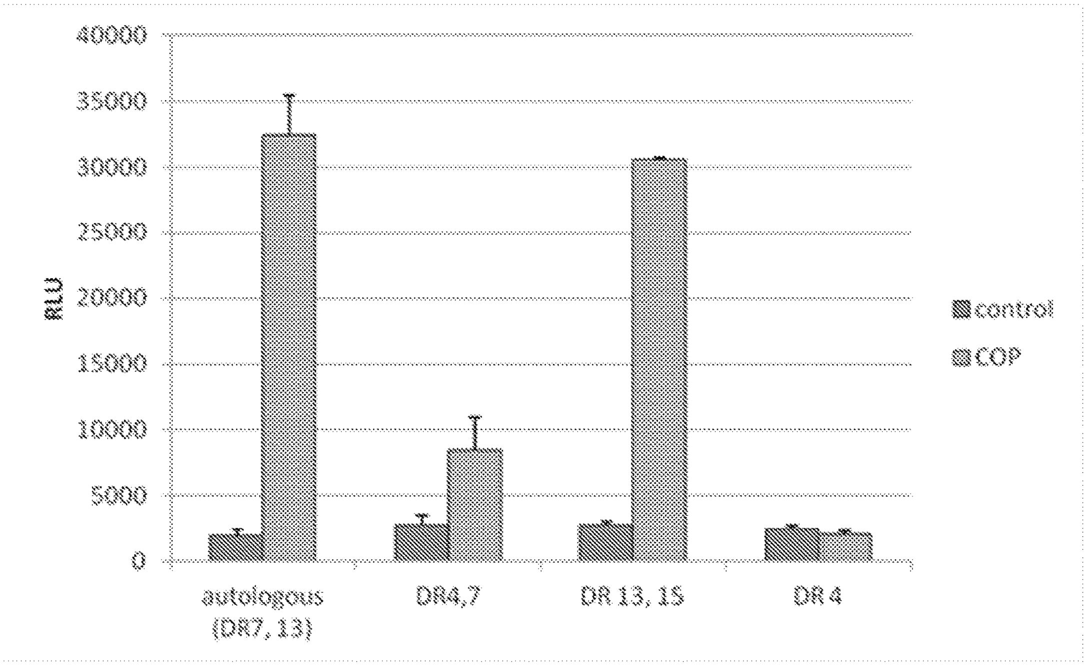

FIGURE 15
15A
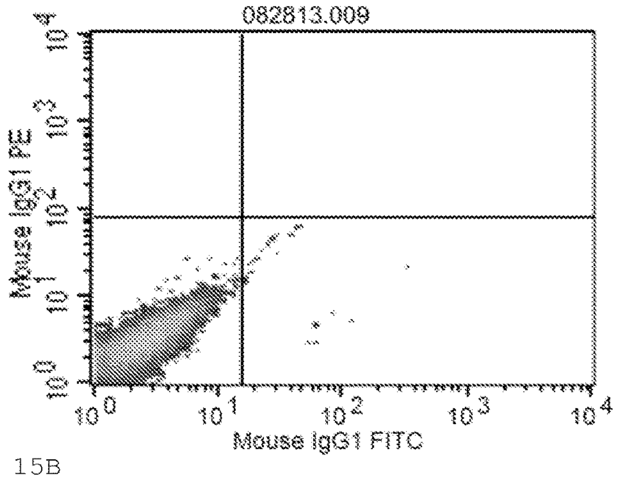
File: 082813.009
Sample ID: E9G 06JUL13
Acquisition Date: 28-Aug-13
Gate: G1
| Quad | % Gated | % Total |
|---|---|---|
| UL | 0.00 | 0.00 |
| UR | 0.00 | 0.00 |
| LL | 99.77 | 46.99 |
| LR | 0.23 | 0.11 |
15B
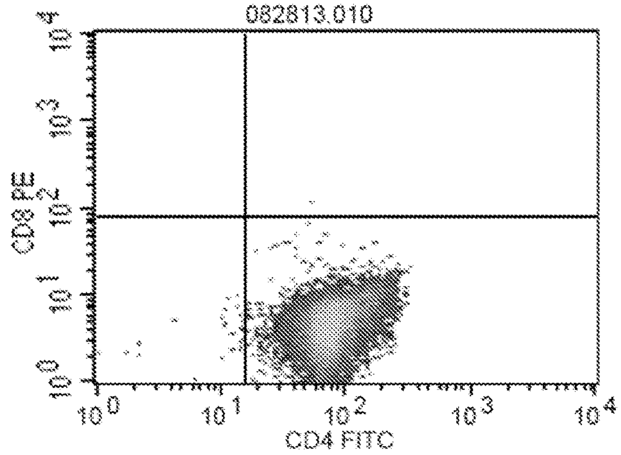
File: 082813.010
Sample ID: E9G 06JUL13
Acquisition Date: 28-Aug-13
Gate: G1
| Quad | % Gated | % Total |
|---|---|---|
| UL | 0.00 | 0.00 |
| UR | 0.01 | 0.00 |
| LL | 0.23 | 0.09 |
| LR | 99.76 | 39.99 |

FIGURE 16
16A
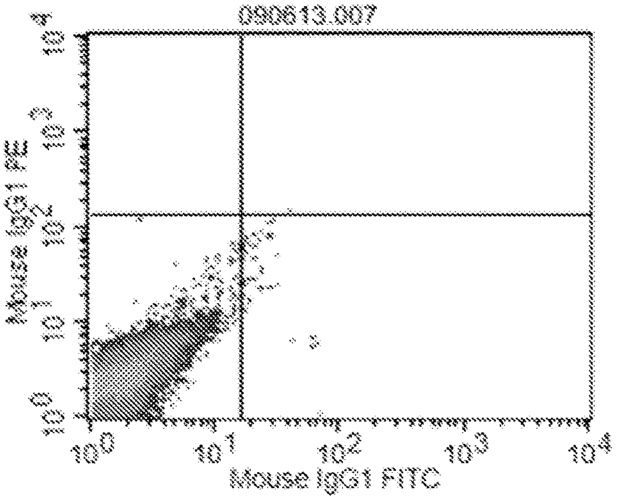
File: 090613.007
Sample ID: 165-F5G
Acquisition Date: 06-Sep-13
Gate: G1
| Quad | % Gated | % Total |
|---|---|---|
| UL | 0.00 | 0.00 |
| UR | 0.01 | 0.00 |
| LL | 99.79 | 75.29 |
| LR | 0.20 | 0.15 |
16B
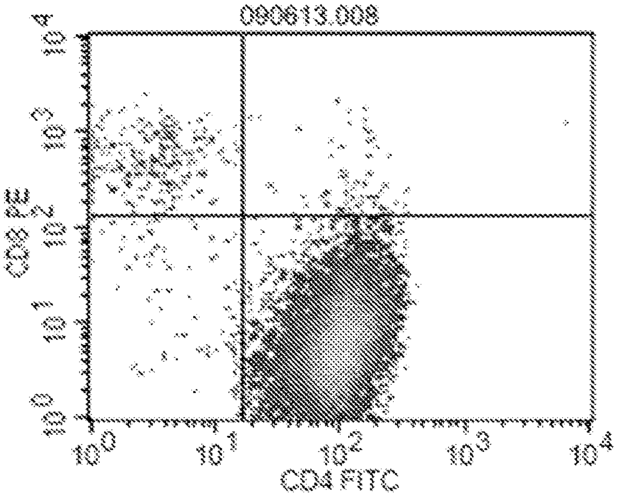
File: 090613.008
Sample ID: 165-F5G
Acquisition Date: 06-Sep-13
Gate: G1
| Quad | % Gated | % Total |
|---|---|---|
| UL | 1.50 | 1.11 |
| UR | 0.50 | 0.37 |
| LL | 0.55 | 0.40 |
| LR | 97.46 | 72.04 |

FIGURE 17
17A
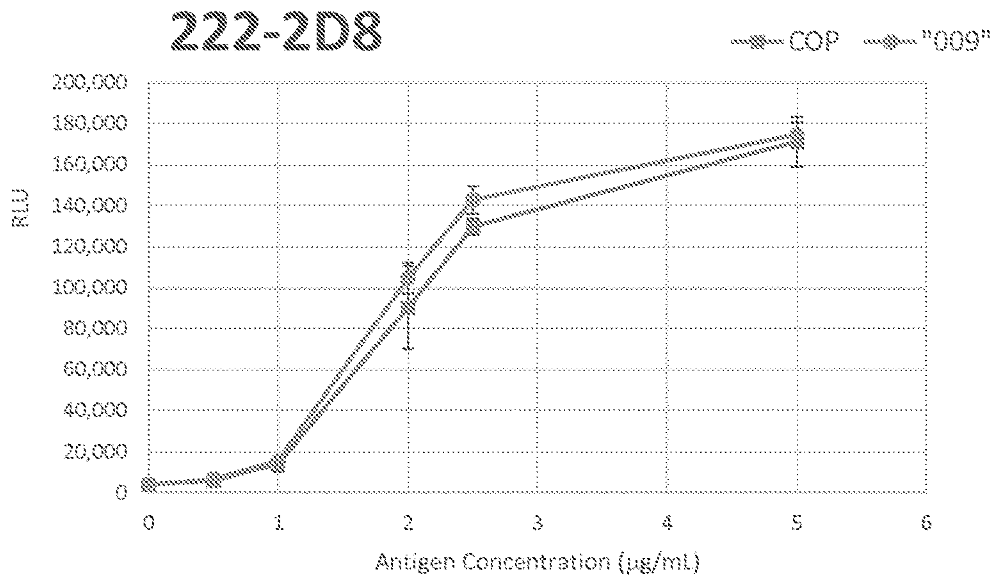
17B
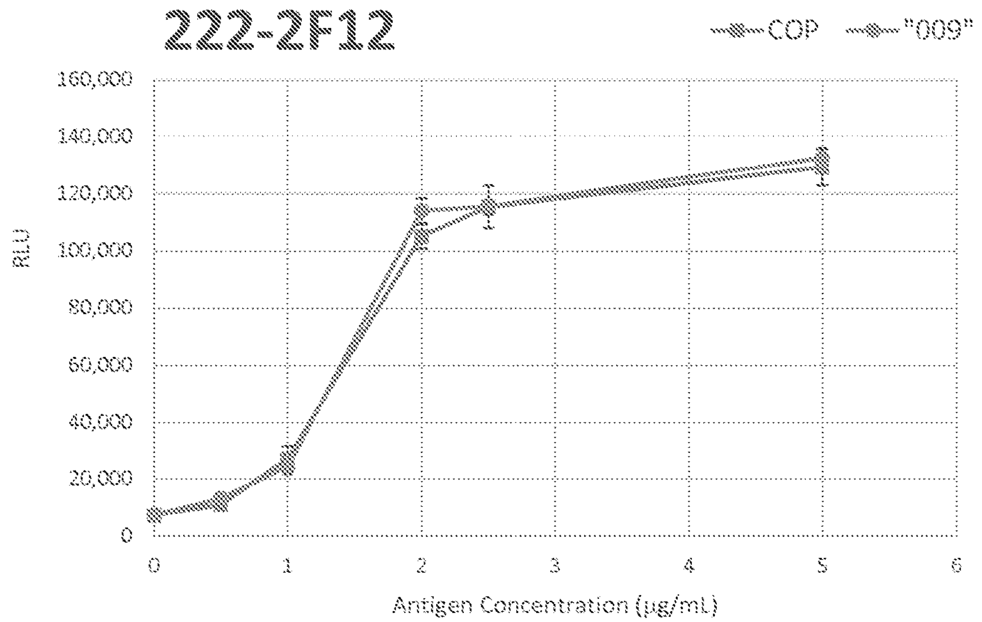

FIGURE 18
18A
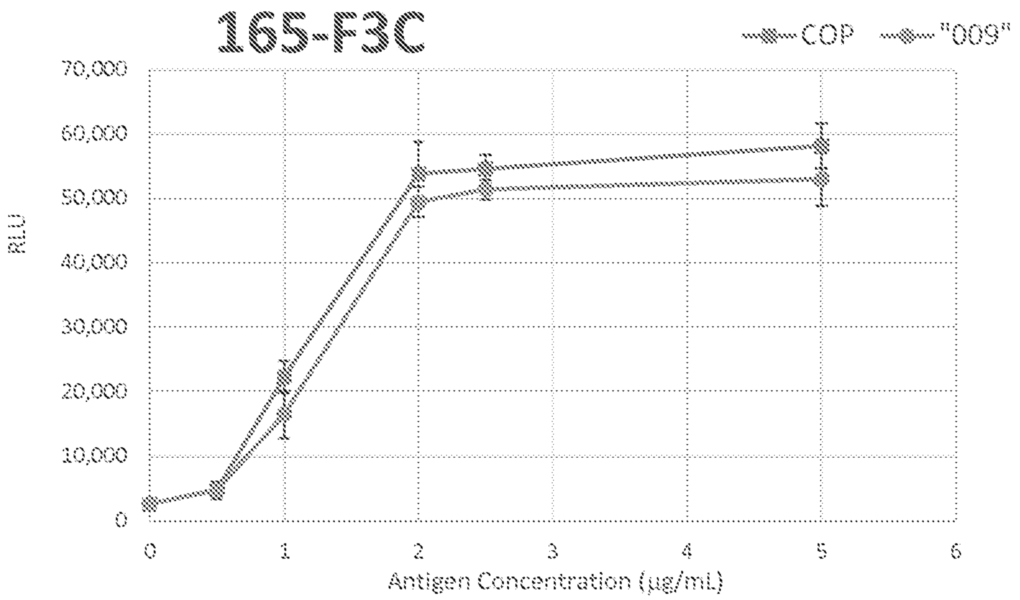
18B
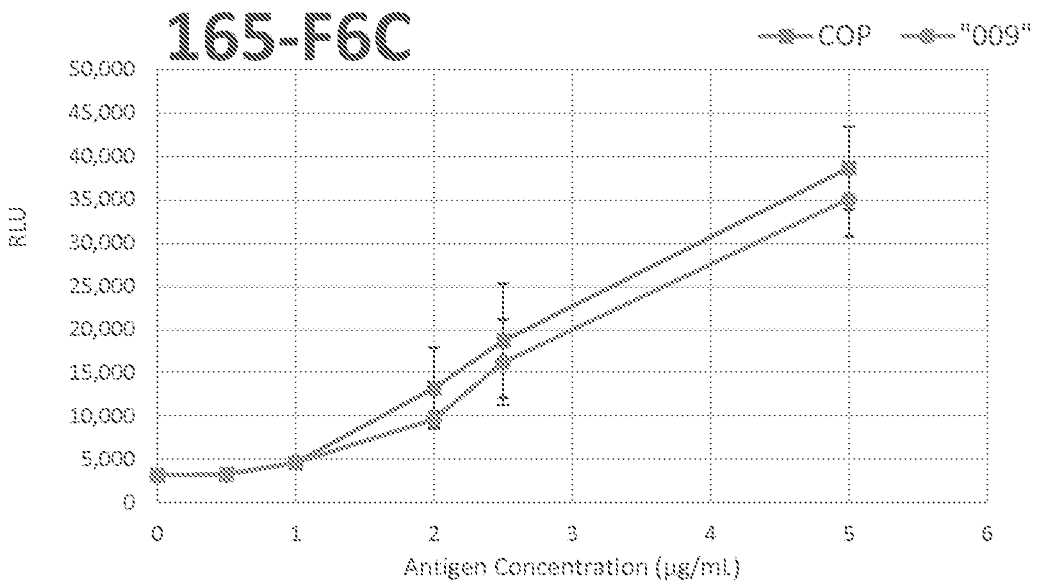

FIGURE 19
19A
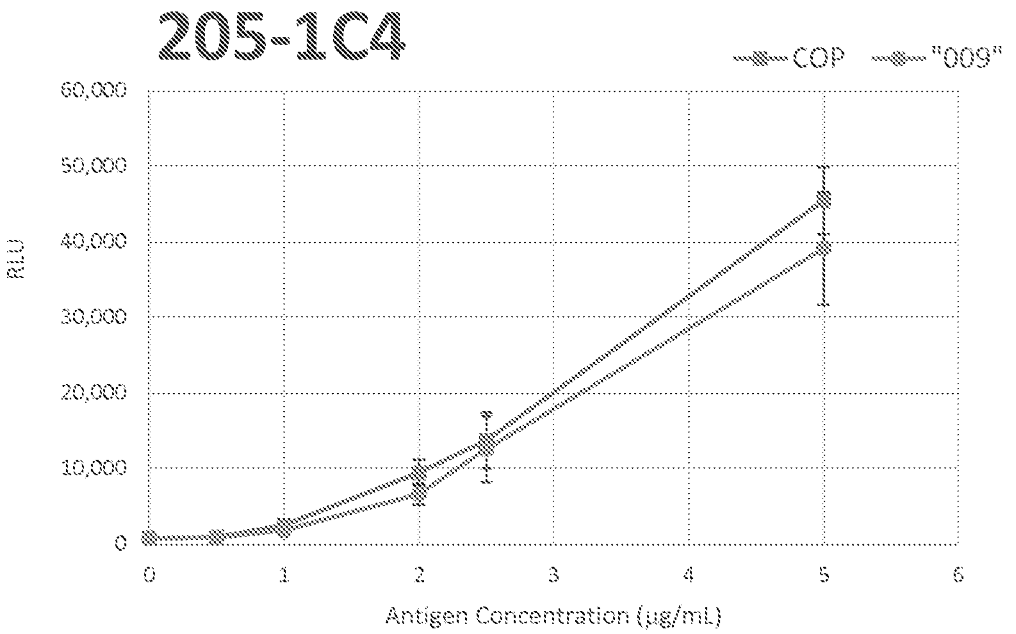
19B
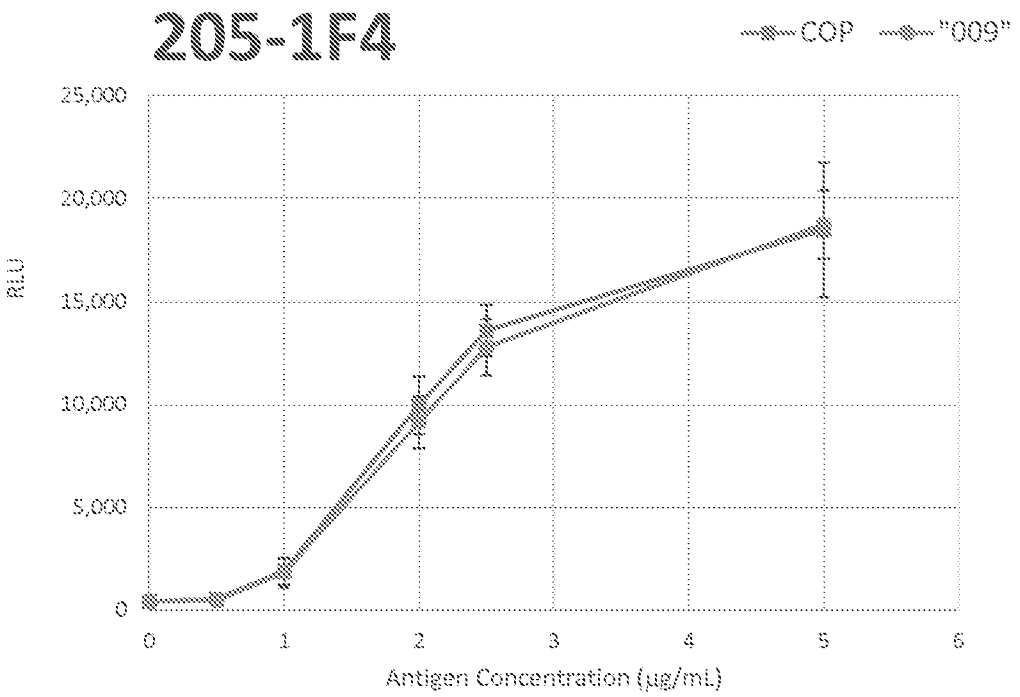

HUMAN T CELL LINE ASSAY FOR EVALUATING THE IMMUNOLOGIC IDENTITY OF GLATIRAMER ACETATE PREPARATIONS

CROSS-REFERENCE

This application claims the benefit of priority of U.S. Provisional Patent Application No. 61/895,370, filed Oct. 24, 2013; which is incorporated herein by reference in its entirety.

BACKGROUND OF THE INVENTION

Glatiramer acetate is a synthetic peptide drug approved for treating multiple sclerosis. It consists of the acetate salts of synthetic polypeptides containing the amino acids L-glutamic acid, L-alanine, L-tyrosine, and L-lysine. Currently sold as Copaxone®, glatiramer acetate injection is indicated for the reduction of the frequency of relapses in patients with Relapsing-Remitting Multiple Sclerosis (RRMS), including patients who have experienced a first clinical episode and have MRI features consistent with Multiple Sclerosis.

Glatiramer acetate is thought to act in multiple sclerosis by modifying immune processes responsible for the pathogenesis of the disease. In particular, it is believed that the mechanism of action of Copaxone® in Multiple Sclerosis is at least in part mediated by immunomodulation of T-cell activity.

During the manufacture of glatiramer acetate, reliable and cost-effective assays for interrogating glatiramer acetate preparations to demonstrate immunological identity and/or comparable potency to reference standard lots of glatiramer acetate are needed for maintaining consistency among drug lots for pharmaceutical use.

SUMMARY OF THE INVENTION

The invention is based on the discovery of methods for generating and identifying glatiramer acetate (GA)-specific human T-cell lines that respond similarly to different GA preparations, but differ in responsiveness to non-canonical GA peptides, have different MHC restriction elements, and produce different cytokines in response to stimulation with GA. The invention relates to methods for obtaining GA-specific human T-cell lines that recognize different GA epitopes, and to methods for using these GA-specific human T-cell lines to determine whether GA preparations are immunologically identical. In embodiments, the invention relates to a method for determining whether a GA test preparation and a GA reference standard preparation are immunologically identical, using at least one GA-specific human T-cell line or a panel of GA-specific human T-cell lines generated using the described methods.

The invention further relates to processes for preparing a drug product or pharmaceutical composition containing GA, comprising determining whether a GA test preparation and a GA reference standard are immunologically identical, and including the GA test lot in the drug product if it is determined to be immunologically identical to the GA reference standard. The invention also relates to a drug product containing GA prepared by the methods of the invention. The invention further relates to human B-cell lines appropriate for use as antigen presenting cells in the methods of the invention.

The assays of the present invention can demonstrate the immunological identity or reveal non-identity of GA product preparations with an accuracy not available using existing GA batch assays. The assays of the present invention do not require animal immunization, thereby eliminating assay-to-assay variability, and they do not require animal sacrifice.

In particular, the present invention relates to a method of determining whether a test preparation of GA and a GA reference standard are immunologically identical, using at least one GA-specific human T-cell line, the method comprising: a) incubating cells of the at least one GA-specific human T-cell line with appropriate antigen presenting cells (APC); b) stimulating at least one sample of the GA-specific human T-cells and appropriate APC incubated in step (a) with an amount of the test preparation of GA, and separately stimulating at least one sample of the GA-specific human T-cells and appropriate APC incubated in step (a) with the same amount of the GA reference standard; c) measuring at least one GA-elicited response of the at least one sample of cells stimulated in step (b) with the test preparation of GA, and measuring the same at least one GA-elicited response of the at least one sample of cells stimulated in step (b) with the GA reference standard; and d) comparing the measurements obtained in step (c); wherein the test preparation of GA and the GA reference standard are determined to be immunologically identical when the comparison of the measurements made in step (d) falls within an acceptable range.

In embodiments, the present invention relates to a method of determining whether a test preparation of glatiramer acetate (GA) and a GA reference standard are immunologically identical, the method comprising: measuring at least one GA-elicited response of at least one GA-specific human T-cell line to stimulation with the test preparation of GA in the presence of appropriate APC to obtain a first measurement, and at least one GA-elicited response of the at least one GA-specific human T-cell line to a GA reference standard in the presence of appropriate APC to obtain a second measurement; and comparing the first and second measurements; wherein the test preparation of GA and the GA reference standard are determined to be immunologically identical when the comparison of the first and second measurements falls within an acceptable range.

In the above embodiments, the appropriate APC can comprise cells selected from the group consisting of: Epstein Barr Virus-transformed (EBV-transformed) human B-cells autologous to the GA-specific human T-cells; EBV-transformed human B-cells having the DR molecule involved in antigen presentation to the GA-specific human T-cells; PBMC autologous to the GA-specific human T cells; PBMC having the DR molecule involved in antigen presentation to the GA-specific human T-cells; purified monocytes autologous to the GA-specific human T-cells; purified monocytes having the DR molecule involved in antigen presentation to the GA-specific human T-cells; purified dendritic cells autologous to the GA-specific human T-cells; and purified dendritic cells having the DR molecule involved in antigen presentation to the GA-specific human T-cells.

The invention also relates to a method comprising selecting for pharmaceutical use a test preparation of GA having immunologic identity to a GA reference standard determined according to methods described.

The invention relates to the above methods, wherein the acceptable range is about 80% to about 120%, or about 90% to about 110%. In embodiments of the above methods, the at least one measured GA-elicited response is selected from proliferation, production of a response biomarker, expression of a nucleic acid encoding a response biomarker, and a combination thereof. In embodiments, the at least one measured GA-elicited response is production of a response biomarker, and the response biomarker is a cytokine, a chemokine, or an activation marker. In certain embodiments, the response biomarker is a cytokine selected from: IL-2, IL-4, IL-5, IL-6, IL-10, IL-13, or IL-17, IL-21 IL-22, TNF-γ, TNF-α (TNF), TNF-β (LT), and IL-1b. In embodiments, the response biomarker is an activation marker selected from: CD69, CD25, CD71, CD137, CD154, CD278, CD279, and HLA-DR. In embodiments, the response biomarker is a chemokine selected from: IL-8 (CXCL8), RANTES (CCL5), CCL1, CXCL4, and CXCL7.

The invention relates to the above methods, wherein the at least one measured GA-elicited response is expression of a nucleic acid encoding a response biomarker, and the response biomarker encoded by the nucleic acid is a cytokine, a chemokine, or an activation marker. In embodiments, the encoded response biomarker is a cytokine selected from: IL-2, IL-4, IL-5, IL-6, IL-10, IL-13, or IL-17, IL-21, IL-22, IFN-γ, TNF-α (TNF), TNF-β (LT), TGF-β and IL-1b. In certain embodiments, the encoded response biomarker is an activation marker selected from: CD69, CD25, CD71, CD137, CD154, CD278, CD279, and HLA-DR. In embodiments, the encoded response biomarker is a chemokine selected from: IL-8 (CXCL8), RANTES (CCL5), CCL1, CXCL4, and CXCL7.

The invention relates to the above methods, wherein at least two GA-elicited responses of the cells stimulated with the test preparation of GA are measured, and the same at least two GA-elicited responses of the cells stimulated with the GA reference standard, are measured. In these embodiments, the at least two GA-elicited responses can be selected from the expression of: IL-2, IL-4, IL-5, IL-6, IL-10, IL-13, or IL-17, IL-21, IL-22, IFN-γ, TNF-α (TNF), TNF-β (LT), TGF-β, IL-1b, CD69, CD25, CD71, CD137, CD154, CD278, CD279, HLA-DR, IL-8 (CXCL8), RANTES (CCL5), CCL1, CXCL4, CXCL7, a nucleic acid encoding IL-2; a nucleic acid encoding IL-4, a nucleic acid encoding IL-5, a nucleic acid encoding IL-6, a nucleic acid encoding IL-10, a nucleic acid encoding IL-13, or a nucleic acid encoding IL-17, a nucleic acid encoding IL-22, a nucleic acid encoding IFN-γ, a nucleic acid encoding TNF-α (TNF), a nucleic acid encoding TNF-β (LT), a nucleic acid encoding TGF-β, a nucleic acid encoding IL-1b, a nucleic acid encoding CD69, a nucleic acid encoding CD25, a nucleic acid encoding CD71, a nucleic acid encoding CD137, a nucleic acid encoding CD154, a nucleic acid encoding CD278, a nucleic acid encoding CD279, a nucleic acid encoding HLA-DR, a nucleic acid encoding IL-8 (CXCL8), a nucleic acid encoding RANTES (CCL5), a nucleic acid encoding CCL1, a nucleic acid encoding CXCL4, and a nucleic acid encoding CXCL7, The invention relates to the above methods, wherein the GA reference standard is Copaxone (COP) or Mylan GA (GMA).

The invention relates to the above methods, wherein the appropriate APC have at least one HLA-DR restriction element capable of presenting GA peptides. In certain embodiments, the at least one HLA-DR restriction element capable of presenting GA peptides is selected from: DR-1, DR-2, DR-3, DR-4, DR-7, DR-11, DR-13, and DR-15.

The invention relates to the above methods, wherein the at least one GA-specific human T-cell line incubated in step (a) is a long-term T-cell line. In embodiments, the GA-specific human T-cell line is clonal. In embodiments, the at least one long-term GA-specific human T-cell line has been maintained in culture for at least about four weeks prior to stimulation, previously restimulated at least four times, or both. In embodiments, the at least one long-term GA-specific human T-cell line has been previously restimulated at least eight times. In embodiments, the maintenance in culture of the at least one long-term GA-specific human T-cell line comprises recurrent restimulation with GA and autologous APC, in the absence of mitogen.

The invention relates to the above methods, wherein the stimulation includes stimulating each of at least three samples of GA-specific human T-cells, incubated with or in the presence of APC, with one of a series of amounts of the test preparation of GA, and stimulating each of at least three samples of GA-specific human T-cells, incubated with or in the presence of APC, with one of the same series of amounts of the GA reference standard. In embodiments, the series of amounts of the test preparation of GA, and the series of amounts of the GA reference standard, comprise escalating doses of GA of about 1 ng/mL to about 1 mg/mL GA. In embodiments, the series of amounts of the test preparation of GA, and the series of amounts of the GA reference standard, are escalating doses of GA of about 1 μg/mL to about 30 μg/mL GA.

In embodiments, the invention relates to a process for preparing a drug product or pharmaceutical composition containing GA, comprising: 1) reacting protected glatiramer acetate with hydrobromic acid to form trifluoroacetyl GA, treating said trifluoroacetyl copolymer-1 with aqueous piperidine solution to form a test preparation of GA, and purifying the test preparation of GA; 2) determining whether the test preparation of GA and a GA reference standard are immunologically identical, by: a) incubating cells of at least one GA-specific human T-cell line with appropriate antigen presenting cells (APC); b) stimulating at least one sample of the GA-specific human T-cells and appropriate APC incubated in step (a) with an amount of the test preparation of GA, and separately stimulating at least one sample of the GA-specific human T-cells and appropriate APC incubated in step (a) with the same amount of the GA reference standard; c) measuring at least one GA-elicited response of the at least one sample of cells stimulated in step (b) with the test preparation of GA, and measuring the same at least one GA-elicited response of the at least one sample of cells stimulated in step (b) with the GA reference standard; and d) comparing the measurements obtained in step (c); wherein the test preparation of GA and the GA reference standard are determined to be immunologically identical when the comparison of the measurements of step (d) falls within an acceptable range, and wherein the test preparation of GA is admixed in the drug product or pharmaceutical composition if it is determined to be immunologically identical to the GA reference standard.

In these embodiments, the appropriate APC can comprise cells selected from the group consisting of: Epstein Barr Virus-transformed (EBV-transformed) human B-cells autologous to the GA-specific human T-cells; EBV-transformed human B-cells having the DR molecule involved in antigen presentation to the GA-specific human T-cells; PBMC autologous to the GA-specific human T cells; PBMC having the DR molecule involved in antigen presentation to the GA-specific human T-cells; purified monocytes autologous to the GA-specific human T-cells; purified monocytes having the DR molecule involved in antigen presentation to the GA-specific human T-cells; purified dendritic cells autologous to the GA-specific human T-cells; and purified dendritic cells having the DR molecule involved in antigen presentation to the GA-specific human T-cells.

In embodiments, the acceptable range is about 80% to about 120%, or about 90% to about 110%. In certain embodiments of the above methods, the at least one measured GA-elicited response is selected from proliferation, production of a response biomarker, expression of a nucleic acid encoding a response biomarker, and a combination thereof. In embodiments, the at least one measured GA-elicited response is production of a response biomarker, and the response biomarker is a cytokine, a chemokine, or an activation marker. In certain embodiments, the response biomarker is a cytokine selected from: IL-2, IL-4, IL-5; IL-6, IL-10, IL-13, or IL-17, IL-21 IL-22, IFN-γ, TNF-α (TNF), TNF-β (LT), and IL-1b. In embodiments, the response biomarker is an activation marker selected from: CD69, CD25, CD71, CD137, CD154, CD278, CD279, and HLA-DR. In embodiments, the response biomarker is a chemokine selected from: IL-8 (CXCL8), RANTES (CCL5), CCL1, CXCL4, and CXCL7.

In embodiments, the at least one measured GA-elicited response is expression of a nucleic acid encoding a response biomarker, and the response biomarker encoded by the nucleic acid is a cytokine, a chemokine, or an activation marker. In embodiments, the encoded response biomarker is a cytokine selected from: IL-2, IL-4, IL-5, IL-6, IL-10, IL-13, or IL-17, IL-21, IL-22, IFN-γ, TNF-α (TNF), TNF-β (LT), TGF-β and IL-1b. In certain embodiments, the encoded response biomarker is an activation marker selected from: CD69, CD25, CD71, CD137, CD154, CD278, CD279, and HLA-DR. In embodiments, the encoded response biomarker is a chemokine selected from: IL-8 (CXCL8), RANTES (CCL5), CCL1, CXCL4, and CXCL7.

In embodiments, wherein at least two GA-elicited responses of the cells stimulated with the test preparation of GA are measured, and the same at least two GA-elicited responses of the cells stimulated with the GA reference standard, are measured. In these embodiments, the at least two GA-elicited responses can be selected from the expression of: IL-2, IL-4, IL-5, IL-6, IL-10, IL-13, or IL-17, IL-21, IL-22, IFN-γ, TNF-α (TNF), TNF-β (LT), TGF-β, IL-1b, CD69, CD25, CD71, CD137, CD154, CD278, CD279, HLA-DR, IL-8 (CXCL8), RANTES (CCL5), CCL1, CXCL4, CXCL7, a nucleic acid encoding IL-2, a nucleic acid encoding IL-4, a nucleic acid encoding IL-5, a nucleic acid encoding IL-6, a nucleic acid encoding IL-10, a nucleic acid encoding IL-13, or a nucleic acid encoding IL-17, a nucleic acid encoding a nucleic acid encoding IFN-γ, a nucleic acid encoding TNF-α (TNF), a nucleic acid encoding TNF-β (LT), a nucleic acid encoding TGF-β, a nucleic acid encoding IL-1b, a nucleic acid encoding CD69, a nucleic acid encoding CD25, a nucleic acid encoding CD71, a nucleic acid encoding CD137, a nucleic acid encoding CD154, a nucleic acid encoding CD278, a nucleic acid encoding CD279, a nucleic acid encoding HLA-DR, a nucleic acid encoding IL-8 (CXCL8), a nucleic acid encoding RANTES (CCL5), a nucleic acid encoding CCL1, a nucleic acid encoding CXCL4, and a nucleic acid encoding CXCL7.

In embodiments, the GA reference standard is Copaxone or GMA.

In embodiments, the appropriate APC have at least one HLA-DR restriction element capable of presenting GA peptides. In certain embodiments, the at least one HLA-DR restriction element capable of presenting GA peptides is selected from: DR-1, DR-2, DR-3, DR-4, DR-7, DR-11, DR-13, and DR-15.

In embodiments, the at least one GA-specific human T-cell line incubated in step (a) is a long-term T-cell line. In embodiments, the at least one GA-specific human T-cell line is clonal. In embodiments, the at least one long-term GA-specific human T-cell line has been maintained in culture for at least about four weeks prior to stimulation, previously restimulated at least four times, or both. In embodiments, the at least one long-term GA-specific human T-cell line has been previously restimulated at least eight times. In embodiments, the maintenance in culture of the at least one long-term GA-specific human T-cell line comprises recurrent restimulation with GA and autologous APC, in the absence of mitogen.

In embodiments, the stimulation includes stimulating each of at least three samples of GA-specific human T-cells, incubated with or in the presence of APC, with one of a series of amounts of the test preparation of GA, and stimulating each of at least three samples of GA-specific human T-cells, incubated with or in the presence of APC, with one of the same series of amounts of the GA reference standard. In embodiments, the series of amounts of the test preparation of GA, and the series of amounts of the GA reference standard, comprise escalating doses of GA of about 1 ng/mL to about 1 mg/mL GA. In embodiments, the series of amounts of the test preparation of GA, and the series of amounts of the GA reference standard, are escalating doses of GA of about 1 μg/mL to, about 30 μm/mL GA.

The invention further relates to a method for generating and identifying a GA-specific human T-cell line, the method comprising: a) obtaining a sample of cells, wherein the sample of cells comprises T-cells from a human donor and appropriate APC; b) preparing a culture from the sample of cells of step (a), wherein the culture comprises GA; c) incubating the culture of step (b) with IL-2; d) assaying the culture of step (c) by preparing at least one test culture comprising cells from the culture of step (c), appropriate APC, and a test preparation of GA, preparing at least one control culture from the culture of step (c), and (i) measuring at least one GA-elicited response of the at least one test culture; (ii) measuring the same at least one GA-elicited response of the control culture; and e) comparing the measurement of step (d)(i) with the measurement of step (d)(ii); wherein the generated GA-specific human T-cell line is identified based on an increase in the at least one GA-elicited response measured in step (d)(i) relative to the at least one GA-elicited response measured in step (d)(ii); and f) optionally expanding the culture, and repeating steps (d) and (e) using the expanded culture, to further characterize the identified GA-specific human T-cell line.

In these embodiments, the at least one measured GA-elicited response can be selected from proliferation, production of a response biomarker, expression of a nucleic acid encoding a response biomarker, and a combination thereof. In related embodiments, the at least one measured GA-elicited response is production of a response biomarker, and the response biomarker is a cytokine, an activation marker, or a chemokine. In certain embodiments, the response biomarker is a cytokine selected from: IL-2, IL-4, IL-5, IL-6, IL-10, IL-13, or IL-17, IL-21, IL-22, IFN-γ, TNF-α (TNF), TNF-β (LT), TGF-β, and IL-1b. In embodiments, the response biomarker is an activation marker selected from: CD69, CD25, CD71, CD137, CD154, CD278, CD279, and HLA-DR. In embodiments, the response biomarker is a chemokine selected from: IL-8(CXCL8), RANTES (CCL5), CCL1, CXCL4, and CXCL7. In related embodiments, the at least one measured GA-elicited response is expression of a nucleic acid encoding a response biomarker, and the encoded response biomarker is a cytokine, an activation marker, or a chemokine. In certain embodiments, the encoded response biomarker is a cytokine selected from: IL-2, IL-4, IL-5, IL-6, IL-10, IL-13, or IL-17, IL-21, IL-22, IFN-γ, TNF-α (TNF), TNF-β (LT), TGF-β, and IL-1b. In embodiments, the encoded response biomarker is a chemokine selected from: IL-8 (CXCL8), RANTES (CCL5), CCL1, CXCL4, and CXCL7. In embodiments, the encoded response biomarker is an activation marker selected from: CD69, CD25, CD71, CD137, CD154, CD278, CD279, and HLA-DR.

In embodiments of the invention, step (e) comprises measuring at least two GA-elicited responses of the cultured T-cells to the GA, and step (f) comprises measuring the same at least two GA-elicited responses of the cultured T-cells to the control antigen. In related embodiments, the at least two GA-elicited responses are selected from the expression of: IL-2, IL-4, IL-5, IL-6, IL-10, IL-13, or IL-17, IL-21, IL-22, IFN-γ, TNF-α (TNF), TNF-β (LT), TGF-β, CD69, CD25, CD71, CD137, CD154, CD278, CD279, HLA-DR, IL-8 (CXCL8), RANTES (CCL5), CCL1, CXCL4, CXCL7, a nucleic acid encoding IL-2, a nucleic acid encoding IL-4, a nucleic acid encoding IL-5, a nucleic acid encoding IL-6, a nucleic acid encoding IL-10, a nucleic acid encoding IL-13, or a nucleic acid encoding IL-17, a nucleic acid encoding IL-21, a nucleic acid encoding IL-22, a nucleic, acid encoding IFN-γ, a nucleic acid encoding TNF-α (TNF), a nucleic acid encoding TNF-ρ (LT), a nucleic acid encoding TGF-β, a nucleic acid encoding IL-1b, a nucleic acid encoding CD69, a nucleic acid encoding CD25, a nucleic acid encoding CD71, a nucleic acid encoding CD137, a nucleic acid encoding CD154, a nucleic acid encoding CD278, a nucleic acid encoding CD279, a nucleic acid encoding HLA-DR, a nucleic acid encoding IL-8(CXCL8), a nucleic acid encoding RANTES (CCL5), a nucleic acid encoding CCL1, a nucleic acid encoding CXCL4, and a nucleic acid encoding CXCL7.

In embodiments, the appropriate APC are autologous cells. In embodiments, the appropriate APC are autologous PBMC. In embodiments, the appropriate APC are autologous PBMC treated with a an anti-mitotic agent, e.g., mitomycin C. In embodiments, the appropriate APC have at least one HLA-DR restriction element capable of presenting GA peptides. In certain embodiments, the at least one HLA-DR restriction element capable of presenting GA peptides is selected from: DR-1, DR-2, DR-3, DR-4, DR-7, DR-11, DR-13, and DR-15.

The invention also relates to a GA-specific human T-cell line obtained according to these methods. In embodiments, the generated GA-specific human T-cell line is a long-term T-cell line. In embodiments, the generated GA-specific human T-cell line is clonal.

In embodiments of the invention, no mitogen is added to the culture of step (b) or (c).

In embodiments, the method further comprises characterizing the identified GA-specific human T-cell line, wherein the characterization comprises one or more of: a) confirming or reconfirming the GA-specificity of the identified GA-specific human T-cell line; b) determining the MHC restriction of the identified GA-specific human T-cell line; c) determining a response biomarker profile of the identified GA-specific human T-cell line; and d) determining the reactivity of the identified GA-specific human T-cell line to at least one non-canonical GA peptide.

In embodiments, the method further comprises characterizing the response of the identified GA-specific human T-cell line to a non-canonical GA peptide by: preparing at least one test culture comprising cells of the identified GA-specific human T-cell line, appropriate APC, and a non-canonical GA peptide; preparing at least one control culture comprising cells of the identified GA-specific human T-cell line; measuring at least one GA-elicited response of the at least one test culture; measuring the same at least one GA-elicited response of the control culture; and comparing the measurement of the GA-elicited responses of the test and control cultures; wherein the GA-specific human T-cell line that responds to stimulation with the non-canonical GA peptide is identified by an increase in the at least one GA-elicited response of the test culture relative to the control culture.

The invention also relates to a long-term GA-specific human T-cell line, wherein the long-term GA-specific human T-cell line is capable of producing at least one measured response to stimulation with a test preparation of GA that is increased relative to the same at least one measured response to stimulation with a control antigen, said at least one measured response comprising proliferation, production of a response biomarker, expression of a nucleic acid encoding a response biomarker, or a combination thereof. In embodiments, the GA-specific human T-cell line is clonal.

In embodiments, the at least one measured GA-elicited response is selected from proliferation, production of a response biomarker, expression of a nucleic acid encoding a response biomarker, and a combination thereof. In embodiments, the at least one measured GA-elicited response is production of a response biomarker, and the response biomarker is a cytokine, a chemokine, or an activation marker. In certain embodiments, the response biomarker is a cytokine selected from: IL-2, IL-4, IL-5, IL-6, IL-10, IL-13, or IL-17, IL-21 IL-22, IFN-γ, TNF-α (TNF), TNF-β (LT), and IL-1b. In embodiments, the response biomarker is an activation marker selected from: CD69, CD25, CD71, CD137, CD154, CD278, CD279, and HLA-DR. In embodiments, the response biomarker is a chemokine selected from: IL-8 (CXCL8), RANTES (CCL5), CCL1, CXCL4, and CXCL7.

In embodiments, the at least one measured GA-elicited response is expression of a nucleic acid encoding a response biomarker, and the response biomarker encoded by the nucleic acid is a cytokine, a chemokine, or an activation marker. In embodiments, the encoded response biomarker is a cytokine selected from: IL-2, IL-4, IL-5, IL-6, IL-10, IL-13, or IL-17, IL-21, IL-22, IFN-γ, TNF-α (TNF), TNF-β (LT), TGF-β and IL-1b. In certain embodiments, the encoded response biomarker is an activation marker selected from: CD69, CD25, CD71, CD137, CD154, CD278, CD279, and HLA-DR. In embodiments, the encoded response biomarker is a chemokine selected from: IL-8 (CXCL8), RANTES (CCL5), CCL1, CXCL4, and CXCL7.

In embodiments, at least two GA-elicited responses of the cells stimulated with the test preparation of GA are measured, and the same at least two GA-elicited responses of the cells stimulated with the GA reference standard, are measured. In these embodiments, the at least two GA-elicited responses can be selected from the expression of: IL-2, IL-4, IL-5, IL-6, IL-10, IL-13, or IL-17, IL-21, IL-22, IFN-γ, TNF-α (TNF), TNF-β (LT), TGF-β, IL-1b, CD69, CD25, CD71, CD137, CD154, CD278, CD279, HLA-DR, IL-8 (CXCL8), RANTES (CCL5), CCL1, CXCL4, CXCL7, a nucleic acid encoding IL-2, a nucleic acid encoding IL-4, a nucleic acid encoding IL-5, a nucleic acid encoding IL-6, a nucleic acid encoding IL-10, a nucleic acid encoding IL-13, or a nucleic acid encoding IL-17, a nucleic acid encoding IL-22, a nucleic acid encoding IFN-γ, a nucleic acid encoding TNF-α (TNF), a nucleic acid encoding TNF-β (LT), a nucleic acid encoding TGF-β, a nucleic acid encoding IL-1b, a nucleic acid encoding CD69, a nucleic acid encoding CD25, a nucleic acid encoding CD71, a nucleic acid encoding CD137, a nucleic acid encoding CD154, a nucleic acid encoding CD278, a nucleic acid encoding CD279, a nucleic acid encoding HLA-DR, a nucleic acid encoding IL-8 (CXCL8), a nucleic acid encoding RANTES (CCL5), a nucleic acid encoding CCL1, a nucleic acid encoding CXCL4, and a nucleic acid encoding CXCL7. An APC line comprising antigen presenting cells capable of presenting antigen to the long-term GA-specific human T-cell line of claim 90.

In embodiments, the APC line is selected from: Epstein Barr Virus-transformed (EBV-transformed) human B-cells autologous to the GA-specific human T-cells; EBV-transformed human B-cells having the DR molecule involved in antigen presentation to the GA-specific human T-cells; PBMC autologous to the GA-specific human T cells; PBMC having the DR molecule involved in antigen presentation to the GA-specific human T-cells; purified monocytes autologous to the GA-specific human T-cells; purified monocytes having the DR molecule involved in antigen presentation to the GA-specific human T-cells; purified dendritic cells autologous to the GA-specific human T-cells; and purified dendritic cells having the DR molecule involved in antigen presentation to the GA-specific human T-cells.

In embodiments, the long-term GA-specific human T-cell line is generated by culturing for at least about four weeks. In embodiments, the long-term GA-specific human T-cell line is generated by stimulation with a GMA or COP preparation.

The present invention also relates to an assay panel of GA-specific human T-cell lines for use in determining whether a test preparation of GA and a GA reference standard are immunologically identical, wherein the assay panel comprises the following GA-specific human T-cell lines: a) a GA-specific human T-cell line generated by culturing human T-cells in the presence of a first preparation of GA; b) a GA-specific human T-cell line generated by culturing human T-cells in the presence of a second preparation of GA; and c) a GA-specific human T-cell line that is not reactive to at least one non-canonical GA peptide. In embodiments, the GA-specific human T-cell line of (a) or (b) also is the GA-specific human T-cell line of (c).

In embodiments, the non-canonical GA peptide of (c) consists of the amino acids tyrosine (Y), glutamic acid (E), alanine (A), and lysine (K) at a molar ratio that differs from the ratio of the amino acids tyrosine (Y), glutamic acid (E), alanine (A), and lysine (K) in Copaxone®. In embodiments, the assay panel of claim 105, wherein the non-canonical GA peptide of (c) consists of any one, two, or three of the amino acids tyrosine (Y), glutamic acid (E), alanine (A), and lysine (K). In embodiments, the assay panel of claim 105, further comprising a GA-specific human T-cell line that is reactive to the at least one non-canonical GA peptide.

In certain embodiments, the invention relates to the above assay panel wherein the GA-specific human T-cell line of (a) is selected from the group consisting of 222-AG12, 222-BA11, 222-BC11, 165-B5G, 165-C4G, 165-C5G, 165-C8G, 165-D8G, 165-E7G, 165-E9G, 165-F10G, 165-F5G, 165-F8G, and 165-H11G; the GA-specific human T-cell line of (b) is selected from the group consisting of 222-1C5, 222-1H12, 222-2B11, 222-2B8, 222-2C1, 222-2C3, 222-2D2, 222-2D8, 222-2E1, 222-1F8, 222-2F12, 222-2G4, 222-1G8, 222-2G12, 165-B6C, 165-B10C, 165-C4C, 165-C7C, 165-D2C, 165-D3C, 165-D11C, 165-E3C, 165-F3C, 165-F6C, 205-1B4, 205-1B7, 205-1C4, 205-1D1, 205-1E1, 205-1F2, 205-1F4, 205-1H1, 205-1H3, 205-1H5, 205-1H7, 205-1H9, and 205-1H11; and the GA-specific human T-cell line of (c) is selected from the group consisting of 222-AG12, 165-B5G, 165-D8G, 165-E7G, 165-E9G, 165-F5G, 165-F10G, 222-1H12, 222-2F12, 165-B10C, 165-C4C, 165-C7C, 165-D11C, 165-E3C, 165-F3C, 165-F6C, and 205-1H7.

In embodiments, the GA-specific human T-cell line of (a) is selected from the group consisting of 222-AG12, 222-AG12, 222-BA11, 222-BC11, 165-B5G, 165-C5G, 165-C8G, 165-D8G, 165-E9G, 165-F10G, 165-F5G, 165-F8G, and 165-H11G; the GA-specific human T-cell line of (b) is selected from the group consisting of 222-1C5, 222-1H12, 222-2B8, 222-2C3, 222-2E1, 222-1F8, 222-2F12, 222-2G4, 222-1G8, 165-C4C, 165-C7C, 165-D2C, 165-D3C, 205-1B4, 205-1B7, 205-1C4, and 205-1F4; and the GA-specific human T-cell line of (c) is selected from the group consisting of 222-AG12, 165-B5G, 165-D8G, 165-E7G, 165-E9G, 165-F5G, 165-F10G, 222-1H12, 222-2F12, 165-B10C, 165-C4C, 165-C7C, 165-D11C, 165-E3C, 165-F3C, 165-F6C, and 205-1H7.

In certain embodiments, the GA-specific human T-cell line of (a) is selected from the group consisting of 165-B5G or 165-D8G; the GA-specific human T-cell line of (b) is selected from the group consisting of 222-1H12 or 222-2E1; and the GA-specific human T-cell line of (c) is 222-AG12.

In embodiments, the assay panel comprises or further comprises at least one GA-specific human T cell line that has a first known GA response biomarker profile, and comprising or further comprising at least one GA-specific human T cell line that has a second known GA response biomarker profile that is different from the first known GA response biomarker profile.

In embodiments, the assay panel comprises or further comprises at least one GA-specific human T cell line that has a first known MHC restriction, and comprising or further comprising at least one GA-specific human T cell line that has a second known MHC restriction that is different from the first known MHC restriction. In embodiments, the assay panel comprises or further comprises at least one GA-specific human T-cell line having an HLA-DR restriction element capable of presenting GA peptides. In embodiments, the first HLA-DR restriction element is selected from: DR-1, DR-2, DR-3, DR-4, DR-7, DR-11, DR-13, and DR-15; and wherein the second HLA-DR restriction element is selected from: DR-4, DR-7, DR-11, DR-13, and DR-15.

In embodiments, the assay panel comprises or further comprises at least one GA-specific human T-cell line that has a first known GA biomarker response profile, and at least one GA-specific human T-cell line that has a second known GA biomarker response profile. In embodiments, the first and second known biomarker response profiles each comprise at least one cytokine, at least one chemokine, at least one activation marker, at least one nucleic acid encoding a cytokine, at least one nucleic acid encoding a chemokine, or at least one nucleic acid encoding an activation marker. In embodiments, the first and second known GA biomarker response profiles each comprise at least one cytokine selected from: IL-2, IL-4, IL-5, IL-6, IL-10, IL-13, or IL-17, IL-21, IL-22, IFN-γ, TNF-α (TNF), TNF-β (LT), TGF-β, and IL-1b. In certain embodiments, the first and second known GA biomarker response profiles each comprise an activation marker selected from: CD69, CD25, CD71, CD137, CD154, CD278, CD279, and HLA-DR. In embodiments, the first and second known GA biomarker response profiles each comprise a chemokine selected from: IL-8 (CXCL8), RANTES (CCL5), CCL1, CXCL4, and CXCL7. In embodiments, the first and second known GA biomarker response profiles each comprise at least one nucleic acid encoding a cytokine selected from the group consisting of: IL-2, IL-4, IL-5, IL-6, IL-10, IL-13, IL-17, IL-21, IL-22, TNF-α (TNF), TNF-β (LT), TGF-β, and IL-1b. In embodiments, the first and second known GA biomarker response profiles each comprise at least one nucleic acid encoding an activation marker selected from: CD69, CD25, CD71, CD137, CD154, CD278, CD279, and HLA-DR. In embodiments, the first and second known GA biomarker response profiles each comprise at least one nucleic acid encoding a chemokine selected from: IL-8 (CXCL8), RANTES (CCL5), CCL1, CXCL4, and CXCL7.

In embodiments, the GA-specific human T-cell lines in the assay panel are long-term T-cell lines. In embodiments, the GA-specific human T-cell lines in the assay panel are clonal. In related embodiments, the GA-specific human T-cell lines have been cultured for at least about four weeks and/or restimulated at least four times. In embodiments, the GA-specific human T-cell lines have been restimulated at least eight times.

In embodiments, the non-canonical peptide is selected from peptide 026, GLT 631, GAT 631, GAT111, LT11, GT11, GT 41, GL 14, and GA 64. In embodiments, the non-canonical peptide is peptide 026. In embodiments, the assay panel comprises or further comprises two to six GA-specific human T-cell lines not reactive to a non-canonical GA peptide, wherein each GA-specific human T-cell line is not reactive to a different non-canonical GA peptide. In embodiments, the assay panel comprises or further comprises two GA-specific human T-cell lines not reactive to a non-canonical GA peptide, wherein one of the two GA-specific human T-cell lines is not reactive to a non-canonical GA peptide selected from peptide 026, GLT 631, GAT 631, GAT111, LT11, GT11, GT 41, GL 14, GT41S, and GA 64, and the second of the two GA-specific human T-cell lines is not reactive to a non-canonical GA peptide selected from peptide 026, GLT 631, GAT 631, GAT111, LT11, GT11, GT 41, GL 14, GT 41S, and GA 64. In embodiments, one of the two GA-specific human T-cell lines is not reactive to a non-canonical GA peptide selected from peptide 026, GLT 631, GAT 631, LT11, and GL 14, and the second of the two GA-specific human T-cell lines is not reactive to a non-canonical GA peptide selected from peptide 026, GLT 631, GAT 631, LT11, and GL 14. In embodiments, one of the two GA-specific human T-cell lines is not reactive to peptide 026, and the second of the two GA-specific human T-cell lines is not reactive to GLT 631, GAT 631, LT11, or GL 14.

In certain embodiments, each GA-specific human T-cell line of (a), (b), and (c) is. $CD4^+$. In related embodiments, each GA-specific human T-cell line of (a), (b), and (c) comprises more than 98% $CD4^+$ cells. In embodiments, each GA-specific human T-cell line of (a), (b), and (c) comprises more than 99% $CD4^+$ cells. In embodiments, each GA-specific human T-cell line of (a), (b), and (c) is not $CD8^+$. In related embodiments, each GA-specific human T-cell line of (a), (b), and (c) comprises less than 2% $CD8^+$ cells. In certain embodiments, each GA-specific human T-cell line of (a), (b), and (c) comprises less than 1% CD8+ cells.

The invention also relates to a method of determining whether a test preparation of glatiramer acetate (GA) and a GA reference standard are immunologically identical using an assay panel, the method comprising: 1) incubating cells of each GA-specific human T-cell line in the assay panel with appropriate APC; 2) stimulating a predetermined number of cells of each of the GA-specific human T-cell lines incubated in step (1) with an amount of the test preparation of GA; 3) separately stimulating the same predetermined number of cells of each of the GA-specific human T-cell lines incubated in step (1) with the same amount of the GA reference standard; 4) measuring at least one GA-elicited response of each of the GA-specific human T-cell lines stimulated in steps (2) and (3); and 5) comparing the measurement of the at least one GA-elicited response obtained for each GA-specific human T-cell line stimulated with the test preparation of GA with the measurement of the at least one GA-elicited response obtained for the same GA-specific human T-cell line stimulated with the GA reference standard; wherein the test preparation of GA and the GA reference standard are determined to be immunologically identical when the comparison of the measurements of step (5) falls within an acceptable range.

In embodiments, the appropriate APC can comprise cells selected from the group consisting of: Epstein Barr Virus-transformed (EBV-transformed) human B-cells autologous to the GA-specific human T-cells; EBV-transformed human B-cells having the DR molecule involved in antigen presentation to the GA-specific human T-cells; PBMC autologous to the GA-specific human T cells; PBMC having the DR molecule involved in antigen presentation to the GA-specific human T-cells; purified monocytes autologous to the GA-specific human T-cells; purified monocytes having the DR molecule involved in antigen presentation to the GA-specific human T-cells; purified dendritic cells autologous to the GA-specific human T-cells; and purified dendritic cells having the DR molecule involved in antigen presentation to the GA-specific human T-cells.

In embodiments, the acceptable range is about 80% to about 120%, or about 90% to about 110%. In embodiments of the above methods, the at least one measured GA-elicited response is selected from proliferation, production of a response biomarker, expression of a nucleic acid encoding a response biomarker, and a combination thereof. In embodiments, the at least one measured GA-elicited response is production of a response biomarker, and the response biomarker is a cytokine, a chemokine, or an activation marker. In certain embodiments, the response biomarker is a cytokine selected from: IL-2, IL-4, IL-5, IL-6, IL-10, IL-13, or IL-17, IL-21 IL-22, IFN-γ, TNF-α (TNF), TNF-β (LT), and IL-1b. In embodiments, the response biomarker is an activation marker selected from: CD69, CD25, CD71, CD137, CD154, CD278, CD279, and HLA-DR. In embodiments, the response biomarker is a chemokine selected from: IL-8 (CXCL8), RANTES, (CCL5), CCL1, CXCL4, and CXCL7.

In embodiments, the at least one measured GA-elicited response is expression of a nucleic acid encoding a response biomarker, and the response biomarker encoded by the nucleic acid is a cytokine, a chemokine, or an activation marker. In embodiments, the encoded response biomarker is a cytokine selected from: IL-2, IL-4, IL-5, IL-6, IL-10, IL-13, or IL-17, IL-21, IL-22, IFN-γ, TNF-α, (TNF), TNF-β (LT), TGF-β and IL-1b. In certain embodiments, the encoded response biomarker is an activation marker selected from: CD69, CD25, CD71, CD137, CD154, CD278, CD279, and HLA-DR. In embodiments, the encoded response biomarker is a chemokine selected from: IL-8 (CXCL8), RANTES (CCL5), CCL1, CXCL4, and CXCL7.

In embodiments, at least two GA-elicited responses of the cells stimulated with the test preparation of GA are measured, and the same at least two GA-elicited responses of the cells stimulated with the GA reference standard, are measured. In these embodiments, the at least two GA-elicited responses can be selected from the expression of: IL-2, IL-4, IL-6, IL-10, IL-13, or IL-17, IL-21, IL-22, IFN-γ, TNF-α (TNF), TNF-β (LT), TGF-β, IL-1b, CD69, CD25, CD71, CD137, CD154, CD278, CD279, HLA-DR, IL-8 (CXCL8), RANTES (CCL5), CCL1, CXCL4, CXCL7, a nucleic acid encoding IL-2, a nucleic acid encoding IL-4, a nucleic acid encoding IL-5, a nucleic acid encoding IL-6, a nucleic acid encoding IL-10, a nucleic acid encoding IL-13, or a nucleic acid encoding IL-17, a nucleic acid encoding IL-22, a nucleic acid encoding IFN-γ, a nucleic acid encoding TNF-α (TNF), a nucleic acid encoding TNF-β (LT), a nucleic acid encoding TGF-β, a nucleic acid encoding IL-1b, a nucleic acid encoding CD69, a nucleic acid encoding CD25, a nucleic acid encoding CD71, a nucleic acid encoding CD137, a nucleic acid encoding CD154, a nucleic acid encoding CD278, a nucleic acid encoding CD279, a nucleic acid encoding HLA-DR, a nucleic acid encoding IL-8 (CXCL8), a nucleic acid encoding RANTES (CCL5), a nucleic acid encoding CCL1, a nucleic acid encoding CXCL4, and a nucleic acid encoding CXCL7.

In embodiments, the GA reference standard is Copaxone or GMA.

In embodiments, wherein the appropriate APC have at least one HLA-DR restriction element capable of presenting GA peptides. In certain embodiments, the at least one HLA-DR restriction element capable of presenting GA peptides is selected from: DR-1, DR-2, DR-3, DR-4, DR-7, DR-11, DR-13, and DR-15.

In embodiments, wherein the at least one GA-specific human T-cell line incubated in step (a) is a long-term T-cell line. In embodiments, the at least one GA-specific human T-cell line is clonal. In embodiments, the at least one long-term GA-specific human T-cell line has been maintained in culture for at least about four weeks prior to stimulation, previously restimulated at least four times, or both. In embodiments, the at least one long-term GA-specific human T-cell line has been previously restimulated at least eight times. In embodiments, the maintenance in culture of the at least one long-term GA-specific human T-cell line comprises recurrent restimulation with GA and autologous APC, in the absence of mitogen.

In embodiments, the stimulation includes stimulating each of at least three samples of GA-specific human T-cells, incubated with or in the presence of APC, with one of a series of amounts of the test preparation of GA, and stimulating each of at least three samples of GA-specific human T-cells, incubated with or in the presence of APC, with one of the same series of amounts of the GA reference standard. In embodiments, the series of amounts of the test preparation of GA, and the series of amounts of the GA reference standard, comprise escalating doses of GA of about 1 ng/mL to about 1 mg/mL GA. In embodiments, the series of amounts of the test preparation of GA, and the series of amounts of the GA reference standard, are escalating doses of GA of about 1 μg/mL to about 30 μg/mL GA.

The invention also relates to a drug product or pharmaceutical composition containing GA, prepared by a process comprising: 1) preparing a test preparation of GA by reacting protected glatiramer acetate with hydrobromic acid to form trifluoroacetyl GA, treating said trifluoroacetyl copolymer-1 with aqueous piperidine solution to form GA, and purifying said GA; 2) determining whether the test preparation of GA and a GA reference standard are immunologically identical, by: a) incubating cells of the at least one GA-specific human T-cell line with appropriate antigen presenting cells (APC); b) stimulating at least one sample comprising a predetermined number of cells of the at least one GA-specific human T-cell line incubated in (a) with an amount of the test preparation of GA, and separately stimulating at least one sample comprising the same predetermined number of cells of the at least one GA-specific human T-cell line incubated in step (a) with the amount of the GA reference standard; c) measuring at least one GA-elicited response of the at least one GA-specific human T-cell line stimulated in step (b) with the test preparation of GA, and measuring the same at least one GA-elicited response of the at least one GA-specific human T-cell lines stimulated in step (b) with the GA reference standard; and d) comparing the measurement of the at least one GA-elicited response of the at least one sample of cells of the at least one GA-specific human T-cell line stimulated in step (b) with the test preparation of GA, with the measurement of the same at least one GA-elicited response of the at least one sample of cells of the at least one GA-specific human T-cell line stimulated in step (b) with the GA reference standard; wherein the test preparation of GA and the GA reference standard are determined to be immunologically identical when the comparison of the measurements of step (d) falls within an acceptable range, and wherein the test preparation of GA is admixed in the drug product or pharmaceutical composition if it is determined to have immunologic identity to the GA reference standard.

The invention additionally relates to a drug product or pharmaceutical composition containing GA, prepared by a process comprising: 1) preparing a test preparation of GA by reacting protected glatiramer acetate with hydrobromic acid to form trifluoroacetyl GA, treating said trifluoroacetyl copolymer-1 with aqueous piperidine solution to form GA, and purifying said GA; 2) determining whether the test preparation of GA and the GA reference standard are immunologically identical using the method of claim 1-24, 25-46, or 139-160.

The invention further relates to a kit comprising an assay panel of the invention, appropriate APC for each GA-specific human T-cell line in the assay panel, and a GA reference standard.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIGS. 2A and 2B. Proliferation of Donor 1 GMA Expanded T-Cell Lines AG12, BC11, AG11 and BAH in Response to GMA Presented by Autologous APC. This figure shows the results of ATP assays of cellular proliferation carried out using four Donor 1 GMA expanded T-cell lines incubated with 0, 1, 10, or 100 μg/mL GMA (Mylan Pharmaceuticals, Inc.) in the presence of autologous APC. The zero control sample was incubated with APC but no antigen. 2A. Proliferation of Donor 1 T-cell lines AG12 (dark gray bars) and BC11 (light gray bars) in response to increasing concentrations of GA in the presence of autologous APC. 2B. Proliferation of Donor 1 T-cell lines AG11 (dark gray bars) and BA11 (light gray bars) response to increasing concentrations of GA in the presence of autologous APC.

FIGS. 3A-3C. Proliferation of Donor 1 GMA Expanded T-Cell lines in Response to GMA or COP Presented by Autologous APC. This figure shows the results of ATP assays carried out using three Donor 1 GMA T-cell lines incubated with increasing concentrations of GA and autologous APC. 3A. Proliferation of Donor 1 T-cell line BA11 incubated with 0, 0.3, 1, 3, 10, or 30 μg/mL GMA (Mylan Pharmaceuticals, Inc.; dark gray bars) or Copaxone (Teva Pharmaceuticals USA, Inc.; light gray bars) and autologous APC. 3B. Proliferation of Donor 1 T-cell line BC11 (light gray bars) incubated with 0, 1, 3, or 10 μg/mL GMA (dark gray bars) or Copaxone (light gray bars) and autologous APC. 3C. Proliferation of Donor 1 T-cell line AG12 incubated with 0, 3, 10, and 30 μg/mL GMA (dark gray bars) or Copaxone (light gray bars) and autologous APC.

FIGS. 4A and 4B. IFN-γ Production by Donor 1 GMA Expanded T-Cell lines in Response to GMA or COP Presented by EBV-transformed B-LCL. This figure shows the results of IFN-γ assays carried out using supernatants of two Donor 1 GMA expanded T-cell lines incubated with GMA, COP, or Tetanus Toxoid in the presence of autologous EBV-transformed B-LCL. 4A. IFN-γ produced by Donor 1 T-cell line AG11 in the presence of either autologous EBV-transformed B-LCL (dark gray bars) or EBV-transformed B-LCL from a donor matched at one allele (206 B-LCL; light gray bars). 4B. IFN-γ produced by Donor 1 T-cell line AG12 in the presence of either autologous EBV-transformed B-LCL (dark gray bars) or EBV-transformed B-LCL from a donor matched at one allele (206 B-LCL; light gray bars).

FIG. 5A-5G. Proliferation of Seven Donor 1 COP Expanded T-Cell lines in Response to GMA or COP Presented by Autologous APC. This figure shows the results of ATP assays of proliferation carried out using four Donor 1 COP T-cell lines incubated with 0, 1, 3, or 10 μg/mL GMA (Mylan Pharmaceuticals, Inc.) and autologous APC. The zero control sample was incubated with autologous APC but no antigen. 5A. Proliferation of Donor 1 T-cell line 2D8 in response to GMA (dark gray bars) or COP (light gray bars). 5B. Proliferation of Donor 1 T-cell line 1H12 in response to GMA (dark gray bars) or COP (light gray bars). 5C. Proliferation of Donor 1 T-cell line 2F12 in response to GMA (dark gray bars) or COP (light gray bars). 5D. Proliferation of Donor 1 T-cell line 2B8 in response to GMA (dark gray bars) or COP (light gray bars). 5E. Proliferation of Donor 1 T-cell line 1C5 in response to GMA (dark gray bars) or COP (light gray bars). 5F. Proliferation of Donor 1 T-cell line 2B11 in response to GMA (dark gray bars) or COP (light gray bars). 5G. Proliferation of Donor 1 T-cell line 2E1 in response to GMA (dark gray bars) or COP (light gray bars).

FIG. 6A-6F. Cytokine Secretion by Donor 1 COP Expanded T-Cell lines in Response to GMA or COP Presented by Autologous APC. 6A. Cytokine secretion by Donor 1 T-cell line 2D8 in response to each of three concentrations of GMA. 6B. Cytokine secretion by Donor 1 T-cell line 2D8 in response to each of three concentrations of COP. 6C. Cytokine secretion by Donor 1 T-cell line 1H12 in response to each of three concentrations of GMA. 6D. Cytokine secretion by Donor 1 T-cell line 1H12 in response to each of three concentrations of COP. 6E. Cytokine secretion by Donor 1 T-cell line 2F12 in response to each of three concentrations of GMA. 6F. Cytokine secretion by Donor 1 T-cell line 2F12 in response to each of three concentrations of COP. The arrows indicate the position of the control sample secretion level in each cytokine dataset, followed from left to right by the secretion levels of cells stimulated with 1 g/mL GA, 3 μg/mL GA, 10 μg/mL GA, and MBP as a control presented by autologous APC.

FIGS. 7A and 7B. Donor 2 T-Cell Line 1A7 Proliferation and IFN-γ Production in Response to GMA or COP in the Presence of Autologous APC. 7A. Proliferation of Donor 2 T-cell line 1A7 in response to stimulation with GMA at 0, 0.1, 0.3, 1, 3, 10, 30, or 100 μg/mL is shown. 7B. IFN-γ secretion by Donor 2 T-cell line 1A7 in response to stimulation with GMA at 0, 0.1, 0.3, 1, 3, 10, 30, or 100 μg/mL is shown. In each experiment, the light gray 0 μg/mL antigen bar represents a control sample containing 1 μg/mL Tetanus Toxoid, autologous APC, and no GA, and the dark gray 0 μg/mL antigen bar represents a control sample containing autologous APC and no GA.

FIGS. 9A and 9B. HLA-DR Restriction of Donor 3 T-Cell Line 165-B5G and 165-C4G. 9A. Donor 3 T-cell line 165-B5G proliferation in the presence of Donor 3, 5, or 6 mitomycin-treated APC incubated with or without COP. 9B. Donor 3 T-cell line 165-C4G proliferation in the presence of Donor 3, 5 or 6 mitomycin-treated APC incubated with or without GMA. In both figures: open bars=no antigen; solid bars=20 μg/mL GA.

FIGS. 10A and 10B. HLA-DR Restriction of Donor 3 T-Cell Line 165-05G and 165-E9G. 10A. Donor 3 T-cell line 165-05G proliferation in the presence of Donor 3, 5, or 6 mitomycin-treated APC incubated with or without COP. 10B. Donor 3 T-cell line 165-E9G in the presence of Donor 3, 5 or 6 mitomycin-treated APC incubated with or without COP. In both figures: open bars=no antigen; solid bars=20 μg/mL COP.

FIGS. 11A and 11B. HLA-DR Restriction of Donor 3 T-Cell Line 165-F5G and 165-F10G. 11A. Donor 3 T-cell line 165-F5G proliferation in the presence of Donor 3, 5, or 6 mitomycin-treated APC incubated with or without COP. 11B. Donor 3 T-cell line 165-F10G proliferation in the presence of Donor 3, 5 or 7 mitomycin-treated APC incubated with or without GMA. In both figures: open bars=no antigen; solid bars=20 μg/mL GA.

FIGS. 12A and 12B. HLA-DR Restriction of Donor 3 T-Cell Line 165-B6C and 165-C7C. 12A. Donor 3 T-cell line 165-B6C proliferation in the presence of mitomycin-treated Donor 3, 5, or 6 APC incubated with or without COP. 12B. Donor 3 T-cell line 165-C7C proliferation in the presence of Donor 3, 5 or 6 APC incubated with or without COP. In both figures: open bars=no antigen; solid bars=20 μg/mL COP.

FIGS. 13A and 13B. HLA-DR Restriction of Donor 3 T-Cell Line 165-D3C and 165-F3C. 13A. Donor 3 T-cell line 165-D3C proliferation in the presence of mitomycin-treated Donor 3, 5, or 7 APC incubated with or without GMA. 13B. Donor 3 T-cell line 165-F3C proliferation in the presence of Donor 3, 5 or 6 APC incubated with or without COP. In both figures: open bars=no antigen; solid bars=20 μg/mL GA.

FIGS. 14A and 14B. HLA-DR Restriction of Donor 3 T-Cell Line 165-F6C and 205-1H7. 14A. Donor 3 T-cell line 165-F6C proliferation after stimulation in the presence of Donor 3, 5, or 7 mitomycin-treated APC incubated with or without COP. 14B. Donor 4 T-cell line 205-1H7 proliferation in the presence of Donor 3, 5 or 6 mitomycin-treated APC incubated with or without COP. In both figures: left bar in each pair=no antigen; right bar in each pair=20 μg/mL COP.

FIGS. 15A and 15B. Characterization of GA-Specific Human T-Cell Line 165-E9G Expression of CD4 and CD8 by Flow Cytometry. 15A. Binding to nonspecific control mouse anti-IgG1 monoclonal antibodies labeled with PE or FITC as indicated. 15B. Binding to an anti-CD8 monoclonal antibody labeled with PE and an anti-CD4 monoclonal antibody labeled with FITC as indicated.

FIGS. 16A and 16B. Characterization of GA-Specific Human T-Cell Line 165-F5G Expression of CD4 and CD8 by Flow Cytometry. 16A. Binding to nonspecific control mouse anti-IgG1 monoclonal antibodies labeled with PE or FITC as indicated. 16B. Binding to an anti-CD8 monoclonal antibody labeled with PE and an anti-CD4 monoclonal antibody labeled with FITC as indicated.

FIGS. 17A and 17B. Donor 1 T-Cell Line Proliferation in Response to Altered GA Lot 009. 17A. Proliferation of Donor 1 T-cell Line 222-2D8 in response to stimulation with at 0, 1, 2, 2.5, and 5 μg/mL COP, and altered GA lot 009 is shown. 17B. Proliferation of Donor 1 T-cell Line 222-2F12 in response to stimulation with at 0, 1, 2, 2.5, and 5 μg/mL COP, and altered GA lot 009 is shown.

FIGS. 18A and 18B. Donor 3 T-Cell Line Proliferation in Response to Altered GA Lot 009. 18A. Proliferation of Donor 3 T-cell Line 165-F3C in response to stimulation with at 0, 1, 2, 2.5, and 5 μg/mL COP, and altered GA lot 009 is shown. 18B. Proliferation of Donor 1 T-cell Line 165-F6C in response to stimulation with at 0, 1, 2, 2.5, and 5 μg/mL COP, and altered GA lot 009 is shown.

FIGS. 19A and 19B. Donor 4 T-Cell Line Proliferation in Response to Altered GA Lot 009. 19A. Proliferation of Donor 4 T-cell Line 205-1C4 in response to stimulation with at 0, 1, 2, 2.5, and 5 μg/mL COP, and altered GA lot 009 is shown. 19B. Proliferation of Donor 1 T-cell Line 205-1F4 in response to stimulation with at 0, 1, 2, 2.5, and 5 μg/mL COP, and altered GA lot 009 is shown.

DETAILED DESCRIPTION OF THE INVENTION

Figure 1:
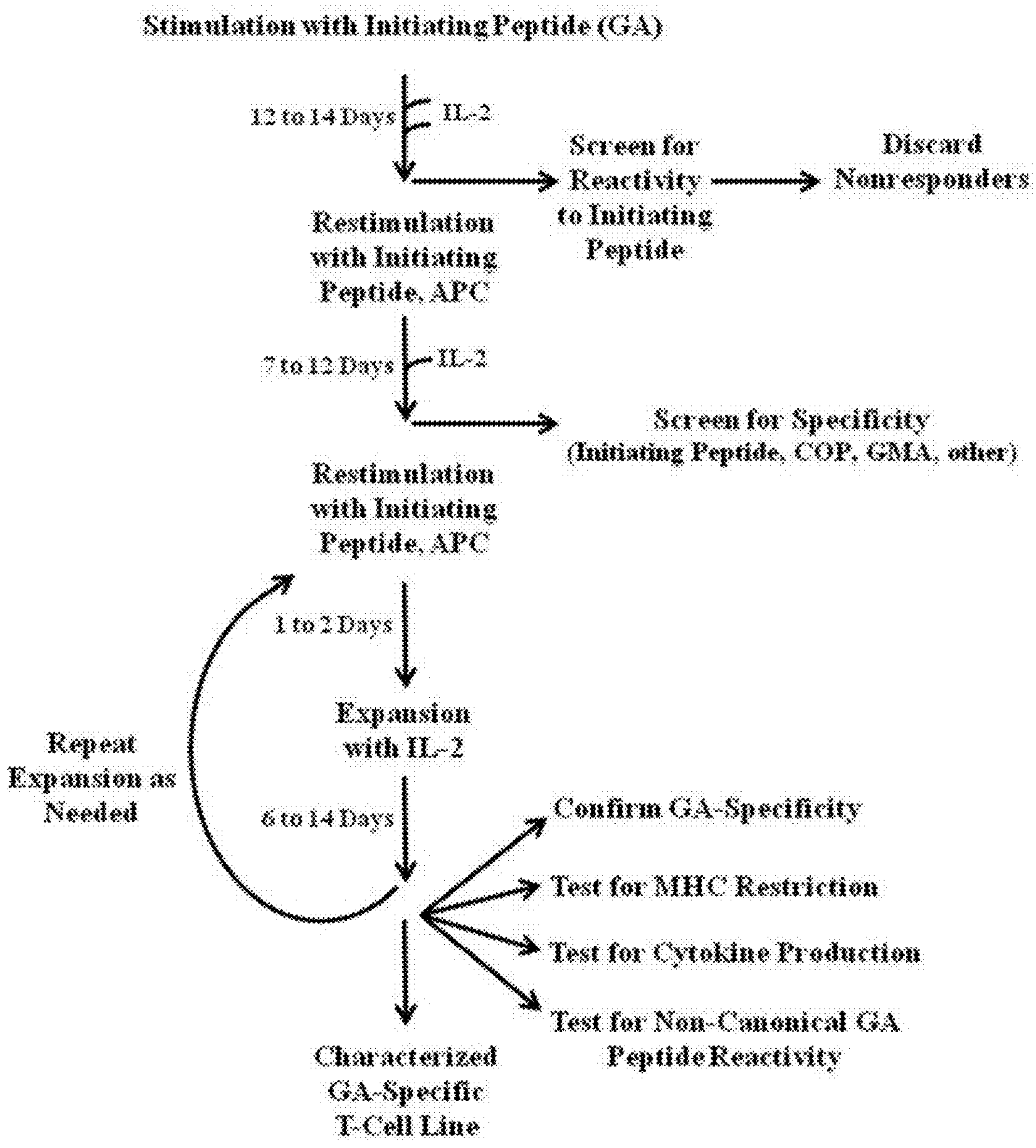
FIG. 1. A Process for Identifying a GA-Specific Human T-Cell Line. This drawing shows a series of steps that can be used to identify GA-specific human T-cell lines according to methods of the invention.

The mechanism of action of Copaxone® in Multiple Sclerosis is at least in part mediated by immunomodulation of T-cell activity, and the immunologic response of T-cells to GA is a specific and sensitive measure of epitopes present in a GA preparation. Because of the unique ability of individual T-cells to distinguish between different but very similar peptides, analyzing GA-elicited responses of GA-specific human T-cells in culture can distinguish immunologically relevant differences between preparations of GA. In this regard, equivalent GA-elicited responses of a GA-specific T-cell line to a test preparation of GA and a GA reference standard can indicate that the GA reference standard and GA test preparation have immunological identity. The present invention is based on the demonstration that GA-specific human T-cell lines can be generated and identified and used to test the immunological identity of different GA preparations. Further, it has been shown that GA-specific human T-cell lines that recognize different epitopes of GA can be generated. As a result, GA-specific human T-cell lines that recognize many if not all different epitopes of GA can be generated, identified, and used in parallel in assay panels to allow determination with a high degree of confidence that compared GA preparations have immunological identity.

Glatiramer Acetate

Glatiramer acetate (GA) consists of the acetate salts of synthetic polypeptides that contain four naturally occurring amino acids: L-glutamic acid, L-alanine, L-tyrosine, and L-lysine with an average molar fraction of 0.141, 0.427, 0.095, and 0.338, respectively. The average molecular weight of GA is 5,000-9,000 daltons. Chemically, GA is designated L-glutamic acid polymer with L-alanine, L-lysine and L-tyrosine, acetate (salt). The empirical formula of glatiramer acetate is $(C_5H_9NO_4.C_3H_7NO_2.C_6H_{14}N_2O_2.C_9H_{11}NO_3)_x.xC_2H_4O_2$ (CAS-147245-92-9, Physician's Desk Reference). As used herein, "GA" refers to glatiramer acetate, including, e.g., "GMA," glatiramer acetate produced by Mylan Pharmaceuticals, Inc., and "COP," or "Copaxone," glatiramer acetate produced and sold by Teva Pharmaceuticals USA, Inc. Copaxone was approved by the FDA in 1996 for the treatment of relapsing-remitting multiple sclerosis (RRMS). Its composition is described in the literature, e.g., in U.S. Pat. No. 3,849,550, "Therapeutic copolymer," and U.S. Pat. No. 5,800,808, "Copolymer-1 improvements in compositions of copolymers," and in the product labeling for Copaxone (Teva Pharmaceuticals USA, Inc.), each incorporated by reference herein in its entirety.

Production of Glatiramer Acetate

GA can be produced by known and published methods. Methods for producing Copaxone have been described in, e.g., in U.S. Pat. No. 3,849,550, "Therapeutic copolymer," and U.S. Pat. No. 5,800,808, "Copolymer-1 improvements in compositions of copolymers." According to U.S. Pat. No. 5,800,808, Copolymer-1 may be prepared by methods known in the art, for example, by the process disclosed in U.S. Pat. No. 3,849,550, wherein the N-carboxyanhydrides of tyrosine, alanine, y-benzyl glutamate and E-N-trifluoroacetyllysine are polymerised at ambient temperature in anhydrous dioxane with diethylamine as initiator. The deblocking of the y-carboxyl group of the glutamic acid is effected by hydrogen bromide in glacial acetic acid and is followed by the removal of the trifluoroacetyl groups from the lysine residues by 1M piperidine.

GA Test Preparations

In embodiments of the methods of the present invention, a GA-elicited response of a GA-specific human T-cell line to a test or production preparation, lot, or batch of GA is compared to the same GA-elicited response of a reference standard preparation of GA. In embodiments, a test preparation of GA is any preparation, lot or batch of GA desired to be tested. In embodiments, the test preparation of GA is a newly manufactured preparation of GA. In other embodiments, the test preparation of GA is not newly manufactured but is desired to be tested nonetheless, e.g., to evaluate shelf-life of the preparation. A reference standard lot of GA, or GA reference standard, also can be any preparation, lot or batch of GA as desired, e.g., GMA or COP. In embodiments, the methods of the invention are used to compare two or more test or production preparations to GA, to each other, or to any another preparation of GA as desired. In embodiments, the GA test preparation is a preparation of GMA. In embodiments, the GA test preparation and GA reference standard are different preparations of GMA. In embodiments, multiple test preparations of GA are compared with a GA reference standard. In embodiments, the preparations of GA compared are, e.g., a preparation of GMA and a preparation of COP, two preparations of GMA, or a preparation of GA made by another manufacturer and GMA or COP.

Testing GA Preparations

The present invention relates to GA-specific human T-cell-line assays useful for evaluating GA preparations. These assays can ensure consistency of GA preparations, e.g., during manufacturing or following changes in manufacturing processes. In embodiments, the methods of the invention are used to determine whether a test preparation of GA and a GA reference standard are immunologically identical, by comparing at least one GA-elicited response of a GA-specific human T-cell line after separately stimulating the cell line with either the test preparation of GA or the GA reference standard. Based on the results presented herein, GA-specific human T-cell lines capable of discerning subtle differences in the composition of a stimulating preparation of GA can be generated and identified. When used to stimulate the GA-specific T-cell lines, subtle differences in stimulating antigen result in measurable differences in GA-elicited responses of the GA-specific human T-cell lines.

Assays of the invention also are useful for determining the relative GA potency of a test preparation of GA, e.g., the potency of the GA test preparation as compared to that of a GA reference standard. These methods are useful for ensuring consistent potency among drug preparations in the manufacture of glatiramer acetate acceptable for pharmaceutical use.

In embodiments of the invention, at least one GA-elicited response is measured in an assay of a test preparation of GA and compared to the same GA-elicited response to a GA reference standard to give a desired relative potency. Desired relative potency can be expressed, e.g., as a ratio of the response to the GA test preparation to the response to the GA reference standard, or as a part, fraction, or percentage, where the percentage is 100 when the measurements are equal.

In embodiments of the present invention, the relative potency of GA in a production or test preparation is determined by comparing a value representing the immunologic response of a GA-specific human T-cell line to a test preparation of GA, to a value representing the same response of the same cell line to a GA reference standard. This potency determination describes the stimulation capacity of a test preparation of GA. In embodiments, a potency assay of the present invention is used to determine whether a preparation of GA has a desired potency.

Generation and Identification of GA-Specific Human T-Cell Lines

FIG. 1 shows a general scheme for generating and identifying COP or GMA-specific human T-cell lines according to the methods of the present invention.

Initially, a sample of cells is obtained from a normal, healthy, GA-naïve donor. Donor PBMC are collected for use, e.g., by leukapheresis or venipuncture. The collected cells are stimulated at Day 0 with an amount of initiating peptide (a preparation of GA) at a density of about $5\times10^5$ to about $1\times10^6$ cells/mL. In embodiments, the collected cells initially are stimulated at a density of about $5\times10^5$ cells/mL, about $6\times10^5$ cells/mL, about $7\times10^5$ cells/mL, about $8\times10^5$ cells/mL, about $9\times10^5$ cells/mL, or about $1\times10^6$ cells/mL, cells/mL. The stimulated cells are cultured and in embodiments periodically are treated with a growth promoter, e.g., IL-2, before screening a portion for reactivity to the initiating peptide. A remaining portion of the culture of a cell line that is reactive to the initiating peptide is restimulated with the initiating peptide and appropriate APC, and a growth promoter added as needed. A portion of the restimulated GA-reactive cell line culture then is screened for antigen specificity by comparing the cells' response to stimulation with the initiating peptide in the presence of MHC-matched APC, and appropriate controls, e.g., other preparations of GA, and other (non-relevant) antigens, e.g., tetanus toxoid, in the presence of MHC-matched APC, using a specificity assay as described herein. A line that responds to GA and not to a non-relevant antigen is identified as a GA-specific human T-cell line. The remaining cell line culture is restimulated as before with the initiating peptide and appropriate APC, and a growth promoter added as needed, e.g., for cell line expansion or in preparation for an assay to confirm GA-specificity or further characterize the cell line. Characterization assays further test an identified GA-responsive human T-cell line, e.g., for MHC-restriction, response biomarker production in response to GA stimulation, or reactivity to a non-canonical GA peptide.

In certain embodiments, screening a T-cell line for GA-reactivity and screening for GA-specificity are carried out together following the initial stimulation. In these embodiments, use of both a no antigen control and a non-relevant antigen control, each in the presence of MHC-matched APC, are contemplated. In embodiments, an initial determination of GA-specificity of a human T-cell line is confirmed following restimulation of the cell line. In embodiments, an identified GA-specific human T-cell line is demonstrated to be GA-specific after multiple rounds of restimulation, e.g., after at least 2 to 10 rounds of restimulation or more. In embodiments, an identified GA-specific human T-cell line is demonstrated to be GA-specific after at least 2, at least 3, at least 4, at least 5, at least 6, at least 7, at least 8, at least 9, at least 10, 3 to 10, 4 to 10, 5 to 10, 6 to 10, 7 to 10, 8 to 10, 9 to 10, 2 to 9, 2 to 8, 2 to 7, 2 to 6, 2 to 5, 2 to 4, 3 to 9, 3 to 8, 3 to 7, 3 to 6, 3 to 5, 4 to 9, 4 to 8, 4 to 7, 4 to 6, 5 to 9, 5 to 8, 5 to 7, 6 to 9, 6 to 8, 7 to 9, or 8 to 10 rounds of restimulation.

In embodiments, the collected cells are restimulated at a density of about $1\times10^5$ to about $1\times10^6$ cells/mL, about $0.1\times10^5$ cells/mL, about $1.5\times10^5$ cells/mL, about $2\times10^5$ cells/mL, about $2.5\times10^5$ cells/mL, about $3\times10^5$ cells/mL, about $3.5\times10^5$ cells/mL, about $4\times10^5$ cells/mL, about $4.5\times10^5$ cells/mL, about $5\times10^5$ cells/mL, about $6\times10^5$ cells/mL, about $7\times10^5$ cells/mL, about $8\times10^5$ cells/mL, about $9\times10^5$ cells/mL, or about $1\times10^6$ cells/mL.

In other embodiments of the present invention, GA-specific human T-cell lines identified by the described method, including GA-specific T-cell lines that respond to non-canonical GA peptides, are contemplated for use in the methods of the invention for determining immunological identity of GA preparations.

The initiating peptide used for initial stimulation can be any GA preparation as desired, including, but not limited to, any preparation of COP or any preparation of GMA. In embodiments, the peptide used for restimulation is the same GA preparation as the initiating peptide. In embodiments, the concentration of peptide used for restimulation is the same as that used for the initial stimulation. In embodiments, the stimulating peptide (also referred to as "initiating peptide") or restimulating peptide is added at a concentration of about 1 ng/mL to about 1 mg/mL. In embodiments, the concentration of peptide used for the initial stimulation or for restimulation is about 1 ng/mL to about 1 mg/mL, about 1 ng/mL to about 500 µg/mL, about 1 ng/mL to about 100 µg/mL, about 1 ng/mL to about 50 µg/mL, about 1 ng/mL to about 10 µg/mL, about 1 ng/mL to about 1 µg/mL, about 1 ng/mL to about 500 ng/mL, about 1 ng/mL to about 100 ng/mL, about 100 ng/mL to about 1 mg/mL, about 100 ng/mL to about 500 µg/mL, about 100 ng/mL to about 100 µg/mL, about 100 ng/mL to about 10 µg/mL, about 100 ng/mL to about 1 µg/mL, about 100 ng/mL to about 500 ng/mL, about 500 ng/mL to about 1 mg/mL, about 500 ng/mL to about 500 μg/mL, about 500 ng/mL to about 100 μg/mL, about 500 ng/mL to about 10 μg/mL, about 500 ng/mL to about 1 μg/mL, about 1 μg/mL to about 1 mg/mL, about 1 μg/mL to about 900 μg/ml, about 1 μg/mL to about 800 μg/mL, about 1 μg/mL to about 700 μg/mL, about 1 μg/mL to about 600 μg/mL, about 1 μg/mL to about 500 μg/mL, about 1 μg/mL to about 400 μg/mL, about 1 μg/mL to about 300 μg/mL, about 1 μg/mL to about 200 μg/mL, 1 μg/mL to about 100 μg/mL, 1 μg/mL to about 90 μg/mL, 1 μg/mL to about 80 μg/mL, 1 μg/mL to about 70 μg/mL, 1 μg/mL to about 60 μg/mL, 1 μg/mL to about 50 μg/mL, 1 μg/mL to about 40 μg/mL, 1 μg/mL to about 30 μg/mL, about 10 μg/mL to about 1 mg/mL, about 10 μg/mL to about 900 μg/mL, about 10 μg/mL to about 800 μg/mL, about 10 μg/mL to about 700 μg/mL, about 10 μg/mL to about 600 μg/mL, about 10 μg/mL to about 500 μg/mL, about 10 μg/mL to about 400 μg/mL, about 10 μg/mL to about 300 μg/mL, about 10 μg/mL to about 200 μg/mL, about 10 μg/mL to about 100 μg/mL, about 10 μg/mL to about 90 μg/mL, about 10 μg/mL to about 80 μg/mL, about 10 μg/mL to about 70 μg/mL, about 10 μg/mL to about 60 μg/mL, about 10 μg/mL to about 50 μg/mL, about 10 μg/mL to about 40 μg/mL, about 10 μg/mL to about 30 μg/mL, about 50 μg/mL to about 1 mg/mL, about 50 μg/mL to about 900 μg/mL, about 50 μg/mL to about 800 μg/mL, about 50 μg/mL to about 700 μg/mL, about 50 μg/mL to about 600 μg/mL, about 50 μg/mL to about 500 μg/mL, about 50 μg/mL to about 400 μg/mL, about 50 μg/mL to about 300 μg/mL, about 50 μg/mL to about 200 μg/mL, about 50 μg/mL to about 500 μg/mL, about 50 μg/mL to about 90 μg/mL, about 50 μg/mL to about 80 μg/mL, about 50 μg/mL to about 70 μg/mL, about 100 μg/mL to about 1 mg/mL, about 100 μg/mL to about 900 μg/mL, about 100 μg/mL to about 800 μg/mL, about 100 μg/mL to about 700 μg/mL, about 100 ninth to about 600 μg/mL, about 100 μg/mL to about 500 μg/mL, about 100 μg/mL to about 400 μg/mL, about 100 μg/mL to about 300 μg/mL, about 100 μg/mL to about 200 μg/mL, about 100 μg/mL to about 150 μg/mL, about 200 μg/mL to about 1 mg/mL, about 200 μg/mL to about 900 μg/mL, about 200 μg/mL to about 800 μg/mL, about 200 μg/mL to about 700 μg/mL, about 200 μg/mL to about 600 μg/mL, about 200 μg/mL to about 500 μg/mL, about 200 μg/mL to about 400 μg/mL, about 200 μg/mL to about 300 μg/mL, about 200 μg/mL to about 250 μg/mL, about 300 μg/mL to about 1 mg/mL, about 300 μg/mL to about 900 μg/mL, about 300 μg/mL to about 800 μg/mL, about 300 μg/mL to about 700 μg/mL, about 300 μg/mL to about 600 μg/mL, about 300 μg/mL to about 500 μg/mL, about 300 μg/mL to about 400 μg/mL, about 400 μg/mL to about 1 mg/mL, about 400 μg/mL to about 900 μg/mL, about 400 μg/mL to about 800 μg/mL, about 400 μg/mL to about 700 μg/mL, about 400 μg/mL to about 600 μg/mL, about 400 μg/mL to about 500 μg/mL, about 500 μg/mL, to about 1 mg/mL, about 500 μg/mL to about 900 μg/mL, about 500 μg/mL to about 800 μg/mL, about 500 μg/mL to about 700 μg/mL, about 500 μg/mL to about 600 μg/mL, about 750 μg/mL to about 1 mg/mL, about 750 μg/mL to about 900 μg/mL, about 750 μg/mL to about 800 μg/mL, or about 800 μg/mL to about 1 mg/mL.

In embodiments, initial stimulation is carried out by adding the initiating peptide at the desired concentration to a cell sample containing about $1\times10^5$ cells to about $2\times10^5$ cells. In embodiments, the cell sample volume is 100 to 200 and the cell density in the sample is about $5\times10^5$ cells/mL to about $1\times10^6$ cells/mL. In embodiments, the initiating peptide is added to the cell sample at a final peptide concentration of about 1 μg/mL to about 100 μg/mL.

In embodiments, one or more growth promoter is added one or more times to the cell culture or sample following initial stimulation or restimulation. In embodiments, the growth promoter is IL-2. The growth promoter can be added at regular or irregular intervals during the culturing, e.g., every 2 to 10 days as needed, depending on, e.g., the rate of cell growth. In embodiments, growth promoter is added every 2 days, every 3 days, every 4 days, every 5 days, every 6 days, every 7 days, every 8 days, every 9 days, or every 10 days. As known to one of skill in the art, the appropriate amount of growth promoter to add can be determined based on the growth characteristics of the culture, e.g., cell health as examined microscopically, and media pH as indicated by a pH indicator dye. In embodiments, about 5 to about 30 units (U) of IL-2 is added per mL of cell culture. In embodiments, about 10, about 15, about 17, about 18, about 19, about 20, about 21, about 22, about 23, about 5 to about 30, about 5 to about 25, about 5 to about 20, about 5 to about 15, about 5 to about 10, about 10 to about 30, about 10 to about 25, about 10 to about 20, about 10 to about 15, about 15 to about 30, about 15 to about 25, about 15 to about 20, about 20 to about 30, about 20 to about 25, about 25 to about 30, about 17 to about 23, about 18 to about 22, or about 19 to about 21 units of IL-2 are added to each mL of cell culture. In embodiments, about 20 U/mL IL-2 is added to the cell culture on D3 and D6 following initial stimulation. In embodiments, about 15 to about 25 U/mL IL-2 is added to the cell culture every 3 days following initial stimulation. In embodiments, about 15 to about 25 U/mL IL-2 is added to the cell culture 18 hours to 2 days following restimulation. In embodiments, about 20 U/mL IL-2 is added to the cell culture 18 hours to 24 hours following restimulation. In embodiments, the initiating peptide is added to a cell sample containing about $5\times10^5$ cells/mL to about $1\times10^6$ cells/mL. In embodiments, the initiating peptide is added to the cell sample at a final peptide concentration of about 1 μg/mL to about 100 μg/mL at a final concentration of about 1 μg/mL to about 100 μg/mL, and IL-2 is added to the cell sample at a final concentration of about 15 to about 25 U/mL. In embodiments, the initiating peptide is added to a cell sample containing about $5\times10^5$ cells/mL to about $1\times10^6$ cells/mL at a final concentration of about 1 μg/mL to about 100 μg/mL, and IL-2 is added to the cell sample at a final concentration of about 15 to about 25 U/mL at least twice after initial stimulation and before screening for reactivity. In embodiments, the initiating peptide is added to a cell sample containing about $5\times10^5$ cells/mL to about $1\times10^6$ cells/mL cells at a final concentration of about 1 μg/mL to about 100 μg/mL, and IL-2 is added to the cell sample at a final concentration of about 15 to about 25 U/mL at D3 and D6 following initial stimulation. In embodiments, the initiating peptide is added to a cell sample containing about $5\times10^5$ cells/mL to about $1\times10^6$ cells/mL at a final concentration of about 1 μg/mL to about 100 μg/mL, and IL-2 is added to the cell sample at a final concentration of about 15 to about 25 U/mL every 3 days following initial stimulation.

At least about 7 to about 16 days after stimulation with the initiating peptide, as shown in FIG. 1, the cell lines are screened for reactivity to the initiating peptide. In embodiments, the cell lines are screened for reactivity to the initiating peptide after at least about 7, at least about 8, at least about 9, at least about 10, at least about 11, at least about 12, at least about 13, at least about 14, at least about 15, at least about 16 days, about 7 to about 16, about 8 to about 14, about 8 to about 12, about 8 to about 10, about 10 to about 16, about 10 to about 14, about 12 to about 16 days, or about 12 to about 14 days after the initial stimulation with initiating peptide at Day 0, or as long as the culture remains healthy without restimulation. In embodiments, the cell lines are screened for reactivity to the initiating peptide after at least one restimulation with the initiating peptide and appropriate APC. In embodiments, the stimulated cell cultures are screened for reactivity to the initiating peptide after 2 to 10 rounds of restimulation following the initial stimulation with initiating peptide at Day 0. Thus, the stimulated cell cultures can be screened for reactivity to the initiating peptide at any time, e.g., after more than about 14 days, provided they are restimulated when necessary as determined by one of skill in the art.

The GA initiating peptide can be prepared by diluting the peptide in solution according to methods known in the art, e.g., by suspension in water and about 20 mg/mL mannitol, or in culture medium. GA preparation for bioassays is described, e.g., in U.S. Pat. No. 7,429,374, "Process for the measurement of the potency of glatiramer acetate," incorporated by reference herein.

Screening for Reactivity to GA

As described and as depicted in FIG. 1, a T-cell culture is screened for GA-reactivity following the initial stimulation. Screening is carried out by preparing a test mature containing GA and appropriate APC, and measuring a resulting GA-elicited response of the T-cell culture. In embodiments wherein donor PBMC are used, the donor PBMC already contain autologous APC. Appropriate APC for use in the methods of the invention are cells capable of presenting antigen to the T-cells, including, e.g., Epstein Barr Virus-transformed (EBV-transformed) human B-cells autologous to the GA-specific human T-cells, purified monocytes autologous to the GA-specific human T-cells, purified dendritic cells autologous to the GA-specific human T-cells, PBMC autologous to the GA-specific human T-cells, EBV-transformed human B-cells having the DR molecule involved in antigen presentation to the GA-specific human T-cells, purified monocytes having the DR molecule involved in antigen presentation to the GA-specific human T-cells, purified dendritic cells having the DR molecule involved in antigen presentation to the GA-specific human T-cells, and PBMC having the DR molecule involved in antigen presentation to the GA-specific human T-cells.

In embodiments, proliferation of the APC prior to use is inhibited, by any known method, including exposure to γ-radiation or to an anti-mitotic agent, e.g., mitomycin C.

In embodiments, a T-cell culture is screened for GA-reactivity at a cell density of about $1\times10^5$ to about $5\times10^5$ cells/mL, about $1\times10^5$ cells/mL, about $1.5\times10^5$ cells/mL, about $2\times10^5$ cells/mL, about $2.5\times10^5$ cells/mL, about $3\times10^5$ cells/mL, about $3.5\times10^5$ cells/mL, about $4\times10^5$ cells/mL, about $4.5\times10^5$ cells/mL, or about $5\times10^5$ cells/mL.

In embodiments, the APC are present at a number equal to the number of T-cells used to twice the number of T-cells used. In embodiments, autologous mitomycin-treated PBMC are present at about $2.5\times10^5$ to about $5\times10^6$ cells/mL. In embodiments, autologous mitomycin-treated PBMC are present at $1\times10^6$-$2\times10^6$ cells/mL. In embodiments, autologous mitomycin-treated PBMC are present at $2.5\times10^6$ cells/mL.

In embodiments, autologous mitomycin-treated B-LCL are present at about $1\times10^5$-$1\times10^6$ cells/mL. In embodiments, autologous mitomycin-treated B-LCL are present at about $1\times10^5$-$5\times10^5$ cells/mL. In embodiments, autologous mitomycin-treated B-LCL are present at about $1\times10^5$ cells/mL, about $1.5\times10^5$ cells/mL, about $2\times10^5$ cells/mL, about $2.5\times10^5$ cells/mL, or about $5\times10^5$ cells/mL. In embodiments, the number of APC used in a screening or characterization assay in the methods of the invention is adjusted as needed to increase the GA-elicited response, for example, to a minimum desired level relative to a negative control. In embodiments, the minimum desired level of the GA-elicited response relative to the negative control is 1.5-fold (i.e., the response is about 50% higher) to about 1000-fold, as described below.

The GA-elicited response measured is compared with the same response measured in a control, e.g., the response of the same T-cell line in a culture containing appropriate APC in the absence of antigen (GA), or in the presence of a non-relevant antigen suitable for serving as a negative control. The screening readout can be from any appropriate assay for a GA-elicited response preferred, including, but not limited to, a proliferation assay, or a response biomarker assay in which the amount of at least one cytokine, cytokine receptor, chemokine, or T-cell activation marker produced, by the culture is measured. In embodiments, the GA-elicited response is the expression of a nucleic acid that encodes a response biomarker. Based on comparison of the GA-elicited response(s) measured in the T-cell lines cultured with GA and a control culture, GA-specific T-cell lines are identified.

In embodiments, a GA-reactive or responsive T-cell line is identified by an increase in the at least one GA-elicited response measured in the test culture stimulated with GA that is statistically greater than the same at least one GA-elicited response measured in a no-antigen control culture or a non-relevant antigen control culture. In embodiments, a GA-reactive or responsive T-cell line is identified by an increase in a GA-elicited response of the test culture relative to the control of about 1.5-fold (i.e., the response is about 50% higher) to about 1000-fold, about 1.5 to about 2-fold, about 1.5 to about 3-fold, about 1.5 to about 4-fold, about 1.5 to about 5-fold, about 1.5 to about 6-fold, about 1.5 to about 7-fold, about 1.5 to about 8-fold, about 1.5 to about 9-fold, about 2 to about 3-fold, about 2 to about 4-fold, about 2 to about 5-fold, about 2 to about 6-fold, about 2 to about 7-fold, about 2 to about 8-fold, about 2 to about 9-fold, about 2 to about 10-fold, about 3 to about 4-fold, about 3 to about 5-fold, about 3 to about 6-fold, about 3 to about 7-fold, about 3 to about 8-fold, about 3 to about 9-fold, about 3 to about 10-fold, about 4 to about 5-fold, about 4 to about 6-fold, about 4 to about 7-fold, about 4 to about 8-fold, about 4 to about 9-fold, about 4 to about 10-fold, about 5 to about 6-fold, about 5 to about 7-fold, about 5 to about 8-fold, about 5 to about 9-fold, about 5 to about 10-fold, about 6 to about 7-fold, about 6 to about 8-fold, about 6 to about 9-fold, about 6 to about 10-fold, about 7 to about 8-fold, about 7 to about 9-fold, about 7 to about 10-fold, about 8 to about 9-fold, about 8 to about 10-fold, about 1.5-fold to about 80-fold, about 1.5-fold to about 70-fold, about 1.5-fold to about 60-fold, about 1.5-fold to about 50-fold, about 1.5-fold to about 40-fold, about 1.5-fold to about 30-fold, about 1.5-fold to about 20-fold, about 2-fold to about 80-fold, about 1.5-fold to about 70-fold, about 1.5-fold to about 60-fold, about 1.5-fold to about 50-fold, about 1.5-fold to about 40-fold, about 1.5-fold to about 30-fold, about 1.5-fold to about 20-fold, about 2-fold to about 80-fold, about 2-fold to about 70-fold, about 2-fold to about 60-fold, about 2-fold to about 50-fold, about 2-fold to about 40-fold, about 2-fold to about 30-fold, about 2-fold to about 20-fold, about 3-fold to about 80-fold, about 3-fold to about 70-fold, about 3-fold to about 60-fold, about 3-fold to about 50-fold, about 3-fold to about 40-fold, about 3-fold to about 30-fold, about 3-fold to about 20-fold, about 5-fold to about 80-fold, about 5-fold to about 70-fold, about 5-fold to about 60-fold, about 5-fold to about 50-fold, about 5-fold to about 40-fold, about 5-fold to about 30-fold, about 3-fold to about 20-fold, about 10-fold to about 80-fold, about 10-fold to about 60-fold, about 10-fold to about 40-fold, or about 10-fold to about 20-fold, at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, or at least about 10-fold.

In certain embodiments, a GA-reactive or responsive T-cell line is identified by an increase of at least 50% in proliferation of the test culture stimulated with GA, relative to proliferation of a no-antigen control culture or a non-relevant antigen control culture. In embodiments, a GA-reactive or responsive T-cell line is identified by an increase in two or more GA-elicited responses measured in the test culture stimulated with GA, relative to the same two or more GA-elicited response measured in a no-antigen control culture or a non-relevant antigen control culture. In embodiments, 2, 3, 4, 5, 6, 7, 8, 9, 10, or more GA-elicited responses are measured.

Screening T-Cell Lines for GA-Specificity

As further shown in FIG. 1, the GA-reactive T-cell lines are screened for GA-specificity. In embodiments, a test for GA-specificity is carried out in conjunction with a GA-reactivity assay, by additionally screening for T-cell lines that do not respond to an appropriate negative control antigen, e.g., a peptide from an unrelated protein. In embodiments, the GA-specificity of a T-cell line is tested by comparing at least one GA-elicited response measured in a test culture stimulated with GA, relative to the same at least one GA-elicited response measured in a culture containing a negative control antigen. In embodiments, a negative control antigen culture comprises a negative control antigen, e.g., tetanus toxoid, MBP, CMV, PPD, or allogeneic MHC.

A test of an identified GA-reactive T-cell line for GA specificity can serve as a confirmatory test for GA reactivity. In embodiments, GA-reactivity is confirmed before specificity testing. In embodiments, GA-reactivity of an identified GA-reactive or GA-specific human T-cell line is reconfirmed at any point during culturing, e.g., after thawing a frozen culture. In embodiments, when a confirmatory test for reactivity of a T-cell line to a GA reference standard is negative, the T-cell line no longer is considered GA-specific or reactive and can be discarded.

In embodiments, a GA-specific human T-cell line is identified by a (mean) GA-elicited response measured in response to GA stimulation that is statistically greater than the (mean) negative control GA-elicited response.

In embodiments, a GA-specific T-cell line is identified by an increase in the at least one GA-elicited response measured in the test culture stimulated with GA, relative to the same at least one GA-elicited response measured in the negative control culture. In embodiments, the increase is about 1.5 to about 10-fold (i.e., the response is about 50% higher to about 1000% higher), about 1.5 to about 2-fold, about 1.5 to about 3-fold, about 1.5 to about 4-fold, about 1.5 to about 5-fold, about 1.5 to about 6-fold, about 1.5 to about 7-fold, about 1.5 to about 8-fold, about 1.5 to about 9-fold, about 2 to about 10-fold, about 2 to about 3-fold, about 2 to about 4-fold, about 2 to about 5-fold, about 2 to about 6-fold, about 2 to about 7-fold, about 2 to about 8-fold, about 2 to about 9-fold, about 3 to about 10-fold, about 3 to about 4-fold, about 3 to about 5-fold, about 3 to about 6-fold, about 3 to about 7-fold, about 3 to about 8-fold, about 3 to about 9-fold, about 4 to about 10-fold, about 4 to about 5-fold, about 4 to about 6-fold, about 4 to about 7-fold, about 4 to about 8-fold, about 4 to about 9-fold, about 5 to about 10-fold, about 5 to about 6-fold, about 5 to about 7-fold, about 5 to about 8-fold, about 5 to about 9-fold, about 6 to about 10-fold, about 6 to about 7-fold, about 6 to about 8-fold, about 6 to about 9-fold, about 7 to about 10-fold, about 7 to about 8-fold, about 7 to about 9-fold, about 8 to about 10-fold, about 8 to about 9-fold, at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, or at least about 10-fold.

In embodiments, a GA-specific human T-cell line is identified using the following formula:

GA-elicited response to test antigen minus the same response to control÷GA-elicited response to reference antigen minus response to control=0.8 to 1.2, or 80% to 120%. The comparison is thus within acceptable range or limits. In these embodiments, the T-cell line is determined to be GA-specific based on a "single reference lot, single dose analysis." In embodiments, the GA-specificity of a human T-cell line is identified when the single reference, single dose analysis comparison value is within the acceptable range at one GA dose, two different GA doses, three different GA doses, or more.

In embodiments, the reference antigen used to obtain the denominator value of the formula above is the same antigen that was used to initiate and stimulate the T-cell line. In embodiments, the GA-elicited response observed after stimulation with the test antigen is not more than 20% above or below the value observed after stimulation with the antigen used to obtain the cell line. In embodiments, human T-cell lines are identified as GA-specific if they meet these criteria in the majority of assays run, show no major deviation at any concentration tested, and have similar dose-response curves with no major deviation in curve shape for test and reference antigen response values.

Any appropriate control can be used in the above embodiments, e.g., a no antigen control or a non-relevant antigen control.

In the above embodiments, the acceptable range is, e.g., about 80% to about 120%, about 75% to about 120%, about 75% to about 115%, about 75% to about 110%, about 75% to about 105%, about 75% to about 100%, about 80% to about 125%, about 85% to about 125%, about 90% to about 125%, about 95% to about 125%, about 100% to about 125%, about 80% to about 118%, about 80% to about 115%, about 80% to about 112%, about 80% to about 110%, about 80% to about 108%, about 80% to about 105%, about 80% to about 102%, about 80% to about 101%, about 80% to about 100%, about 80% to about 99%, about 80% to about 98%, about 80% to about 97%, about 80% to about 95%, about 80% to about 92%, about 80% to about 90%, about 82% to about 120%, about 82% to about 118%, about 82% to about 115%, about 82% to about 112%, about 82% to about 110%, about 82% to about 108%, about 82% to about 105%, about 82% to about 102%, about 82% to about 101%, about 82% to about 100%, about 82% to about 99%, about 82% to about 98%, about 82% to about 97%, about 82% to about 95%, about 82% to about 92%, about 82% to about 90%, about 84% to about 120%, about 84% to about 118%, about 84% to about 115%, about 84% to about 112%, about 84% to about 110%, about 84% to about 108%, about 84% to about 105%, about 84% to about 102%, about 84% to about 101%, about 84% to about 100%, about 84% to about 99%, about 84% to about 98%, about 84% to about 97%, about 84% to about 95%, about 84% to about 92%, about 84% to about 90%, about 86% to about 120%, about 86% to about 118%, about 86% to about 115%, about 86% to about 112%, about 86% to about 110%, about 86% to about 108%, about 86% to about 105%, about 86% to about 102%, about 86% to about 101%, about 86% to about 100%, about 86% to about 99%, about 86% to about 98%, about 86% to about 97%, about 86% to about 95%, about 86% to about 92%, about 88% to about 120%, about 88% to about 118%, about 88% to about 115%, about 88% to about 112%, about 88% to about 110%, about 88% to about 108%, about 88% to about 105%, about 88% to about 102%, about 88% to about 101%, about 88% to about 100%, about 88% to about 99%, about 88% to about 98%, about 88% to about 97%, about 88% to about 95%, about 90% to about 120%, about 90% to about 118%, about 90% to about 115%, about 90% to about 112%, about 90% to about 110%, about 90% to about 108%, about 90% to about 105%, about 90% to about 102%, about 90% to about 101%, about 90% to about 100%, about 90% to about 99%, about 90% to about 98%, about 90% to about 97%, about 90% to about 95%, about 92% to about 120%, about 92% to about 118%, about 92% to about 115%, about 92% to about 112%, about 92% to about 110%, about 92% to about 108%, about 92% to about 105%, about 92% to about 102%, about 92% to about 101%, about 92% to about 100%, about 92% to about 99%, about 92% to about 98%, about 95% to about 120%, about 95% to about 118%, about 95% to about 115%, about 95% to about 112%, about 95% to about 110%, about 95% to about 108%, about 95% to about 105%, about 95% to about 102%, about 95% to about 101%, about 95% to about 100%, about 97% to about 120%, about 97% to about 118%, about 97% to about 115%, about 97% to about 112%, about 97% to about 110%, about 97% to about 108%, about 97% to about 105%, about 97% to about 102%, about 98% to about 120%, about 98% to about 118%, about 98% to about 115%, about 98% to about 112%, about 98% to about 110%, about 98% to about 108%, about 98% to about 105%, about 99% to about 120%, about 99% to about 118%, about 99% to about 115%, about 99% to about 112%, about 99% to about 110%, about 99% to about 108%, about 99% to about 105%, about 100% to about 120%, about 100% to about 118%, about 100% to about 115%, about 100% to about 112%, about 100% to about 110%, about 100% to about 108%, about 100% to about 105%, about 101% to about 120%, about 101% to about 118%, about 101% to about 115%, about 101% to about 112%, about 101% to about 110%, about 101% to about 108%, about 102% to about 120%, about 102% to about 118%, about 102% to about 115%, about 102% to about 112%, about 102% to about 110%, about 102% to about 108%, about 105% to about 120%, about 105% to about 118%, about 105% to about 115%, about 105% to about 112%, about 105% to about 110%, about 110% to about 120%, about 110% to about 118%, or about 110% to about 115%.

In embodiments, a GA-specific T-cell line is identified by an increase in at least 2, at least 3, at least 4, or more, different GA-elicited responses measured in the test culture stimulated with GA, relative to the same GA-elicited responses of the negative control culture.

In embodiments, a GA-elicited response measured at different GA doses is used to generate a dose response curve, and GA-specificity is identified by comparison of the dose response curve obtained using the test GA lot to that obtained using the reference GA lot. In these embodiments, the GA-specificity of a human T-cell line is identified based on a "single-reference lot dose response curve analysis." In these embodiments, the GA-specificity of a human T-cell line can be identified when the slopes in the linear range of the test GA lot and reference GA lot dose-response curves are statistically similar or identical as determined according to any appropriate statistical methods known in the art.

In embodiments, to reach a determination of GA-specificity, the slope ($\beta$*) of the reference lot dose response curve must meet appropriate acceptance criteria. Appropriate acceptance criteria can be predetermined by those of skill in the art. In certain embodiments, appropriate acceptance criteria are:

Coefficient of correlation (r) is ≥0.90

The slope is ≥0.60

The back-calculated concentration of GA standards is within E30% of the nominal concentration The precision of a GA sample is ≤0% of coefficient of variation (CV).

In embodiments, the GA-elicited response in 75% of positive control samples (e.g., cells stimulated with ConA) must be above the highest response elicited when the same cells are stimulated with any concentration of GA. In embodiments, the GA-elicited response in 75% of negative control samples (e.g., cells treated with a control peptide such as myelin basic protein, MBP) must be below or close to the lowest response elicited with any concentration of GA.

Linear regression can be performed on the GA reference lot sample set, where the data points are plotted on a log-log scale. The log GA-elicited response values (by increasing concentration of analyte, shown below as IL-2) are on the Y-axis, and the log GA reference lot concentration (dose) values are on the X-axis.

The best fit linear regression model used for the above data set is as follows:

$$Y=\alpha+\beta\cdot X \quad (1)$$

where $Y=\log_{10}$(mIL−2 concentration) and $X=\log_{10}$(GA concentration). Substituting X and Y variables with the appropriate representations, the above model becomes the following:

$$\log_{10}(mIL\text{-}2\ \text{concentration})=\alpha+\beta\cdot\log_{10}(\text{GA-concentration}) \quad (2)$$

In embodiments, GA-specificity is established when the slope of the test lot curve is within acceptable limits. The acceptable limits for the slope of the test lot curve are determined based on the reference lot curve using the following series of equations:

The back-calculated dose value for a given log (response) is:

$$X_{back}=10^{(Y-\alpha)/\beta} \text{ where } Y=\text{Log}_{10}(mIL\text{-}2\ \text{concentration}) \quad (3)$$

The accuracy can be calculated by the following:

$$\text{accuracy}=\left[\frac{10^{(Y-\alpha)/\beta}-X_{true}}{X_{true}}\right]*100\% \quad (4)$$

$Y_{low}$ and $Y_{high}$ are the lowest and highest log (response) values permitted by the highest allowable accuracy of ±(Mean+2*SD), where Mean+2*SD is the highest limit of the approximate 95% individual tolerance region.

Therefore, the region where the hypothesis of the equality of the slopes is to be accepted is:

$$\begin{cases} \left[\frac{10^{(Y_{low}-\alpha)/\beta} - X_1}{X_1}\right] * 100\% \geq -(\text{Mean} + 2 * SD) \\ \left[\frac{10^{(Y_{high}-\alpha)/\beta} - X_2}{X_2}\right] * 100\% \leq (\text{Mean} + 2 * SD) \end{cases} \tag{5}$$

$$\begin{cases} Y_{low} = \alpha + \beta * \log\left(X_1 * \left(1 - \frac{(\text{Mean} + 2 * SD)}{100}\right)\right) \\ Y_{high} = \alpha + \beta * \log\left(X_2 * \left(1 + \frac{(\text{Mean} + 2 * SD)}{100}\right)\right) \end{cases} \tag{6}$$

β* is calculated as follows:

$$\left\{\beta^* = \frac{Y_{high} - Y_{low}}{\log X_2 - \log X_1}\right. \tag{7}$$

Subsequently, the above region is reduced to the following for determination of the acceptable β* limits:

$$\begin{cases} \beta^* \geq \beta * (\text{lower limit}) \\ \beta^* \leq \beta * (\text{upper limit}) \end{cases} \tag{8}$$

where β is the slope of the GA reference lot curve. Therefore, the acceptable range for the GA test lot slope, β*, determined by equation (6) can be displayed as:

$$\beta\cdot(\text{lower limit}) \leq \beta^* \leq \beta\cdot(\text{upper limit}) \tag{9}$$

If •β* is within the above acceptable limits, parallelism can be concluded.

In embodiments, the coefficient of correlation is 0.90 to 0.98. In embodiments, the coefficient of correlation is greater than or equal to 0.90, greater than or equal to 0.91, greater than or equal to 0.92, greater than or equal to 0.93, greater than or equal to 0.94, greater than or equal to 0.95, greater than or equal to 0.96, greater than or equal to 0.97, greater than or equal to 0.98, 0.90 to 0.98, 0.91 to 0.98, 0.92 to 0.98; 0.93 to 0.98, 0.94 to 0.98, 0.95 to 0.98, 0.96 to 0.98, 0.90 to 0.97, 0.91 to 0.97, 0.92 to 0.97, 0.93 to 0.97, 0.94 to 0.97, 0.95 to 0.97, or 0.96 to 0.98.

In embodiments, a true hypothesis test for equal slope is used.

In embodiments, the GA-specific human T-cell lines are long-term GA-specific human T-cell lines, that is, they are demonstrated to maintain GA-specificity for an extended culturing period. In embodiments, the long-term GA-specific human T-cell lines of the invention are demonstrated to maintain GA-specificity after culturing for at least about 4 weeks to at least about 10 weeks, or longer, e.g., by rescreening to confirm GA-specificity. In embodiments, the GA-specific human T-cell lines of the invention are demonstrated to maintain GA-specificity after culturing at least about 4 weeks to at least about 12 weeks, or longer, not including any time spent in frozen storage. In embodiments, the GA-specific human T-cell lines of the invention are demonstrated to maintain GA-specificity after culturing at least about 4, at least about 5, at least about 6, at least about 7, at least about 8, at least about 9, at least about 10 weeks, at least about 11 weeks, at least about 12 weeks, about 4 to about 12 weeks, about 4 to about 11 weeks, about 4 to about 10 weeks, about 4 to about 9 weeks, about 4 to about 8 weeks, about 4 to about 7 weeks, about 4 to about 6 weeks, about 5 to about 12 weeks, about 5 to about 11 weeks, about 5 to about 10 weeks, about 5 to about 9 weeks, about 5 to about 8 weeks, about 5 to about 7 weeks, about 6 to about 12 weeks, about 6 to about 11 weeks, about 6 to about 10 weeks, about 6 to about 9 weeks, about 6 to about 8 weeks, about 7 to about 12 weeks, about 7 to about 11 weeks, about 7 to about 10 weeks, about 7 to about 9 weeks, about 8 to about 12 weeks, about 8 to about 11 weeks, about 8 to about 10 weeks, about 9 to about 12 weeks, or about 9 to about 11 weeks, not including any time spent in frozen storage.

In embodiments, the long-term GA-specific human T-cell lines of the invention are demonstrated to maintain GA-specificity for an extended culturing period when grown in the presence of appropriate APC as described herein. In embodiments, the appropriate APC are autologous APC. In specific embodiments, the long-term GA-specific human T-cell lines of the invention are demonstrated to maintain GA-specificity long-term when grown in the absence of a mitogen. In embodiments, the mitogen that is absent is, e.g., phytohemagglutinin (PHA), Concanavalin A (ConA), lipopolysaccharide, or Staphylococcal enterotoxin B (SEB). Long-term growth with maintenance of GA-specificity in the absence of a mitogen is a notable feature of GA-specific human T-cell lines of the present invention. In specific embodiments, the long-term GA-specific human T-cell lines of the invention are demonstrated to maintain GA-specificity in culture for at least about 4 weeks in culture or for at least 1 to 10 rounds of restimulation and expansion, when grown in the presence of GA and appropriate autologous APC, without added mitogen. In embodiments, an identified GA-specific human T-cell line is demonstrated to be GA-specific after multiple rounds of restimulation and expansion, e.g., after at least 1 to 10 rounds of restimulation and expansion or more. In embodiments, a long-term GA-specific human T-cell line is demonstrated to be GA-specific after at least 1, at least 2, at least 3, at least 4, at least 5, at least 6, at least 7, at least 8, at least 9, at least 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 1 to 8, 2 to 8, 3 to 8, 4 to 8, 5 to 8, 6 to 8, 1 to 7, 2 to 7, 3 to 7, 4 to 7, 5 to 7, 1 to 6, 2 to 6, 3 to 6, 4 to 6, 1 to 5, 2 to 5, 3 to 5, 1 to 4, 2 to 4, or 1 to 3, rounds of restimulation and expansion.

In embodiments, the GA-specific human T-cell lines are maintained at a cell density of about $1\times10^5$ to about $1\times10^6$ cells/mL, about $1\times10^5$ cells/mL, about $1.5\times10^5$ cells/mL, about $2\times10^5$ cells/mL, about $2.5\times10^5$ cells/mL, about $3\times10^5$ cells/mL, about $3.5\times10^5$ cells/mL, about $4\times10^5$ cells/mL, about $4.5\times10^5$ cells/mL, about $5\times10^5$ cells/mL, about $6\times10^5$ cells/mL, about $7\times10^5$ cells/mL, about $8\times10^5$ cells/mL, about $9\times10^5$ cells/mL, or about $1\times10^6$ cells/mL, during expansion.

In embodiments, a GA-specific human T-cell line is determined to be GA-specific based on a comparison of the value obtained by measuring a GA-elicited response when the T-cell line is stimulated with a first preparation of GA, to the value obtained by measuring the same GA-elicited response when the T-cell line is stimulated with a second preparation of GA, wherein the comparison of the response value of the second preparation of GA to the response value of the first preparation of GA is within a predetermined acceptable range, and wherein the GA-specific human T-cell line is a long-term GA-specific human T-cell line.

In embodiments, a GA-specific human T-cell line is determined to be GA-specific based on a comparison of the dose response curve obtained by measuring a GA-elicited response when the GA-specific human T-cell line is stimulated at multiple doses with a first preparation of GA, to the dose response curve obtained by measuring the same GA-elicited response when the GA-specific human T-cell line is stimulated at multiple doses with a second preparation of GA, wherein the comparison of the slope of the dose response curve of the second preparation of GA to the slope of the dose response curve of the first preparation of GA is within acceptable limits, and wherein the GA-specific human T-cell line is a long-term GA-specific human T-cell line.

In either of the above two embodiments, the first preparation of GA can be the same preparation used to generate the GA-specific human T-cell line. In embodiments, the first preparation of GA is COP. In embodiments, the GA-specific human T-cell line is clonal. In embodiments, the GA-specific human T-cell line has a known MHC restriction. In embodiments, the GA-specific human T-cell line has a known MHC restriction selected from: DR-1, DR-2, DR-3, DR-4, DR-7, DR-11, DR-13, and DR-15. In embodiments, the GA-specific human T-cell line comprises at least 98% CD4+ T-cells, and not more than 2% CD8+ T-cells.

In embodiments, the GA-specific human T-cell line is reactive to a noncanonical GA peptide. In embodiments, the GA-specific human T-cell line is reactive to a noncanonical GA peptide selected from: Peptide 026, GLT 631, GAT 631, GAT 111, GL 14, LT 11, GA 41S, GA 64, and GT 11.

In embodiments, the GA-specific human T-cell line is not reactive to a noncanonical GA peptide. In embodiments, the GA-specific human T-cell line is not reactive to a noncanonical GA peptide selected from Peptide 026, GLT 631, GAT 631, GAT 111, GL 14, LT 11, GA 41S, GA 64, and GT 11.

Expansion of GA-Specific Human T-Cell Lines

In embodiments, a cell line used in the methods of the present invention, e.g., an initial human T-cell line (unscreened), a GA-reactive human T-cell line (shown to be GA-reactive), or an identified GA-specific human T-cell line (shown to be GA-specific), is expanded before or after one or more screening stages. Expansion increases the number of cells in the culture and can be carried out at any time, and as many times, during the GA-specific T-cell line identification and characterization process described, as desired. Typically, expansion of a human T-cell line is carried out after establishing or after confirming the GA-specificity of the line. In embodiments, a cell line is expanded prior to being frozen for storage, or after thawing. In embodiments, a human T-cell line is expanded multiple times during a process as generally outlined in FIG. 1. In embodiments, the GA-specificity of an identified GA-specific human T-cell line is retested following expansion and before use in a method for determining whether it has immunological identity to another GA preparation.

Expansion of a T-cell line is carried out by restimulating the T-cell line with the initiating peptide as described above for initial stimulation, in the presence of appropriate APC, and if needed, a growth promoter, e.g., IL-2. In embodiments, 11-2 is added about 12 to about 36 hours following restimulation and the culture is incubated for about 6 to about 14 days. In embodiments, this process is repeated, and portions of the culture frozen, as desired. In embodiments, expansion of a confirmed GA-specific human T-cell line is carried out by restimulating the cells with initiating peptide at a final concentration of about 1 μg/mL to about 100 μg/mL, adding APC at an amount that is about equal to the number of T-cells used to an amount that is about twice the number of T-cells used, and after about 12 to about 36 hours adding IL-2 at a final concentration of about 10 to about 25 U/mL. In embodiments, this process is repeated multiple times at intervals of about 6 days, about 7 days, about 8 days, about 9 days, about 10 days, about 11 days, about 12 days, about 13 days, about 14 days, about 7 to about 14 days, about 7 to about 13 days, about 7 to about 12 days, about 7 to about 11 days, about 7 to about 10 days, about 7 to about 9 days, about 8 to about 14 days, about 8 to about 13 days, about 8 to about 12 days, about 8 to about 11 days, about 8 to about 10 days, about 9 to about 14 days, about 9 to about 13 days, about 9 to about 12 days, about 9 to about 11 days, about 10 to about 14 days, about 10 to about 13 days, about 10 to about 12 days, about 10 to about 11 days, about 11 to about 14 days, about 11 to about 13 days, or about 12 to about 14 days. In certain embodiments, expansion of a confirmed GA-specific human T-cell line is carried out by restimulating the cells with initiating peptide at a final concentration of about 1 μg/mL to about 100 μg/mL, adding APC at an amount that is about equal to the number of T-cells used to an amount that is about twice the number of T-cells used, and after about 12 to about 36 hours adding IL-2 at a final concentration of about 10 to about 25 U/mL, and further, incubating the cells for about 7 to about 10 days. The incubation time before restimulating to initiate another cycle of expansion, if desired, can be determined by any method known to one of skill in the art of tissue culture, e.g., by evaluating pH indicator dye color in the medium, and cell characteristics. In embodiments, at the end of the incubation period the expansion process is repeated by splitting the cultures according to methods known in the art and restimulating for further expansion. In embodiments, the expanded cells are frozen for storage, restimulated and tested for GA-specificity, or used in characterization tests as described herein.

Any suitable T-cell expansion medium (permissive for development of the lymphoid lineage) known in the art can be used for growing the T-cell lines according to the methods of the present invention. In embodiments, a serum-free medium is used. In embodiments, the medium used is, e.g., AIM V (Invitrogen), X-VIVO 15® Medium (Lonza), Stemline® T Cell Expansion Medium (Sigma-Aldrich). In embodiments, the medium lacks animal serum, feeder cells, and cell-based extracellular matrices. The formulations of suitable media, including serum-free media, are known and described in the art, e.g., in U.S. Pat. No. 6,733,746, "Hematopoietic cell culture nutrient supplement" and U.S. Pat. No. 8,481,315, "Methods of expanding myeloid cell populations and uses thereof" both incorporated by reference herein.

Characterization of GA-Specific Human T-Cell Lines

The GA-specific human T-cell lines of the present invention can be characterized as described herein. Based on the characteristics, e.g., immunological characteristics, of each GA-specific human T-cell line, panels comprising cell lines having different MHC restrictions, different biomarker profiles, and different responses to non-canonical GA peptides are assembled for use in a parallel assay format for comprehensive interrogation of the GA epitopes in a GA preparation. This strategy enables determination of the immunologic identity between different GA preparations with greater accuracy than possible using any previously described assay.

As described, GA consists of the acetate salts of synthetic polypeptides that contain four naturally occurring amino acids: L-glutamic acid, L-alanine, L-tyrosine, and L-lysine. These amino acids are present at an average molar fraction of 0.141, 0.427, 0.095, and 0.338, respectively, in random sequence. Multiple epitopes undoubtedly are present on a given GA molecule. The more GA epitopes interrogated in an assay for determining whether GA test and reference standard preparations have immunologic identity, the more accurately the assay can identify a GA test preparation having a comparable clinical effect to the reference standard, e.g., the FDA-approved drug, Copaxone. However, the identification of antigenic epitopes in GA has eluded researchers, primarily because GA, as a mixture of peptides having many different amino acid sequences, is difficult to characterize using conventional techniques such as X-ray crystallography.

The present invention overcomes this problem by using individual T-cells' unique ability to distinguish between different but similar antigen structures. The invention is based on the discovery that GA-specific human T-cell lines that recognize different epitopes in a GA preparation can be generated and identified. Using the methods of the present invention, GA-specific human T-cell lines that recognize different GA epitopes based on the cell lines' antigen recognition properties are obtained. A panel comprising GA-specific human T-cell lines that together recognize many different GA epitopes can be assembled and used to interrogate GA preparations.

Characterization can be carried out by the methods described herein, or by any other method known in the art for characterizing antigen-specific T-cell lines, for example, as described by using T cell receptor spectratyping as described by Gorski, et al., 1994 May 15, ("Circulating T cell repertoire complexity in normal individuals and bone marrow recipients analyzed by CDR3 size spectratyping. Correlation with immune status," J Immunol. 152(10):5109-19), or identifying T cell receptor Vβ chain expression using PCR as described by Choi, et al., 1989 November, "Interaction of *Staphylococcus aureus* toxin 'superantigens' with human T cells," Proc Natl Acad Sci USA 86(22):8941-5.

Characterization of GA-Specific Human T-Cell Lines Reactive to Non-Canonical GA Peptides In embodiments of the present invention, GA-specific human T-cell lines that recognize different epitopes in GA are identified based on their reactivity to stimulation with non-canonical GA peptides. Non-canonical GA peptides are peptides consisting of any subset of the four GA amino acids, or all four GA amino acids, in different average molar fraction than described for COP. Examples of non-canonical GA peptides are poly-glutamic acid, poly-alanine, poly-tyrosine, and poly-lysine, peptides containing only two or only three of the four GA amino acids (in any average molar fraction), and peptides having all four of the GA amino acids in different average molar fraction than described for Copaxone. Table 1 in the Examples provides a non-limiting list of certain non-canonical GA peptides, including peptide 026, which contains all four GA amino acids but was synthesized by withholding tyrosine for the first 5 minutes of GA manufacturing. Methods for synthesizing non-canonical GA peptides useful in the methods of the invention are described in the literature. Peptide 026 contains less tyrosine than GA and an altered distribution of amino acids over the length of each polypeptide species in the preparation. Many peptides suitable for use as non-canonical GA peptides in the methods of the present invention are commercially available, e.g., from Sigma-Aldrich (St. Louis, Mo.).

The epitopes in a non-canonical GA peptide are expected to be present in canonical GA. A non-canonical peptide containing fewer than the four amino acids that make up GA is expected to contain a smaller number of different epitopes than GA. A non-canonical peptide containing all four GA amino acids, in an altered molar ratio relative to GA (i.e., the ratio described for Copaxone), is expected to contain GA epitopes in different relative proportion to that found in Copaxone, depending on the alteration. The successful identification of GA-specific human T-cell lines that are not reactive to a non-canonical peptide containing all four GA amino acids, e.g., peptide 026, as well as GA-specific human T-cell lines that are reactive to the same non-canonical peptide, demonstrates that GA-specific human T-cell lines having very fine differences in specificity can be generated. These GA-specific human T-cell lines can be useful for detecting an aberrant GA preparation. Thus, characterizing GA-specific human T-cell lines based on reactivity to different non-canonical GA peptides allows the identification of GA-specific human T-cell lines that when used in parallel in an assay panel can determine accurately whether GA preparations have immunological identity.

A T-cell line assay panel that includes multiple GA-specific T-cell lines that each recognize a different epitope of GA can determine with greater accuracy the immunological identity of GA preparations when compared to a test that measures reactivity to only a single epitope, or a test that cannot distinguish between reactivity to different epitopes, e.g., an assay using a primary polyclonal T-cell culture obtained from a GA-immunized animal. In embodiments, the GA-specific human T-cell lines of the present invention are derived from one clone and therefore are clonal, i.e., monoclonal. In embodiments, they are derived from multiple clones. In embodiments where the GA-specific human T-cell lines are derived from multiple clones, they are derived from a few clones and are oligoclonal.

A GA-specific human T-cell line that is reactive to a non-canonical. GA peptide is expected to recognize a different epitope in GA than a GA-specific human T-cell line that does not react to the same non-canonical GA peptide. Thus, a GA-specific human T-cell line that reacts to a first non-canonical GA peptide but does not react to a second non-canonical peptide, a GA-specific human T-cell line that does not react to the first non-canonical GA peptide but does react to the second non-canonical peptide, and a GA-specific human T-cell line that reacts to neither the first or second non-canonical peptide, each can be presumed to recognize a different epitope of GA. As an example, a first GA-specific human T-cell line that reacts to GL 41, poly (Glu-Tyr; 4:1) but not to GL 14 (Glu-Lys; 1:4), a second GA-specific human T-cell line that reacts to GL 14 but not GL 41, and a third GA-specific human T-cell line that does not react to either GL 41 or GL 14, each recognizes a different GA epitope. In embodiments of the present invention, a combination of two or more GA-specific human T-cell lines that each react to a different non-canonical peptide are identified and used together in an assay panel to determine whether a GA test preparation contains the epitopes recognized by the GA-specific human T-cell lines in the panel. In embodiments, the assay panel includes two or more GA-specific human T-cell lines determined not to react to the non-canonical peptides.

In embodiments, use of the panel includes testing the reactivity of one or more GA-specific human T-cell, lines in the panel to a non-canonical peptide, by measuring a response of the T-cell line following stimulation with the non-canonical peptide. In embodiments, the response measured is a GA-elicited response as described above, e.g., proliferation, production of a response biomarker, or expression of a nucleic acid encoding a response biomarker. In embodiments, the reactivity of a GA-specific human T-cell line to a non-canonical peptide is tested by measuring a GA-elicited response at multiple timepoints following stimulation, or after stimulation with a series of different GA concentrations, to obtain a dose-response profile or curve, as described above.

Reactivity to a non-canonical peptide can be determined using the same methods for determining reactivity to GA, that is, by measuring a GA-elicited response to stimulation with the non-canonical peptide and comparing the measurement with a negative control, e.g., a no antigen control.

In embodiments, a T-cell line that is reactive to a non-canonical peptide is identified by an increase in at least one GA-elicited response measured in a test culture of the T-cell line stimulated with the non-canonical peptide that is statistically greater than the same at least one GA-elicited response measured in a no-antigen control culture or a non-relevant antigen control culture. In embodiments, a T-cell line that is reactive to a non-canonical peptide is identified by an increase in a GA-elicited response of the test culture relative to the control of about 1.5 to about 10-fold (i.e., the response is about 50% higher to about 1000% higher), about 1.5 to about 2-fold, about 1.5 to about 3-fold, about 1.5 to about 4-fold, about 1.5 to about 5-fold, about 1.5 to about 6-fold, about 1.5 to about 7-fold, about 1.5 to about 8-fold, about 1.5 to about 9-fold, about 2 to about 10-fold, about 2 to about 3-fold, about 2 to about 4-fold, about 2 to about 5-fold, about 2 to about 6-fold, about 2 to about 7-fold, about 2 to about 8-fold, about 2 to about 9-fold, about 3 to about 10-fold, about 3 to about 4-fold, about 3 to about 5-fold, about 3 to about 6-fold, about 3 to about 7-fold, about 3 to about 8-fold, about 3 to about 9-fold, about 4 to about 10-fold, about 4 to about 5-fold, about 4 to about 6-fold, about 4 to about 7-fold, about 4 to about 8-fold, about 4 to about 9-fold, about 5 to about 10-fold, about 5 to about 6-fold, about 5 to about 7-fold, about 5 to about 8-fold, about 5 to about 9-fold, about 6 to about 10-fold, about 6 to about 7-fold, about 6 to about 8-fold, about 6 to about 9-fold, about 7 to about 10-fold, about 7 to about 8-fold, about 7 to about 9-fold, about 8 to about 10-fold, about 8 to about 9-fold, at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, or at least about 10-fold.

Characterization of GA-Specific Human T-Cells Based on Response Biomarker Production In embodiments of the present invention, a GA-specific human T-cell line is characterized by measuring the production and/or expression of at least one GA response biomarker by the GA-specific T-cell line after it is restimulated with GA. In embodiments, the GA-specific human T-cell line is characterized by measuring the production and/or expression of a set of GA response biomarkers, to generate a response biomarker profile. As shown herein in the Examples, different GA-specific human T-cell lines were demonstrated to have different GA-response biomarker profiles, that is, different lines produced different amounts of GA response biomarkers following restimulation with GA. Such differences can reflect subtle differences in the binding specificities of GA-specific human T-cell lines that make the use of these cell lines particularly useful for recognizing a difference between a GA test preparation and a GA reference standard. In embodiments, as described herein, the GA response biomarker profile of one or more GA-specific human T-cell line is characterized and the line used in the methods and/or assay panels of the invention to determine whether a GA test preparation and a GA reference standard are immunologically identical. The expression levels of the biomarkers in the GA response biomarker profile of a GA-specific human T-cell line stimulated with a GA test preparation are compared with the respective biomarker expression levels of the same GA-specific human T-cell line stimulated with the GA reference standard. The GA test preparation and GA reference standard are determined to be immunologically identical when the comparison value, of the expression level of each biomarker by the GA-specific human T-cell line following stimulation with the GA test preparation, and the expression level of each respective biomarker by the GA-specific human T-cell line following stimulation with the GA reference standard, falls within an acceptable range. In embodiments, the acceptable range for the comparison value is about 75% to about 125%, about 80% to about 120%, or about 90% to about 110%. In embodiments, the acceptable range is about 75% to about 120%, about 75% to about 115%, about 75% to about 110%, about 75% to about 105%, about 75% to about 100%, about 80% to about 125%, about 85% to about 125%, about 90% to about 125%, about 95% to about 125%, about 100% to about 125%, about 80% to about 118%, about 80% to about 115%, about 80% to about 112%, about 80% to about 110%, about 80% to about 108%, about 80% to about 105%, about 80% to about 102%, about 80% to about 101%, about 80% to about 100%, about 80% to about 99%, about 80% to about 98%, about 80% to about 97%, about 80% to about 95%, about 80% to about 92%, about 80% to about 90%, about 82% to about 120%, about 82% to about 118%, about 82% to about 115%, about 82% to about 112%, about 82% to about 110%, about 82% to about 108%, about 82% to about 105%, about 82% to about 102%, about 82% to about 101%, about 82% to about 100%, about 82% to about 99%, about 82% to about 98%, about 82% to about 97%, about 82% to about 95%, about 82% to about 92%, about 82% to about 90%, about 84% to about 120%, about 84% to about 118%, about 84% to about 115%, about 84% to about 112%, about 84% to about 110%, about 84% to about 108%, about 84% to about 105%, about 84% to about 102%, about 84% to about 101%, about 84% to about 100%, about 84% to about 99%, about 84% to about 98%, about 84% to about 97%, about 84% to about 95%, about 84% to about 92%, about 84% to about 90%, about 86% to about 120%, about 86% to about 118%, about 86% to about 115%, about 86% to about 112%, about 86% to about 110%, about 86% to about 108%, about 86% to about 105%, about 86% to about 102%, about 86% to about 101%, about 86% to about 100%, about 86% to about 99%, about 86% to about 98%, about 86% to about 97%, about 86% to about 95%, about 86% to about 92%, about 88% to about 120%, about 88% to about 118%, about 88% to about 115%, about 88% to about 112%, about 88% to about 110%, about 88% to about 108%, about 88% to about 105%, about 88% to about 102%, about 88% to about 101%, about 88% to about 100% about 88% to about 99%, about 88% to about 98%, about 88% to about 97%, about 88% to about 95%, about 90% to about 120%, about 90% to about 118%, about 90% to about 115%, about 90% to about 112%, about 90% to about 110%, about 90% to about 108%, about 90% to about 105%, about 90% to about 102%, about 90% to about 101%, about 90% to about 100%, about 90% to about 99%, about 90% to about 98%, about 90% to about 97%, about 90% to about 95%, about 92% to about 120%, about 92% to about 118%, about 92% to about 1.15%, about 92% to about 112%, about 92% to about 110%, about 92% to about 108%, about 92% to about 105%, about 92% to about 102%, about 92% to about 101%, about 92% to about 100%, about 92% to about 99%, about 92% to about 98%, about 95% to about 120%, about 95% to about 118%, about 95% to about 115%, about 95% to about 112%, about 95% to about 110%, about 95% to about 108%, about 95% to about 105%, about 95% to about 102%, about 95% to about 101%, about 95% to about 100%, about 97% to about 120%, about 97% to about 118%, about 97% to about 115%, about 97% to about 112%, about 97% to about 110%, about 97% to about 108%, about 97% to about 105%, about 97% to about 102%, about 98% to about 120%, about 98% to about 118%, about 98% to about 115%, about 98% to about 112%, about 98% to about 110%, about 98% to about 108%, about 98% to about 105%, about 99% to about 120%, about 99% to about 118%, about 99% to about 115%, about 99% to about 112%, about 99% to about 110%, about 99% to about 108%, about 99% to about 105%, about 100% to about 120%, about 100% to about 118%, about 100% to about 115%, about 100% to about 112%, about 100% to about 110%, about 100% to about 108%, about 100% to about 105%, about 101% to about 120%, about 101% to about 118%, about 101% to about 115%, about 101% to about 112%, about 101% to about 110%, about 101% to about 108%, about 102% to about 120%, about 102% to about 118%, about 102% to about 115%, about 102% to about 112%, about 102% to about 110%, about 102% to about 108%, about 105% to about 120%, about 105% to about 118%, about 105% to about 115%, about 105% to about 112%, about 105% to about 110%, about 110% to about 120%, about 110% to about 118%, or about 110% to about 115%.

In embodiments, more than one GA-specific human T-cell line, each having a different GA response biomarker profile, are used in an assay panel of GA-specific human T-cell lines to determine whether a test preparation of GA and a GA reference standard are immunologically identical.

A GA response biomarker measured in the characterization of a GA-specific human T-cell line is, e.g., a cytokine, cytokine receptor, chemokine, T-cell activation marker, or a nucleic acid that encodes a cytokine, cytokine receptor, chemokine, or T-cell activation marker.

In embodiments, a response biomarker measured in the characterization of a GA-specific human T-cell line is a cytokine selected from, e.g., IL-2, IL-4, IL-5, IL-6, IL-10, IL-13, or IL-17, IL-21, IL-22, IFN-γ, TNF-α (TNF), TNF-β (LT), TGF-β, and IL-1b. In embodiments, a response biomarker is an activation marker selected from, e.g., CD69, CD25, CD71, CD137, CD154, CD278, CD279, and HLA-DR. In embodiments, a response biomarker is a chemokine, selected from, e.g., IL-8 (CXCL8), RANTES (CCL5), CCL1, CXCL4, and CXCL7. In embodiments, a response biomarker is a Th1-associated cytokine, a Th2-associated cytokine, a Th17-associated cytokine, or a $Th_{FH}$-associated cytokine. In embodiments, a response biomarker is a Th1-associated cytokine and is IFN-γ. In embodiments, a response biomarker is a Th2-associated cytokine selected from: IL-4, IL-5, and IL-13. In embodiments, a response biomarker is a Th17-associated cytokine selected from: IL-17, and IL-22. In embodiments, a response biomarker is a $Th_{FH}$-associated cytokine selected from: IL-21, and TGF-β. In embodiments, a response biomarker is a key regulatory associated cytokine selected from IL-10 and TGF-β.

In embodiments, a response biomarker measured in the characterization of a GA-specific human T-cell line is a nucleic acid encoding a cytokine selected from, e.g., IL-2, IL-4, IL-5, IL-6, IL-10, IL-13, or IL-17, IL-21, IL-22, IFN-γ, TNF-α (TNF), TNF-β (LT), TGF-β, and IL-1b. In embodiments, a response biomarker is a nucleic acid encoding an activation marker selected from, e.g., CD69, CD25, CD71, CD137, CD154, CD278, CD279, and HLA-DR. In embodiments, a response biomarker is a nucleic acid encoding chemokine, selected from, e.g., IL-8 (CXCL8), RANTES (CCL5), CCL1, CXCL4, and CXCL7. In embodiments, a response biomarker is a nucleic acid encoding Th1-associated cytokine, a nucleic acid encoding Th2-associated cytokine, a nucleic acid encoding Th17-associated cytokine, or a nucleic acid encoding $Th_{FH}$-associated cytokine. In embodiments, a response biomarker is a nucleic acid encoding Th1-associated cytokine and is IFN-γ. In embodiments, a response biomarker is a nucleic acid encoding Th2-associated cytokine selected from: IL-4, IL-5, and IL-13. In embodiments, a response biomarker is a nucleic acid encoding Th17-associated cytokine selected from: IL-17, and IL-22. In embodiments, a response biomarker is a nucleic acid encoding a $Th_{FH}$-associated cytokine selected from: IL-21, and TGF-β. In embodiments, a response biomarker is a nucleic acid encoding a key regulatory associated cytokine selected from IL-10 and TGF-β.

Characterization of GA-Specific Human T-Cell Lines Based on MHC Restriction

In embodiments of the present invention, a GA-specific human T-cell line is characterized by testing its MHC restriction. T-cell lines that react to the same antigen through different MHC restriction elements may recognize different epitopes. MHC restriction therefore offers another parameter for immunologically distinguishing the epitope specificity of the GA-specific human T-cell lines of the invention, and thereby for selecting an appropriate panel of GA-specific human T-cell lines for use in an assay to determine whether GA preparations are immunologically identical.

MHC restriction can be tested using any method known in the art e.g., as described by Oftung, et al. (Oftung F., et al., 1994, "Mapping of multiple HLA class II restricted T-cell epitopes of the mycobacterial 70-kilodalton heat shock protein," Infect. Immun. 62:5411-5418), or as set forth herein in the Examples.

Characterization of GA-Specific Human T-Cell Lines Based on Analysis of Surface Marker Expression In embodiments of the present invention, a GA-specific human T-cell line is characterized by analyzing its expression of cell surface markers. In embodiments, a GA-specific human T-cell line used in the methods of the invention is $CD4^+$. CD4 expression can be analyzed, and a $CD4^+$ T-cell line identified, using methods known in the art. In embodiments, CD4 is analyzed by flow cytometry using a fluorochrome-labeled monoclonal antibody having specificity for CD4. In embodiments, a GA-specific human T-cell line is determined to be $CD4^+$ when 98% or more, of the cells in a sample tested are $CD4^+$. In embodiments, a GA-specific human T-cell line is determined to be $CD4^+$ when 99% or more of the cells in a sample tested are $CD8^+$. In embodiments, a GA-specific human T-cell line determined to contain 97% or more, more than 97%, 97.5% or more, more than 97.5%, 98% or more, more than 98%, 98.5% or more, more than 98.5%, 99% or more, or more than 99% $CD4^+$ cells is included in an assay panel of the invention.

In embodiments, the GA-specific human T-cell line is $CD8^-$. As with CD4, the presence of the CD8 marker can be analyzed using methods known in the art, e.g., by flow cytometry using a fluorochrome-labeled monoclonal antibody having reactivity to CD8. In embodiments, a GA-specific human T-cell line used in the methods of the invention is $CD8^-$. In embodiments, CD8 is analyzed by flow cytometry using a fluorochrome-labeled monoclonal antibody having specificity for CD8. In embodiments, a control using nonspecific antibodies, e.g., fluorochrome-labeled mouse isotype matched control monoclonal antibody is included. In embodiments, a GA-specific human T-cell line used in the methods of the invention is $CD4^+$ and $CD8^-$. In embodiments, a GA-specific human T-cell line is determined to be $CD8^-$ when 2% or fewer of the cells in a sample tested are $CD8^+$. In embodiments, a GA-specific human T-cell line is determined to be $CD8^-$ when 1% or fewer of the cells in a sample tested are $CD8^+$. In embodiments, a GA-specific human T-cell line determined to contain 3% or less, less than 3%, 2.5% or less, less than 2.5%, 2% or less, less than 2%, 1.5% or less, less than 1.5%, 1% or less, or less than 1% $CD8^+$ cells is included in an assay panel of the invention.

In embodiments, a control using nonspecific antibodies, e.g., fluorochrome-labeled mouse isotype matched control monoclonal antibody IgG1 antibodies, is included as described in the Examples herein.

GA-Elicited Responses

As described, in the methods of the present invention GA elicited responses are measured in the context of identifying and characterizing GA-specific human T-cell lines. Reactivity and specificity screenings of human T-cell lines are carried out by measuring at least one GA-elicited response of a human T-cell line to stimulation with GA and comparison with a measurement of the same response of an appropriate control, e.g., in the absence of antigen. Similarly, a GA-specific human T-cell line of the invention can be further characterized as reactive to a non-canonical GA peptide by measurement of a response elicited by a GA-specific human T-cell line after stimulation with the non-canonical GA peptide. "GA-elicited response" as used herein refers to a response elicited by stimulation of a GA-specific human T-cell line after stimulation with GA or a non-canonical GA peptide.

A GA-elicited response measured in the context of the present invention is a response observed following treatment of a T-cell line with a stimulating peptide (in the presence of appropriate APC) that is not observed in a suitable control, e.g., the same T-cell line treated with APC and no peptide, or the same T-cell line treated with APC and a non-relevant control antigen (a negative control). Evaluation of a GA-elicited response of a GA-specific T-cell line following stimulation with GA preparations can reveal the presence of minute differences between epitopes present in the GA preparations tested. In certain methods of the invention, a GA-elicited response of an identified GA-specific human T-cell line to a test preparation of GA and a GA reference standard is measured, and the measured GA-elicited responses are compared. Based on the comparison, it is determined whether the preparations of GA are immunologically identical. In related methods, comparing a GA-elicited response of an identified GA-specific human T-cell line allows determination of the potency of a first GA preparation, e.g., a GA test preparation, relative to that of a second GA preparation, e.g., a GA reference standard. In other methods described herein, a GA-elicited response is measured in the characterization of a GA-specific human T-cell line.

A GA-elicited response in the context of the present invention can be a measure of, e.g., T-cell proliferation, production of a response biomarker, or expression of a nucleic acid encoding a response biomarker. In embodiments, a GA-elicited response is measured at multiple timepoints following restimulation. In embodiments, a GA-elicited response is measured after restimulation of a T-cell line with a series of different concentrations of a GA test preparation and a GA reference standard. In embodiments, this data is used to plot a dose-response curve, and the dose-response curve obtained for each GA preparation compared. In embodiments, compared GA preparations are determined to be immunologically identical when the slopes in the linear range of their respective dose-response curves are statistically similar or identical.

T-Cell Proliferation

Proliferation of T-cell lines in response to antigen can be evaluated using any suitable method known in the art. For example, proliferation can be evaluated by measuring uptake of tritiated thymidine, BrdU uptake (using, e.g., Millipore cat. #2752), by CFSE assay (using, e.g., CellTrace™ CFSE Cell Proliferation Kit, Life Technologies, and as described by Quah, et al., 2007, "Monitoring lymphocyte proliferation in vitro and in vivo with the intracellular fluorescent dye carboxyfluorescein diacetate succinimidyl ester," Nature Protocols 2(9): 2049-2056), or by ATP quantification to determine viable cell number (using, e.g., CellTiter Glo® Luminescent Cell Viability Assay, Promega, catalog #G7571). Methods for evaluating antigen-specific T-cells are described in the literature, e.g., in "Techniques for Immune Function Analysis," Application Handbook 1st Edition, 2006, Becton, Dickinson and Company.

A GA-specific T-cell line can be identified based on an increase in proliferation of the T-cell line after stimulation with GA and appropriate APC, when compared to the level after stimulation with no antigen or a control antigen and appropriate APC. In embodiments, a GA-specific T-cell line is identified based on an increase in proliferation represented by an increase in cell number, DNA synthesis (e.g., in a BrdU assay), or increased dilution of an intracellular dye (e.g., in a CFSE assay), wherein the increase is about 2-fold to about 10 fold relative to a control. In embodiments, the increase is at least about 2-fold, at least about 3-fold, at least about 4-fold, at least about 5-fold, at least about 6-fold, at least about 7-fold, at least about 8-fold, at least about 9-fold, at least about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 10-fold, about 4-fold to about 9-fold, about 4-fold to about 8-fold, about 4-fold to about 7-fold, about 4-fold to about 6-fold, about 4-fold to about 5-fold, about 5-fold to about 10-fold, about 5-fold to about 9-fold, about 5-fold to about 8-fold, about 5-fold to about 7-fold, about 5-fold to about 6-fold, about 6-fold to about 10-fold, about 6-fold to about 9-fold, about 6-fold to about 8-fold, about 6-fold to about 7-fold, about 7-fold to about 10-fold, about 7-fold to about 9-fold, about 7-fold to about 8-fold, about 8-fold to about 10-fold, about 8-fold to about 9-fold, or about 9-fold to about 10-fold.

In embodiments, a test preparation of GA and a GA reference standard are demonstrated to be immunologically identical when the comparison of the measurements (expressed as, e.g., a ratio, fraction, or percentage) of proliferation of a sample of GA-specific T-cells stimulated with the test preparation of GA and a sample of GA-specific T-cells stimulated with a GA reference standard falls within an acceptable range.

Comparison of GA-Elicited Responses of GA-Specific Human T-Cell Lines to Test and Reference Standard GA Preparations In embodiments of the present invention, measurement of a GA-elicited response of a GA-specific human T-cell line to a test preparation of GA, and measurement of the same GA-elicited response of the GA-specific human T-cell line to a GA reference standard are compared. Based on the comparison, the test preparation of GA and the GA reference standard are determined to be immunologically identical. In embodiments, the test preparation of GA and the GA reference standard are determined to be immunologically identical when the comparison value falls within an acceptable range. In embodiments, the comparison value is expressed as a percentage, where the percentage is 100 when the measurements are equal. In these embodiments, the acceptable range for the comparison value is about 75% to about 125%, about 80% to about 120%, or about 90% to about 110%. In embodiments, the acceptable range is about 75% to about 120%, about 75% to about 115%, about 75% to about 110%, about 75% to about 105%, about 75% to about 100%, about 80% to about 125%, about 85% to about 125%, about 90% to about 125%, about 95% to about 125%, about 100% to about 125%, about 80% to about 118%, about 80% to about 115%, about 80% to about 112%, about 80% to about 110%, about 80% to about 108%, about 80% to about 105%, about 80% to about 102%, about 80% to about 101%, about 80% to about 100%, about 80% to about 99%, about 80% to about 98%, about 80% to about 97%, about 80% to about 95%, about 80% to about 92%, about 80% to about 90%, about 82% to about 120%, about 82% to about 118%, about 82% to about 115%, about 82% to about 112%, about 82% to about 110%, about 82% to about 108%, about 82% to about 105%, about 82% to about 102%, about 82% to about 101%, about 82% to about 100%, about 82% to about 99%, about 82% to about 98%, about 82% to about 97%, about 82% to about 95%, about 82% to about 92%, about 82% to about 90%, about 84% to about 120%, about 84% to about 118%, about 84% to about 115%, about 84% to about 112%, about 84% to about 110%, about 84% to about 108%, about 84% to about 105%, about 84% to about 102%, about 84% to about 101%, about 84% to about 100%, about 84% to about 99%, about 84% to about 98%, about 84% to about 97%, about 84% to about 95%, about 84% to about 92%, about 84% to about 90%, about 86% to about 120%, about 86% to about 118%, about 86% to about 115%, about 86% to about 112%, about 86% to about 110%, about 86% to about 108%, about 86% to about 105%, about 86% to about 102%, about 86% to about 101%, about 86% to about 100%, about 86% to about 99%, about 86% to about 98%, about 86% to about 97%, about 86% to about 95%, about 86% to about 92%, about 88% to about 120%, about 88% to about 118%, about 88% to about 115%, about 88% to about 112%, about 88% to about 110%, about 88% to about 108%, about 88% to about 105%, about 88% to about 102%, about 88% to about 101%, about 88% to about 100%, about 88% to about 99%, about 88% to about 98%, about 88% to about 97%, about 88% to about 95%, about 90% to about 120%, about 90% to about 118%, about 90% to about 115%, about 90% to about 112%, about 90% to about 110%, about 90% to about 108%, about 90% to about 105%, about 90% to about 102%, about 90% to about 101%, about 90% to about 100%, about 90% to about 99%, about 90% to about 98%, about 90% to about 97%, about 90% to about 95%, about 92% to about 120%, about 92% to about 118%, about 92% to about 115%, about 92% to about 112%, about 92% to about 110%, about 92% to about 108%, about 92% to about 105%, about 92% to about 102%, about 92% to about 101%, about 92% to about 100%, about 92% to about 99%, about 92% to about 98%, about 95% to about 120%, about 95% to about 118%, about 95% to about 115%, about 95% to about 112%, about 95% to about 110%, about 95% to about 108%, about 95% to about 105%, about 95% to about 102%, about 95% to about 101%, about 95% to about 100%, about 97% to about 120%, about 97% to about 118%, about 97% to about 115%, about 97% to about 112%, about 97% to about 110%, about 97% to about 108%, about 97% to about 105%, about 97% to about 102%, about 98% to about 120%, about 98% to about 118%, about 98% to about 115%, about 98% to about 112%, about 98% to about 110%, about 98% to about 108%, about 98% to about 105%, about 99% to about 120%, about 99% to about 118%, about 99% to about 115%, about 99% to about 112%, about 99% to about 110%, about 99% to about 108%, about 99% to about 105%, about 100% to about 120%, about 100% to about 118%, about 100% to about 115%, about 100% to about 112%, about 100% to about 110%, about 100% to about 108%, about 100% to about 105%, about 101% to about 120%, about 101% to about 118%, about 101% to about 115%, about 101% to about 112%, about 101% to about 110%, about 101% to about 108%, about 102% to about 120%, about 102% to about 118%, about 102% to about 115%, about 102% to about 112%, about 102% to about 110%, about 102% to about 108%, about 105% to about 120%, about 105% to about 118%, about 105% to about 115%, about 105% to about 112%, about 105% to about 110%, about 110% to about 120%, about 110% to about 118%, or about 110% to about 115%.

In related methods, the comparison value is used as a measure of the potency of a first GA preparation, e.g., a GA test preparation, relative to that of a second GA preparation, e.g., a GA reference standard.

GA Response Biomarker Production

In embodiments, the GA-elicited response measured in the methods of the invention is the production of a response biomarker. In embodiments, the response biomarker is a cytokine, cytokine receptor, chemokine, T-cell activation marker, or a nucleic acid that encodes a cytokine, cytokine receptor, chemokine, or T-cell activation marker (which can be a cytokine receptor). In embodiments, a GA-response biomarker is a cytokine, cytokine receptor, chemokine, T-cell activation marker, or a nucleic acid that encodes a cytokine, cytokine receptor, chemokine, or T-cell activation marker. In embodiments, a response biomarker is a cytokine selected from, e.g., IL-2, IL-4, IL-5, IL-6, IL-10, IL-13, or IL-17, IL-21, IL-22, IFN-γ, TNF-α (TNF), TNF-β (LT), TGF-β, and IL-1b. In embodiments, a response biomarker is an activation marker selected from, e.g., CD69, CD25, CD71, CD137, CD154, CD278, CD279, and HLA-DR. In embodiments, a response biomarker is a chemokine, selected from, e.g., IL-8 (CXCL8), RANTES (CCL5), CCL1, CXCL4, and CXCL7. In embodiments, a response biomarker is a Th1-associated cytokine, a Th2-associated cytokine, a Th17-associated cytokine, or a $Th_{FH}$-associated cytokine. In embodiments, a response biomarker is a Th1-associated cytokine and is IFN-γ. In embodiments, a response biomarker is a Th2-associated cytokine selected from: IL-4, IL-5, and IL-13. In embodiments, a response biomarker is a Th17-associated cytokine selected from: IL-17, and IL-22. In embodiments, a response biomarker is a $Th_{FH}$ associated cytokine selected from: IL-21, and TGF-β. In embodiments, a response biomarker is a key regulatory associated cytokine selected from IL-10 and TGF-β.

In embodiments, a response biomarker is a nucleic acid encoding a cytokine selected from, e.g., IL-2, IL-4, IL-5, IL-6, IL-10, IL-13, or IL-17, IL-21, IL-22, IFN-γ, TNF-α, (TNF), TNF-β (LT), TGF-β, and IL-1b. In embodiments, a response biomarker is a nucleic acid encoding an activation marker selected from, e.g., CD69, CD25, CD71, CD137, CD154, CD278, CD279, and HLA-DR. In embodiments, a response biomarker is a nucleic acid encoding chemokine, selected from, e.g., IL-8 (CXCL8), RANTES (CCL5), CCL1, CXCL4, and CXCL7. In embodiments, a response biomarker is a nucleic acid encoding Th1-associated cytokine, a nucleic acid encoding Th2-associated cytokine, a nucleic acid encoding Th17-associated cytokine, or a nucleic acid encoding $Th_{FH}$-associated cytokine. In embodiments, a response biomarker is a nucleic acid encoding Th1-associated cytokine and is IFN-γ. In embodiments, a response biomarker is a nucleic acid encoding Th2-associated cytokine selected from: IL-4, IL-5, and IL-13. In embodiments, a response biomarker is a nucleic acid encoding Th17-associated cytokine selected from: IL-17, and IL-22. In embodiments, a response biomarker is a nucleic acid encoding $Th_{FH}$-associated cytokine selected from: IL-21, and TGF-β. In embodiments, a response biomarker is a nucleic acid encoding a key regulatory associated cytokine selected from IL-10 and TGF-β.

The production of a response biomarker protein can be measured in according to any suitable method known in the art and published in the literature, e.g., by ELISA, Western Blot assay, flow cytometric assay, or any appropriate multiplex assay. Commercial assays are available for measuring production of cytokines, chemokines, cytokine receptors, and activation markers as Called for in the methods of the present invention. For example, multiplex assays for detection of human cytokines and chemokines can be created using the BD™ Cytometric Bead Array Flex Set system (BD Biosciences, San Jose, Calif.).

A GA-specific human T-cell line can be identified or characterized by comparing the production of a response biomarker after restimulation with GA in the presence of appropriate APC, to the amount of response biomarker produced in an appropriate negative control, e.g., after restimulation with no antigen or a non-relevant control antigen (in the presence of appropriate APC). In embodiments, a GA-specific human T-cell line is identified based on an increase in response biomarker production relative to the control. In embodiments, the increase observed in production of the response biomarker relative to a negative control is about 1.5-fold to about 1000-fold. response of the test culture relative to the control of about 1.5-fold (i.e., the response is about 50% higher) to about 1000-fold, about 1.5 to about 2-fold, about 1.5 to about 3-fold, about 1.5 to about 4-fold, about 1.5 to about 5-fold, about 1.5 to about 6-fold, about 1.5 to about 7-fold, about 1.5 to about 8-fold, about 1.5 to about 9-fold, about 2 to about 3-fold, about 2 to about 4-fold, about 2 to about 5-fold, about 2 to about 6-fold, about 2 to about 7-fold, about 2 to about 8-fold, about 2 to about 9-fold, about 2 to about 10-fold, about 3 to about 4-fold, about 3 to about 5-fold, about 3 to about 6-fold, about 3 to about 7-fold, about 3 to about 8-fold, about 3 to about 9-fold, about 3 to about 10-fold, about 4 to about 5-fold, about 4 to about 6-fold, about 4 to about 7-fold, about 4 to about 8-fold, about 4 to about 9-fold, about 4 to about 10-fold, about 5 to about 6-fold, about 5 to about 7-fold, about 5 to about 8-fold, about 5 to about 9-fold, about 5 to about 10-fold, about 6 to about 7-fold, about 6 to about 8-fold, about 6 to about 9-fold, about 6 to about 10-fold, about 7 to about 8-fold, about 7 to about 9-fold, about 7 to about 10-fold, about 8 to about 9-fold, about 8 to about 10-fold, about 1.5-fold to about 80-fold, about 1.5-fold to about 70-fold, about 1.5-fold to about 60-fold, about 1.5-fold to about 50-fold, about 1.5-fold to about 40-fold, about 1.5-fold to about 30-fold, about 1.5-fold to about 20-fold, about 2-fold to about 80-fold, about 1.5-fold to about 70-fold, about 1.5-fold to about 60-fold, about 1.5-fold to about 50-fold, about 1.5-fold to about 40-fold, about 1.5-fold to about 30-fold, about 1.5-fold to about 20-fold, about 2-fold to about 80-fold, about 2-fold to about 70-fold, about 2-fold to about 60-fold, about 2-fold to about 50-fold, about 2-fold to about 40-fold, about 2-fold to about 30-fold, about 2-fold to about 20-fold, about 3-fold to about 80-fold, about 3-fold to about 70-fold, about 3-fold to about 60-fold, about 3-fold to about 50-fold, about 3-fold to about 40-fold, about 3-fold to about 30-fold, about 3-fold to about 20-fold, about 5-fold to about 80-fold, about 5-fold to about 70-fold, about 5-fold to about 60-fold, about 5-fold to about 50-fold, about 5-fold to about 40-fold, about 5-fold to about 30-fold, about 3-fold to about 20-fold, about 10-fold to about 80-fold, about 10-fold to about 60-fold, about 10-fold to about 40-fold, or about 10-fold to about 20-fold, at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, or at least about 10-fold.

A nucleic acid encoding a response biomarker can be quantitatively measured using any of a number of commercially available assay kits and systems, or according to any method described in the art. In embodiments, a response biomarker mRNA is measured by Real-Time PCR. The use of any appropriate quantitative method for measuring mRNA expression levels known in the art is contemplated. For example, mRNA can be copied by reverse transcriptase, and amplified using a appropriate PCR method, including RT-PCR, and real time reverse-transcription PCR (qRT-PCR). PCR methods for quantitating gene expression are described by, e.g., VanGuilder, et al., 2008, "Twenty-five years of quantitative PCR for gene expression analysis," Biotechniques 44: 619-626, and Bustin, et al., 2005, "Quantitative real-time RT-PCR—a perspective," Journal of Molecular Endocrinology, 34:597-601, each incorporated herein by reference in its entirety. Quantitative PCR of mouse cytokine mRNAs is described by, e.g., Overbergh, et al., 1999, "Quantification of murine cytokine mRNAs using real time quantitative reverse transcriptase PCR," Cytokine 11(4): 305-312, incorporated herein by reference, describing probes and primers for quantifying IL-1, IL-2, IL-4, IL-5, IL-6, IL-7, IL-10, IL-12, p40, IL-13, IL-15, IFN-γ, TNF-α, TGF-β and iNOS. Methods for measuring response biomarker mRNAs following ex vivo GA stimulation of mouse lymph node cells, are described in, e.g., U.S. Pat. App. Pub. No. 2014/0272987, "Glatiramer Acetate Response Biomarker mRNA Potency Assay," incorporated by reference in its entirety herein.

A GA-specific human T-cell line can be identified or characterized by comparing the production of a nucleic acid encoding a response biomarker after restimulation with GA in the presence of appropriate APC, to the amount of the nucleic acid encoding the response biomarker produced in an appropriate negative control, e.g., after restimulation with no antigen or a non-relevant control antigen (in the presence of appropriate APC). In embodiments, a GA-specific human T-cell line is identified based on an increase in production of a nucleic acid encoding a response biomarker relative to the control. In embodiments, the increase observed in production of the nucleic acid encoding the response biomarker relative to a negative control is about 1.5-fold to about 1000-fold. In embodiments, the increase is about 1.5-fold to about 100-fold, about 1.5-fold to about 50-fold, about 1.5-fold to about 45-fold, about 1.5-fold to about 40-fold, about 1.5-fold to about 35-fold, about 1.5-fold to about 30-fold, about 1.5-fold to about 25-fold, about 1.5-fold to about 22-fold, about 1.5-fold to about 20-fold, about 1.5-fold to about 15-fold, about 1.5-fold to about 12-fold, about 1.5-fold to about 10-fold, about 1.5-fold to about 9-fold, about 1.5-fold to about 8-fold, about 1.5-fold to about 7-fold, about 1.5-fold to about 6-fold, about 1.5-fold to about 5-fold, about 1.5-fold to about 4-fold, about 1.5-fold to about 3-fold, about 2-fold to about 100-fold, about 2-fold to about 50-fold, about 2-fold to about 45-fold, about 2-fold to about 40-fold, about 2-fold to about 35-fold, about 2-fold to about 30-fold, about 2-fold to about 25-fold, about 2-fold to about 22-fold, about 2-fold to about 20-fold, about 2-fold to about 15-fold, about 2-fold to about 12-fold, about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 3-fold to about 100-fold, about 3-fold to about 50-fold, about 3-fold to about 45-fold, about 3-fold to about 40-fold, about 3-fold to about 35-fold, about 3-fold to about 30-fold, about 3-fold to about 25-fold, about 3-fold to about 22-fold, about 3-fold to about 20-fold, about 3-fold to about 15-fold, about 3-fold to about 12-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 4-fold to about 100-fold, about 4-fold to about 50-fold, about 4-fold to about 45-fold, about 4-fold to about 40-fold, about 4-fold to about 35-fold, about 4-fold to about 30-fold, about 4-fold to about 25-fold, about 4-fold to about 22-fold, about 4-fold to about 20-fold, about 4-fold to about 15-fold, about 4-fold to about 12-fold, about 4-fold to about 10-fold, about 4-fold to about 9-fold, about 4-fold to about 8-fold, about 4-fold to about 7-fold, about 4-fold to about 6-fold, about 5-fold to about 100-fold, about 5-fold to about 50-fold, about 5-fold to about 45-fold, about 5-fold to about 40-fold, about 5-fold to about 35-fold, about 5-fold to about 30-fold, about 5-fold to about 25-fold, about 5-fold to about 22-fold, about 5-fold to about 20-fold, about 5-fold to about 15-fold, about 5-fold to about 12-fold, about 5-fold to about 10-fold, about 5-fold to about 9-fold, about 5-fold to about 8-fold, about 5-fold to about 7-fold, about 7-fold to about 100-fold, about 7-fold to about 50-fold, about 7-fold to about 45-fold, about 7-fold to about 40-fold, about 7-fold to about 35-fold, about 7-fold to about 30-fold, about 7-fold to about 25-fold, about 7-fold to about 22-fold, about 7-fold to about 20-fold, about 7-fold to about 15-fold, about 7-fold to about 12-fold, about 7-fold to about 10-fold, about 7-fold to about 9-fold, about 10-fold to about 100-fold, about 10-fold to about 50-fold, about 10-fold to about 45-fold, about 10-fold to about 40-fold, about 10-fold to about 35-fold, about 10-fold to about 30-fold, about 10-fold to about 25-fold, about 10-fold to about 22-fold, about 10-fold to about 20-fold, about 10-fold to about 15-fold, about 15-fold to about 100-fold, about 15-fold to about 50-fold, about 15-fold to about 45-fold, about 15-fold to about 40-fold, about 15-fold to about 35-fold, about 15-fold to about 30-fold, about 15-fold to about 25-fold, about 15-fold to about 22-fold, about 15-fold to about 20-fold, about 20-fold to about 100-fold, about 20-fold to about 50-fold, about 20-fold to about 45-fold, about 20-fold to about 40-fold, about 20-fold to about 35-fold, about 20-fold to about 30-fold, about 20-fold to about 25-fold, about 25-fold to about 100-fold, about 25-fold to about 50-fold, about 25-fold to about 45-fold, about 25-fold to about 40-fold, about 25-fold to about 35-fold, about 25-fold to about 30-fold, about 30-fold to about 100-fold, about 30-fold to about 50-fold, about 40-fold to about 100-fold, about 50-fold to about 100-fold, about 60-fold to about 100-fold, about 70-fold to about 100-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, at least about 100-fold, at least about 250-fold, at least about 500-fold, or at least about 1000-fold.

Preparation of a Drug Product of GA

The invention relates to a process for preparing a drug product or pharmaceutical composition containing GA. In embodiments of this process, glatiramer acetate is prepared according to standard methods known in the art and described in the literature, e.g., in U.S. Pat. Nos. 3,849,550 and 5,800,808. In embodiments, a drug product or pharmaceutical composition containing GA is prepared by: reacting protected glatiramer acetate with hydrobromic acid to form trifluoroacetyl GA, treating said trifluoroacetyl copolymer-1 with aqueous piperidine solution to form the test preparation of GA, and purifying the test preparation of GA. The test preparation of GA and the GA reference standard are determined to be immunologically identical or not immunologically identical, using the methods and/or assay panels as described herein. For example, the test preparation of GA and the GA reference standard are determined to be immunologically identical or not immunologically identical, by (a) incubating cells of at least one GA-specific human T-cell line with appropriate antigen presenting cells (APC), (b) stimulating at least one sample of the GA-specific human T-cells and appropriate APC incubated in step (a) with an amount of the test preparation of GA, and separately stimulating at least one sample of the GA-specific human T-cells and appropriate APC incubated in step (a) with the same amount of the GA reference standard, (c) measuring at least one GA-elicited response of the at least one sample of cells stimulated in step (b) with the test preparation of GA, and measuring the same at least one GA-elicited response of the at least one sample of cells stimulated in step (b) with the GA reference standard, and (d) comparing the measurements obtained in step (c), wherein the test preparation of GA and the GA reference standard are determined to be immunologically identical when the comparison of the measurements of step (d) falls within an acceptable range, and wherein the test preparation of GA is admixed into the drug product or pharmaceutical composition if it is determined to be immunologically identical to the GA reference standard. In embodiments, the drug product or pharmaceutical composition additionally contains excipients and/or diluents, for example, as described in the package labeling for Copaxone®.

In certain embodiments, the methods of the invention are used to determine whether a GA test preparation and a GA reference standard are immunologically identical, or have an acceptable relative potency, prior to potential addition of a GA preparation to a drug product or pharmaceutical composition after addition of the GA preparation, or at any other time as desired. In embodiments, a test preparation of GA is added to other components, e.g., a diluent, an excipient, or another active ingredient, of a GA drug product or pharmaceutical composition, only if it is determined to have immunologic identity or comparable potency to the GA reference standard. Potency assays including methods for evaluating data comparing GA preparations are described in the literature, e.g., in U.S. Pat. No. 7,429,374, "Process for the measurement of the potency of glatiramer acetate," incorporated by reference herein in its entirety.

Identification of New Biomarkers

Additional response biomarkers can be identified by comparing the amount of a potential response biomarker, present in a GA-specific T-cell culture stimulated with GA in the presence of appropriate APC, to the amount of the response biomarker present in a control culture incubated with appropriate APC but not antigen stimulated, or a control culture stimulated with a control antigen.

A suitable GA response biomarker for use in the methods of the invention can be identified by comparing the amount of a potential GA response biomarker protein or a nucleic acid encoding the protein, present in a GA-specific human T-cell line stimulated with GA in the presence of appropriate APC, to the amount of the same potential GA response biomarker protein or a nucleic acid encoding the protein in an appropriate negative control. A suitable GA response biomarker is significantly modulated (increased or decreased) in a GA-specific human T-cell line stimulated with GA in the presence of appropriate APC relative to the negative control. In embodiments, a GA response biomarker for a GA-specific human T-cell line is identified based on an increase in its production after GA restimulation of the GA-specific human T-cell line of about 2-fold to about 1000-fold relative to a negative control.

Assay Panels of GA-Specific Human T-Cell Lines

As described, the invention contemplates the use of at least one GA-specific human T-cell line in a method for determining the immunological identity of GA preparations, e.g., a GA test preparation and a GA reference standard. Because GA contains a number of epitopes, generating and identifying GA-specific human T-cell lines by stimulating them with GA and testing their responsiveness to GA, it was not necessarily known that GA-specific human T-cell lines having the ability to recognize different epitopes could be obtained. Based on the discovery that GA-specific human T-cell lines with distinguishable epitope binding specificities can be obtained, the present invention provides assays using multiple GA-specific human T-cell lines to determine with greater accuracy the immunological identity of GA preparations.

In embodiments of the invention, an assay panel of GA-specific human T-cell lines is used to analyze GA preparations, e.g., to test for immunological identity and/or determine their degree of similarity or dissimilarity. In embodiments, the assay panel comprises multiple GA-specific human T-cell lines. In embodiments, the assay panel comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 different GA-specific human T-cell lines. In embodiments, the assay panel comprises at least 2, at least 3, at least 4, at least 5, at least 6, at least 7, at least 8, at least 9, at least 10, at least 15, at least 20, at least 25, at least 30, at least 40, at least 50, at least 60, at least 70, at least 80, at least 90, or at least 100 different GA-specific human T-cell lines. In embodiments, the assay panel comprises 2 to 100, 2 to 50, 2 to 25, 2 to 10, 5 to 100, 5 to 50, 5 to 25, 5 to 10, 10 to 100, 10 to 50, 10 to 25, or 50 to 100, different GA-specific human T-cell lines.

In embodiments of the invention, the assay panel comprises clonal GA-specific human T-cell lines, oligoclonal GA-specific human T-cell lines, or a combination of both. In embodiments, the assay panel comprises a combination of clonal and oligoclonal GA-specific human T-cell lines, wherein the majority (>50%) are clonal GA-specific human T-cell lines. In embodiments, the assay panel comprises a combination of clonal and oligoclonal GA-specific human T-cell lines, wherein the panel is comprised of about 20% or greater, about 25% or greater, about 30% or greater, about 35% or greater, about 40% or greater, about 45% or greater, about 50% or greater, about 55% or greater, about 60% or greater, about 65% or greater, about 70% or greater, about 75% or greater, about 80% or greater, about 85% or greater, about 90% or greater, about 95% or greater, or about 100%, clonal GA-specific human T-cell lines. In embodiments, the assay panel comprises a combination of clonal and oligoclonal GA-specific human T-cell lines, wherein the panel is comprised of about 20% to about 100%, about 25% to about 100%, about 30% to about 100%, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, or about 95% to about 100%, clonal GA-specific human T-cell lines. In embodiments, the assay panel comprises a combination of clonal and oligoclonal GA-specific human T-cell lines, wherein the panel is comprised of ⅙ or greater, ⅓ or greater, ⅔ or greater, ¾ or greater, or ⅚ or greater, clonal GA-specific human T-cell lines.

In embodiments, all GA-specific human T-cell lines in an assay panel are clonal. A T-cell line can be cloned from a population of T cells using any method known to those of skill in the art and described in the literature, for example, limiting dilution cloning. In limiting dilution cloning, a candidate cell line is cultured in multiple wells at limiting dilution (e.g., 0.3 cells/well, or not more than one cell/well) with antigen, and APC. The resulting cells are restimulated as described herein. Methods for T-cell cloning are widely known and described in the literature, e.g., by Mariotti, S., and Nisini, R., 2009, "Generation of Human T Cell Clones," in T Cell Protocols, Gennaro de Libero (ed.), Humana Press, Second edition, vol. 514, pages 65-93, incorporated herein by reference in its entirety. In embodiments, the limiting dilution cloning process is repeated one or more times to obtain a clonal GA-specific human T-cell line. A T-cell line also can be cloned using flow cytometry methods, e.g., as described by Lee, S-T, et al., 2008, "A Novel Strategy for Rapid and Efficient Isolation of Human Tumor-Specific CD4+ and CD8+ T-Cell Clones," J. Imm. Meth. 331(1-2): 13-26, incorporated herein by reference in its entirety. In embodiments, clonality of a T-cell line is confirmed by T-cell receptor sequencing according to methods known to those of skill in the art and published in the literature.

In embodiments, an assay panel comprises GA-specific human T-cell lines generated by culturing human T-cells in the presence of a first preparation of GA, and at least one GA-specific human T-cell line generated by culturing human T-cells in the presence of a second preparation of GA. In embodiments, the first preparation of GA is COP and the second preparation of GA is GMA. In embodiments, the first and second preparations of GA are different COP preparations or different GMA preparations.

In embodiments, an assay panel of GA-specific human T-cell lines comprises at least one GA-specific human T-cell line that produces a similar or identical GA-elicited response following stimulation with a first preparation of GA as it does following stimulation with a second preparation of GA. In embodiments, the first preparation of GA is COP and the second preparation of GA is GMA. In embodiments, the first and second preparations of GA are different COP preparations or different GMA preparations.

In embodiments, the panel comprises at least one GA-specific human T-cell line that responds to stimulation with a first non-canonical GA peptide. In embodiments, the panel comprises at least one GA-specific human T-cell line that responds to stimulation with a first non-canonical GA peptide, and at least one GA-specific human T-cell line that responds to stimulation with a second non-canonical GA peptide. In embodiments, the panel comprises at least two GA-specific human T-cell lines that each produce a different response biomarker profile in response to stimulation with GA. In embodiments, the assay panel comprises at least two GA-specific human T-cell lines that each has a different MHC restriction.

In embodiments, the assay panel of GA-specific human T-cell lines comprises at least two GA-specific human T-cell lines, wherein at least one of the at least two GA-specific cell lines is:

a) a GA-specific human T-cell line that does not respond to stimulation with a non-canonical GA peptide;

b) a GA-specific human T-cell line that has a known biomarker response profile; and c) a GA-specific human T-cell line that has a known MHC restriction.

In embodiments, an assay panel of the invention comprises at least one GA-specific human T-cell line generated by culturing human T-cells in the presence of a first preparation of GA, and at least one GA-specific human T-cell line generated by culturing human T-cells in the presence of a second preparation of GA. In embodiments, this assay panel further comprises at least one GA-specific human T-cell line that does not react to a non-canonical GA peptide. In embodiments, the at least one GA-specific human T-cell line generated by culturing human T-cells in the presence of a first preparation of GA is generated by culturing human T-cells in the presence of GMA.

In embodiments, the GA-specific human T-cell lines in an assay panel are selected from:

1) a GA-specific human T-cell line that was generated by culturing with a first preparation of GA 2) a GA-specific human T-cell line that was generated by culturing with a second preparation of GA 3) a GA-specific human T-cell line that does not respond to stimulation with a first non-canonical GA peptide;

4) a GA-specific human T-cell line that responds to stimulation with the first non-canonical GA peptide;

5) a GA-specific human T-cell line that does not respond to stimulation with a second non-canonical GA peptide;

6) a GA-specific human T-cell line that responds to stimulation with a second non-canonical GA peptide;

7) a GA-specific human T-cell line that has a known biomarker response profile;

8) a GA-specific human T-cell line that has a known biomarker response profile different from that of the GA-specific human T-cell line of (7);

9) a. GA-specific human T-cell line that has a known MHC restriction; and 10) a GA-specific human T-cell line that has a known MHC restriction different from that of the GA-specific human T-cell line of (9).

In embodiments, the GA-specific human T-cell lines are long-term GA-specific human T-cell lines, and/or clonal GA-specific human T-cell lines, and/or CD4+GA-specific human T-cell lines, and/or CD8-GA-specific human T-cell lines.

In embodiments, the assay panel includes one or more T-cell lines listed in Table A.

TABLE A

| COP and GMA-Reactive T Cell Lines | | | |
|---|---|---|---|
| No | Cell Line | Donor | Culturing Antigen |
| 1 | 222-AG11 | 1 | GMA |
| 2 | 222-AG12 | 1 | GMA |
| 3 | 222-BA11 | 1 | GMA |
| 4 | 222-BC11 | 1 | GMA |
| 5 | 165-B2G | 3 | GMA |
| 6 | 165-B5G | 3 | GMA |
| 7 | 165-C4G | 3 | GMA |
| 8 | 165-C5G | 3 | GMA |
| 9 | 165-C8G | 3 | GMA |
| 10 | 165-D8G | 3 | GMA |
| 11 | 165-E7G | 3 | GMA |
| 12 | 165-E9G | 3 | GMA |
| 13 | 165-F10G | 3 | GMA |
| 14 | 165-F5G | 3 | GMA |
| 15 | 165-F8G | 3 | GMA |
| 16 | 165-H11G | 3 | GMA |
| 17 | 222-1C5 | 1 | COP |
| 18 | 222-1H12 | 1 | COP |
| 19 | 222-2B11 | 1 | COP |
| 20 | 222-2B8 | 1 | COP |
| 21 | 222-2C3 | 1 | COP |
| 22 | 222-2D8 | 1 | COP |
| 23 | 222-2E1 | 1 | COP |
| 24 | 222-2F12 | 1 | COP |
| 25 | 222-1G8 | 1 | COP |
| 26 | 222-2G12 | 1 | COP |
| 27 | 165-B6C | 3 | COP |
| 28 | 165-B10C | 3 | COP |
| 29 | 165-C4C | 3 | COP |
| 30 | 165-C7C | 3 | COP |
| 31 | 165-D2C | 3 | COP |
| 32 | 165-D3C | 3 | COP |
| 33 | 165-D11C | 3 | COP |
| 34 | 165-E3C | 3 | COP |
| 35 | 165-F3C | 3 | COP |
| 36 | 165-F6C | 3 | COP |
| 37 | 165-F9C | 3 | COP |
| 38 | 205-1B4 | 4 | COP |
| 39 | 205-1B7 | 4 | COP |
| 40 | 205-1C4 | 4 | COP |
| 41 | 205-1D1 | 4 | COP |
| 42 | 205-1E1 | 4 | COP |
| 43 | 205-1F2 | 4 | COP |
| 44 | 205-1F4 | 4 | COP |
| 45 | 205-1H3 | 4 | COP |
| 46 | 205-1H5 | 4 | COP |
| 47 | 205-1H7 | 4 | COP |
| 48 | 205-1H9 | 4 | COP |
| 49 | 205-1H11 | 4 | COP |
| 50 | 224-D2-001 | 6 | GMA |
| 51 | 224-G11-001 | 6 | GMA |
| 52 | 224-G2-001 | 6 | GMA |
| 53 | 224-C4-001 | 6 | GMA |
| 54 | 224-F4-001 | 6 | GMA |
| 55 | 224-B6-001 | 6 | GMA |
| 56 | 224-B7-001 | 6 | GMA |
| 57 | 224-G10-001 | 6 | GMA |
| 58 | 224-D6-001 | 6 | GMA |
| 59 | 224-E7-001 | 6 | GMA |
| 60 | 224-B11-001 | 6 | GMA |
| 61 | 224-C11-001 | 6 | GMA |
| 62 | 224-E2-001 | 6 | GMA |

In embodiments, the assay panel includes one or more T-cell lines listed in Table B.

TABLE B

GMA and Copaxone-Specific* T Cell Lines

| No. | Cell Line | Initiating Antigen | MHC Restriction | Non-Canonical Peptide Reactivity** | Non-Canonical Peptide Non-Reactivity*** |
|---|---|---|---|---|---|
| 1 | 222-AG12 | GMA | | | Peptide 026<br>GLT 631<br>GAT 631<br>GAT 111<br>GL 14<br>LT 11<br>GT 11 |
| 2 | 222-BC11 | GMA | | | |
| 3 | 165-B5G | GMA | DR-11 | GL 14 | Peptide 026<br>GLT 631<br>GAT 631<br>GAT 111<br>LT 11<br>GT 11 |
| 4 | 165-C4G | GMA | DR-15 | | GT 11 |
| 5 | 165-C5G | | | GL 14<br>LT 11 | GLT 631<br>GAT 631<br>GAT 111<br>GT 11 |
| 6 | 165-D8G | GMA | | | Peptide 026 |
| 7 | 165-E7G | GMA | | GLT 631<br>GAT 631<br>GL 14 | Peptide 026<br>GAT 111<br>LT 11<br>GT 11 |
| 8 | 165-E9G | GMA | DR-11 | GL 14 | GLT 631<br>GAT 631<br>GAT 111<br>LT 11<br>GT 11 |
| 9 | 165-F5G | GMA | DR-11 | GL 14 | Peptide 026<br>GLT 631<br>GAT 631<br>GAT 111<br>LT 11<br>GT 11 |
| 10 | 165-F8G | GMA | | | GT 11 |
| 11 | 165-F10G | GMA | DR-15 | GL 14<br>LT 11 | GLT 631<br>GAT 631<br>GAT 111<br>GT 11 |
| 12 | 165-H11G | GMA | | GLT 631<br>GAT 631<br>GL 14 | GAT 111<br>LT 11<br>GT 11 |
| 13 | 222-2D8 | COP | | | |
| 14 | 222-2E1 | COP | | | |
| 15 | 222-2F12 | COP | | GL 14 | GLT 631<br>GAT 631<br>GAT 111 |
| 16 | 165-B6C | COP | DR-11 | Peptide 026 | GLT 631<br>GAT 631<br>GT 11 |
| 17 | 165-B10C | COP | | | Peptide 026<br>GT 11 |
| 18 | 165-C4C | COP | | GL 14<br>LT 11 | GLT 631<br>GAT 631<br>GAT 111<br>GT 11<br>GT41S<br>GA64 |
| 19 | 165-C7C | COP | DR-11 | GL 14<br>LT 11 | GLT 631<br>GAT 631<br>GAT 111<br>GT 11 |
| 20 | 165-D2C | COP | | | GT 11 |
| 21 | 165-D3C | COP | DR-15 | Peptide 026 | GT 11 |
| 22 | 165-U3C | COP | | | Peptide 026<br>GLT 631<br>GAT 631<br>GAT 111<br>GT 11 |
| 23 | 165-F3C | COP | DR-11 | Peptide 026<br>GL 14<br>LT 11 | GLT 631<br>GAT 631<br>GAT 111<br>GT 11<br>GT 41S<br>GA 64 |
| 24 | 165-F6C | COP | DR-15 | Peptide 026<br>GL 14 | GT 11<br>GLT 631<br>GAT 631<br>GAT 111<br>LT 11<br>GT 11<br>GT 41S<br>GA64 |
| 25 | 205-1B4 | COP | | | Peptide 026<br>GLT 631<br>GAT 631 |
| 26 | 205-1C4 | COP | | Peptide 026 | GLT 631<br>GAT 631 |
| 27 | 205-1F2 | COP | | | |
| 28 | 205-1F4 | COP | DR-13 | LT 11 | GLT 631<br>GAT 631<br>GAT 111<br>GL 14<br>GT 41S<br>GA 64 |
| 29 | 205-1H3 | COP | | GL 14 | GLT 631<br>GAT 631<br>GAT 111<br>LT 11<br>GT 41S<br>GA 64 |
| 30 | 205-1H5 | COP | | Peptide 026 | GLT 631<br>GAT 631 |
| 31 | 205-1H7 | COP | DR-13 | GLT 631 | GAT 631<br>GAT 111 |
| 32 | 205-1H11 | COP | | Peptide 026 | GLT 631<br>GAT 631<br>GAT 111<br>GL 14<br>LT 11<br>GT 11 |

*Identified based on proliferation response using the equation: (Proliferation response to test antigen - proliferation response to control) ÷ (proliferation response to reference antigen - proliferation response to control) = 0.8 to 1.2.
**Percent proliferation of no antigen control; lines identified based on at least one proliferation value of greater than or equal to 2 times no antigen control value.
***All cell lines in this column identified based on proliferation values of less than 2 times no antigen control value.

In embodiments, the assay panel comprises one or more positive or negative controls.

In embodiments, when the assay panel includes one or more GA-specific human T-cell line that does not respond to stimulation with a non-canonical GA peptide, it further comprises one or more GA-specific human T-cell line that responds to stimulation with the same non-canonical GA peptide. For example, the assay panel can comprise a first characterized GA-specific human T-cell line determined to not respond to stimulation with a non-canonical GA peptide, and a second characterized GA-specific human T-cell line determined to respond to stimulation with the non-canonical GA peptide. In embodiments, the first and second characterized GA-specific human T-cell lines both respond to stimulation with the non-canonical GA peptide but each responds differently (e.g., they each produce a different GA response biomarker profile). In related embodiments, a negative control is included for any GA-specific human T-cell line determined to respond or not to respond to stimulation with a non-canonical GA peptide. In embodiments, the negative control sample contains the cell line, appropriate APC, and no antigen.

In embodiments, the assay panel includes one or more GA-specific human T-cell line that has a known biomarker response profile, and one or more GA-specific human T-cell line that has a different known biomarker response profile. For example, the assay panel comprises a characterized GA-specific human T-cell line determined to have a first known biomarker response profile, and a characterized GA-specific human T-cell line determined to have a second known biomarker response profile different from the first known biomarker response profile. In embodiments, the first and second known biomarker response profiles each comprise at least one cytokine, at least one chemokine, at least one activation marker, at least one nucleic acid encoding a cytokine, at least one nucleic acid encoding a chemokine, or at least one nucleic acid encoding an activation marker.

In related embodiments, a negative control is included for any GA-specific human T-cell line having a known biomarker response profile. In embodiments, the negative control sample contains the cell line, appropriate APC, and no antigen.

In embodiments, the assay panel includes one or more GA-specific human T-cell line that has a known MHC restriction, and one or more GA-specific human T-cell line that has a different known MHC restriction. In embodiments, the assay panel includes one or more GA-specific human T-cell line that has a known MHC restriction wherein the HLA-DR restriction element is selected from: DR-1, DR-2, DR-3, DR-4, DR-7, DR-11, DR-13, and DR-15; and one or more GA-specific human T-cell line that has a different known MHC restriction wherein the HLA-DR restriction element is selected from: DR-4, DR-7, DR-11, DR-13, and DR-15. For example, the assay panel comprises a characterized GA-specific human T-cell line determined to have first a known MHC restriction, and a characterized GA-specific human T-cell line determined to have a second known MHC restriction different from the first known MHC restriction. In related embodiments, a negative control is included for any GA-specific human T-cell line determined to have a different known MHC restriction. In embodiments, the negative control sample contains the cell line, non-matched APC, and GA. In embodiments, the negative control sample contains the cell line, appropriate APC, and no antigen.

In embodiments, an assay panel comprises at least two GA-specific human T-cell lines, wherein each of the at least two GA-specific human T-cell lines is determined to be GA-specific based on a comparison of the response obtained by measuring a GA-elicited response when the T-cell line is stimulated with a first preparation of GA, to the response obtained by measuring the same GA-elicited response when the T-cell line is stimulated with a second preparation of GA, and wherein the comparison of the response of the second preparation of GA to the response of the first preparation of GA is within acceptable range or limits, and wherein each of the at least two GA-specific human T-cell lines is a long-term GA-specific human T-cell line. In embodiments, the first preparation of GA was used to generate the GA-specific human T-cell line. In embodiments, the first preparation of GA is Copaxone.

In embodiments, an assay panel comprises at least two GA-specific human T-cell lines, wherein each of the at least two GA-specific human T-cell lines is determined to be GA-specific based on a comparison of the dose response curve obtained by measuring a GA-elicited response when the GA-specific human T-cell line is stimulated at multiple doses with at least a first preparation of GA, to the dose response curve obtained by measuring the same GA-elicited response when the GA-specific human T-cell line is stimulated at multiple doses with a second preparation of GA, wherein the comparison of the slope of the dose response curve of die second preparation of GA to the slope of the dose response curve of the first preparation of GA is within acceptable range or limits, and wherein each of the at least two GA-specific human T-cell lines is a long-term GA-specific human T-cell line. In embodiments, the first preparation of GA was used to generate the GA-specific human T-cell line. In embodiments, the first preparation of GA is Copaxone.

In embodiments, at least one of the at least two GA-specific human T-cell lines in the assay panel is reactive to a noncanonical GA peptide. In embodiments, at least one of the at least two GA-specific human T-cell lines in the assay panel is reactive to a noncanonical GA peptide selected from: Peptide 026, GLT 631, GAT 631, GAT 111, GL 14, LT 11, GA 41S, GA 64, and GT 11.

In embodiments, at least one of the at least two GA-specific human T-cell lines in the assay panel is not reactive to a noncanonical GA peptide. In embodiments, at least one of the at least two GA-specific human T-cell lines in the assay panel is not reactive to a noncanonical GA peptide selected from Peptide 026, GLT 631, GAT 631, GAT 111, GL 14, LT 11, GA 41S, GA 64, and GT 11.

In embodiments, at least one of the at least two GA-specific human T-cell lines in the assay panel is reactive to a noncanonical GA peptide and wherein at least one of the at least two GA-specific human T-cell lines in the assay panel is not reactive to the same noncanonical GA peptide. In embodiments, at least one of the at least two GA-specific human T-cell lines in the assay panel is reactive to a noncanonical GA peptide selected from Peptide 026, GLT 631, GAT 631, GAT 111, GL 14, LT 11, GA 41S, GA 64, and GT 11, and wherein at least one of the at least two GA-specific human T-cell lines in the assay panel is not reactive to the same noncanonical GA peptide.

In embodiments, at least one of the at least two GA-specific human T-cell lines in the assay panel is clonal. In embodiments, all of the at least two GA-specific human T-cell lines in the assay panel are clonal. In embodiments, the at least two GA-specific human T-cell lines in the assay panel have different MHC restrictions. In embodiments, at least two GA-specific human T-cell lines in the assay panel include one or more GA-specific human T-cell line that has a known MHC restriction wherein the HLA-DR restriction element is selected from: DR-1, DR-2, DR-3, DR-4, DR-7, DR-11, DR-13, and DR-15; and one or more GA-specific human T-cell line that has a different known MHC restriction wherein the HLA-DR restriction element is selected from: DR-4, DR-7, DR-11, DR-13, and DR-15. In embodiments, the at least two GA-specific human T-cell lines in the assay panel comprise at least 98% CD4+ T-cells and not more than 2% CD8+ T-cells.

Use of an Assay Panel of GA-Specific Human T-Cell Lines

In embodiments of the invention, an assay panel of the invention is used in a method of determining whether a test preparation of GA and a GA reference standard are immunologically identical. In these embodiments, cell samples are prepared using a predetermined number of cells of each GA-specific human T-cell line in the panel, appropriate APC, and an amount of the test preparation of GA. Cell samples also are prepared using the same predetermined number of cells of each GA-specific human T-cell line in the panel, appropriate APC, and an amount of the GA reference standard. In embodiments, control samples are prepared. In embodiments, a negative control is prepared using the same predetermined number of cells of each GA-specific human T-cell line in the panel, no APC, and no antigen. In embodiments, a control is prepared using the same predetermined number of cells of each GA-specific human T-cell line in the panel, appropriate APC, and a non-relevant antigen. In embodiments, a negative control is prepared using the same predetermined number of cells of each GA-specific human T-cell line in the panel, and non-matched APC.

In embodiments, the same at least one to at least 25 GA-elicited responses are measured in each cell sample. In embodiments, 2, 3, 4, 5, 6, 7, 8, 9, 10, 11, 12, 13, 14, 15, 16, 17, 18, 19, 20, 21, 22, 23, 24, 25, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25, GA-elicited responses are measured in each cell sample.

The measurements obtained using an assay panel of the invention can be used to determine whether a test preparation of GA and a GA reference standard are immunologically identical by comparing the measurement of a given GA-elicited response in the T-cell line sample stimulated with the GA test preparation to the same GA-elicited response in the T-cell line sample stimulated with the GA reference standard. In embodiments, these measurements are normalized to take into account any background observed in the negative control sample before the comparison is made.

Determining Immunological Identity

As described herein, the immunological identity of a GA test preparation and a GA reference standard can be determined using the methods of the invention by comparing the measurement of at least one GA-elicited response in a GA-specific T-cell line stimulated with the GA test preparation and the same least one GA-elicited response in the GA-specific T-cell line stimulated with the GA reference standard.

As described elsewhere herein, the GA-elicited response measured can be proliferation, production of a response biomarker, expression of a nucleic acid encoding a response biomarker, or a combination thereof.

In embodiments, wherein the GA-elicited response measured in the methods of the invention is the production of a response biomarker, the response biomarker can be, e.g., a cytokine, cytokine receptor, chemokine, T-cell activation marker, or a nucleic acid that encodes a cytokine, cytokine receptor, chemokine, or T-cell activation marker. Response biomarkers can be measured according to methods known in the art and described elsewhere herein.

In embodiments, the response biomarker is a cytokine selected from, e.g., IL-2, IL-4, IL-5, IL-6, IL-10, IL-13, or IL-17, IL-21, IL-22, TNF-α (TNF), TNF-β (LT), TGF-β, and IL-1b. In embodiments, the response biomarker is an activation marker selected from, e.g., CD69, CD25, CD71, CD137, CD154, CD278, CD279, and HLA-DR. In embodiments, the response biomarker is a chemokine, selected from, e.g., IL-8 (CXCL8), RANTES (CCL5), CCL1, CXCL4, and CXCL7. In embodiments, theresponse biomarker is a Th1-associated cytokine, a Th2-associated cytokine, a Th17-associated cytokine, or a $Th_{FH}$-associated cytokine. In embodiments, the response biomarker is a Th1-associated cytokine and is IFN-γ. In embodiments, the response biomarker is a Th2-associated cytokine selected from: IL-4, IL-5, and IL-13. In embodiments, the response biomarker is a Th17-associated cytokine selected from: IL-17, and IL-22. In embodiments, the response biomarker is a $Th_{FH}$-associated cytokine selected from: IL-21, and TGF-β. In embodiments, the response biomarker is a key regulatory associated cytokine selected from IL-10 and TGF-β.

In embodiments, the response biomarker is a nucleic acid encoding a cytokine selected from, e.g., IL-2, IL-4, IL-5, IL-10, IL-13, or IL-17, IL-21, IL-22, TNF-α (TNF), TNF-β (LT), TGF-β, and IL-1b. In embodiments, the response biomarker is a nucleic acid encoding an activation marker selected from, e.g., CD69, CD25, CD71, CD137, CD154, CD278, CD279, and HLA-DR. In embodiments, the response biomarker is a nucleic acid encoding chemokine, selected from, e.g., IL-8 (CXCL8), RANTES (CCL5), CCL1, CXCL4, and CXCL7. In embodiments, the response biomarker is a nucleic acid encoding Th1-associated cytokine, a nucleic acid encoding Th2-associated cytokine, a nucleic acid encoding Th17-associated cytokine, or a nucleic acid encoding $Th_{FH}$-associated cytokine. In embodiments, the response biomarker is a nucleic acid encoding Th1-associated cytokine and is IFN-γ. In embodiments, the response biomarker is a nucleic acid encoding Th2-associated cytokine selected from: IL-4, IL-5, and IL-13. In embodiments, the response biomarker is a nucleic acid encoding Th17-associated cytokine selected from: IL-17, and IL-22. In embodiments, the response biomarker is a nucleic acid encoding a $Th_{FH}$-associated cytokine selected from: IL-21, and TGF-β. In embodiments, the response biomarker is a nucleic acid encoding a key regulatory associated cytokine selected from IL-10 and TGF-β. Additional response biomarkers can be identified according to methods described herein.

In embodiments, a determination of immunological identity of the GA test preparation and the GA reference standard is made when each comparison of a respective pair of GA test preparation and GA reference standard measurements (e.g., expressed as a fraction, ratio, or percentage) falls within an acceptable range or acceptable limits.

In embodiments of the invention, immunological identity between the GA preparations is determined using a panel of GA-specific human T-cell lines. In embodiments, a measurement of at least one GA-elicited response in each GA-specific human T-cell line in the panel stimulated with a GA test preparation, and the same at least one GA-elicited response in the respective GA-specific human T-cell line in the panel stimulated with a GA reference standard, are compared. As described, in certain embodiments, each GA-elicited response measurement is normalized to take into account any signal observed in a suitable negative control sample prior to the comparison. In embodiments, wherein a panel of multiple GA-specific T-cell lines is used to evaluate at least one test lot of GA, the dose response curves for any/all cell lines in the panel stimulated with the reference lot(s) must meet predetermined criteria, e.g., as described below wherein the coefficient of correlation (r) is ≥0.90, the slope is ≥0.60, the back-calculated concentration of GA standards is within ±30% of the nominal concentration, and the precision of a GA sample is ≤20% of coefficient of variation (CV). In embodiments, the dose response curve for the at least one test lot of GA must be within predetermined acceptable limits to be determined immunologically identical to the GA reference lot. In embodiments, the coefficient of correlation is 0.90 to 0.98. In embodiments, the coefficient of correlation is greater than or equal to 0.90, greater than or equal to 0.91, greater than or equal to 0.92, greater than or equal to 0.93, greater than or equal to 0.94, greater than or equal to 0.95, greater than or equal to 0.96, greater than or equal to 0.97, greater than or equal to 0.98, 0.90 to 0.98, 0.91 to 0.98, 0.92 to 0.98, 0.93 to 0.98, 0.94 to 0.98, 0.95 to 0.98, 0.96 to 0.98, 0.90 to 0.97, 0.91 to 0.97, 0.92 to 0.97, 0.93 to 0.97, 0.94 to 0.97, 0.95 to 0.97, or 0.96 to 0.98.

In embodiments, a determination of immunological identity is made when the comparison (the GA-elicited response measurement in the GA-specific human T-cell line stimulated with the GA test preparation, relative to the GA-elicited response measurement in the GA-specific human T-cell line stimulated with the GA reference standard) is 75% to 125%. In embodiments, an appropriate negative control value, e.g., a no antigen control, is subtracted from the test values prior to making the comparison. In embodiments, a no antigen control value is not subtracted from the test values prior to making the comparison. In embodiments, the values are compared directly.

In embodiments, the acceptable range or limits for the comparison value is about 80% to about 120%, or about 90% to about 110%. In embodiments, the acceptable range is about 75% to about 120%, about 75% to about 115%, about 75% to about 110%, about 75% to about 105%, about 75% to about 100%, about 80% to about 125%, about 85% to about 125%, about 90% to about 125%, about 95% to about 125%, about 100% to about 125%, about 80% to about 118%, about 80% to about 115%, about 80% to about 112%, about 80% to about 110%, about 80% to about 108%, about 80% to about 105%, about 80% to about 102%, about 80% to about 101%, about 80% to about 100%, about 80% to about 99%, about 80% to about 98%, about 80% to about 97%, about 80% to about 95%, about 80% to about 92%, about 80% to about 90%, about 82% to about 120%, about 82% to about 118%, about 82% to about 115%, about 82% to about 112%, about 82% to about 110%, about 82% to about 108%, about 82% to about 105%, about 82% to about 102%, about 82% to about 101%, about 82% to about 100%, about 82% to about 99%, about 82% to about 98%, about 82% to about 97%, about 82% to about 95%, about 82% to about 92%, about 82% to about 90%, about 84% to about 120%, about 84% to about 118%, about 84% to about 115%, about 84% to about 112%, about 84% to about 110%, about 84% to about 108%, about 84% to about 105%, about 84% to about 102%, about 84% to about 101%, about 84% to about 100%, about 84% to about 99%, about 84% to about 98%, about 84% to about 97%, about 84% to about 95%, about 84% to about 92%, about 84% to about 90%, about 86% to about 120%, about 86% to about 118%, about 86% to about 115%, about 86% to about 112%, about 86% to about 110%, about 86% to about 108%, about 86% to about 105%, about 86% to about 102%, about 86% to about 101%, about 86% to about 100%, about 86% to about 99%, about 86% to about 98%, about 86% to about 97%, about 86% to about 95%, about 86% to about 92%, about 88% to about 120%, about 88% to about 118%, about 88% to about 115%, about 88% to about 112%, about 88% to about 110%, about 88% to about 108%, about 88% to about 105%, about 88% to about 102%, about 88% to about 101%, about 88% to about 100%, about 88% to about 99%, about 88% to about 98%, about 88% to about 97%, about 88% to about 95%, about 90% to about 120%, about 90% to about 118%, about 90% to about 115%, about 90% to about 112%, about 90% to about 110%, about 90% to about 108%, about 90% to about 105%, about 90% to about 102%, about 90% to about 101%, about 90% to about 100%, about 90% to about 99%, about 90% to about 98%, about 90% to about 97%, about 90% to about 95%, about 92% to about 120%, about 92% to about 118%, about 92% to about 115%, about 92% to about 112%, about 92% to about 110%, about 92% to about 108%, about 92% to about 105%, about 92% to about 102%, about 92% to about 101%, about 92% to about 100%, about 92% to about 99%, about 92% to about 98%, about 95% to about 120%, about 95% to about 118%, about 95% to about 115%, about 95% to about 112%, about 95% to about 110%, about 95% to about 108%, about 95% to about 105%, about 95% to about 102%, about 95% to about 101%, about 95% to about 100%, about 97% to about 120%, about 97% to about 118%, about 97% to about 115%, about 97% to about 112%, about 97% to about 110%, about 97% to about 108%, about 97% to about 105%, about 97% to about 102%, about 98% to about 120%, about 98% to about 118%, about 98% to about 115%, about 98% to about 112%, about 98% to about 110%, about 98% to about 108%, about 98% to about 105%, about 99% to about 120%, about 99% to about 118%, about 99% to about 115%, about 99% to about 112%, about 99% to about 110%, about 99% to about 108%, about 99% to about 105%, about 100% to about 120%, about 100% to about 118%, about 100% to about 115%, about 100% to about 112%, about 100% to about 110%, about 100% to about 108%, about 100% to about 105%, about 101% to about 120%, about 101% to about 118%, about 101% to about 115%, about 101% to about 112%, about 101% to about 110%, about 101% to about 108%, about 102% to about 120%, about 102% to about 118%, about 102% to about 115%, about 102% to about 112%, about 102% to about 110%, about 102% to about 108%, about 105% to about 120%, about 105% to about 118%, about 105% to about 115%, about 105% to about 112%, about 105% to about 110%, about 110% to about 120%, about 110% to about 118%, or about 110% to about 115%.

In embodiments, a determination of immunological identity of the GA test preparation and the GA reference standard using an assay panel of GA-specific T-cell lines is identified by comparing at least 2, at least 3, at least 4, or more, different GA-elicited responses measured following stimulation with the GA test and GA reference standard preparations.

In embodiments, a determination of immunological identity of the GA test preparation and the GA reference standard using an assay panel of GA-specific T-cell lines is made when the comparison of each respective pair of measurements in the assay panel is within a predetermined acceptable range. In embodiments, a determination of immunological identity of the GA test preparation and the GA reference standard is made when the comparison of 80 to 100%, 85 to 100%, 90 to 100%, or 95 to 100%, 80%, 85%, 90%, 95%, or 100% of respective pairs of measurements in an assay panel are within an acceptable range.

In embodiments wherein the test and reference standard GA preparations are determined to be immunologically identical based on a use of a single reference lot and comparison of a GA-elicited response at a single dose, the determination of immunological identity is made based on a "single reference lot, single dose analysis" In embodiments, the immunological identity of two GA preparations is determined when the single reference, single dose analysis comparison value is within a predetermined acceptable range at each of one GA dose, two different GA doses, three different GA doses, or more.

In embodiments, the GA-elicited response to each GA lot is measured at a series of increasing GA doses, and a dose-response curve is generated for each lot using the resulting response values. In embodiments, the lots are determined to be immunologically identical (or not immunologically identical), by comparing the slope ($\beta^*$) of the reference lot dose response curve with the slope of the test lot dose response curve. In these embodiments, the GA-specificity of a human T-cell line is identified based on a "single-reference lot dose response curve analysis." In embodiments, the test preparation of GA and the GA reference standard are confirmed as immunologically identical when the slopes in the linear range of their respective dose-response curves are statistically similar or identical.

In embodiments, the immunological identity of two GA preparations can be determined when the slopes in the linear range of the test GA lot and reference GA lot dose-response curves are statistically similar or identical as determined according to any appropriate statistical methods known to those of skill in the art. In embodiments, immunological identity of the GA test preparation and the GA reference standard are determined using an $EC_{50}$ comparison and/or regression analysis, or another appropriate method known in the art or described in the literature.

In embodiments, to reach a determination of immunological identity by comparing dose response curves, the slope (β*) of the reference lot dose response curve must meet appropriate acceptance criteria. Appropriate acceptance criteria can be predetermined by those of skill in the art. In certain embodiments, appropriate acceptance criteria are:

Coefficient of correlation (r) is ≥0.90

The slope is ≥0.60

The back-calculated concentration of GA standards is within ±30% of the nominal concentration The precision of a GA sample is ≤20% of coefficient of variation (CV).

In embodiments, the GA-elicited response in 75% of positive control samples (e.g., cells stimulated with ConA) must be above the highest response elicited when the same cells are stimulated with any concentration of GA. In embodiments, the GA-elicited response in 75% of negative control samples (e.g., cells treated with a control peptide such as myelin basic protein, MBP) must be below or close to the lowest response elicited with any concentration of GA.

Linear regression can be performed on the GA reference lot sample set, where the data points are plotted on a log-log scale. The log GA-elicited response values (by increasing concentration of analyte, shown below as IL-2) are on the Y-axis, and the log GA reference lot concentration (dose) values are on the X-axis.

The best fit linear regression model used for the above data set is as follows:

$$Y = \alpha + \beta \cdot X \quad (1)$$

where $Y=\log_{10}$(mIL−2 concentration) and $X=\log_{10}$(GA concentration). Substituting X and Y variables with the appropriate representations, the above model becomes the following:

$$\log_{10}(mIL\text{-}2\ \text{concentration}) = \alpha + \beta \cdot \log_{10}(\text{GA-concentration}) \quad (2)$$

In embodiments, immunological identity is established when the slope of the test lot curve is within acceptable limits. The acceptable range for the slope of the test lot curve is determined based on the reference lot curve using the following series of equations:

The back-calculated dose value for a given log (response) is:

$$X_{back} = 10^{(Y-\alpha)/\beta} \text{ where } Y = \text{Log}_{10}(mIL\text{-}2\ \text{concentration}) \quad (3)$$

The accuracy can be calculated by the following:

$$\text{accuracy} = \left[\frac{10^{(Y-\alpha)/\beta} - X_{true}}{X_{true}}\right] * 100 \quad (4)$$

$Y_{low}$ and $Y_{high}$ are the lowest and highest log (response) values permitted by the highest allowable accuracy of ±(Mean+2*SD), where Mean+2*SD is the highest limit of the approximate 95% individual tolerance region.

Therefore, the region where the hypothesis of the equality of the slopes is to be accepted is:

$$\begin{cases} \left[\dfrac{10^{(Y_{low}-\alpha)/\beta} - X_1}{X_1}\right] * 100\% \geq -(\text{Mean} + 2*SD) \\ \left[\dfrac{10^{(Y_{high}-\alpha)/\beta} - X_2}{X_2}\right] * 100\% \leq (\text{Mean} + 2*SD) \end{cases} \quad (5)$$

$$\begin{cases} Y_{low} = \alpha + \beta * \log\left(X_1 * \left(1 - \dfrac{(\text{Mean} + 2*SD)}{100}\right)\right) \\ Y_{high} = \alpha + \beta * \log\left(X_2 * \left(1 + \dfrac{(\text{Mean} + 2*SD)}{100}\right)\right) \end{cases} \quad (6)$$

β* is calculated as follows:

$$\left\{\beta^* = \frac{Y_{high} - Y_{low}}{\log X_2 - \log X_1}\right. \quad (7)$$

Subsequently, the above region is reduced to the following for determination of the acceptable β* limits:

$$\begin{cases} \beta^* \geq \beta * (\text{lower limit}) \\ \beta^* \leq \beta * (\text{upper limit}) \end{cases} \quad (8)$$

where β is the slope of the GA-RS curve. Therefore, the acceptable range for the GA-Batch slope, β*, determined by equation (6) can be displayed as:

$$\beta \cdot (\text{lower limit}) \leq \beta^* \leq \beta \cdot (\text{upper limit}) \quad (9)$$

If β* is within the above acceptable limits, parallelism can be concluded.

In embodiments, a true hypothesis test for equal slope is used.

In embodiments, a calibration curve is generated using multiple assays of the reference lot (to account for assay variation), or assays of multiple reference lots (to account for variation among reference lots, e.g., multiple lots of commercially available COP). In embodiments wherein multiple COP reference lots are included in the assay, to provide multiple datasets, e.g., to account for lot-to-lot variation, the data from the multiple reference lots are used to determine acceptable variation from the reference slope. In these embodiments, the test and reference GA lots are determined to be immunologically identical based on a "multiple-reference dose-response curve analysis."

In embodiments wherein multiple samples of the same Copaxone reference lot are included in the assay, to provide repeat data, e.g., to account for assay variation, the reference lot repeat data are used to determine acceptable variation from the reference slope. In these embodiments, the test and reference GA lots are determined to be immunologically identical based on a "repeated reference dose-response curve analysis."

In embodiments, multiple GA-specific human T-cell lines with known characteristics, e.g., MHC restriction and reactivity to non-canonical peptides, are employed in a panel. In these embodiments, each GA-specific T-cell line in the panel can be stimulated with a reference GA lot or multiple reference GA lots, and one or more test lots of GA. To establish immunological identity between the reference lot(s) and a test lot of GA, the dose response curves for the reference lot(s) must meet appropriate acceptance criteria, e.g., as discussed above, and the dose response curve for the test lot of GA must be within the acceptable limits as described.

In embodiments, a single GA-specific T-cell line or multiple GA-specific T-cell lines are stimulated with a reference GA lot, a non-canonical GA peptide synthesized in a manner that alters the primary amino acid composition as described elsewhere herein, and a test lot of GA. Using the approach described above the acceptable limits for β* for the reference peptide can be determined, as well as the slope generated by the dose response curve of a non-canonical peptide. Statistical comparison of the similarity or dissimilarity of the slope of the test peptide with the slopes of the dose response curves of both the standard and the non-canonical peptides simultaneously can provide a determination of the degree of similarity or dissimilarity of the test peptide. Using this comparison, the immunological identity or non-identity of a test lot of GA can be determined.

Identification of GA Response Biomarkers

A GA response biomarker produced in the context of a GA-elicited response measured in the methods of the present invention can be identified by comparing the amount of a candidate GA response biomarker, produced in a GA-specific T-cell culture stimulated with GA in the presence of appropriate APC, to the amount of the same biomarker produced in a control culture incubated with appropriate APC but not stimulated with antigen, or in a control culture stimulated with a negative control antigen: In embodiments, a GA response biomarker is identified based on an increase relative to a control following GA stimulation of about 1.5-fold (i.e., the response is about 50% higher) to about 1000-fold, about 1.5 to about 2-fold, about 1.5 to about 3-fold, about 1.5 to about 4-fold, about 1.5 to about 5-fold, about 1.5 to about 6-fold, about 1.5 to about 7-fold, about 1.5 to about 8-fold, about 1.5 to about 9-fold, about 2 to about 3-fold, about 2 to about 4-fold, about 2 to about 5-fold, about 2 to about 6-fold, about 2 to about 7-fold, about 2 to about 8-fold, about 2 to about 9-fold, about 2 to about 10-fold, about 3 to about 4-fold, about 3 to about 5-fold, about 3 to about 6-fold, about 3 to about 7-fold, about 3 to about 8-fold, about 3 to about 9-fold, about 3 to about 10-fold, about 4 to about 5-fold, about 4 to about 6-fold, about 4 to about 7-fold, about 4 to about 8-fold, about 4 to about 9-fold, about 4 to about 10-fold, about 5 to about 6-fold, about 5 to about 7-fold, about 5 to about 8-fold, about 1.5 to about 9-fold, about 5 to about 10-fold, about 6 to about 7-fold, about 6 to about 8-fold, about 6 to about 9-fold, about 6 to about 10-fold, about 7 to about 8-fold, about 7 to about 9-fold, about 7 to about 10-fold, about 8 to about 9-fold, about 8 to about 10-fold, about 1.5-fold to about 80-fold, about 1.5-fold to about 70-fold, about 1.5-fold to about 60-fold, about 1.5-fold to about 50-fold, about 1.5-fold to about 40-fold, about 1.5-fold to about 30-fold, about 1.5-fold to about 20-fold, about 2-fold to about 80-fold, about 1.5-fold to about 70-fold, about 1.5-fold to about 60-fold, about 1.5-fold to about 50-fold, about 1.5-fold to about 40-fold, about 1.5-fold to about 30-fold, about 1.5-fold to about 20-fold, about 2-fold to about 80-fold, about 2-fold to about 70-fold, about 2-fold to about 60-fold, about 2-fold to about 50-fold, about 2-fold to about 40-fold, about 2-fold to about 30-fold, about 2-fold to about 20-fold, about 3-fold to about 80-fold, about 3-fold to about 70-fold, about 3-fold to about 60-fold, about 3-fold to about 50-fold, about 3-fold to about 40-fold, about 3-fold to about 30-fold, about 3-fold to about 20-fold, about 5-fold to about 80-fold, about 5-fold to about 70-fold, about 5-fold to about 60-fold, about 5-fold to about 50-fold, about 5-fold to about 40-fold, about 5-fold to about 30-fold, about 3-fold to about 20-fold, about 10-fold to about 80-fold, about 10-fold to about 60-fold, about 10-fold to about 40-fold, or about 10-fold to about 20-fold, at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, or at least about 10-fold.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Methods

The following methods were used in the Examples herein unless otherwise specified. Assay samples were run in triplicate.

1. Preparation and Initial Stimulation of Human T-Cell Lines

T-cell lines were isolated using a method described by Good et al, and Ota, et al. (Good, et al., 1987; Ota, et al., 1990). PBMC were collected by leukapheresis using acid citrate dextrose (ACD) as an anticoagulant, separated by Ficoll-Paque gradient centrifugation according to the manufacturer's protocol (Amersham Pharmacia Biotech, Uppsala, Sweden), and cryopreserved in PBS containing 2% human serum albumin and 10% DMSO. PBMC cultures were prepared in AIM V® medium (Invitrogen) or X-VIVO 15® medium (Lonza). On Day 1, 10 μg/mL of antigen (GMA, Mylan Pharmaceuticals, Inc., or Copaxone, Teva Pharmaceuticals USA, Inc.) was added to U-bottom 96-well plates containing $5\times10^5$ to $2\times10^6$ cells/mL ($1\text{-}4\times10^5$ cells per 200 μl well). The plates were incubated at 37° C., 6% $CO_2$. On Day 3 or 4, 10 U/mL IL-2 (2 U/well, eBioscience cat#14-8029-63 or R&D Systems cat#202-IL-010/CF) was added. IL-2 was prepared by diluting stock IL-2 to 40 U/mL in medium and adding 50 μl of the diluted stock IL-2 (2 U) to each well. IL-2 was added again in the same amount on Day 6 or 7, and potentially again on or around Day 10 if needed based on evaluation of cell growth.

2. Screening of Human T-Cell Lines for Reactivity to GA by Proliferation Assay

On Day 12-14, the cell lines were subjected to an initial screening for reactivity to GA restimulation by assaying for proliferation in the presence of APC. Confirmatory assays were carried out following at least 3 total rounds of restimulation (at least about 31 days or longer).

Proliferation was evaluated by measuring ATP content using a luminescent method (CellTiter Glo Luminescent Cell Viability Assay, Promega, Madison, Wis., cat. #G7571) or by measuring BrdU uptake by ELISA (Millipore cat. #2752), in both cases following kit instructions. A split well format was used. Cells in each well were resuspended and 65 μl transferred to the wells of each of two new U-bottom 96-well plates, to generate the replicate plates. For the initial screening, the original 96-well plate received mitomycin-treated autologous PBMC as APC plus 10 μg/mL antigen (GA). A first replicate plate received 100 μl., mitomycin-treated PBMC alone ($2\times10^5$), and no antigen, and a second replicate plate received 100 μL mitomycin-treated PBMC plus GA at a final concentration of 10 μg/mL. Therefore, all three plates received autologous APC (PBMC) treated with mitomycin C to prevent cell division. Each well had a total volume of 200 μL. The latter two plates were incubated for 3 days at 37° C., 6% $CO_2$ before adding CellTiter Glo or BrdU and measuring signal. IL-2 was added at 10 U/mL to the original 96-well plate for expansion on Day 17. For subsequent screenings, mitomycin-treated EBV-transformed autologous B-LCL ($2\times10^5$ to $5\times10^5$ cells/mL) were used as APC.

Potential antigen-reactive wells were identified by the increase in response relative to the corresponding well in the control (APC added, no antigen) plate. The original wells identified as antigen-reactive typically were transferred to 24-well plates 7-10 days after the screening, and restimulated/expanded with GA in the presence of mitomycin-treated autologous PBMC as described below.

3. Expansion/Restimulation of GA-Specific T-Cells

At the time of initial screening for GA reactivity, the original replicate plate containing one third of the cells from the original stimulation were restimulated/expanded. Cell lines in the original plate were restimulated with 10 μg/mL GA (same preparation used for initial stimulation) and mitomycin C-treated PBMC at about Day 12-14 when assay plates were restimulated. IL-2 was added at 10 U/mL on about Day 17. About 7-12 days after the initial screening (about Day 19 to 26), wells in the original plates corresponding to the positive wells were expanded/restimulated again. Cells in presumptive positive wells were collected and cultured in a 24-well plate with GA added at the initial stimulation concentration (10 μg/mL), and mitomycin-treated APC. APC were adjusted to $2.5\times10^6$ per mL (if PBMC) or $5\times10^5$ per mL (if B-LCL). 1 mL APC was added per well to a 24-well plate containing T-cells, and the plates were incubated for 24 hours at 37° C. with 6% $CO_2$. IL-2 was added to each well at a final IL-2 concentration of 10 U/mL or as otherwise specified. The cultures were continued for 6-13 days, and stimulation repeated. T-cells were stimulated every 7 to 14 days during expansion.

Volumes used in culture vessels for the procedures described herein: 200 μL/well of a 96-well plate; 2 mL/well of a 24-well plate; 4 mL/well of a 12-well plate; 10 mL in a T-25 flask; and 20 mL in a T-75 flask.

4. Screening T-Cell Lines for GA-Specificity

Culture medium was removed from cultures prepared as for proliferation assay and utilized to measure cytokine production. In most cases culture medium was collected 18-24 hours after mixing T-cells, APC, and stimulating antigen. Cytokine production was measured by ELISA or bead assay. For measuring cytokine production, 100-150 μL culture medium (100 μL if culture was to be continued, otherwise 150 μL) was removed from each well. In some cases, the culture was continued 48 hours, for a total of 72 hours of culture, and the proliferative response measured.

IFN-γ ELISA

IFN-γ concentration in culture supernatants was measured by a sandwich ELISA using two anti-IFN-γ monoclonal antibodies. Clone 2G1 was used for capture, and biotinylated antibody from clone B133.5 was used for detection (both from Endogen). Recombinant IFN-γ was used to construct a standard curve ranging from 1000 to 15 pg/mL.

ELISA plates were coated with capture antibody by diluting antibody to 1 μg/mL in PBS and adding 100 μl of diluted antibody per well. Plates were incubated overnight at 4° C. The coating antibody was removed and 100 μl of PBS-BSA added to all wells. The plates were incubated for one hour at room temperature. A standard curve was prepared. Standards were prepared using 1 μl of stock IFN-γ (100 μg/mL) in 1 mL of PBS-BSA (100 ng/mL final concentration) diluted in PBS-BSA (1 g BSA/100 mL PBS) as follows:

a. Take 10 μl of 100 ng/mL IFN-γ and dilute in 1 mL of PBS-BSA.=1000 pg/mL b. Mix 500 μl of 1000 pg/mL with 500 ul of PBS-BSA.=500 μg/mL c. Mix 500 μl of 500 pg/mL with 500 ul of PBS-BSA.=250 pg/mL d. Mix 500 μl of 250 pg/mL with 500 ul of PBS-BSA.=125 pg/mL e Mix 500 μl of 125 pg/mL with 500 ul of PBS-BSA.=62.5 pg/mL f. Mix 500 μl of 62.5 pg/mL with 500 ul of PBS-BSA.=31.25 pg/mL g. Mix 500 μl of 31.25 pg/mL with 500 ul of PBS-BSA.=15.625 pg/mL.

Biotinylated antibody was diluted to 0.5 μg/mL in PBS-BSA. 5 μl of antibody was diluted in 5 mL of PBS-BSA for each plate. After incubation with PBS-BSA, the plate was washed four times using a plate washer and PBS 0.05% Tween 20 as wash solution. 50 μl of biotinylated antibody was added to all wells. 50 μl of samples or standards were added to appropriate wells. Standards and samples were run in duplicate or triplicate. Plates were incubated for 90 minutes at room temperature. Streptavidin-peroxidase was diluted 1:10,000 in PBS-Tween. 1 μl of streptavidin-peroxidase in 10 mL of PBS-Tween was used for each plate. The plate was washed four times, 100 μl of streptavidin-peroxidase added to each well, an d the plate incubated 30 minutes at room temperature. The plate was washed four times with PBS-Tween. 100 μl of TMB (3,3',5,5"-tetramethylbenzidine) was added to each well, and the plate was incubated 15-30 minutes at room temperature. The reaction was stopped by adding 100 μl of 0.2N $NH_2SO_4$ per well, and the plate was read at 450 nm with a 630 nm reference.

The capture antibody used was monoclonal anti-human IFN-γ (Endogen catalog no. IL-700A). The biotinylated anti-IFN-γ was Endogen catalog no. M-701B. The streptavidin peroxidase was Zymed catalog no. 43-4323. TMB used was Ultra TMB, Thermo Scientific cat no. 34028. Standard formulation TMB also can be used.

Multiplex Assay

The concentration of multiple cytokines was measured simultaneously using FlowCytoMix™ kits (eBioscience, San Diego Calif.). These are fluorescent bead based assays consisting of beads conjugated to anti cytokine antibodies. Beads specific for each cytokine are distinguished by size and fluorescence at 670 run. Cytokine bound to each bead is detected using a phycoerythrin conjugated antibody so that the fluorescence at 585 nm reflects the concentration of cytokine in the sample. Two kits were utilized which measured different cytokine panels. The TH1/TH2 kit measures IFN-γ, IL-1β, IL-2, IL-4, IL-5, IL-6, IL-8, IL-10, IL-12p70, TNF-α (TNF) and TNF-β (LT). The TH1/TH2/TH9/TH17/TH22 kit measures IFN-β, IL-1β, IL-2, IL-4, IL-5, IL-6, IL-9, IL-10, IL-12p70, IL-13, IL-17, IL-22, and TNF-α (TNF). Both kits were used following the manufacturer's instructions.

5. Preparation of Antigen Presenting Cells

PBMC for use as APC were prepared by thawing frozen PBMC and adjusting the cell concentration to $5\times10^6$ cells per mL in PBS. Mitomycin C (Sigma-Aldrich cat#M4287 or EMD Millipore cat#475820-10MG) was added to a final concentration of 25 μg/mL. Plates were incubated for 30-45 minutes at 37° C., then the cells were washed 3 times with PBS to remove the mitomycin C. The PBMC concentration was adjusted to $1\text{-}1.5\times10^6$ cells per mL.

Human B-cells were immortalized using Epstein-Barr virus to use as APC. PBMC were thawed according to standard protocol and the cells suspended at a concentration of $10^7$ cells per mL. Aliquots of PBMC were infected with Epstein-Barr virus (ATCC VR-1492) for use as immortalized B lymphoblastoid cell lines (B-LCL). Infection was carried out by culturing PBMC with virus in RPMI 1640 medium containing 10% fetal bovine serum and 1 μg/mL cyclosporin A (cyclosporine) to prevent the activation and proliferation of T-cells. Two mL of Epstein-Barr virus (ATCC VR-1492) were added to 2 mL of cells in a 15 mL centrifuge tube, mixed well, and incubated at 37° C. for one hour in a water bath. Eight mL of culture medium (RPMI 1640 medium with 10% fetal bovine serum) and 10 μg of cyclosporine (prepared by dissolving 1 mg of cyclosporine in 1 mL of 100% ethanol and 100 uL of Tween 80, and bringing volume to 10 mL with PBS) were added to the cells and the mixture transferred to a 25 $cm^2$ flask. The flask was incubated upright in a 37° C. incubator with 5-10% $CO_2$, and the flask left undisturbed for 2 to 6 weeks.

Successful transformation was apparent after 2-6 weeks of culture when clusters of large lymphoblasts were observed microscopically. At this point the cultures were maintained and expanded by keeping the cell concentration between $2\times10^5$ and $1\times10^6$ cells per mL. This typically was accomplished by diluting the cells 1:4-1:5 every 3 to 5 days. For restimulation, $5\times10^5$ mitomycin-treated B-LCL or mitomycin-treated autologous PBMC were added to each well.

When B-LCL were used as APC, 50 μg/mL mitomycin C was added to a cell suspension of $2\times10^6$ cells per mL. Cells were incubated with mitomycin C for 45 minutes and then washed three times to remove excess mitomycin C. After the wash to remove mitomycin C, cells were adjusted to $2\text{-}5\times10^5$ per mL.

6. Maintenance of EBV Transformed B Cells (B-LCL)

As described above, transformed B cells were established in the laboratory by infecting peripheral blood mononuclear cells (PBMC) with virus and adding cyclosporine to the medium (RPMI 1640 10% fetal calf serum) to prevent the activation and proliferation of T-cells. Stimulation of PBMC with autologous EBV-B cells potentially results in stimulation of any EBV specific T-cells resulting in virus-specific T-cell lines. Therefore, EBV-B cells were not used with primary cultures or early passage T-cell lines except as otherwise specified. EBV-B cells can be used to restimulate T cell lines that have been passaged several times.

Because EBV-B cells grow in suspension and tend to form clumps of cells, the cell concentration was kept between $2\times10^5$/mL and $10^6$/mL. Cultures were split 1:4-1:5 every 3 to 5 days by pipetting cells up and down to break up cell clumps and remove 80% of the suspension. An equal volume of fresh medium was added, and the culture incubated.

7. MHC DR Restriction Testing

MHC DR restriction testing of cell lines was carried out by measuring the proliferation response of the cell lines as described above in the presence of an array of APC selected based on the known HLA-DR loci of the original PBMC donor for the cell line tested, including autologous APC (B-LCL). The donors used are described in Table 2.

To define the MHC molecule used to present antigen to GA specific T cell lines, GA specific responses were measured in the presence of autologous APC and in the presence of APC matching one of the T cell donor's HLA-DR alleles. Therefore at least 3 APC were used in each experiment: autologous APC, APC matching DR allele 1 but not allele 2 and a third APC matching allele 2 but not allele 1. In some experiments a fourth APC B-LCL was used. A no antigen negative control was used. APC were inactivated by incubation with 50 ug/mL mitomycin C. Following inactivation, cells were washed three times to remove mitomycin C and suspended in X-VIVO 15 medium at $1\times10^6$ cells per mL. GA was added to the cell suspension to a final concentration of 20-60 μg/mL. The cells were incubated with antigen for 1 hour at 37° C. to allow antigen uptake and binding. The cell suspension was then centrifuged to pellet the cells and the cell pellet was washed once with medium. APC were adjusted to $2\times10^5$ cells per mL in X-VIVO 15 medium and added to opaque 96-well plates at 100 μL per well. T-cell suspensions of $2\text{-}4\times10^5$ cells per mL (unless otherwise specified) were added to the 96-well plates at 100 μL per well and the cultures incubated 4 days before measuring cell numbers using CellTiter Glo® (to evaluate proliferation).

Alternatively, APC were not pulsed. Instead, each well contained 10 ug/mL antigen, 50 μl APC and 100 μL of T cells.

After incubating for 4 days at 37° C. (5% $CO_2$), 100 μL were removed from each well, combined with 100 μL CellTiterGlo reagent, and luminescence was measured using a Packard Fusion. Results were expressed in relative light units (RLU).

8. Donor HLA Typing

Donor HLA typing shown in Table 2 was carried out by the Puget Sound Blood Center (Seattle, Wash.) following standards set by the American Society for Histocompatibility and Immunogenetics (ASHI) and by the Clinical Laboratory Improvement Act (CLIA). Polymerase chain amplification-based testing was used to assign HLA class I and class II alleles.

9. Thawing Cryopreserved Cells

Cryopreserved cells were thawed by immersing the vial in a 37° C. water bath and agitating for 2-3 minutes. As soon as the cell suspension was completely liquid it was transferred to a 15 mL centrifuge tube containing 10 mL warm X-VIVO 15 medium. The tube was inverted gently two to three times to mix. A 50 μL aliquot of the suspension was removed to obtain a cell count and the remaining suspension was centrifuged at 200×g for 10 minutes to pellet the cells. The medium was decanted and the cell pellet was resuspended in X-VIVO 15 medium at the desired cell concentration.

10. Reagents

GA preparations were Copaxone (COP, Teva Pharmaceuticals USA, Inc.) or GMA (Mylan Pharmaceuticals, Inc.) each diluted to 20 mg/mL in mannitol (40 mg/mL). Peptide 026 was prepared by withholding tyrosine for the first five minutes of synthesis. Tetanus toxoid was supplied by Astarte Biologics. The Stern peptide is described by Stern, et al., 2005, "Peptide 15-mers of defined sequence that substitute for random amino acid copolymers in amelioration of experimental autoimmune encephalomyelitis," Proc. Nat. Acad. Sci. 102:1620-1625).

TABLE 1

| Peptides | |
|---|---|
| Peptide | Composition |
| 026 | YEAK polymer; tyrosine withheld for first five minutes of manufacture |
| GLT 631 (GLT) | poly (Glu-Lys-Tyr; 6:3:1) (Sigma-Aldrich, St. Louis, MO) |
| GAT 631 | poly (Glu-Ala-Tyr; 6:3:1) (Sigma-Aldrich, St. Louis, MO) |
| GAT 111 | poly (Glu-Ala-Tyr; 1:1:1) (Sigma-Aldrich, St. Louis, MO) |
| LT 11 | poly (Lys-Tyr; 1:1) (Sigma-Aldrich, St. Louis, MO) |
| GT 11 | poly (Glu-Tyr; 1:1) (Sigma-Aldrich, St. Louis, MO) |
| GT 41 | poly (Glu-Tyr; 4:1) (Sigma-Aldrich, St. Louis, MO) |
| GL 14 | poly (Glu-Lys; 1:4) (Sigma-Aldrich, St. Louis, MO) |
| GA 64 | poly (Glu-Ala; 6:4) (Sigma-Aldrich, St. Louis, MO) |
| MBP | FFKNIVTPRTPPPSQGK (Myelin basic protein peptide, residues 84-102) (AnaSpec, Fremont, CA) |
| ST (STERN) | EKPKVEAYKAAAAPA (Bachem H-6292, Torrance, CA) |

Example I. Generation of GA-Specific Human T-Cell Lines

Human T-cell lines were prepared from PBMC, obtained as described above from each of several different donors with no previous exposure to GA, and shown to respond specifically to GA. Characteristics of the donors used for studies described herein are summarized in Table 2.

TABLE 2

| Donor HLA-DR Loci | | | | |
|---|---|---|---|---|
| Donor | Age | Gender | Race | MHC Class II HLA-DRβ1 |
| Donor 1 (222) | 25 | Female | Caucasian | *04:01, *07:01 |
| Donor 2 (206) | 63 | Female | Caucasian | *04:01, *04:04 |
| Donor 3 (165) | 51 | Male | Caucasian | *15, *11 |
| Donor 4 (205) | 21 | Male | Caucasian | *07, *13 |
| Donor 5 (213) | 23 | Female | Caucasian | *11, *1 |
| Donor 6 (224) | 49 | Female | Caucasian | *13, *15:01 |
| Donor 7 (228) | 30 | Male | Caucasian | *15, *03 |

More than sixty GA-reactive T-cell lines were generated by culturing PBMC nom these donors according to the methods described above, in the presence of either GMA or Copaxone. These cell lines, listed in Table 3 by donor and stimulating antigen used, were demonstrated to have reactivity to GA based on proliferation assay, GA-specificity based on proliferation or cytokine production assay, or both.

TABLE 3

| T Cell Lines Obtained | | | |
|---|---|---|---|
| No | Cell Line | Donor | Culturing Antigen |
| 1 | 222-AG11 | 1 | GMA |
| 2 | 222-AG12 | 1 | GMA |
| 3 | 222-BA11 | 1 | GMA |
| 4 | 222-BC11 | 1 | GMA |
| 5 | 206-1A7 | 2 | GMA |
| 6 | 165-B2G | 3 | GMA |
| 7 | 165-B5G | 3 | GMA |
| 8 | 165-B11G | 3 | GMA |
| 9 | 165-C4G | 3 | GMA |
| 10 | 165-C5G | 3 | GMA |
| 11 | 165-C8G | 3 | GMA |
| 12 | 165-D8G | 3 | GMA |
| 13 | 165-E7G | 3 | GMA |
| 14 | 165-E9G | 3 | GMA |
| 15 | 165-F10G | 3 | GMA |
| 16 | 165-F2G | 3 | GMA |
| 17 | 165-F5G | 3 | GMA |
| 18 | 165-F8G | 3 | GMA |
| 19 | 165-H11G | 3 | GMA |
| 20 | 222-1C5 | 1 | COP |
| 21 | 222-1H12 | 1 | COP |
| 22 | 222-2B11 | 1 | COP |
| 23 | 222-2B8 | 1 | COP |
| 24 | 222-2C1 | 1 | COP |
| 25 | 222-2C3 | 1 | COP |
| 26 | 222-2D2 | 1 | COP |
| 27 | 222-2D8 | 1 | COP |
| 28 | 222-2E1 | 1 | COP |
| 29 | 222-1F8 | 1 | COP |
| 30 | 222-2F12 | 1 | COP |
| 31 | 222-2G4 | 1 | COP |
| 32 | 222-1G8 | 1 | COP |
| 33 | 222-2G12 | 1 | COP |
| 34 | 165-B6C | 3 | COP |
| 35 | 165-B10C | 3 | COP |
| 36 | 165-C4C | 3 | COP |
| 37 | 165-C7C | 3 | COP |
| 38 | 165-C9C | 3 | COP |
| 39 | 165-D2C | 3 | COP |
| 40 | 165-D3C | 3 | COP |
| 41 | 165-D11C | 3 | COP |
| 42 | 165-E3C | 3 | COP |
| 43 | 165-E9C | 3 | COP |
| 44 | 165-F3C | 3 | COP |
| 45 | 165-F4C | 3 | COP |
| 46 | 165-F6C | 3 | COP |
| 47 | 165-F9C | 3 | COP |
| 48 | 165-F11C | 3 | COP |
| 49 | 165-G7C | 3 | COP |
| 50 | 205-1B4 | 4 | COP |
| 51 | 205-1B7 | 4 | COP |
| 52 | 205-1C4 | 4 | COP |
| 53 | 205-1D1 | 4 | COP |
| 54 | 205-1E1 | 4 | COP |
| 55 | 205-1F2 | 4 | COP |
| 56 | 205-1F4 | 4 | COP |
| 57 | 205-1G3 | 4 | COP |
| 58 | 205-1H1 | 4 | COP |
| 59 | 205-1H3 | 4 | COP |
| 60 | 205-1H4 | 4 | COP |
| 61 | 205-1H5 | 4 | COP |
| 62 | 205-1H7 | 4 | COP |
| 63 | 205-1H9 | 4 | COP |
| 64 | 205-1H11 | 4 | COP |

Donor 1: Cell Lines Initially Stimulated with GMA

GMA-responsive cell lines were obtained from Donor 1 PBMC as described above ($2\times10^5$ cells/well, i.e., $1\times10^6$ cells/mL, plated with 10 μg/mL GMA; IL-2 added on Days 3 and 7). In a split well assay begun on Day 12 the cells were stimulated with 10 μg/mL GMA and $1\times10^5$ mitomycin-treated autologous PBMC as APC. BrdU was added on Day 3, cells were incubated 4.5 hours and fixed, and uptake measured. Table 4 shows the proliferative response measured for eight presumptive GA-specific human T-cell lines obtained from Donor 1 PBMC were selected. These cell lines each produced an increase in signal of at least 50% relative to (no antigen) control.

TABLE 4

| BrdU Uptake by Eight Donor 1 Human T-Cell Lines after Stimulation with GMA. | | |
|---|---|---|
| Donor 1 Cell Line | Control ($OD_{450}$) | GMA ($OD_{450}$) |
| 222-AF2 | 0.454 | 1.119 |
| 222-AF5 | 0.606 | 1.133 |
| 222-AC11 | 0.680 | 1.244 |
| 222-BA4 | 0.370 | 0.603 |
| 222-AG11 | 0.359 | 0.875 |
| 222-BA11 | 0.255 | 0.783 |
| 222-AG12 | 0.448 | 0.949 |
| 222-BC11 | 0.499 | 0.921 |

Figure 3C:
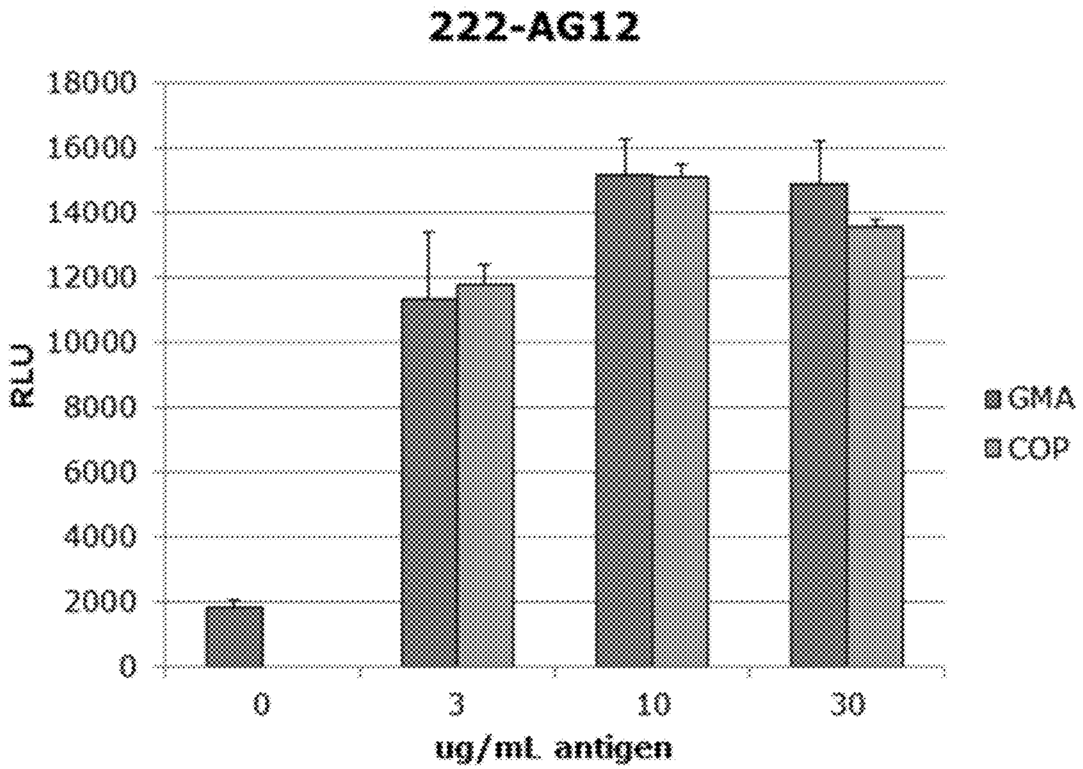

On Day 24, cells from the wells corresponding to the eight presumptive GA-specific human T-cell lines listed in Table 4 were transferred to a 24-well plate and expanded by stimulating with 10 μg/mL GMA and mitomycin-treated autologous PBMC as APC ($3\times10^6$ per well, i.e., $1.5\times10^6$/mL). On Day 32 four of the eight lines, 222-BA11, 222-BC11, 222-AG11, and 222-AG12, were stimulated with 0, 1, 10 and 100 μg/mL GMA and tested in a 96-well plate for a proliferative response to GMA using an ATP assay, again using autologous PBMC as APC ($2\times10^5$ per well, i.e., $1\times10^6$/mL). The best proliferative response relative to control was observed in the cells stimulated with 10 μg/mL GMA. FIGS. 2A and B show the results of the ATP proliferation assay carried out using 222-AG12, 222-BC11, 222-AG11, and 222-BA11 at Day 35 (control=no antigen). FIGS. 3A-C compare the results of ATP proliferation assays carried out after stimulation with varying concentrations of GMA or Copaxone as indicated, using cell lines 222-BA11, 222-BC11, and 222-AG12.

Cytokine Production by Donor 1 Human T-Cell Lines Stimulated with GMA

222-AG11 and 222-AG12 vials frozen at Day 32 were thawed and the cells tested for cytokine production. The lines were stimulated with 10 μg/mL GMA, 10 μg/mL Copaxone, or 1 μg/mL Tetanus Toxoid (control antigen) in the presence of either autologous EBV-transformed B-LCL or EBV-transformed B-LCL from a donor matched at one allele (Donor 2 B-LCL). Control samples to which APC but no antigen was added were included. Culture medium was collected after 24 hours and assayed by ELISA for IFN-γ as described above. FIGS. 4A and B show the IFN-γ produced by lines 222-AG11 and 222-AG12.

Donor 1: Cell Lines Initially Stimulated with Copaxone

COP-responsive T-cell lines were obtained from Donor 1. In the initial stimulation, isolated PBMC were plated at $1\times10^5$ cells per well ($5\times10^5$ cells/mL) with 10 μg/mL Copaxone and cultured as described above. IL-2 was added to all wells on Days 4 and 7 of culture, and the wells screened for reactivity on Day 14 using a luminescent proliferation assay in split well format. The original plate was restimulated, and IL-2 added 4 days after restimulation. Table 5 shows the proliferation assay results for the fifteen Donor 1 COP T-cell lines (producing at least twice the signal as control).

TABLE 5

| Donor 1 Presumptive COP T Cell Lines - ATP Proliferation Assay | | |
|---|---|---|
| Donor 1 Cell Line | Control | COP 10 μg/mL |
| 222-1C5 | 7087 | 14906 |
| 222-1F8 | 2308 | 6519 |
| 222-1G8 | 4030 | 8308 |
| 222-1H12 | 8141 | 23836 |

TABLE 5-continued

| Donor 1 Presumptive COP T Cell Lines - ATP Proliferation Assay | | |
|---|---|---|
| Donor 1 Cell Line | Control | COP 10 μg/mL |
| 222-2B8 | 5543 | 13600 |
| 222-2B11 | 6340 | 16460 |
| 222-2C1 | 8350 | 20166 |
| 222-2C3 | 6839 | 14045 |
| 222-2C5 | 4695 | 9577 |
| 222-2D2 | 7135 | 16271 |
| 222-2D8 | 13024 | 26495 |
| 222-2E1 | 8035 | 17064 |
| 222-2F12 | 9703 | 28022 |
| 222-2G4 | 2566 | 6812 |
| 222-2G12 | 3913 | 9899 |

(Data in RLU.)

T-cell line 222-2D8, generated from Donor 1 by initial stimulation with COP, was shown in at least two experiments to proliferate comparably following restimulation with GMA and COP. Table 6 shows the results of an ATP proliferation assay carried out on Day 56 of culturing following stimulation with 3 or 10 μg/mL of GMA or COP. ATP levels were measured at 48 hours after stimulation. The control in the GMA series was no antigen, and the control in the COP series was MBP. The response to GMA in comparison to COP at the 10 μg/mL dose in this assay was 103.4%.

TABLE 6

Figure 5G:
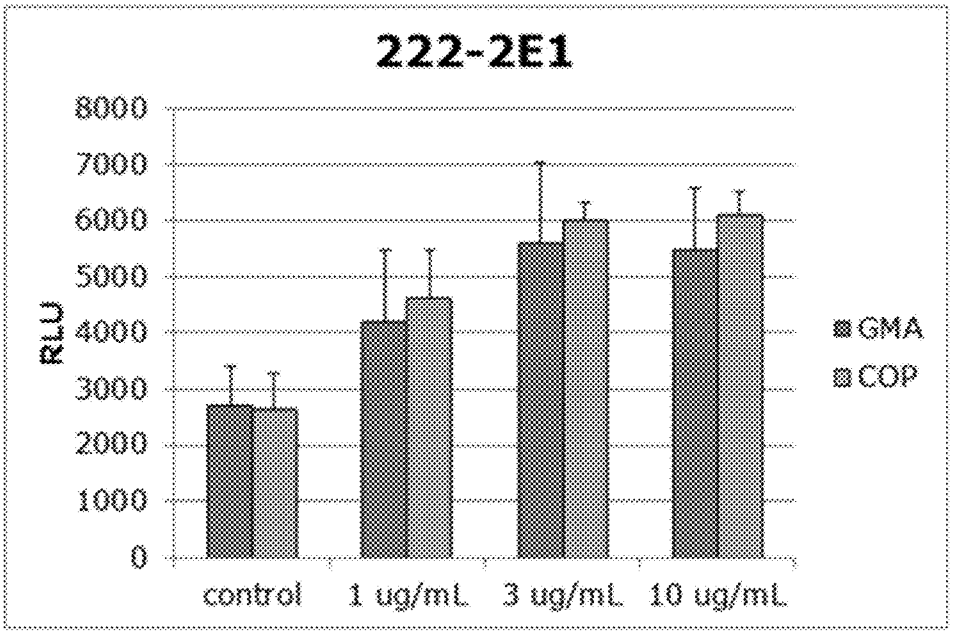

| Antigen Reactivity of Cell Line 222-2D8 (Data from FIG. 5A) | | |
|---|---|---|
| | GMA | COP |
| No Antigen | 2290 | 1999 |
| 1 μg/mL | 4369 | 4888 |
| 3 μg/mL | 7480 | 6392 |
| 10 μg/mL | 12793 | 12161 |

In a second ATP proliferation assay, carried out on Day 56 or culturing following stimulation with 1, 3, or 10 μg/mL of GMA or COP, the response to GMA in comparison to COP at the 10 μg/mL dose was 107.1%. The results are shown in Table 7.

TABLE 7

| Antigen Reactivity of Cell Line 222-2D8 (Day 56) | | | | |
|---|---|---|---|---|
| | GMA | | COP | |
| | Mean | Std dev | Mean | Std dev |
| No Antigen | 697 | 18 | | |
| 1 μg/mL | 2078 | 50.5 | 7229 | 1968 |
| 3 μg/mL | 149752 | 7960.4 | 134127 | 15480 |
| 10 μg/mL | 156417 | 21302.6 | 146092 | 13377 |

T-cell line 222-2F1, generated from Donor 222 by initial stimulation with COP, was shown in at least two experiments to proliferate comparably following restimulation with GMA and COP. Table 8 shows the results of an ATP proliferation assay carried out on Day 56 of culturing following stimulation with 3 or 10 μg/mL of GMA or COP. ATP levels were measured at 48 hours after stimulation. The control in the GMA series was no antigen, and the control in the COP series was MBP. The response to GMA in comparison to COP at the 10 μg/mL dose in this assay was 85.1%.

TABLE 8

| Antigen Reactivity of Cell Line 222-2F12 (Data from FIG. 5C) | | |
|---|---|---|
| | GMA | COP |
| No Antigen | 4442 | 2417 |
| 1 μg/mL | 6500 | 5281 |
| 3 μg/mL | 8520 | 8684 |
| 10 μg/mL | 12382 | 11747 |

On Day 56 of culturing, after six total rounds of stimulation, cell line 222-2F12 was assayed for proliferation in response to stimulation with GA and a series of non-canonical peptides. For the assay, 0, 3, 10, or 30 μg/mL of each of peptides GL 14, GLT 631, GAT 111, and GAT 631, COP, and GMA, were added to the T-cell lines at $1\times10^5$ cells/mL, in the presence of mitomycin C-treated autologous B-LCL. Proliferation was measured by luminescent ATP assay. Cell line 222-2F12 responded to GL 14 at 3 μg/mL, and not to the other non-canonical GA peptides tested. The response to GMA in comparison to COP at the 10 μg/mL dose in this assay was 99.4%. The data are shown in Table 9.

Cytokine Production by Donor 1 Human T-Cell Lines Stimulated with Copaxone

Based on the increases in ATP level observed (i.e., a ratio of relative luminescence in wells with antigen to control wells without antigen of two or more), fifteen presumptive GA-specific T-cell lines in the original plate were moved to a 24-well plate at Day 26 and restimulated with 10 μg/mL Copaxone in the presence of autologous EBV-transformed B-LCL ($5\times10^5$ per well, i.e., $2.5\times10^5$/mL). At Day 27 IL-2 was added. On Day 34, the fifteen presumptive lines were restimulated with 10 μg/mL GMA or 10 μg/mL COP in the presence of mitomycin-treated autologous B-LCL ($4\times10^4$ per well; $2\times10^5$ per mL), or incubated with mitomycin-treated autologous B-LCL and no antigen. On Day 35 IL-2 was added to continued cultures. On Day 36 culture supernatant was collected from test cultures and IFN-γ production measured by ELISA (48 hours after restimulation). The results are shown in Table 10. IFN-γ protein concentrations were determined using a TMB standard curve.

TABLE 10

IFN-γ Produced by Donor 1 COP T-Cell Lines in Response to Stimulation with GMA or COP.

| | IFN-γ: T-Cells Alone | | IFN-γ: T-Cells + B-LCL | | IFN-γ: T-Cells + GMA, B-LCL | | IFN-γ: T-Cells + Copaxone, B-LCL | |
|---|---|---|---|---|---|---|---|---|
| Line | Mean | Std Dev | Mean | Std Dev | Mean | Std Dev | Mean | Std Dev |
| 222-2D8 | 224 | 38 | 270 | 18 | >1000 | | >1000 | |
| 222-1C5 | 849 | 37 | 821 | 118 | 776 | 53 | 700 | 49 |
| 222-2E1 | 303 | 32 | 457 | 23 | >1000 | | >1000 | |
| 222-1H12 | 943 | 13 | >1000 | | >1000 | | >1000 | |
| 222-2B11 | 389 | 20 | 354 | 8 | >1000 | | >1000 | |
| 222-2D2 | 25 | 7 | 68 | 11 | 131 | 13 | 133 | 11 |
| 222-2C3 | 489 | 32 | 538 | 32 | >1000 | | >1000 | |
| 222-2B8 | 686 | 10 | 599 | 44 | >1000 | | >1000 | |
| 222-2G12 | 294 | 11 | 515 | 35 | >1000 | | >1000 | |
| 222-2C5 | 306 | 12 | 325 | 56 | 245 | 45 | 273 | 8 |
| 222-2F12 | 232 | 17.9 | 295 | 17.1 | >1000 | | >1000 | |
| 222-2G4 | 94 | 3.2 | 280 | 26.2 | 438 | 12.8 | 416 | 29.0 |
| 222-1F8 | 28 | 9.3 | 120 | 7.5 | 169 | 14.4 | 156 | 16.2 |
| 222-1G8 | 907 | | >1000 | | >1000 | | >1000 | |
| 222-2C1 | 206 | 33 | 369 | 28 | 392 | 56 | 417 | 48 |

(Data in mean pg/mL of triplicate cultures.)

TABLE 9

Reactivity of Donor 1 COP T-Cell Line 222-2F12 to Non-Canonical Peptides (Day 56)

| | 0 μg/mL | | 3 μg/mL | | 10 μg/mL | | 30 μg/mL | |
|---|---|---|---|---|---|---|---|---|
| | Mean | Std dev | Mean | Std dev | Mean | Std dev | Mean | Std dev |
| COP | 5673 | 664 | 233087 | 4 | 230009 | 3534 | 118769 | 7210 |
| GLT 631 | | | 5277 | 1002 | 4934 | 809 | 5217 | 1933 |
| GAT 631 | | | 4342 | 187 | 3226 | 378 | 3071 | 923 |
| GAT 111 | | | 3914 | 333 | 3590 | 748 | 2430 | 288 |
| GL 14 | | | 17007 | 350 | 331 | 288 | 203 | 175 |
| GMA | | | 232779 | 451 | 228761 | 2425 | 125994 | 7400 |

At least seven Donor 1 COP T-cell lines, 222-2D8, 222-2E1, 222-2B11, 222-2C3, 222-2B8, 222-2G12, and 222-2F12, produced IFN-γ in response to GA, and the cell lines reacted to both Copaxone and GMA.

The 222-2D8, 222-1H12, 222-105, and 222-2D2 Day 34 supernatants also were tested in triplicate for IFN-γ, IL-2, IL-10, IL-8, IL-5, IL-113, TNF-α, and TNF-β secretion in response to GMA, COP, or no antigen (as a control) by immunofluorescent bead assay (FlowCytoMix™ kit). Little or no IL-4, IL-6, or IL-12 was detected. Table 11 shows the resulting cytokine secretion profiles of lines 222-2D8 and 222-1H12. Table 12 shows the resulting cytokine secretion profiles of lines 222-105, and 222-2D2. It is important to note that in Table 12 supernatants of T-cell line 1H12 were titrated, demonstrating that this cell line also produced interferon in response to both GMA and COP.

TABLE 11

Cytokine Production by Donor 1 COP T-Cell Lines 222-2D8, 222-1H12

| | IFN-γ (pg/mL) | IL-2 (pg/mL) | IL-10 (pg/mL) | IL-5 (pg/mL) | IL-1β (pg/mL) | IL-4 (pg/mL) | TNF-α (pg/mL) | TNF-β (pg/mL) |
|---|---|---|---|---|---|---|---|---|
| 222-2D8 Control | 92 | 0 | 56 | 22 | 0 | 0 | 0 | 0 |
| 222-2D8 GMA | 2616 | 52 | 107 | 1501 | 2420 | 41 | 405 | 243 |
| 222-2D8 COP | 3296 | 0 | 100 | 1587 | 2535 | 0 | 493 | 267 |
| 222-1H12 Control | 785 | 125 | 72 | 83 | 0 | 89 | 20 | 44 |
| 222-1H12 GMA | 3138 | 152 | 234 | 336 | 20 | 99 | 83 | 102 |
| 222-1H12 COP | 3626 | 0 | 240 | 398 | 59 | 0 | 22 | 98 |

TABLE 12

Cytokine Production by Donor 1 COP T-Cell Lines 222-1C5 and 222-2D2

| | IFN-γ (pg/mL) | IL-2 (pg/mL) | IL-10 (pg/mL) | IL-5 (pg/mL) | IL-8 (pg/mL) | IL-1β (pg/mL) | TNF-α (pg/mL) | TNF-β (pg/mL) |
|---|---|---|---|---|---|---|---|---|
| 222-1C5 Control | 590.55 | 145.76 | 74.93 | 95.43 | <= 0 | 88.72 | 6.64 | 19.5 |
| 222-1C5 GMA | 511.42 | 185.35 | 77.88 | 67.83 | <= 0 | 94.12 | 31.35 | 29.94 |
| 222-1C5 COP | 416.83 | <= 0 | 50.58 | 56.39 | <= 0 | <= 0 | <= 0 | 15.34 |
| 222-2D2 Control | 9.11 | 24.59 | 35.81 | 14.93 | <= 0 | 22.54 | <= 0 | 5.79 |
| 222-2D2 GMA | 53.75 | 55.42 | 26.12 | 29.13 | <= 0 | 103.85 | 5.35 | 5.79 |
| 222-2D2 COP | 120 | 210.47 | 45.09 | 38.13 | 0.85 | 130.9 | 30.87 | 23.15 |

The cultures were restimulated on days 46, 56, 67 and 75. On Day 56, cell lines 222-2D8, 222-1H12, 222-2F12, 222-2B8, 222-105, 222-2B11, and 222-2E1 again were tested for reactivity to stimulation with 1, 3, or 10 μg/mL of GMA or COP in a proliferation assay. ATP levels were measured in all seven cell lines at 48 hours (results in FIGS. 5A-G) after stimulation. The control in the GMA series was no antigen, and the control in the COP series was MBP.

Four culture supernatants (from 222-2B8, 222-105, 222-2B11, and 222-2E1) taken 24 hours after the Day 56 restimulation were assayed for cytokines, using a bead-based multiplex assay (results in Tables 13-16). All cytokine values represent the mean of triplicate values in pg/mL. In both the proliferation and cytokine assay the lines showed reactivity to both GMA and COP stimulation. Line 105, previously identified as not making IFN-γ in response to stimulation with GA, was found, after appropriate dilution of supernatants to produce IFN-γ in response to both GMA and COP, and in comparable amounts (see Table 14).

TABLE 13

Cytokine Production by Donor 1 COP T-Cell Line 222-2B8

| | IFN-γ (pg/mL) | IL-2 (pg/mL) | IL-10 (pg/mL) | IL-22 (pg/mL) | IL-13 (pg/mL) | IL-5 (pg/mL) | TNF-α (pg/mL) |
|---|---|---|---|---|---|---|---|
| Control | 0 | 0 | 0 | 57.94 | 11.85 | 0 | 0 |
| GMA-1 μg/mL | 1.88 | 0 | 0 | 0 | 183.09 | 0 | 0 |
| GMA-3 μg/mL | 44.52 | 1.6 | 1.8 | 63.98 | 1214.45 | 78.29 | 0 |
| GMA-10 μg/mL | 140.65 | 0 | 41 | 124.15 | 3162.51 | 400.46 | 96.57 |
| MBP | 0 | 0 | 0 | 20.62 | 26.77 | 0 | 0 |
| Control | 0 | 0 | 0 | 57.94 | 11.85 | 0 | 0 |
| COP-1 μg/mL | 8.46 | 0 | 2.99 | 83.01 | 204.31 | 0 | 0 |

TABLE 13-continued

Cytokine Production by Donor 1 COP T-Cell Line 222-2B8

| | IFN-γ (pg/mL) | IL-2 (pg/mL) | IL-10 (pg/mL) | IL-22 (pg/mL) | IL-13 (pg/mL) | IL-5 (pg/mL) | TNF-α (pg/mL) |
|---|---|---|---|---|---|---|---|
| COP-3 μg/mL | 39.91 | 19.65 | 2.83 | 77.82 | 1028.23 | 30.3 | 0 |
| COP-10 μg/mL | 119.12 | 0 | 36.16 | 143.57 | 2825.8 | 314.77 | 91.29 |
| MBP | 0 | 0 | 0 | 20.62 | 26.77 | 0 | 0 |

TABLE 14

Cytokine Production by Donor 1 COP T-Cell Line 222-1C5

| | IFN-γ (pg/mL) | IL-2 (pg/mL) | IL-10 (pg/mL) | IL-22 (pg/mL) | IL-13 (pg/mL) | IL-5 (pg/mL) | TNF-α (pg/mL) |
|---|---|---|---|---|---|---|---|
| Control | 84 | 80 | 5 | 105 | 107 | 0 | 14 |
| GMA-1 μg/mL | 181 | 30 | 11 | 39 | 154 | 0 | 3 |
| GMA-3 μg/mL | 325 | 83 | 38 | 101 | 316 | 0 | 72 |
| GMA-10 μg/mL | 664 | 0 | 55 | 0 | 942 | 0 | 80 |
| MBP | 64 | 0 | 0 | 36 | 82 | 0 | 9 |
| Control | 84 | 80 | 5 | 105 | 107 | 0 | 14 |
| COP-1 μg/mL | 158 | 0 | 11 | 0 | 129 | 0 | 11 |
| COP-3 μg/mL | 256 | 0 | 16 | 32 | 254 | 0 | 42 |
| COP-10 μg/mL | 585 | 40 | 49 | 42 | 837 | 0 | 42 |
| MBP | 64 | 0 | 0 | 36 | 82 | 0 | 9 |

TABLE 15

Cytokine Production by Donor 1 COP T-Cell Line 222-B11

| | IFN-γ (pg/mL) | IL-2 (pg/mL) | IL-10 (pg/mL) | IL-22 (pg/mL) | IL-13 (pg/mL) | IL-5 (pg/mL) | TNF-α (pg/mL) |
|---|---|---|---|---|---|---|---|
| Control | 0 | 19.65 | 3.79 | 84.94 | 36.59 | 0 | 0 |
| GMA-1 μg/mL | 0 | 0 | 1.3 | 42.51 | 29.41 | 0 | 0 |
| GMA-3 μg/mL | 0 | 0 | 0 | 51.87 | 133.55 | 0 | 0 |
| GMA-10 μg/mL | 37.79 | 0 | 0.4 | 0 | 1563.22 | 94.56 | 0 |
| MBP | 0 | 0 | 0 | 0 | 0.83 | 0 | 0 |
| Control | 0 | 19.65 | 3.8 | 84.94 | 36.59 | 0 | 0 |
| COP-1 μg/mL | 0.65 | 63.02 | 0 | 69.37 | 47.69 | 0 | 0 |
| COP-3 μg/mL | 0 | 0 | 0 | 45.67 | 105.51 | 0 | 0 |
| COP-10 μg/mL | 47.35 | 0 | 11.27 | 19.45 | 1839.63 | 119 | 13.51 |
| MBP | 0 | 0 | 0 | 0 | 0.83 | 0 | 0 |

TABLE 16

Cytokine Production by Donor 1 COP T-Cell Line 222-2E1

| | IFN-γ (pg/mL) | IL-2 (pg/mL) | IL-10 (pg/mL) | IL-22 (pg/mL) | IL-13 (pg/mL) | IL-5 (pg/mL) | TNF-α (pg/mL) |
|---|---|---|---|---|---|---|---|
| Control | 22.54 | 67.91 | 0 | 75.29 | 54.48 | 0 | 0 |
| GMA-1 μg/mL | 49.11 | 0 | 0 | 21.77 | 146.02 | 0 | 9.36 |
| GMA-3 μg/mL | 162.68 | 0 | 7.1 | 25.71 | 1050.77 | 0 | 65.44 |
| GMA-10 μg/mL | 349.76 | 0 | 16.33 | 0 | 2036.36 | 128.4 | 170.24 |
| MBP | 20.69 | 42.43 | 2.28 | 107.54 | 51.1 | 0 | 13.51 |
| Control | 22.54 | 67.91 | 0 | 75.29 | 54.48 | 0 | 0 |
| COP-1 μg/mL | 53.73 | 26.46 | 5.3 | 72.54 | 165.79 | 0 | 25.28 |
| COP-3 μg/mL | 163.61 | 40.39 | 12.19 | 40.37 | 1037.93 | 0 | 0 |
| COP-10 μg/mL | 405.26 | 0 | 22 | 60.95 | 2046.94 | 106.24 | 333.22 |
| MBP | 20.69 | 42.43 | 2.3 | 107.54 | 51.1 | 0 | 13.51 |

Cell lines 222-2D8, 222-1H12, and 222-2F12 were further assayed after 48 hours (on Day 56, following the 6th stimulation) for cytokine secretion by immunofluorescent bead assay (results in FIGS. 6A-F). IL-12p70, IFN-γ, IL-2, IL-10, IL-8, IL-6, IL-5, IL-4, IL-1β, TNF-α (TNF), and TNF-β (LT) secretion were measured in response to stimulation with 1, 3, or 10 μg/mL GMA, or 1, 3, or 10 μg/mL COP, as well as a no-antigen control and an MBP control, in the presence of autologous EBV-transformed B-LCL. FIGS. 6A, C, and E show cytokine secretion by the three Donor 1 cell lines in response to the three concentrations of GMA and FIGS. 6B, D, and F show their cytokine secretion in response to three concentrations of COP. The arrows indicate the position of the first bar in each cytokine dataset, i.e., the control sample, followed toward the right by the secretion levels in cells treated with 1 μg/mL GA, 3 μg/mL GA, 10 μg/mL GA, and MBP, in that order. Each of the three cell lines gave a different cytokine secretion profile. The cell lines treated with 10 μg/mL GA produced the highest levels of cytokines (the fourth bar from left in each set).

Donor 2: Cell Lines Stimulated with GMA

PBMC were obtained from a normal, healthy, 63-year old female donor having MHC Class II HLA-DRβ1 04:01, 04:04 (Donor 2). The isolated PBMC were cultured on Day 0 at $2\times10^5$ cells per well ($1\times10^6$ cells/mL) with 100 μg/mL GMA in AIM V medium, and cultured as described in the Methods. The cultures were screened for proliferation at Day 13 using a BrdU uptake assay after stimulation with 100 μg/mL GMA using mitomycin-treated autologous PBMC as APC. Nine presumptive GA-specific human T-cell lines were selected for expansion and further analysis based on an increase in the OD of the GA-stimulated test sample of at least 50% relative to an unstimulated control sample. Table 17 shows the BrdU proliferation data for the nine presumptive GA-specific human T-cell lines obtained from Donor 2 PBMC. It is notable that for all of these T-cell lines the difference in BrdU uptake from control was greater than two-fold.

TABLE 17

BrdU Uptake by Donor 2 Human T-Cell Lines after GMA Stimulation.

| Donor 2 Cell Line | Control ($OD_{450}$) | GMA ($OD_{450}$) |
|---|---|---|
| 206-1A6 | 0.220 | 0.563 |
| 206-1A7 | 0.329 | 0.688 |
| 206-1A11 | 0.151 | 0.452 |
| 206-1C12 | 0.272 | 0.626 |
| 206-1H1 | 0.109 | 0.447 |
| 206-1H2 | 0.095 | 0.526 |
| 206-2A1 | 0.259 | 0.548 |
| 206-2A10 | 0.162 | 0.444 |
| 206-2C3 | 0.146 | 0.358 |

These presumptive Donor 2 T-cell lines were expanded by stimulation with 10 μg/mL GMA and mitomycin-treated autologous PBMC and later with autologous EBV-transformed B-LCL. Line 206-1A7 was switched to X-VIVO 15 medium. On Day 88 line 206-1A7 was stimulated with B-LCL and 10 μg/mL GMA or 1 μg/mL Tetanus Toxoid (TT). After four days the culture was tested for proliferation by ATP assay and supernatants were tested for IFN-γ and TNF-α secretion by ELISA. FIG. 7A shows proliferation of T-cell line 206-1A7 in response to stimulation with GMA at concentrations ranging from 0 to 100 μg/mL as indicated. FIG. 7B shows IFN-γ secretion by line 206-1A7. In both experiments, the 0 concentration controls contain no GMA. The light gray 0 concentration bars in FIGS. 7A and B represent samples treated with 1 μg/mL TT. TNF-α was not detectable. This cell line was lost to bacterial contamination.

Donor 3: Cell Lines Stimulated with GMA

PBMC were obtained from Donor 3, a normal, healthy, 52-year old male donor having MHC. Class II HLA-DRβ1*15, *11. Cultures were stimulated at $1\times10^5$ cells per well ($1\times10^6$ cells/mL) in a U bottom 96-well plate with 10 μg/mL GMA. IL-2 was added on Days 3 and 7, and cultures were restimulated with 10 μg/mL GMA on Day 14 in the presence of $2\times10^4$ autologous B-LCL per well, and screened by ATP proliferation assay. Based on the assay data (Table 18), fourteen presumptive GA-specific T-cell lines were selected and expanded to a 24-well plate on Day 24. IL-2 was added on Day 25.

TABLE 18

Donor 3 Presumptive GMA Cell Lines - ATP Proliferation Assay

| Donor 3 Cell Line | Control | GMA 10 μg/mL |
|---|---|---|
| 165-B2G | 9692 | 28770 |
| 165-B5G | 15423 | 63023 |
| 165-B11G | 18412 | 56588 |
| 165-C4G | 14869 | 62306 |
| 165-C5G | 14240 | 76296 |
| 165-C8G | 18205 | 79281 |
| 165-D8G | 30331 | 136938 |
| 165-E7G | 18215 | 66364 |
| 165-E9G | 17059 | 52948 |
| 165-F2G | 14734 | 44951 |
| 165-F5G | 16943 | 100677 |
| 165-F8G | 17986 | 72716 |
| 165-F10G | 13314 | 42447 |
| 165-H11G | 17149 | 52850 |

(Data in RLU.)

For these cell lines, the ratio of proliferation in response to GMA:control (APC only) was greater than 3.0. On Day 32 these cell lines were restimulated at 1-$2.5\times10^5$ cells/mL with 10 μg/mL GMA in the presence of $2.5\times10^5$ autologous B-LCL and rescreened by proliferation assay. For the assay, stimulation with 10 μg/mL GMA, 10 μg/mL COP, or 1 μg/mL Tetanus Toxoid (as a control) was tested. All 8 cell lines tested were responsive to GMA and COP (Table 19).

TABLE 19

Confirmation of Donor 3 GMA Culture Antigen Reactivity by ATP Proliferation Assay

| | 165-F2G | | 165-B5G | | 165-F8G | | 165-H11G | |
|---|---|---|---|---|---|---|---|---|
| Antigen | Mean | Std dev | Mean | Std dev | Mean | Std dev | Mean | Std dev |
| None | 17575 | 570 | 27019 | 2046 | 20130 | 954 | 12847 | 591 |
| COP | 79071 | 2082 | 51934 | 2971 | 40596 | 2709 | 59388 | 1477 |
| GMA | 74327 | 5970 | 51364 | 1200 | 35103 | 1993 | 54450 | 498 |
| Tetanus | 17519 | 649 | 20861 | 81 | 19132 | 1294 | 9511 | 962 |

| | 165-F5G | | 165-D8G | | 165-E9G | | 165-F10G | |
|---|---|---|---|---|---|---|---|---|
| Antigen | Mean | Std dev | Mean | Std dev | Mean | Std dev | Mean | Std dev |
| None | 40831 | 2747 | 39276 | 453 | 17077 | 1992 | 15039 | 1436 |
| COP | 114287 | 3327 | 83592 | 4132 | 64509 | 6068 | 120610 | 1200 |
| GMA | 108326 | 11172 | 81880 | 2323 | 62461 | 3778 | 111713 | 3974 |
| Tetanus | 29012 | 1074 | 27814 | 2555 | 11745 | 2413 | 9121 | 2749 |

(Data in RLU.)

Cytokine Production by Donor 3 Human T-Cell Lines Stimulated with Different Concentrations of GMA Culture medium from six of the cell lines was tested in a cytokine multiplex assay, confirming reactivity and revealing production of IL-13, IL-22, IL-5 and IFN-γ (Table 20).

TABLE 20

Cytokine Production by Donor 3 GMA Responsive T Cells

| | IFN-γ (pg/mL) | IL-22 (pg/mL) | IL-13 (pg/mL) | IL-4 (pg/mL) | IL-5 (pg/mL) |
|---|---|---|---|---|---|
| 165-B5G CONTROL | 0 | 40 | 321 | 2 | 4 |
| 165-B5G GMA | 201 | 248 | 2930 | 47 | 399 |
| 165-B5G COP | 190 | 106 | 2927 | 17 | 374 |
| 165-B5G TETANUS | 0 | 98 | 294 | 16 | 14 |
| 165-D8G CONTROL | 0 | 143 | 172 | 13 | 0 |
| 165-D8G GMA | 121 | 405 | 3326 | 12 | 309 |
| 165-D8G COP | 115 | 365 | 3121 | 14 | 309 |
| 165-D8G TETANUS | 0 | 146 | 186 | 0 | 0 |
| 165-F8G CONTROL | 235 | 143 | 378 | 4 | 145 |
| 165-F8G GMA | 889 | 197 | 1193 | 5 | 370 |
| 165-F8G COP | 771 | 198 | 1017 | 0 | 297 |
| 165-F8G TETANUS | 286 | 156 | 407 | 3 | 179 |
| 165-E9G CONTROL | 0 | 126 | 87 | 0 | 0 |
| 165-E9G GMA | 837 | 245 | 1499 | 6 | 236 |
| 165-E9G COP | 638 | 192 | 1232 | 12 | 208 |
| 165-E9G TETANUS | 0 | 96 | 83 | 5 | 0 |
| 165-H11G CONTROL | 94 | 123 | 93 | 13 | 9 |
| 165-H11G GMA | 724 | 201 | 1058 | 7 | 320 |
| 165-H11G COP | 724 | 190 | 1095 | 9 | 321 |
| 165-H11G TETANUS | 84 | 163 | 107 | 17 | 0 |
| 165-F10G CONTROL | 7 | 176 | 263 | 13 | 63 |
| 165-F10G GMA | 1108 | 680 | 10897 | 114 | 2589 |
| 165-F10G COP | 1165 | 686 | 11285 | 122 | 2586 |
| 165-F10G TETANUS | 2 | 54 | 248 | 0 | 44 |

On Day 33 the cell lines were expanded into T-25 flasks (10 mL volume with 10 U IL-2 per mL). On Day 40, 12 cell lines were again tested for reactivity using 1, 3 or 10 μg/mL GMA or COP, or 10 μg/mL MBP as a control. Eleven of the 12 cell lines (all but F2G) were responsive to both antigen preparations. The results are shown in Table 21.

TABLE 21

Donor 3 Confirmation of GMA Cell Line Antigen Reactivity by ATP Proliferation Assay

| | 165-B5G | | 165-F8G | | 165-F5G | | 165-D8G | |
|---|---|---|---|---|---|---|---|---|
| | Mean | Std dev | Mean | Std dev | Mean | Std dev | Mean | Std dev |
| No Antigen | 4422 | 577 | 4857 | 367 | 3704 | 517 | 9496 | 763 |
| GMA 1 μg/mL | 3866 | 374 | 4804 | 684 | 5669 | 324 | 9427 | 957 |
| GMA 3 μg/mL | 6591 | 792 | 6841 | 115 | 14024 | 943 | 12644 | 817 |
| GMA 10 μg/mL | 12367 | 2111 | 11880 | 1318 | 23774 | 1393 | 31264 | 529 |
| COP 1 μg/mL | 3672 | 567 | 3690 | 902 | 4332 | 204 | 8088 | 899 |
| COP 3 μg/mL | 3673 | 781 | 3184 | 527 | 6099 | 670 | 8722 | 2268 |
| COP 10 μg/mL | 14282 | 516 | 10663 | 880 | 19498 | 2649 | 28872 | 1737 |
| MBP | 3398 | 622 | 3366 | 404 | 2904 | 233 | 6909 | 320 |
| | 165-C5G | | 165-H11G | | 165-E9G | | 165-F10G | |
| | Mean | Std dev | Mean | Std dev | Mean | Std dev | Mean | Std dev |
| No Antigen | 3398 | 474 | 2541 | 219 | 2882 | 301 | 3977 | 444 |
| GMA 1 μg/mL | 12236 | 932 | 10205 | 715 | 2961 | 273 | 6015 | 702 |
| GMA 3 μg/mL | 36288 | 763 | 27515 | 3713 | 7837 | 98 | 17900 | 875 |
| GMA 10 μg/mL | 45444 | 2719 | 44067 | 1144 | 24935 | 1588 | 30198 | 2512 |
| COP 1 μg/mL | 12667 | 933 | 9102 | 561 | 3216 | 928 | 8427 | 923 |
| COP 3 μg/mL | 24835 | 2274 | 15637 | 2647 | 5584 | 1143 | 31303** | 2532 |
| COP 10 μg/mL | 47537 | 1478 | 43786 | 1906 | 25454 | 2250 | 29986 | 1994 |
| MBP | 3401 | 538 | 2925 | 265 | 2892 | 312 | 3585 | 542 |
| | 165-B2G | | 165-C4G | | 165-E7G | | 165-F2G | |
| | Mean | Std dev | Mean | Std dev | Mean | Std dev | Mean | Std dev |
| No Antigen | 2149 | 176 | 2558 | 131 | 2083 | 147 | 1659 | 137 |
| GMA 1 μg/mL | 4034 | 456 | 3434 | 309 | 2569 | 221 | 1753 | 226 |
| GMA 3 μg/mL | 20994 | 1235 | 6312 | 527 | 6610 | 700 | 1422 | 181 |
| GMA 10 μg/mL | 38244 | 3194 | 19169 | 1494 | 14279 | 967 | 1502 | 116 |
| COP 1 μg/mL | 3779 | 446 | 3143 | 608 | 3794 | 695 | 1700 | 120 |
| COP 3 μg/mL | 11983 | 1946 | 3959 | 393 | 4147 | 1073 | 1332 | 86 |
| COP 10 μg/mL | 10980* | 1844 | 3717* | 308 | 12565 | 240 | 1554 | 61 |
| MBP | 3320 | 440 | 3482 | 404 | 2989 | 438 | 2345 | 1269 |

*Well contained 3 μg/mL COP.
**Well contained 10 μg/mL COP.

Donor 3: Cell Lines Stimulated with COP

In an initial stimulation, isolated PBMC were plated on Day 0 at $2\times10^5$ cells per well ($1\times10^6$ cells/mL) with 100 μg/mL COP in AIM V medium, and cultured as described above in the Methods. Similarly, PBMC were plated on Day 0 at $2\times10^5$ cells per well with 100 μg/mL GMA in AIM V medium. The cultures were stimulated with 100 μg/mL of the respective antigen (COP or GMA) in the presence of mitomycin-treated autologous APC, and screened for proliferation at Day 13 using a BrdU uptake assay. None of the lines tested showed GA-specific reactivity. Significant loss of cells was observed following addition of GA, suggesting use of a lower concentration of GA. GA titration studies showed better proliferative and cytokine responses at 10 and 30 μg/mL GA than at 100 μg/mL GA.

A second set of presumptive COP-responsive T-cell lines was generated by plating PBMC plated on Day 0 at $1\times10^5$ cells per well with 10 μg/mL COP in X VIVO-15 medium. IL-2 was added at 2 U per well on days 3 and 7, and on Day 14 the cultures were screened for proliferation by split well assay. The lines were restimulated (in a first restimulation) with 10 μg/mL COP in the presence of $2\times10^4$ autologous B-LCL as APC and a luminescent ATP assay used to measure proliferation. Fourteen wells were selected for expansion if the ratio of proliferation after stimulation with COP to proliferation in response to the APC control was greater than 3.0 (Table 22).

TABLE 22

Donor 3 Presumptive COP Responsive T Cell Lines - ATP Proliferation Assay

| Donor 3 Cell Line | Control | COP 10 μg/mL |
|---|---|---|
| 165-B6C | 14966 | 77564 |
| 165-B10C | 10604 | 54779 |
| 165-C4C | 23510 | 108089 |
| 165-C7C | 12707 | 63491 |
| 165-C9C | 22840 | 113199 |
| 165-D2C | 12767 | 54895 |
| 165-D3C | 18380 | 119241 |
| 165-D11C | 13302 | 82759 |
| 165-E3C | 12219 | 69893 |
| 165-E9C | 22512 | 98168 |
| 165-F3C | 13157 | 93437 |
| 165-F4C | 13598 | 96289 |
| 165-F6C | 23457 | 135516 |
| 165-F9C | 19736 | 145768 |

(Data in RLU.)

On Day 24 the continued cultures of the lines listed in Table 22 were expanded into a 24-well plate (2 mL/well) and restimulated with 10 μg/mL COP in the presence of $5\times10^4$ autologous B-LCL in a second restimulation. On Day 25, 10 U/mL IL-2 were added. On Day 32, 2-$5\times10^5$ T-cells from each of six of the cell lines were restimulated with 10 μg/mL COP or tetanus toxoid in the presence of $5\times10^4$ autologous B-LCL for confirmatory proliferation testing by luminescent ATP proliferation assay. All six lines showed reactivity to both COP and GMA (Table 23).

TABLE 23

Confirmation of Antigen Reactivity of Six Donor 3 COP Cell Lines by ATP Proliferation Assay

| | 165-D3C | | 165-F3C | | 165-E3C | |
|---|---|---|---|---|---|---|
| Antigen | Mean | Std dev | Mean | Std dev | Mean | Std dev |
| None | 1283 | 32 | 245 | 32 | 1351 | 114 |
| COP | 3362 | 314 | 1141 | 21 | 3778 | 78 |
| GMA | 3436 | 125 | 1257 | 74 | 3723 | 389 |
| Tetanus | 1282 | 56 | 239 | 23 | 1205 | 67 |
| | **165-B6C** | | **165-F6C** | | **165-D11C** | |
| Antigen | Mean | Std dev | Mean | Std dev | Mean | Std dev |
| None | 259 | 33 | 563 | 27 | 220 | 16 |
| COP | 952 | 82 | 1484 | 49 | 525 | 96 |
| GMA | 1058 | 69 | 1489 | 94 | 416 | 16 |
| Tetanus | 211 | 31 | 510 | 3 | 178 | 22 |

(Data in RLU.)

On Day 32, the continued cultures corresponding to the assayed cultures also were restimulated, and on Day 33 seven cell lines (165-B6C, 165-D11C, 165-D11C, 165-F6C, 165-D3C, 165-E3C, and 165-F3C) were expanded to T-25 flasks (10 mL total volume, 10 U/mL IL-2). Seven others were left in the 24-well plate for two additional days before expanding to flasks. Four of the cell lines in the 24-well plate (165-F4C, 165-C9C, 165-E9C, and 165-F9C) were lost. On Day 39, three of the cell lines (165-D2C, 165-C7C, and 165-C4C) in the 24-well plate again were tested for reactivity to three concentrations of COP and GMA, including a no antigen and an MBP control (all in the presence of $5\times10^4$ autologous mitomycin-treated B-LCL as APC) by ATP proliferation assay. All three cell lines responded comparably to COP and GMA (Table 24). At Day 40, after the fourth restimulation on Day 39, the continued cultures corresponding to the assayed cell lines were expanded from the 24-well plate to T-25 flasks with IL-2 as described above.

TABLE 24

Confirmation of Antigen Reactivity of Three Donor 3 COP Cell Lines by ATP Proliferation Assay

| | 165-D2C | | 165-C7C | | 165-C4C | |
|---|---|---|---|---|---|---|
| | Mean | Std dev | Mean | Std dev | Mean | Std dev |
| No Antigen | 2407 | 344 | 1702 | 211 | 1783 | 29 |
| GMA 1 µg/mL | 3881 | 159 | 3307 | 306 | 9367 | 174 |
| GMA 3 µg/mL | 7503 | 808 | 12832 | 1361 | 26279 | 1785 |
| GMA 10 µg/mL | 13253 | 2024 | 42739 | 3834 | 31014 | 3030 |
| COP 1 µg/mL | 3955 | 655 | 3670 | 332 | 11653 | 1386 |
| COP 3 µg/mL | 7378 | 934 | 16527 | 1385 | 28474 | 2184 |
| COP 10 µg/mL | 14239 | 315 | 40194 | 3057 | 28262 | 749 |
| MBP 10 µg/mL | 1927 | 489 | 1673 | 92 | 1631 | 131 |

Seven Donor 3 COP lines were tested on Day 46 of culture. The cell lines were restimulated using 3 concentrations of COP and GMA, including a no antigen and an MBP control as before (all in the presence of $5\times10^4$ autologous B-LCL). Proliferation was measured by ATP assay after 3 days. The results are shown below in Table 25.

TABLE 25

Donor 3 COP Responsive T Cell Lines-ATP Proliferation Assay at Different Antigen Doses

| | 165-B6C | | 165-B10C | | 165-F6C | | 165-F3C | |
|---|---|---|---|---|---|---|---|---|
| | Mean | Std dev | Mean | Std dev | Mean | Std dev | Mean | Std dev |
| No antigen | 4966 | 484 | 4739 | 280 | 4876 | 506 | 9937 | 1476 |
| GMA 1 µg/mL | 9925 | 1683 | 5592 | 1290 | 18511 | 5644 | 45592 | 3040 |
| GMA 3 µg/mL | 38105 | 2486 | 13012 | 928 | 43634 | 1648 | 101328 | 8124 |
| GMA 10 µg/mL | 25839 | 2638 | 19866 | 3407 | 34321 | 3367 | 84268 | 6292 |
| COP 1 µg/mL | | | | | | | | |
| COP 3 µg/mL | 29815 | 930 | 8450 | 582 | 31382 | 4713 | 75407 | 5826 |
| COP 10 µg/mL | 34502 | 1598 | 19792 | 441 | 34071 | 279 | 85442 | 13367 |
| MBP 10 µg/mL | 3216 | 963 | 3003 | 165 | 2214 | 630 | 9849 | 1475 |
| | **165-D3C** | | **165-D11C** | | **165-E3C** | | **165-C8G** | |
| | Mean | Std dev | Mean | Std dev | Mean | Std dev | Mean | Std dev |
| No antigen | 11537 | 1527 | 7630 | 1028 | 4874 | 386 | 2598 | 570 |
| GMA 1 µg/mL | 61535 | 6445 | 15655 | 758 | 10662 | 1175 | 5605 | 1712 |
| GMA 3 µg/mL | 80112 | 15879 | 17777 | 3266 | 35044 | 5182 | 5002 | 201 |
| GMA 10 µg/mL | 107772 | 19471 | 56609 | 3513 | 68577 | 2466 | 30200 | 2759 |
| COP 1 µg/mL | 1248 | 303 | 486 | 49 | 364 | 17 | 400 | 65 |
| COP 3 µg/mL | 79792 | 9655 | 19410 | 1034 | 23785 | 2625 | 4821 | 766 |
| COP 10 µg/mL | 86270 | 20682 | 42017 | 3161 | 51822 | 1083 | 22961 | 2140 |
| MBP 10 µg/mL | 15482 | 2939 | 8406 | 495 | 7662 | 3966 | 5279 | 821 |

(Data in RLU.)

The continuing cell line cultures were restimulated (in the cell lines' fifth restimulation) on Day 46 by expanding to a 12-well plate at a 4 mL/well volume (each well containing $1\times10^6$ T-cells, $1\times10^6$ APC, with 10 µg/mL COP). The remaining cells were cryopreserved. On Day 47 the cell culture from each well of the 12-well plate was expanded into T-75 flasks (20 mL, 10 U/mL IL-2). A sixth restimulation was carried out on Day 53 by expanding into a 24-well plate (each well containing $5\times10^5$ T-cells and $5\times10^5$ APC per well, with 10 µg/mL COP), and remaining cells cryopreserved. On Day 54 the cell culture from each well of the 24-well plate was expanded into T-75 flasks as before. A seventh restimulation was carried out on Day 60 by expanding to into a 24-well plate (each well containing $5\times10^5$ T-cells, $5\times10^5$ APC, with 10 µg/mL COP), and remaining cells cryopreserved. On Day 61 the cell culture from each well of the 24-well plate was expanded into T-25 flasks. These cells were harvested and cryopreserved on Day 67, after a total of seven rounds of restimulation/expansion.

Donor 4: Cell Lines Stimulated with Copaxone

PBMC were obtained from a normal, healthy, 21-year old male donor having MHC Class II DRβ1*07, 13 (Donor 4). PBMC were collected by leukapheresis using ACD as an anticoagulant and separated by Ficoll-Paque gradient centrifugation.

Cultures were initiated in 96-well plates at $1\times10^5$ cells per well ($5\times10^5$ cells per mL) in X-VIVO 15 medium with 10 μg/mL COP, and cultured as described in the Methods. IL-2 was added at 10 U/mL on days 3 and 6 of culture. The cultures were screened for proliferation on Day 13 by luminescent ATP assay after restimulation with 10 μg/mL COP in the presence of $2\times10^5$ mitomycin-treated autologous PBMC per well ($1\times10^6$ cells per mL). Fifteen wells were scored as presumptively responsive based on an ATP ratio (COP stimulated:unstimulated control) of two or greater (Table 26).

TABLE 26

Donor 4 Presumptive COP Responsive T Cell Lines-ATP Proliferation Assay

| Donor 4 Cell Line | Control | COP 10 μg/mL |
|---|---|---|
| 205-1B4 | 41950 | 84937 |
| 205-1B7 | 32281 | 74147 |
| 205-1C4 | 35104 | 69861 |
| 205-1D1 | 31270 | 63419 |
| 205-1E1 | 19150 | 44198 |
| 205-1F2 | 27423 | 71947 |
| 205-1F4 | 16172 | 33143 |
| 205-1G3 | 24326 | 54211 |
| 205-1H1 | 14255 | 29824 |
| 205-1H3 | 24304 | 55518 |
| 205-1H4 | 19145 | 50307 |
| 205-1H5 | 26809 | 57608 |
| 205-1H7 | 19483 | 64436 |
| 205-1H9 | 15320 | 52972 |
| 205-1H11 | 20205 | 54232 |

(Data in RLU.)

T-cell line 205-1F4, generated from Donor 205 by initial stimulation with COP, was shown in at least two experiments to proliferate comparably following restimulation with GMA and COP.

Table 27 shows reactivity of 205-1F4 to GMA and COP assayed on Day 50 of culture, after four restimulations. The cell lines were restimulated in the presence of autologous B-LCL using three concentrations of COP and GMA, including a no antigen control. Proliferation was measured by luminescent ATP assay. The response to GMA in comparison to COP at the 10 μg/mL dose in this assay was 102.7%.

TABLE 27

Antigen Reactivity of Cell Line 205-1F4 (Day 50)

| | GMA | | COP | |
|---|---|---|---|---|
| | Mean | Std dev | Mean | Std dev |
| No Antigen | 2076 | 497 | 2076 | 497 |
| 1 μg/mL | 17341 | 4286 | 47254 | 19915 |
| 3 μg/mL | 195335 | 4478 | 169021 | 13990 |
| 10 μg/mL | 218954 | 7589 | 213196 | 4628 |

Table 28 shows reactivity of 205-1F4 to GMA and COP assayed on Day 58 of culture, after four restimulations. The cell lines were restimulated in the presence of autologous B-LCL using four concentrations of COP and GMA, including a no antigen control. Proliferation was measured by luminescent ATP assay. The response to GMA in comparison to COP at the 10 μg/mL dose in this assay was 98.5%.

TABLE 28

Antigen Reactivity of Cell Line 205-1F4 (Day 58)

| | GMA | | COP | |
|---|---|---|---|---|
| | Mean | Std dev | Mean | Std dev |
| No Antigen | 3193 | 462 | | |
| 3 μg/mL | 29921 | 4413 | 21031 | 1489 |
| 10 μg/mL | 30998 | 1112 | 31423 | 1493 |
| 30 μg/mL | 33915 | 652 | 31323 | 1133 |
| 100 μg/mL | 32698 | 1743 | 31188 | 3568 |

Cell lines 205-1H7 and 205-1H11 were stimulated on Day 59 of culture after a total of six stimulations (five restimulations). The proliferation responses of lines 205-1H7 and 205-1H11 in response to a range of antigen concentrations were measured by luminescent ATP assay. T-cells were collected from each culture, washed and added to the plates at 20,000 cells per well in a volume of 100 uL. All conditions were tested in triplicate. After 4 days incubation at 37° C., 6% $CO_2$, 100 μL of medium was removed from each well and 100 μL of CellTiterGlo® added to each well. The results are shown in Tables 29 and 30.

TABLE 29

Donor 4 T-Cell Line 205-1H7 Dose Response

| Ag Concentration (μg/mL COP) | Mean RLU | Standard Deviation |
|---|---|---|
| 0 | 3382 | 781 |
| 1 | 13131 | 334 |
| 10 | 175652 | 14847 |
| 30 | 190750 | 8994 |

TABLE 30

Donor 4 T-Cell Line 205-1H11 Dose Response

| Ag Concentration (μg/mL COP) | Mean RLU | Standard Deviation |
|---|---|---|
| 0 | 6941 | 593 |
| 1 | 12243 | 1712 |
| 10 | 147464 | 2228 |
| 30 | 112673 | 6037 |

Cytokine Production by Donor 4 Human T-Cell Lines Stimulated with COP

On Day 23 the positive wells (cell lines listed in Table 26) were transferred to a 24-well plate and restimulated with 10 μg/mL COP in the presence of mitomycin-treated autologous PBMC. IL-2 was added at Day 24. On Day 31 (after four rounds of restimulation) ten lines were restimulated with 10 μg/mL COP to confirm antigen reactivity by a cytokine secretion assay. T-cells were added at $2\times10^4$ cells/well in 96-well plates in X-VIVO 15 medium. Each line was separately stimulated with 10 μg/mL GMA, and 10 μg/mL COP in the presence of ($2\times10^5$ cells/well, i.e., $1\times10^6$ cells/ mL) mitomycin-treated autologous PBMC. Culture medium was collected after 20-24 hours for cytokine assay (Flow-Cytomix multiplex bead assay). The supernatants were tested in triplicate for IL-12 p70, IFN-γ, IL-2, IL-10, IL-6, IL-4, IL-5, TNF-α, and TNF-β secretion. Tables 31 and 32 show the resulting cytokine secretion profiles. Most tested cell lines secreted IFN-γ, IL-5, and TNF-α, in response to both GMA and COP. Secretion of IL-2, 11-10, and IL-4 varied among the lines. All samples also secreted IL-8 (data not shown).

TABLE 31

Cytokine Production by Donor 4 COP Responsive T-Cell Lines

| | IL-12 p70 (pg/mL) | IFN-y (pg/mL) | IL-2 (pg/mL) | IL-10 (pg/mL) | IL-6 (pg/mL) | IL-4 (pg/mL) | IL-5 (pg/mL) | TNF-α (pg/mL) | TNF-β (pg/mL) |
|---|---|---|---|---|---|---|---|---|---|
| 205-1B7 control | 6.48 | 29.28 | <=0 | <=0 | 11.31 | <=0 | 0.82 | 8.36 | 16.12 |
| 205-1B7 GMA | 44.57 | 828.5 | 10.89 | 182.81 | 187.85 | 187.29 | 6854.13 | 1305.37 | 217.5 |
| 205-1B7 COP | 18.39 | 935.78 | 27.99 | 210.01 | 195.27 | 200.19 | 7199.83 | 1286.09 | 244.68 |
| 205-1G3 control | 20.01 | 45.5 | 91.05 | 75.24 | 10.15 | 10.27 | 31.82 | 50.07 | 100.29 |
| 205-1G3 GMA | 2.37 | 193.91 | 5.27 | <=0 | 16.67 | <=0 | 121.17 | 68.79 | 17.66 |
| 205-1G3 COP | <=0 | 211.16 | 10.89 | <=0 | 11.79 | <=0 | 91.11 | 38.56 | <=0 |
| 205-1C4 control | <=0 | 0.04 | <=0 | <=0 | 5.42 | <=0 | <=0 | 10.54 | <=0 |
| 205-1C4 GMA | 46.89 | 1046.32 | 312.13 | 45.24 | 149.35 | 124.7 | 5434.06 | 1059.01 | 81.04 |
| 205-1C4 COP | 51.14 | 1212.03 | 478.51 | 50.31 | 159.24 | 199.97 | 6457.14 | 1529.22 | 69.07 |
| 205-1115 control | 3.18 | 32.31 | <=0 | <=0 | 6.61 | <=0 | 2.65 | 5.47 | 4.73 |
| 205-1H5 GMA | 8.78 | 902.95 | <=0 | <=0 | 52.4 | 46.82 | 2534.09 | 910.83 | 79.8 |
| 205-1H5 COP | 7.96 | 1149.77 | 15.14 | 28.45 | 57.31 | 79.67 | 3106.45 | 1260.75 | 88.62 |
| 205-1F5 control | 30.5 | 79.21 | 115.8 | 97.94 | 9.17 | 12.46 | 62.11 | 112.49 | 99.74 |
| 205-1F5 GMA | 67.53 | 479.26 | 197.46 | 231.63 | 314.54 | 328.72 | 13930.97 | 1084.01 | 260.35 |
| 205-1F5 COP | 55.94 | 452.76 | 205.85 | 323.52 | 318.25 | 293.46 | 13727.89 | 833.39 | 278.68 |
| 205-1H7 control | 2.46 | 3.48 | <=0 | <=0 | 6.76 | <=0 | <=0 | 17.73 | <=0 |
| 205-1H7 GMA | 13.42 | 1275.97 | 176.52 | <=0 | 64.82 | 58.41 | 96.95 | 552.89 | 34.81 |
| 205-1H7 COP | 11.11 | 1617.25 | 351.63 | 10.06 | 69.44 | 90.37 | 101.71 | 1924.81 | 49.17 |
| 1H9 control | <=0 | 5.39 | <=0 | <=0 | <=0 | <=0 | <=0 | 24.29 | <=0 |
| 1H9 GMA | <=0 | 182.77 | <=0 | <=0 | 74.92 | <=0 | <=0 | 161.89 | <=0 |
| 1H9 COP | <=0 | 419.21 | <=0 | <=0 | <=0 | <=0 | <=0 | 159.6 | <=0 |
| 1H11 control | 1.19 | 770.12 | <=0 | <=0 | <=0 | <=0 | 159.49 | 110.13 | <=0 |
| 1H11 GMA | 2.24 | 929 | 22.78 | 145 | 28.28 | <=0 | 3349.8 | 609.49 | <=0 |
| 1H11 COP | 3.68 | 1016.21 | 44.94 | 143.84 | 20.11 | 2.09 | 3665.58 | 754.13 | 1.55 |

Culture medium from each of two Donor 4 cell lines was assayed for an extended panel of cytokines, showing production of IL-13 and IL-22 (Table 32).

TABLE 32

Donor 4 Presumptive COP Responsive T Cell Lines - Extended Cytokine Multiplex Assay

| | IFN-γ | IL-2 | IL-10 | 1L-9 | IL-22 | IL-6 | IL-13 | IL-4 | IL-5 | TNF-α |
|---|---|---|---|---|---|---|---|---|---|---|
| 205-1B4 CONTROL | 54 | 38 | 0 | 7 | 99 | 15 | 217 | 10 | 2 | 133 |
| 205-1B4 GMA | 713 | 0 | 25 | 21 | 478 | 109 | 13895 | 117 | 3104 | 868 |
| 205-1B4 COP | 726 | 0 | 32 | 29 | 668 | 114 | 19288 | 174 | 3660 | 1336 |
| 205-1B4 TET | 1 | 0 | 0 | 1 | 82 | 719 | 168 | 0 | 0 | 342 |
| 205-1F4 CONTROL | 0 | 0 | 0 | 2 | 0 | 11 | 30 | 0 | 0 | 27 |
| 205-1F4 GMA | 1207 | 76 | 16 | 7 | 186 | 73 | 4506 | 7 | 1459 | 323 |

TABLE 32-continued

Donor 4 Presumptive COP Responsive T Cell Lines - Extended Cytokine Multiplex Assay

| | IFN-γ | IL-2 | IL-10 | 1L-9 | IL-22 | IL-6 | IL-13 | IL-4 | IL-5 | TNF-α |
|---|---|---|---|---|---|---|---|---|---|---|
| 205-1F4 COP | 1393 | 110 | 0 | 10 | 168 | 77 | 4502 | 10 | 1440 | 616 |
| 205-1F4 TET | 0 | 0 | 0 | 3 | 96 | 285 | 8 | 0 | 0 | 174 |

Donor 6: Cell Lines Stimulated with GMA

PBMC were obtained from a normal, healthy, 49-year old female donor having MHC Class II HLA-DRβ1*13, *15:01 (Donor 6). PBMC were collected by leukapheresis using ACD as an anticoagulant and separated by Ficoll-Paque gradient centrifugation.

Cultures were initiated in 96-well plates at $1\times10^5$ cells per well ($5\times10^5$ cells per mL) in X-VIVO 15 medium with 10 μg/mL GMA/001/014 (Lot 001), a lot of GA prepared by standard methods. Cells were cultured as described in the Methods. IL-2 was added at 10 U/mL on days 3 and 8 of culture. The cultures were screened for proliferation on Day 16 by luminescent ATP assay and were restimulated with 10 μg/mL GMA/001/014 (Lot 001) in the presence of $2\times10^4$ mitomycin-treated autologous B-LCL per well ($1\times10^5$ cells per mL). Fourteen wells were scored as presumptively responsive based on an ATP ratio (COP stimulated:unstimulated control) of two or greater.

The fourteen T-cell cultures were restimulated on Day 26 (second restimulation), and expanded in 10 U/ml IL-2 on Day 28. On Day 35, all 14 cultures were restimulated (third restimulation), and thirteen were assayed for proliferation in the presence of GMA Lot 001, COP, tetanus toxoid, or no antigen control.

Table 33 shows the results of the proliferation assay.

TABLE 33

Donor 6 GMA-Reactive T-Cell Lines-ATP Proliferation Assay

| Donor 6 Cell Line | Control (No Ag) | GMA Lot 001 10 μg/mL | COP 10 μg/mL | Tetanus Toxoid |
|---|---|---|---|---|
| 224-D2-001 | 8251 | 25144 | 26027 | 7430 |
| 224-G11-001 | 13350 | 85685 | 91466 | 12447 |

TABLE 33-continued

Donor 6 GMA-Reactive T-Cell Lines-ATP Proliferation Assay

| Donor 6 Cell Line | Control (No Ag) | GMA Lot 001 10 μg/mL | COP 10 μg/mL | Tetanus Toxoid |
|---|---|---|---|---|
| 224-G2-001 | 849 | 230429 | 227257 | 833 |
| 224-C4-001 | 1542 | 49779 | 52771 | 1238 |
| 224-F4-001 | 2243 | 116349 | 114667 | 2644 |
| 224-B6-001 | 657 | 75125 | 78357 | 611 |
| 224-B7-001 | 704 | 25730 | 20586 | 435 |
| 224-G10-001 | 3181 | 229901 | 229933 | 3440 |
| 224-D6-001 | 2276 | 51060 | 68767 | 4937 |
| 224-E7-001 | 3023 | 137297 | 137556 | 1777 |
| 224-B11-001 | 2927 | 29729 | 27861 | 3273 |
| 224-C11-001 | 13120 | 85787 | 87933 | 22863 |
| 224-E2-001 | 895 | 233093 | 233094 | 852 |

(Data in RLU.)

Example II. Characterization of GA-Specific Human T-Cell Lines Based on Reactivity to Non-Canonical GA Peptides The reactivities of GA-specific human T-cell lines identified as described above to a series of non-canonical GA peptides (listed in Table 1) were tested. GA-specific T-cell lines identified as reactive to non-canonical GA peptides are shown in Table 34 below. These cell lines were identified based on at least a 50% increase in proliferation relative to a control following stimulation with a non-canonical GA peptide after at least five rounds of GA restimulation/expansion. Each cell line previously had been tested for reactivity to GA at least twice and in many cases more. Certain cell lines responded comparably to GA and the non-canonical peptide, as indicated.

TABLE 34

Examples of GA-Reactive Human T-Cell Lines that React to a Non-Canonical GA Peptide

| Peptide | Composition | Reactive T-Cell Line | Nonreactive T-Cell Line |
|---|---|---|---|
| 026 | YEAK polymer; tyrosine withheld for first 5 minutes of synthesis | 165-B6C (Donor 3)<br>165-D3C (Donor 3)<br>165-F3C (Donor 3)<br>165-F6C (Donor 3)<br>205-1C4 (Donor 4)<br>205-1H5 (Donor 4)<br>205-1H11 (Donor 4) | 222-AG12 (Donor 1)<br>165-B5G (Donor 3)<br>165-D8G (Donor 3)<br>165-E7G (Donor 3)<br>165-F5G (Donor 3)<br>165-B10C (Donor 3)<br>165-D11C (Donor 3)<br>165-E3C (Donor 3)<br>205-1B4 (Donor 4) |
| GLT 631 (GLT) | poly (Glu-Lys-Tyr; 6:3:1) | 222-1H12 (Donor 1)<br>165-H11G (Donor 3)<br>205-1H7 (Donor 4) | 222-AG12 (Donor 1)<br>222-2F12 (Donor 1)<br>165-B5G (Donor 3)<br>165-C5G (Donor 3)<br>165-C8G (Donor 3)<br>165-E7G (Donor 3)<br>165-E9G (Donor 3)<br>165-F5G (Donor 3)<br>165-F10G (Donor 3)<br>165-B6C (Donor 3)<br>165-C4C (Donor 3) |

TABLE 34-continued

Examples of GA-Reactive Human T-Cell Lines that React to a Non-Canonical GA Peptide

| Peptide | Composition | Reactive T-Cell Line | Nonreactive T-Cell Line |
|---|---|---|---|
| | | | 165-C7C (Donor 3)<br>165-E3C (Donor 3)<br>165-F3C (Donor 3)<br>165-F6C (Donor 3)<br>205-1B4 (Donor 4)<br>205-1C4 (Donor 4)<br>205-1F4 (Donor 4)<br>205-1H3 (Donor 4)<br>205-1H5 (Donor 4)<br>205-1H11 (Donor 4) |
| GAT 631 | poly (Glu-Ala-Tyr; 6:3:1) | 165-H11G (Donor 3) | 222-AG12 (Donor 1)<br>222-2F12 (Donor 1)<br>222-1H12 (Donor 1)<br>165-B5G (Donor 3)<br>165-C5G (Donor 3)<br>165-C8G (Donor 3)<br>165-E7G (Donor 3)<br>165-E9G (Donor 3)<br>165-F5G (Donor 3)<br>165-F10G (Donor 3)<br>165-B6C (Donor 3)<br>165-C4C (Donor 3)<br>165-C7C (Donor 3)<br>165-E3C (Donor 3)<br>165-F3C (Donor 3)<br>165-F6C (Donor 3)<br>205-1C4 (Donor 4)<br>205-1F4 (Donor 4)<br>205-1H3 (Donor 4)<br>205-1H5 (Donor 4)<br>205-1H7 (Donor 4)<br>205-1H11 (Donor 4) |
| GAT 111 | poly (Glu-Ala-Tyr; 1:1:1) | — | 222-AG12 (Donor 1)<br>222-2F12 (Donor 1)<br>222-1H12 (Donor 1)<br>165-B5G (Donor 3)<br>165-C5G (Donor 3)<br>165-C8G (Donor 3)<br>165-E7G (Donor 3)<br>165-E9G (Donor 3)<br>165-F5G (Donor 3)<br>165-F5G (Donor 3)<br>165-F10G (Donor 3)<br>165-H11G (Donor 3)<br>165-C4C (Donor 3)<br>165-C7C (Donor 3)<br>165-E3C (Donor 3)<br>165-F3C (Donor 3)<br>165-F6C (Donor 3)<br>205-1F4 (Donor 4)<br>205-1H3 (Donor 4)<br>205-1H7 (Donor 4)<br>205-1H11 (Donor 4) |
| GL 14 | poly (Glu-Lys; 1:4) | 222-2F12 (Donor 1)<br>165-B5G (Donor 3)<br>165-C4C (Donor 3)<br>165-C5G (Donor 3)<br>165-C7C (Donor 3)<br>165-F6C (Donor 3)<br>165-E7G (Donor 3)<br>165-E9G (Donor 3)<br>165-F3C (Donor 3)<br>165-F5G (Donor 3)<br>165-F10G (Donor 3)<br>165-H11G (Donor 3)<br>205-1H3 (Donor 4) | 222-AG12 (Donor 1)<br>222-1H12 (Donor 1)<br>205-1F4 (Donor 4)<br>205-1H11 (Donor 4) |
| LT 11 | poly (Lys-Tyr; 1:1) | 165-C4C (Donor 3)<br>165-C7C (Donor 3)<br>165-F3C (Donor 3)<br>165-C5G (Donor 3)<br>165-F10G (Donor 3)<br>205-1F4 (Donor 4) | 222-AG12 (Donor 1)<br>165-B5G (Donor 3)<br>165-F5G (Donor 3)<br>165-E7G (Donor 3)<br>165-E9G (Donor 3)<br>165-F5G (Donor 3)<br>165-H11G (Donor 3)<br>165-F6C (Donor 3)<br>205-1H3 (Donor 4) |

TABLE 34-continued

Examples of GA-Reactive Human T-Cell Lines that React to a Non-Canonical GA Peptide

| Peptide | Composition | Reactive T-Cell Line | Nonreactive T-Cell Line |
|---|---|---|---|
| GT 11 | poly (Glu-Tyr; 1:1) | — | 222-AG12 (Donor 1) |
| | | | 165-B2G (Donor 3) |
| | | | 165-B5G (Donor 3) |
| | | | 165-C4G (Donor 3) |
| | | | 165-C5G (Donor 3) |
| | | | 165-C8G (Donor 3) |
| | | | 165-E7G (Donor 3) |
| | | | 165-E9G (Donor 3) |
| | | | 165-F2G (Donor 3) |
| | | | 165-F5G (Donor 3) |
| | | | 165-F8G (Donor 3) |
| | | | 165-F10G (Donor 3) |
| | | | 165-H11G (Donor 3) |
| | | | 165-B6C (Donor 3) |
| | | | 165-B10C (Donor 3) |
| | | | 165-C4C (Donor 3) |
| | | | 165-C7C (Donor 3) |
| | | | 165-D2C (Donor 3) |
| | | | 165-D3C (Donor 3) |
| | | | 165-E3C (Donor 3) |
| | | | 165-F3C (Donor 3) |
| | | | 165-F6C (Donor 3) |
| GT41S | | — | 165-C4C (Donor 3) |
| | | | 165-F3C (Donor 3) |
| | | | 165-F6C (Donor 3) |
| | | | 205-1F4 (Donor 4) |
| | | | 205-1H3 (Donor 4) |
| | | | 205-1H11 (Donor 4) |
| GA64 | | — | 165-C4C (Donor 3) |
| | | | 165-F3C (Donor 3) |
| | | | 165-F6C (Donor 3) |
| | | | 205-1F4 (Donor 4) |
| | | | 205-1H3 (Donor 4) |

Reactivity of GA-Specific Human T-Cell Lines to Peptide 026

Peptide 026 is an altered GA peptide consisting of the amino acids tyrosine, glutamic acid, alanine, and lysine, made by withholding tyrosine during the first five minutes of GA synthesis.

T-cell lines from Donors 3 and 4 were tested for reactivity to peptide 026. As summarized in Table 34, at least four Donor 3 and two Donor 4 T-cell lines showed reactivity to peptide 026. One Donor 4 T-cell line showed reactivity to peptide 026 comparable to that observed following stimulation with GA.

On Day 54 of culture seven Donor 3 COP T-cell lines were tested for reactivity to peptide 026 (dissolved in water containing 20 mg/mL mannitol). Four of the cell lines tested (165-B6C, 165-D3C, 165-F3C, and 165-F6C) had low level reactivity to the 026/11 antigen. The remaining cell lines had no significant reactivity to Peptide 026; all cell lines responded well to both GMA and COP. The data in RLU are shown in Table 36.

TABLE 35

Reactivity of Donor 3 COP T-Cell Lines to Peptide 026

| | MBP | | GMA | | COP | | 026 | |
|---|---|---|---|---|---|---|---|---|
| 165-B6C | Mean | Std dev | Mean | Std dev | Mean | Std dev | Mean | Std dev |
| No Antigen | 2358 | 44 | 2358 | 44 | 2358 | 44 | 2358 | 44 |
| 1 μg/mL | | | 3939 | 452 | 3878 | 231 | 2339 | 316 |
| 3 μg/mL | 2205 | 97 | 19344 | 1921 | 21455 | 1153 | 2715 | 326 |

TABLE 35-continued

| | MBP | | GMA | | COP | | 026 | |
|---|---|---|---|---|---|---|---|---|
| 10 μg/mL | 2268 | 143 | 29012 | 2065 | 32197 | 857 | 5989 | 721 |
| 100 μg/mL | 2201 | 196 | 9856 | 1095 | 7969 | 1417 | 10083 | 911 |
| | **MBP** | | **GMA** | | **COP** | | **026** | |
| 165-B10C | Mean | Std dev | Mean | Std dev | Mean | Std dev | Mean | Std dev |
| No Antigen | 2234 | 295 | 2234 | 295 | 2234 | 295 | 2234 | 295 |
| 1 μg/mL | | | 1942 | 155 | 2117 | 192 | 2663 | 126 |
| 3 μg/mL | 2176 | 183 | 2658 | 76 | 2519 | 175 | 2548 | 175 |
| 10 μg/mL | 2320 | 361 | 5854 | 547 | 6701 | 695 | 2667 | 190 |
| 100 μg/mL | 2272 | 177 | 6380 | 382 | 6215 | 1277 | 992 | 181 |
| | **MBP** | | **GMA** | | **COP** | | **026** | |
| 165-D3C | Mean | Std dev | Mean | Std dev | Mean | Std dev | Mean | Std dev |
| No Antigen | 8319 | 1520 | 8319 | 1520 | 8319 | 1520 | 8319 | 1520 |
| 1 μg/mL | | | 24131 | 692 | 22689 | 1733 | 9388 | 1069 |
| 3 μg/mL | 8037 | 1559 | 58814 | 4975 | 50369 | 2258 | 14049 | 1015 |
| 10 μg/mL | 8656 | 1373 | 57024 | 2006 | 52151 | 1613 | 20508 | 3121 |
| 100 μg/mL | 8647 | 1235 | 14205 | 408 | 10140 | 1549 | 9062 | 2296 |
| | **MBP** | | **GMA** | | **COP** | | **026** | |
| 165-D11C | Mean | Std dev | Mean | Std dev | Mean | Std dev | Mean | Std dev |
| No Antigen | 4571 | 353 | 4571 | 353 | 4571 | 353 | 4571 | 353 |
| 1 μg/mL | | | 3636 | 506 | 3410 | 260 | 4297 | 159 |
| 3 μg/mL | 4348 | 443 | 6578 | 570 | 6618 | 216 | 4287 | 453 |
| 10 μg/mL | 4301 | 373 | 16338 | 1033 | 15652 | 1327 | 4050 | 603 |
| 100 μg/mL | 4020 | 476 | 14560 | 437 | 12958 | 1216 | 1931 | 216 |

TABLE 35-continued

| | MBP | | GMA | | COP | | 026 | |
|---|---|---|---|---|---|---|---|---|
| 165-E3C | Mean | Std dev | Mean | Std dev | Mean | Std dev | Mean | Std dev |
| No Antigen | 2797 | 124 | 2797 | 124 | 2797 | 124 | 2797 | 124 |
| 1 μg/mL | | | 2954 | 231 | 2592 | 354 | 3582 | 648 |
| 3 μg/mL | 2898 | 241 | 17065 | 2766 | 14394 | 3211 | 3888 | 61 |
| 10 μg/mL | 2658 | 94 | 37602 | 2580 | 39495 | 2117 | 3443 | 216 |
| 100 μg/mL | 2582 | 305 | 23437 | 4209 | 20538 | 3942 | 2256 | 1189 |

| | MBP | | GMA | | COP | | 026 | |
|---|---|---|---|---|---|---|---|---|
| 165-F3C | Mean | Std dev | Mean | Std dev | Mean | Std dev | Mean | Std dev |
| No Antigen | 3150 | 184 | 3150 | 184 | 3150 | 184 | 3150 | 184 |
| 1 μg/mL | | | 9423 | 835 | 7777 | 52 | 3131 | 226 |
| 3 μg/mL | 3369 | 343 | 37555 | 1427 | 36331 | 1813 | 3776 | 308 |
| 10 μg/mL | 3115 | 266 | 44621 | 1586 | 44047 | 2194 | 8005 | 251 |
| 100 μg/mL | 3017 | 263 | 12391 | 489 | 9932 | 1294 | 6667 | 776 |

TABLE 35-continued

| | MBP | | GMA | | COP | | 026 | |
|---|---|---|---|---|---|---|---|---|
| 165-F6C | Mean | Std dev | Mean | Std dev | Mean | Std dev | Mean | Std dev |
| No Antigen | 2189 | 82 | 2189 | 82 | 2189 | 82 | 2189 | 82 |
| 1 μg/mL | | | 15671 | 823 | 13418 | 267 | 2027 | 57 |
| 3 μg/mL | 1960 | 84 | 40274 | 2355 | 38973 | 1889 | 2816 | 354 |
| 10 μg/mL | 1977 | 210 | 38921 | 1554 | 39560 | 924 | 10332 | 1043 |
| 100 μg/mL | 3672 | 567 | 3690 | 902 | 4332 | 204 | 8088 | 899 |

Donor 3 GMA T-Cell lines 165-B5G, 165-D8G, 165-E7G, and 165-F5G also were tested for reactivity to peptide 026, with negative results. On Day 56 of culturing (described in Example I), the cell lines were stimulated with COP, GMA, and peptide 026, each at 0, 1, 5, 10, and 100 μg/mL. All Donor 3 lines responded well to GMA and COP, and the GMA and COP responses were comparable.

Donor 4 GA-Specific T-Cell Lines: Peptide 026

Figure 8:
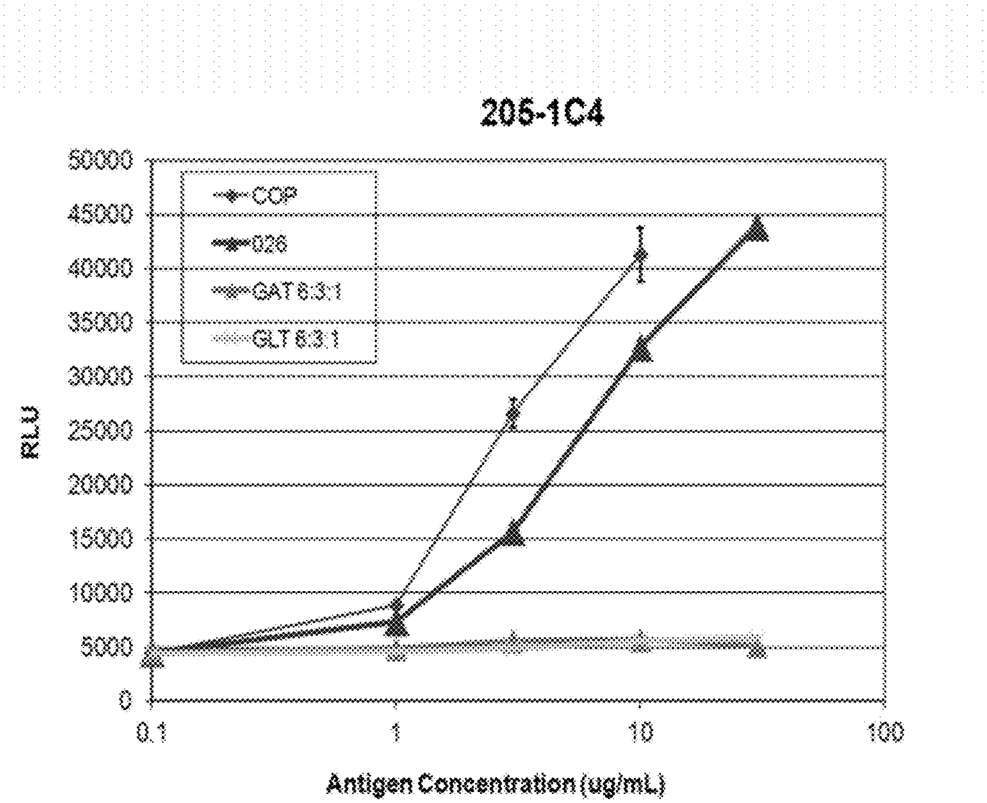
FIG. 8. Donor 4 T-Cell Line 205-1C4 Proliferation in Response to COP, Peptide 026, GAT 631, GLT 631. Proliferation of Donor 4 T-cell Line 205-1C4 in response to stimulation with 0, 1, 10, and 30 μg/mL COP, Peptide 026, GAT 631 and GLT 631 is shown.

Donor 4 COP T-cell lines 205-1B4, 205-1C4, and 205-1H5 were tested for reactivity to peptide 026. Peptides GAT 631, GLT, and COP also were tested at 1, 5, 10, and 30 μg/mL. Cell line 205-1C4 showed reactivity to peptide 026 comparable to its reactivity to GA, while 205-1H5 showed minimal reactivity, and 205-1B4 did not show reactivity (Table 37). FIG. 8 shows the results in RLU for cell line 205-1C4 in graph form.

TABLE 36

Reactivity of Donor 4 COP T-Cell Lines 205-1B4, 205-1C4, and 205-1H5 to Non-Canonical GA Peptides

| | COP | | 026 | | GLT 631 | | GAT 631 | |
|---|---|---|---|---|---|---|---|---|
| 205-1B4 | Mean | Std dev | Mean | Std dev | Mean | Std dev | Mean | Std dev |
| No Antigen | 830 | 45 | 830 | 45 | 830 | 45 | 830 | 45 |
| 1 μg/mL | 1522 | 110 | 870 | 75 | 912 | 72 | 843 | 70 |
| 3 μg/mL | 5501 | 1043 | 1047 | 127 | 1059 | 160 | 890 | 24 |
| 10 μg/mL | 11273 | 493 | 856 | 145 | 1387 | 204 | 845 | 92 |
| 30 μg/mL | | | 1007 | 215 | 1389 | 188 | 766 | 221 |

| | COP | | 026 | | GLT 631 | | GAT 631 | |
|---|---|---|---|---|---|---|---|---|
| 205-1C4 | Mean | Std dev | Mean | Std dev | Mean | Std dev | Mean | Std dev |
| No Antigen | 4464 | 605 | 4464 | 605 | 4464 | 605 | 4464 | 605 |
| 1 μg/mL | 8859 | 211 | 7353 | 623 | 4559 | 355 | 4856 | 369 |
| 3 μg/mL | 26612 | 1314 | 15709 | 243 | 4934 | 314 | 5584 | 419 |
| 10 μg/mL | 41287 | 2529 | 32715 | 1111 | 5616 | 261 | 5666 | 523 |
| 30 μg/mL | | | 43886 | 695 | 5782 | 872 | 5137 | 761 |

| | COP | | 026 | | GLT 631 | | GAT 631 | |
|---|---|---|---|---|---|---|---|---|
| 205-1H5 | Mean | Std dev | Mean | Std dev | Mean | Std dev | Mean | Std dev |
| No Antigen | 749 | 9 | 749 | 9 | 749 | 9 | 749 | 9 |
| 1 μg/mL | 2375 | 494 | 985 | 79 | 710 | 39 | 648 | 132 |
| 3 μg/mL | 7182 | 229 | 1103 | 55 | 885 | 100 | 696 | 65 |
| 10 μg/mL | 8580 | 731 | 1265 | 209 | 1153 | 124 | 698 | 105 |
| 30 μg/mL | | | 1872 | 342 | 1294 | 187 | 669 | 21 |

Donor 4 COP cell line 205-1H11 was tested for reactivity to peptides 026, GLT 631, LT 11, GL 14, GT 41S, GAT 631 and GAT 111. This experiment was performed at the same time as the COP dose response experiment described in Example I, using the same cells and method. Cell line 205-1H11 showed reactivity to peptide 026 at 30 μg/mL of antigen (Table 37).

TABLE 37

Reactivity of Donor 4 COP T-Cell Line 205-1H11 to Non-Canonical GA Peptides

| | 0 μg/mL | | 1 μg/mL | | 10 μg/mL | | 30 μg/mL | |
|---|---|---|---|---|---|---|---|---|
| | Mean | Std dev | Mean | Std dev | Mean | Std dev | Mean | Std dev |
| COP | 6941 | 593 | 12243 | 1712 | 147464 | 228 | 112673 | 6037 |
| 026/11 | | | 5513 | 232 | 11329 | 1298 | 78603 | 1155 |
| GLT (6:3:1) | | | 5627 | 331 | 5915 | 269 | 8542 | 332 |
| GAT (6:3:1) | | | 6244 | 522 | 6604 | 399 | 6089 | 484 |
| GAT (1:1:1) | | | 6121 | 304 | 6448 | 578 | 6253 | 520 |
| LT 11 | | | 5961 | 406 | 6698 | 616 | 4303 | 445 |
| GL 14 | | | 5954 | 532 | 102 | 83 | 74 | 50 |
| GT 41S | | | 5484 | 435 | 5840 | 828 | 5395 | 390 |

(Data in RLU.)

Donor 4 COP cell line 205-1H3 was tested for reactivity to peptides GLT 631, GAT 631, GAT 111, GL 14, LT 11, GA 64, and GT 41S. Cell line 205-1H3 showed reactivity to peptide GL 14 at 1 μg/mL of antigen (Table 38).

TABLE 38

Reactivity of Donor 4 COP T-Cell Line 205-1H3 to Non-Canonical GA Peptides

| | 0 μg/mL | | 1 μg/mL | | 3 μg/mL | | 10 μg/mL | |
|---|---|---|---|---|---|---|---|---|
| | Mean | Std dev | Mean | Std dev | Mean | Std dev | Mean | Std dev |
| COP | 4121.0 | 829.9 | 32122.0 | 7174.4 | 49585.0 | 3808.6 | 60878.3 | 4768.1 |
| GMA | | | 37654.3 | 6157.2 | 55284.3 | 1312.7 | 60841.7 | 4656.5 |
| GLT (6:3:1) | | | 3619.3 | 521.5 | 2923.7 | 422.8 | 3264.7 | 624.6 |
| GAT (6:3:1) | | | 4271.0 | 360.7 | 4577.0 | 233.2 | 4589.0 | 665.3 |
| GAT (1:1:1) | | | 3892.7 | 601.5 | 3227.7 | 714.1 | 3704.3 | 502.7 |
| GL 14 | | | 15619.0 | 1114.2 | 1053.3 | 107.2 | 61.0 | 3.0 |
| LT 11 | | | 4780.3 | 769.3 | 3083.3 | 459.3 | 3381.0 | 512.1 |
| GA 64 | | | 4012.0 | 574.6 | 4246.0 | 1209.8 | 2054.3 | 267.5 |
| GT 41S | | | 3773.3 | 274.2 | 3857.0 | 808.1 | 2349.0 | 124.7 |

Reactivity of GA-Specific Human T-Cell Lines to Peptide GLT 1 and GAT631

Donor 1, 3 and 4 GA-specific T-cell lines were tested for proliferation in response to stimulation with peptide GLT 631 (GLT), poly (Glu-Lys-Tyr; 6:3:1). One Donor 1 cell line, three Donor 3 T-cell lines and one Donor 4 T-cell line showed some reactivity to GLT. Two of the Donor 3 T-cell lines showed reactivity to GLT comparable to that observed following stimulation with GA. Three Donor 3 T-cell lines showed reactivity to GAT.

Donor 1 GA-Specific T-Cell Line 222-1H12: Peptides GLT 631 and GAT

On Day 56 of culturing (described in Example I), after five rounds of stimulation (including the initial stimulation and four rounds of restimulation), Donor 1 COP T-cell line 222-1H12 was assayed for proliferation following addition of 0, 3, 10, and 30 μg/mL of each of peptides GL 14, GLT 631, GAT 111, and GAT 631, COP, and GMA, at a T-cell concentration of $1\times10^5$ cells/mL, in the presence of mitomycin C-treated autologous B-LCL. Proliferation was measured by luminescent ATP assay. Cell line 222-1H12 responded to GLT 631 and not to the other non-canonical GA peptides tested. The data in RLU are shown in Table 39.

TABLE 39

Reactivity of Donor 1 COP T-Cell Line 222-1H12 to Non-Canonical Peptides

| | 0 μg/mL | | 3 μg/mL | | 10 μg/mL | | 30 μg/mL | |
|---|---|---|---|---|---|---|---|---|
| | Mean | Std dev | Mean | Std dev | Mean | Std dev | Mean | Std dev |
| COP | 5974 | 1124 | 146874 | 10577 | 168163 | 10045 | 68492 | 10042 |
| GLT (6:3:1) | | | 11147 | 1604 | 7518 | 1515 | 9490 | 1361 |
| GAT (6:3:1) | | | 5267 | 1022 | 4204 | 736 | 3141 | 472 |

TABLE 39-continued

Reactivity of Donor 1 COP T-Cell Line 222-1H12 to Non-Canonical Peptides

| | 0 μg/mL | | 3 μg/mL | | 10 μg/mL | | 30 μg/mL | |
|---|---|---|---|---|---|---|---|---|
| | Mean | Std dev | Mean | Std dev | Mean | Std dev | Mean | Std dev |
| GAT (1:1:1) | | | 5224 | 784 | 3555 | 406 | 3014 | 370 |
| GL (1:4) | | | 7143 | 805 | 234 | 211 | 131 | 95 |
| GMA | | | 141486 | 15062 | 167193 | 12648 | 82376 | 11177 |

Donor 3 GA-Specific T-Cell Lines: GLT and GAT

On Day 81 of culturing (described in Example I), after nine total rounds of stimulation (including the initial stimulation and eight rounds of restimulation), Donor 3 GMA T-cell lines I65-B5G and 165-E7G were assayed for proliferation. For the assay, 0, 1, 3, 10, and 30 μg/mL of each of peptides GAT 631, GLT 631, and COP were added, at a T-cell concentration of $1\times10^5$ cells/mL, in the presence of mitomycin C-treated autologous B-LCL. Proliferation was measured by luminescent ATP assay. Both lines responded well to GLT 631. 165-B5G and 165-E7G also responded to GAT 631. The data in RLU are shown in Tables 40-41.

TABLE 40

Reactivity of Donor 3 GMA T-Cell Lines 165-B5G to Peptides GLT 631 and GAT 631

| | 1 μg/mL | | 3 μg/mL | | 10 μg/mL | | 30 μg/mL | |
|---|---|---|---|---|---|---|---|---|
| | Mean | Std dev | Mean | Std dev | Mean | Std dev | Mean | Std dev |
| COP | 6275 | 305 | 7499 | 775 | 10914 | 1331 | 13974 | 1841 |
| GAT 631 | 4666 | 1106 | 5536 | 517 | 4997 | 646 | 3637 | 641 |
| GLT 631 | 4288 | 675 | 5153 | 258 | 11847 | 1251 | 11416 | 1591 |

No Antigen Value: 2432 +/− 243

TABLE 41

Reactivity of Donor 3 GMA T-Cell Lines 165-E7G to Peptides GLT 631 and GAT631

| | 1 μg/mL | | 3 μg/mL | | 10 μg/mL | | 30 μg/mL | |
|---|---|---|---|---|---|---|---|---|
| | Mean | Std dev | Mean | Std dev | Mean | Std dev | Mean | Std dev |
| COP | 4217 | 1198 | 5366 | 663 | 7619 | 2756 | 7161 | 342 |
| GAT 631 | 4043 | 600 | 6457 | 2644 | 5499 | 326 | 4178 | 905 |
| GLT 631 | 3992 | 2391 | 5133 | 643 | 12006 | 461 | 12836 | 2611 |

No Antigen Value: 2145 +/− 1180

On Day 50 of culturing (described in Example I), after six total rounds of stimulation, Donor 3 GMA T-cell lines 165-H11G, 165-05G, 165-E9G, and 165-F10G were assayed for proliferation. Cell lines were incubated with 0, 1, 3, 10, and 30 μg/mL of each of peptides GAT 631, GLT 631, GAT 111, GMA, COP, and STERN (165-F10G was stimulated with MBP rather than STERN), at a T-cell concentration of $1\times10^5$ cells/mL, in the presence of mitomycin C-treated autologous B-LCL. Proliferation was measured by luminescent ATP assay. Cell line 165-H11G responded to GLT 631 and GAT 631. The data in RLU are shown in Tables 42-45.

TABLE 42

Reactivity of Donor 3 GMA T-Cell Line 165-H11G to Peptides GLT 631 and GAT631

| | 1 μg/mL | | 3 μg/mL | | 10 μg/mL | | 30 μg/mL | |
|---|---|---|---|---|---|---|---|---|
| | Mean | Std dev | Mean | Std dev | Mean | Std dev | Mean | Std dev |
| GMA | 9569 | 380 | 46539 | 1071 | 49104 | 1175 | 32179 | 1534 |
| COP | 8610 | 2000 | 37551 | 4300 | 50044 | 2322 | 32898 | 2167 |
| GAT 631 | 2413 | 332 | 2969 | 151 | 2995 | 136 | 3115 | 35 |
| GLT 631 | 2763 | 139 | 2875 | 134 | 3028 | 333 | 3093 | 13 |

TABLE 42-continued

Reactivity of Donor 3 GMA T-Cell Line 165-H11G to Peptides GLT 631 and GAT631

| | 1 μg/mL | | 3 μg/mL | | 10 μg/mL | | 30 μg/mL | |
|---|---|---|---|---|---|---|---|---|
| | Mean | Std dev | Mean | Std dev | Mean | Std dev | Mean | Std dev |
| GAT 111 | 2448 | 599 | 2294 | 237 | 2102 | 31 | 1599 | 55 |
| STERN | 2279 | 335 | 2118 | 198 | 2418 | 43 | 2296 | 241 |

No Antigen Value: 1485 +/− 208

TABLE 43

Reactivity of Donor 3 GMA T-Cell Line 165-05G to Peptides GLT 631 and GAT 631

| | 1 μg/mL | | 3 μg/mL | | 10 μg/mL | | 30 μg/mL | |
|---|---|---|---|---|---|---|---|---|
| | Mean | Std dev | Mean | Std dev | Mean | Std dev | MeanStd | dev |
| GMA | 3999 | 413 | 35643 | 2850 | 53130 | 1978 | 55596 | 664 |
| COP | 6791 | 132 | 42584 | 2129 | 56893 | 2843 | 55001 | 2583 |
| GAT 631 | 2004 | 59 | 2207 | 152 | 1928 | 72 | 1829 | 260 |
| GLT 631 | 1871 | 253 | 2268 | 207 | 2256 | 113 | 2137 | 363 |
| GAT 111 | 1778 | 112 | 1661 | 312 | 1569 | 87 | 1449 | 170 |
| STERN | 1750 | 48 | 1606 | 91 | 1650 | 140 | 1572 | 83 |

No Antigen Value : 2149 +/− 361

TABLE 44

Reactivity of Donor 3 GMA T-Cell Line 165-E9G to Peptides GLT 631 and GAT631

| | 1 μg/mL | | 3 μg/mL | | 10 μpg/mL | | 30 μg/mL | |
|---|---|---|---|---|---|---|---|---|
| | Mean | Std dev | Mean | Std dev | Mean | Std dev | Mean | Std dev |
| GMA | 1889 | 115 | 5974 | 911 | 37352 | 1044 | 39472 | 2920 |
| COP | 1999 | 109 | 5538 | 439 | 38813 | 828 | 38286 | 503 |
| GAT 631 | 1482 | 162 | 1593 | 109 | 1454 | 59 | 1382 | 47 |
| GLT 631 | 1630 | 208 | 1600 | 161 | 2341 | 554 | 2152 | 217 |
| GAT 111 | 1528 | 128 | 1454 | 77 | 1462 | 77 | 1301 | 23 |
| MBP | 1527 | 162 | 1428 | 102 | 1247 | 81 | 1208 | 70 |
| STERN | 1673 | 62 | 1480 | 75 | 1471 | 81 | 1487 | 273 |

No Antigen Value : 1742 +/− 146

TABLE 45

Reactivity of Donor 3 GMA T-Cell Line 165-F10G to Peptides GLT 631 and GAT 631

| | 1 μg/mL | | 3 μg/mL | | 10 μg/mL | | 30 μg/mL | |
|---|---|---|---|---|---|---|---|---|
| | Mean | Std dev | Mean | Std dev | Mean | Std dev | Mean | Std dev |
| GMA | 4734 | 539 | 35371 | 2546 | 58913 | 459 | 59173 | 1484 |
| COP | 6350 | 1127 | 40495 | 1593 | 58726 | 2437 | 60488 | 1731 |
| GAT 631 | 3755 | 652 | 3543 | 68 | 3702 | 332 | 3794 | 352 |
| GLT 631 | 3363 | 395 | 3061 | 1076 | 4823 | 370 | 4568 | 699 |
| GAT 111 | 3575 | 552 | 2989 | 196 | 2876 | 263 | 2299 | 248 |
| STERN | 2465 | 153 | 2389 | 31 | 2030 | 214 | 2583 | 552 |

No Antigen Value: 3752 +/− 233

Table 46 below shows reactivity of 165-F6C following stimulation with 0, 1.25, 2.5, 5, and 10 μg/mL each of peptides GLT 631, GAT 631, GAT 111, LT 11, GT 11, GL 14, GT 41S, and GMA, as demonstrated by luminescent ATP proliferation assay. The assay was carried out at Day 76 of culture, after eight restimulations, at a T-cell concentration of $1\times10^5$ cells/mL, in the presence of mitomycin C-treated autologous B-LCL. Line 165-F6C reacted to GL 14, and not to the other non-canonical GA peptides tested. The response to GL 14 relative to the no antigen control reached 4.4-fold at a dose of 2.5 μg/mL antigen.

TABLE 46

| Reactivity of 165-F6C to GA and Non-Canonical GA Peptides (Day 76) | | | | | | | | |
|---|---|---|---|---|---|---|---|---|
| | 1.25 μg/mL | | 2.5 μg/mL | | 5 μg/mL | | 10 μg/mL | |
| | Mean | Std dev | Mean | Std dev | Mean | Std dev | Mean | Std dev |
| GMA | 629 | 18 | 3,197 | 803 | 11,867 | 2,036 | 20,141 | 2,133 |
| GLT 631 | 501 | 104 | 416 | 54 | 482 | 48 | 474 | 19 |
| GAT 631 | 516 | 72 | 479 | 101 | 463 | 49 | 449 | 38 |
| GAT 111 | 576 | 30 | 620 | 83 | 479 | 35 | 411 | 47 |
| LT 11 | 431 | 26 | 518 | 70 | 490 | 49 | 736 | 129 |
| GT 11 | 406 | 84 | 426 | 28 | 388 | 41 | 303 | 29 |
| GL 14 | 699 | 10 | 2,267 | 164 | 114 | 19 | 33 | 2 |
| GT 41S | | | 566 | 42 | 578 | 6 | 600 | 40 |

No Antigen value: 517 +/− 51.

Donor 3 line 165-E3C did not react to GAT 631, GLT 631, GAT 111, or the STERN peptide in a separate experiment.

Donor 4 GA-Specific T-Cell Line 205-1H7: GLT 631, GAT 631 and GAT 611

Donor 4 COP T-cell line 205-1H7 also was shown to have reactivity to peptide GLT 631, and not to GAT 631 and GAT 611. The cell line was assayed for proliferation after seven stimulations. The assay was carried out by adding 0, 1, 10, or 30 μg/mL of peptide GLT 631, to the T-cell lines at $1\times10^5$ cells/mL, in the presence of mitomycin C-treated autologous B-LCL. Proliferation was measured by luminescent ATP assay. The data in RLU are shown in Table 47.

TABLE 47

| Reactivity of Donor 4 COP T-Cell Line 205-1H7 to Peptide GLT 631 | | | | | | | | |
|---|---|---|---|---|---|---|---|---|
| | 0 μg/mL | | 1μg/mL | | 10 μg/mL | | 30 μg/mL | |
| | Mean | std dev | Mean | std dev | Mean | std dev | Mean | std dev |
| COP | 3382 | 781 | 13131 | 334 | 175652 | 14847 | 190750 | 8994 |
| 026/11 | | | 4962 | 319 | 2854 | 728 | 2989 | 515 |
| GLT (6:3:1) | | | 3859 | 1182 | 7376 | 1082 | 6770 | 111 |
| GAT (6:3:1) | | | 2949 | 392 | 3664 | 2027 | 2964 | 674 |
| GAT (1:1:1) | | | 2401 | 44 | 4111 | 674 | 1912 | 331 |

Reactivity of GA-Specific Human T-Cell Lines to GL 14 and LT11

GA-specific T-cell lines from Donors 1 and 3 were tested for proliferation in response to stimulation with peptide GL 14, poly (Glu-Lys 1:4). At least one Donor 1 T-cell line and eight Donor 3 T-cell lines showed reactivity to GL at low concentrations. Two of the Donor 3 T-lines showed reactivity comparable to that observed following stimulation with GA at low concentrations. Separate experiments indicated that GL-14 causes cell death at concentrations approaching and exceeding 10 μg/mL (data not shown).

Donor 1 GA-Specific T-Cell Lines: GL 14

On Day 56 of culturing (described in Example 1), after six total rounds of stimulation, Donor 1 COP T-cell line 222-2F12 was assayed for proliferation. For the assay, 0, 3, 10, or 30 μg/mL of each of peptides GL 14, GLT 631; GAT 111, and GAT 631, COP, and GMA, were added to the T-cell lines at $1\times10^5$ cells/mL, in the presence of mitomycin C-treated autologous B-LCL. Proliferation was measured by luminescent ATP assay. Cell line 222-2F12 responded to GL 14 at 3 μg/mL, and not to the other non-canonical GA peptides tested. The data are shown in Table 48.

TABLE 48

| Reactivity of Donor 1 COP T-Cell Line 222-2F12 to Non-Canonical Peptides | | | | | | | | |
|---|---|---|---|---|---|---|---|---|
| | 0 μg/mL | | 3 μg/mL | | 10 μg/mL | | 30 μg/mL | |
| | Mean | Std dev | Mean | Std dev | Mean | Std dev | Mean | Std dev |
| COP | 5673 | 664 | 233087 | 4 | 230009 | 3534 | 118769 | 7210 |
| GLT (6:3:1) | | | 5277 | 1002 | 4934 | 809 | 5217 | 1933 |
| GAT (6:3:1) | | | 4342 | 187 | 3226 | 378 | 3071 | 923 |
| GAT (1:1:1) | | | 3914 | 333 | 3590 | 748 | 2430 | 288 |
| GL (1:4) | | | 17007 | 350 | 331 | 288 | 203 | 175 |
| GMA | | | 232779 | 451 | 228761 | 2425 | 125994 | 7400 |

Donor 3 GA-Specific T-Cell Lines

Donor 3 COP T-cell lines 165-F3C and 165-C4C were assayed for proliferation following stimulation with 0, 1, 3, and 10 μg/mL each of peptides GLT 631, GAT 631, GAT 111, LT 11, GT 11, GL 14, GT 41S, GA 64, COP, and GMA, at a T-cell concentration of $1\times10^5$ cells/mL, in the presence of mitomycin C-treated autologous B-LCL. Line 165-F3C was assayed at Day 77 of culture, after nine stimulations. Line 165-C4C was assayed at Day 66 of culture, after seven stimulations. Proliferation was measured by luminescent ATP assay. These lines responded well to GL 14 and LT 11, and not to the other non-canonical GA peptides tested. The data are shown in Table 49.

TABLE 49

Reactivity of Donor 3 COP T-Cell Lines 165-F3C and 165-C4C to Non-Canonical Peptides

| | 0 μg/mL | | 1 μg/mL | | 3 μg/mL | | 10 μg/mL | |
|---|---|---|---|---|---|---|---|---|
| 165-F3C | Mean | Std dev | Mean | Std dev | Mean | Std dev | Mean | Std dev |
| GMA | 1563 | 207 | 7277 | 386 | 50400 | 1605 | 70563 | 1724 |
| GLT | 1563 | 207 | 2325 | 313 | 2557 | 123 | 2724 | 302 |
| GAT 631 | 1563 | 207 | 2389 | 106 | 2249 | 191 | 2391 | 166 |
| GAT 111 | 1563 | 207 | 2387 | 140 | 2269 | 360 | 1772 | 51 |
| LT 11 | 1563 | 207 | 2144 | 118 | 2605 | 329 | 3608 | 166 |
| GT 11 | 1563 | 207 | 2108 | 173 | 2152 | 290 | 1652 | 455 |
| GL 14 | 1563 | 207 | 2542 | 532 | 7091 | 239 | 65 | 17 |
| GT 41S | 1563 | 207 | 1962 | 201 | 1778 | 34 | 1997 | 184 |
| GA 64 | 1563 | 207 | 1791 | 122 | 1943 | 230 | 1870 | 208 |
| COP | 1563 | 207 | 5027 | 576 | 32906 | 2723 | 62888 | 2978 |
| | 0 μg/mL | | 1 μg/mL | | 3 μg/mL | | 10 μg/mL | |
| 165-C4C | Mean | Std dev | Mean | Std dev | Mean | Std dev | Mean | Std dev |
| GMA | 1881 | 484 | 2668 | 396 | 16108 | 1188 | 88509 | 7445 |
| GLT | 1881 | 484 | 2465 | 140 | 2677 | 268 | 2939 | 156 |
| GAT 631 | 1881 | 484 | 2489 | 142 | 2687 | 119 | 2682 | 163 |
| GAT 111 | 1881 | 484 | 2330 | 405 | 2392 | 202 | 2233 | 88 |
| LT 11 | 1881 | 484 | 2430 | 261 | 2701 | 187 | 4129 | 254 |
| GT 11 | 1881 | 484 | 2664 | 295 | 2804 | 147 | 2311 | 323 |
| GL 14 | 1881 | 484 | 2833 | 887 | 4920 | 594 | 49 | 4 |
| GT 41S | 1881 | 484 | 2119 | 317 | 1943 | 65 | 2193 | 275 |
| GA 64 | 1881 | 484 | 2205 | 141 | 2229 | 205 | 2244 | 374 |
| COP | 1881 | 484 | 2357 | 201 | 7913 | 430 | 74558 | 5178 |

Donor 3 GMA T-cell lines 165-B5G and 165-E7G were assayed for proliferation at Day 55 of culturing, after five rounds of restimulation (not including the initial stimulation). Peptides GLT 631, GAT 631, GAT 111, LT 11, GT 11, GL 14, MBP, COP, and GMA, were added at 0, 1, 3, or 10 μg/mL, to T-cells at a concentration of $2\times10^6$ cells/mL, in the presence of mitomycin C-treated autologous B-LCL. Proliferation was measured by luminescent ATP assay. These lines responded well to GL 14 and not to the other non-canonical GA peptides tested. The data in RLU are shown in Tables 50 and 51.

TABLE 50

Reactivity of Donor 3 GMA T-Cell Line 165-B5G to Non-Canonical Peptides

| | 1.25 μg/mL | | 2.5 μg/mL | | 5 μg/mL | | 10 μg/mL | |
|---|---|---|---|---|---|---|---|---|
| | Mean | Std dev | Mean | Std dev | Mean | Std dev | Mean | Std dev |
| GMA | 1406 | 11 | 2537 | 342 | 5205 | 321 | 11364 | 973 |
| GLT | 1054 | 130 | 1159 | 109 | 1687 | 396 | 3589 | 169 |

TABLE 50-continued

Reactivity of Donor 3 GMA T-Cell Line 165-B5G to Non-Canonical Peptides

| | 1.25 μg/mL | | 2.5 μg/mL | | 5 μg/mL | | 10 μg/mL | |
|---|---|---|---|---|---|---|---|---|
| | Mean | Std dev | Mean | Std dev | Mean | Std dev | Mean | Std dev |
| GAT 631 | 1133 | 131 | 1288 | 329 | 1511 | 62 | 1645 | 441 |
| GAT 111 | 1005 | 122 | 886 | 187 | 947 | 176 | 931 | 132 |
| LT 11 | 1497 | 164 | 1724 | 631 | 1666 | 320 | 2705 | 785 |
| GT 11 | 2167 | 777 | 1957 | 811 | 1353 | 202 | 1191 | 219 |
| GL 14 | 3912 | 685 | 3245 | 171 | 501 | 55 | 45 | 1 |
| MBP | | | | | | | 871 | 87 |

No Antigen Value: 846 +/− 71

TABLE 51

Reactivity of Donor 3 GMA T-Cell Line 165-E7G to Non-Canonical Peptides

| | 1.25 μg/mL | | 2.5 μg/mL | | 5 μg/mL | | 10 μg/mL | |
|---|---|---|---|---|---|---|---|---|
| | Mean | Std dev | Mean | Std dev | Mean | Std dev | Mean | Std dev |
| GMA | 8875 | 2958 | 10248 | 834 | 26934 | 4062 | 30721 | 255 |
| GLT | 2983 | 754 | 3783 | 834 | 5821 | 918 | 5710 | 737 |
| GAT 631 | 2629 | 554 | 2827 | 193 | 2950 | 131 | 3877 | 972 |
| GAT 111 | 1896 | 248 | 2001 | 587 | 1285 | 107 | 2176 | 575 |
| LT 11 | 2785 | 619 | 5270 | 40 | 3559 | 351 | 1983 | 371 |
| GT 11 | 2821 | 474 | 2914 | 726 | 2332 | 344 | 1848 | 183 |
| GL 14 | 10001 | 457 | 14902 | 1074 | 4087 | 459 | 58 | 3 |
| MBP | | | | | | | 2116 | 233 |

No Antigen Value: 2777 +/− 398

Donor 3 GMA and COP T-cell lines 165-F10G, 165-05G, 165-H11G, 165-C7C, 165-E9G, and 165-F5G were assayed for proliferation following stimulation with 0, 1, 3, and 10 μg/mL each of peptides GLT 631, GAT 631, GAT 111, LT 11, GT 11, GL 14, MBP, COP, and GMA, at a T-cell concentration of 1-2×$10^5$ cells/mL, in the presence of mitomycin C-treated autologous B-LCL. Each cell line was assayed for proliferation after a minimum of 55 days in culture, following at least six stimulations. A luminescent ATP assay was used. These lines responded well to GL 14 and not to the other non-canonical GA peptides tested, except for 165-05G, which also responded to LT11. The data in RLU are shown in Tables 52-57

TABLE 52

Reactivity of Donor 3 GMA T-Cell Line 165-F10G to Non-Canonical Peptides

| | 1.25 μg/mL | | 2.5 μg/mL | | 5 μg/mL | | 10 μg/mL | |
|---|---|---|---|---|---|---|---|---|
| | Mean | Std dev | Mean | Std dev | Mean | Std dev | Mean | Std dev |
| GMA | 5731 | 1930 | 38905 | 3450 | 66355 | 1411 | 57329 | 2055 |
| GLT | 1012 | 88 | 1389 | 172 | 2620 | 397 | 2505 | 184 |
| GAT 631 | 948 | 133 | 1080 | 156 | 1024 | 107 | 944 | 69 |
| GAT 111 | 929 | 61 | 1342 | 52 | 1091 | 160 | 1054 | 115 |
| LT 11 | 1145 | 258 | 1270 | 393 | 1552 | 276 | 8012 | 1258 |
| GT 11 | 1388 | 225 | 1506 | 27 | 1598 | 77 | 1294 | 147 |
| GL 14 | 5153 | 813 | 19489 | 985 | 1990 | 1178 | 53 | 4 |
| MBP | | | | | | | 831 | 39 |

No Antigen Value: 1004 +/− 207

TABLE 53

Reactivity of Donor 3 GMA T-Cell Line 165-C5G to Non-Canonical Peptides

| | 1.25 μg/mL | | 2.5 μg/mL | | 5 μg/mL | | 10 μg/mL | |
|---|---|---|---|---|---|---|---|---|
| | Mean | Std dev | Mean | Std dev | Mean | Std dev | Mean | Std dev |
| GMA | 2511 | 550 | 26253 | 2744 | 67559 | 5332 | 74630 | 2713 |
| GLT | 485 | 45 | 552 | 13 | 585 | 157 | 579 | 111 |
| GAT 631 | 435 | 33 | 465 | 81 | 504 | 68 | 423 | 74 |
| GAT 111 | 445 | 35 | 406 | 41 | 422 | 71 | 430 | 64 |
| LT 11 | 527 | 56 | 680 | 133 | 3010 | 445 | 34438 | 3148 |
| GT 11 | 523 | 83 | 620 | 90 | 428 | 100 | 471 | 47 |
| GL 14 | 1412 | 60 | 5418 | 618 | 703 | 13 | 43 | 1 |
| MBP | | | | | | | 469 | 11 |

No Antigen Value: 450 +/− 92

TABLE 54

Reactivity of Donor 3 GMA T-Cell Line 165-H11G to Non-Canonical Peptides

| | 1.25 μg/mL | | 2.5 μg/mL | | 5 μg/mL | | 10 μg/mL | |
|---|---|---|---|---|---|---|---|---|
| | Mean | Std dev | Mean | Std dev | Mean | Std dev | Mean | Std dev |
| GMA | 8 | 652 | 33793 | 895 | 70949 | 3504 | 72728 | 5989 |
| GLT | 29 | 263 | 344 | 53 | 448 | 57 | 435 | 83 |
| GAT 631 | 43 | 253 | 290 | 31 | 297 | 15 | 305 | 10 |
| GAT 111 | 49 | 340 | 320 | 67 | 304 | 72 | 336 | 22 |
| LT 11 | 15 | 434 | 326 | 60 | 357 | 39 | 178 | 5 |
| GT 11 | 17 | 352 | 354 | 10 | 352 | 2 | 308 | 76 |
| GL 14 | 144 | 532 | 4416 | 51 | 118 | 68 | 40 | 2 |
| MBP | | | | | | | 323 | 31 |

No Antigen Value: 245 +/− 32

TABLE 55

Reactivity of Donor 3 COP T-Cell Line 165-C7C to Non-Canonical Peptides

| | 1.25 μg/mL | | 2.5 μg/mL | | 5 μg/mL | | 10 μg/mL | |
|---|---|---|---|---|---|---|---|---|
| | Mean | Std dev | Mean | Std dev | Mean | Std dev | Mean | Std dev |
| GMA | 610 | 187 | 2699 | 912 | 22588 | 1382 | 24029 | 2844 |
| GLT | 273 | 66 | 219 | 60 | 273 | 79 | 219 | 24 |
| GAT 631 | 232 | 26 | 204 | 36 | 200 | 43 | 184 | 24 |
| GAT 111 | 273 | 81 | 231 | 8 | 224 | 58 | 264 | 88 |
| LT 11 | 418 | 73 | 305 | 16 | 244 | 23 | 119 | 33 |
| GT 11 | 346 | 22 | 265 | 50 | 255 | 19 | 234 | 1 |
| GL 14 | 274 | 23 | 1797 | 405 | 537 | 411 | 39 | 0 |
| MBP | | | | | | | 278 | 14 |

No Antigen Value: 188 +/− 21

TABLE 56

Reactivity of Donor 3 GMA T-Cell Line 165-E9G to Non-Canonical Peptides

| | 1.25 μg/mL | | 2.5 μg/mL | | 5 μg/mL | | 10 μg/mL | |
|---|---|---|---|---|---|---|---|---|
| | Mean | Std dev | Mean | Std dev | Mean | Std dev | Mean | Std dev |
| GMA | 253 | 31 | 1647 | 105 | 12964 | 2092 | 13809 | 961 |
| GLT | 142 | 35 | 195 | 40 | 233 | 26 | 312 | 1 |
| GAT 631 | 122 | 8 | 175 | 35 | 207 | 13 | 179 | 20 |
| GAT 111 | 154 | 10 | 240 | 35 | 240 | 13 | 153 | 55 |
| LT 11 | 132 | 15 | 129 | 9 | 89 | 17 | 91 | 12 |
| GT 11 | 110 | 32 | 119 | 8 | 103 | 15 | 96 | 7 |
| GL 14 | 145 | 57 | 801 | 283 | 268 | 102 | 38 | 2 |
| MBP | | | | | | | 163 | 15 |

No Antigen Value: 125 +/− 30

TABLE 57

Reactivity of Donor 3 GMA T-Cell Line 165-F5G to Non-Canonical Peptides

| | 1.25 μg/mL | | 2.5 μg/mL | | 5 μg/mL | | 10 μg/mL | |
|---|---|---|---|---|---|---|---|---|
| | Mean | Std dev | Mean | Std dev | Mean | Std dev | Mean | Std dev |
| GMA | 1071 | 392 | 19012 | 658 | 45384 | 5165 | 48029 | 1665 |
| GLT 631 | 131 | 30 | 143 | 45 | 176 | 48 | 110 | 40 |
| GAT 631 | 118 | 22 | 160 | 35 | 106 | 24 | 130 | 22 |
| GAT 111 | 139 | 29 | 121 | 45 | 142 | 31 | 122 | 33 |
| LT 11 | 126 | 22 | 113 | 12 | 136 | 31 | 129 | 22 |
| GT 11 | 160 | 50 | 124 | 42 | 124 | 18 | 158 | 35 |
| GL 14 | 559 | 107 | 2779 | 485 | 89 | 8 | 38 | 1 |
| MBP | | | | | | | 138 | 12 |

No Antigen Value: 136 +/− 29

Donor 4 GA-Specific T-Cell Line 205-1F4

Table 58 shows reactivity of 205-1F4 following stimulation with 1, 2, 5, and 10 μg/mL of peptide LT 11 and GMA, as demonstrated by luminescent ATP proliferation assay. The assay was carried out at Day 80 of culture, after seven restimulations, at a T-cell concentration of 1×$10^5$ cells/mL, in the presence of mitomycin C-treated autologous B-LCL. Line 165-1F4 showed reactivity to LT 11. The response to LT 11 relative to the no antigen control reached 17.3-fold at a dose of 10 μg/mL antigen.

TABLE 58

| Reactivity of Donor 4 COP T-Cell Line 205-1F4 to Non-Canonical GA Peptide LT 11(Day 80) | | | | | | | | |
|---|---|---|---|---|---|---|---|---|
| | 1 µg/mL | | 2 µg/mL | | 5 µg/mL | | 10 µg/mL | |
| | Mean | Std dev | Mean | Std dev | Mean | Std dev | Mean | Std dev |
| GMA | 7,477 | 1,628 | 64,999 | 3,444 | 83,107 | 3,193 | 67,482 | 3,285 |
| LT 11 | 3,675 | 488 | 4,589 | 827 | 7,626 | 1,261 | 8,853 | 513 |

GMA no antigen = 812 (SD 71);
LT 11 no antigen = 850 (SD85)

Table 59 shows reactivity of 205-1F4 following stimulation with 1, 2, 5, and 10 µg/mL of peptide LT 11 and GMA, as demonstrated by luminescent ATP proliferation assay. The assay was carried out at Day 80 of culture, after seven restimulations, at a T-cell concentration of $1\times10^5$ cells/mL, in the presence of mitomycin C-treated autologous B-LCL. Line 165-1F4 showed reactivity to LT 11. The response to LT 11 relative to the no antigen control reached 10.4-fold at a dose of 10 µg/mL antigen.

TABLE 59

| Reactivity of Donor 4 COP T-Cell Line 205-1F4 to Non-Canonical GA Peptides (Day 71) | | | | | | | | |
|---|---|---|---|---|---|---|---|---|
| | 0 µg/mL | | 1 µg/mL | | 3 µg/mL | | 10 µg/mL | |
| 205-1F4 | Mean | Std dev | Mean | Std dev | Mean | Std dev | Mean | Std dev |
| COP | 2076 | 497 | 47254 | 19915 | 169021 | 13990 | 213196 | 4628 |
| GMA | | | 17341 | 4286 | 195335 | 4478 | 218954 | 7589 |
| GLT 631 | | | 1938 | 322 | 1863 | 46 | 2504 | 255 |
| GAT 631 | | | 2424 | 143 | 2439 | 136 | 3035 | 374 |
| GAT 111 | | | 2002 | 21 | 2163 | 238 | 2275 | 299 |
| LT 11 | | | 73850 | 16093 | 154321 | 6238 | 158776 | 11492 |
| GL 14 | | | 12630 | 1371 | 1423 | 686 | 158 | 134 |
| GT 41S | | | 2361 | 239 | 1805 | 396 | 1855 | 262 |
| GA 64 | | | 2544 | 220 | 2261 | 80 | 2080 | 250 |

Donor 1 GA-Specific T-Cell Line 222-AG12: Lack of Reactivity to Non-Canonical Peptides Donor 1 GMA T-cell line 222-AG12 was assayed for proliferation following stimulation with 0, 1, 10, and 30 µg/mL each of peptides GLT 631, GAT 631, GAT 111, LT 11, GT 11, GL 14, COP, and GMA, at a T-cell concentration of $2\times10^5$ cells/mL, in the presence of mitomycin C-treated autologous B-LCL. Line 222-AG12 was assayed after 3 rounds of restimulation (4 total stimulations). Proliferation was measured by luminescent ATP assay. This line did not respond to any of the non-canonical GA peptides tested. The data are shown in Table 60.

Table 60 shows reactivity of 205-1F4 following stimulation with 0, 1, 3, and 10 µg/mL of each of peptides GLT 631, GAT 631, GAT 111, LT 11, GL 14, GT 41S, GA 64, COP, and GMA, as demonstrated by luminescent ATP proliferation assay. The response to GMA in comparison to COP at the 10 µg/mL dose in this assay was 101.3%. The assay was carried out at Day 71 of culture, after six restimulations, at a T-cell concentration of $1\times10^5$ cells/mL, in the presence of mitomycin C-treated autologous B-LCL. Line 165-1F4 showed reactivity to LT 11, and not to the other non-canonical GA peptides tested. The response to LT 11 relative to the no antigen control reached 76.5-fold at a dose of 10 µg/mL antigen.

TABLE 60

| Reactivity of Donor 1 GMA T-Cell Line 222-AG12 to Non-Canonical Peptides | | | | | | | | |
|---|---|---|---|---|---|---|---|---|
| | COP | | GLT 631 | | GAT 631 | | GAT 111 | |
| ug/mL | Mean | Std dev | Mean | Std dev | Mean | Std dev | Mean | Std dev |
| 0 | 4071 | 186 | | | | | | |
| 1 | 10056 | 878 | 3801 | 772 | 3442 | 406 | 3391 | 708 |
| 10 | 233083 | 3 | 4002 | 340 | 3217 | 202 | 2568 | 162 |
| 30 | 227055 | 10049 | 5292 | 885 | 3548 | 367 | 2245 | 496 |

TABLE 60-continued

| Reactivity of Donor 1 GMA T-Cell Line 222-AG12 to Non-Canonical Peptides | | | | | | | | |
|---|---|---|---|---|---|---|---|---|
| | Peptide 026 | | LT 11 | | GL 14 | | GT 11 | |
| ug/mL | Mean | Std dev | Mean | Std dev | Mean | Std dev | Mean | Std dev |
| 1 | 4155 | 630 | 3452 | 44 | 3531 | 205 | 2650 | 450 |
| 10 | 4120 | 653 | 4242 | 284 | 55 | 7 | 3285 | 773 |
| 30 | 2683 | 109 | 2347 | 748 | 43 | 2 | 2231 | 179 |

Data in RLU.

Example III. Characterization of GA-Specific Human T-Cell Lines Based on MHC Restriction As described in the Methods, T-cell lines were tested for MHC restriction by measuring proliferation following incubation with APC. Mitomycin-treated autologous APC, and test APC, e.g., from donors having at least one HLA-DR match with the original PBMC donor were employed. The results are summarized in Table 61. The values in the data tables below are in RLU.

TABLE 61

| MHC Restriction of T-Cell Lines | | |
|---|---|---|
| Line | Donor MHC Class II | MHC Restriction |
| 165-B5G (Donor 3) | *15, *11 | DR-11 |
| 165-C4G (Donor 3) | *15, *11 | DR-11 |
| 165-C5G (Donor 3) | *15, *11 | DR-15 |
| 165-E9G (Donor 3) | *15, *11 | DR-11 |
| 165-F5G (Donor 3) | *15, *11 | DR-11 |
| 165-F10G (Donor 3) | *15, *11 | DR-15 |
| 165-B6C (Donor 3) | *15, *11 | DR-11 |
| 165-C7C (Donor 3) | *15, *11 | DR-11 |
| 165-D3C (Donor 3) | *15, *11 | DR-15 |
| 165-F3C (Donor 3) | *15, *11 | DR-11 |
| 165-F6C (Donor 3) | *15, *11 | DR-15 |
| 205-1D1 (Donor 4) | *07, *13 | DR-13 |
| 205-1F4 (Donor 4) | *07, *13 | DR-13 |
| 205-1H7 (Donor 4) | *07, *13 | DR-13 |

Donor 3 T-Cell Line 165-B5G

Donor 3 T-cell line 165-B5G was assayed for proliferation, using mitomycin-treated APC from Donors 3, 5, and 6 that had been incubated in the presence or the absence of 20 μg/mL GMA. T-cell line 165-B5G had been restimulated six times (not including the initial stimulation) with antigen before the MHC restriction assay was carried out. The data, shown in Table 62 and FIG. 9A, indicate that 165-B5G is restricted by HLA-DRβ1*11.

TABLE 62

| MHC Restriction of 165-B5G | | | | | | |
|---|---|---|---|---|---|---|
| B-LCL Donor | Allele 1 | Allele 2 | No Ag | SD | GMA | SD |
| 3 (Autologous) | DRβ1*1501 | DRβ1*11 | 1736 | 449 | 4776 | 560 |
| 5 | DRβ1*01 | DRβ1*11 | 939 | 101 | 5450 | 933 |
| 6 | DRβ1*1501 | DRβ1*13 | 1113 | 120 | 2360 | 354 |

Donor 3 T-Cell Line 165-C4G

Donor 3 T-cell line 165-C4G was assayed for proliferation, using mitomycin-treated APC from Donors 3, 5, and 7 that had been incubated in the presence or the absence of 20 μg/mL GMA. T-cell line 165-C4G had been restimulated five times (not including the initial stimulation) with antigen before the MHC restriction assay was carried out. The data, shown in Table 63 and FIG. 9B, indicate that 165-C4G is restricted by HLA-DRβ1*11.

TABLE 63

| MHC Restriction of 165-C4G | | | | | | |
|---|---|---|---|---|---|---|
| B-LCL Donor | Allele 1 | Allele 2 | No Ag | SD | GMA | SD |
| 3 (Autologous) | DRβ1*1501 | DRβ1*11 | 1657 | 25 | 48711 | 3406 |
| 5 | DRβ1*01 | DRβ1*11 | 1695 | 453 | 41833 | 1884 |
| 7 | DRβ1*1501 | DRβ1*03 | 3126 | 376 | 4870 | 197 |

Donor 3 T-Cell Line 165-05G

Donor 3 T-cell line 165-05G was assayed for proliferation, using mitomycin-treated APC from Donors 3, 5, and 6 that had been incubated in the presence or the absence of 20 μg/mL GMA. T-cell line 165-05G had been restimulated four times (not including the initial stimulation) with antigen before the MHC restriction assay was carried out. The data, shown in Table 64 and FIG. 10A, indicate that 165-05G is restricted by HLA-DRβ1*1501.

TABLE 64

| MHC Restriction of 165-C5G | | | | | | |
|---|---|---|---|---|---|---|
| B-LCL Donor | Allele 1 | Allele 2 | No Ag | SD | GMA | SD |
| 3 (Autologous) | DRβ1*1501 | DRβ1*11 | 2738 | 241 | 16461 | 1924 |
| 5 | DRβ1*01 | DRβ1*11 | 3824 | 352 | 9825 | 798 |
| 6 | DRβ1*1501 | DRβ1*13 | 2341 | 108 | 31717 | 3547 |

Donor 3 T-Cell Line 165-E9G

Donor 3 T-cell line 165-E9G was assayed for proliferation, using mitomycin-treated APC from Donors 3, 5, and 6 that had been incubated in the presence or the absence of 20 μg/mL GMA. T-cell line 165-E9G had been restimulated four times (not including the initial stimulation) with antigen before the MHC restriction assay was carried out. The data, shown in Table 65 and FIG. 10B, indicate that 165-E9G is restricted by HLA-DRβ1*11.

TABLE 65

| MHC Restriction of 165-E9G | | | | | | |
|---|---|---|---|---|---|---|
| B-LCL Donor | Allele 1 | Allele 2 | No Ag | SD | GMA | SD |
| 3 (Autologous) | DRβ1*1501 | DRβ1*11 | 1276 | 295 | 5452 | 452 |
| 5 | DRβ1*01 | DRβ1*11 | 1300 | 124 | 9514 | 460 |
| 6 | DRβ1*1501 | DRβ1*13 | 1255 | 85 | 1442 | 96 |

Donor 3 T-Cell Line 165-F5G

Donor 3 T-cell line 165-F5G was assayed for proliferation, using mitomycin-treated APC from Donors 3, 5, and 6 that had been incubated in the presence or the absence of 20 μg/mL GMA. T-cell line 165-F5G had been restimulated seven times (not including the initial stimulation) with antigen before the MHC restriction assay was carried out. The data, shown in Table 66 and FIG. 11A, indicate that 165-F5G is restricted by HLA-DRβ1*11.

TABLE 66

| MHC Restriction of 165-F5G | | | | | | |
|---|---|---|---|---|---|---|
| B-LCL Donor | Allele 1 | Allele 2 | no Ag | SD | GMA | SD |
| 3 (Autologous) | DRβ1*1501 | DRβ1*11 | 881 | 96 | 2862 | 62 |
| 5 | DRβ1*01 | DRβ1*11 | 1255 | 74 | 3971 | 755 |
| 6 | DRβ1*1501 | DRβ1*13 | 858 | 120 | 1424 | 38 |

Donor 3 T-Cell Line 165-F10G

Donor 3 T-cell line 165-F10G was assayed for proliferation, using mitomycin-treated APC from Donors 3, 5, and 7 that had been incubated in the presence or the absence of 20 μg/mL GMA. T-cell line 165-F10G had been restimulated five times (not including the initial stimulation) with antigen before the MHC restriction assay was carried out. The data, shown in Table 67 and FIG. 11B, indicate that 165-F10G is restricted by HLA-DRβ1*1501.

TABLE 67

| MHC Restriction of 165-F10G | | | | | | |
|---|---|---|---|---|---|---|
| B-LCL Donor | Allele 1 | Allele 2 | no Ag | SD | GMA | SD |
| 3 (Autologous) | DRβ1*1501 | DRβ1*11 | 2603 | 107 | 120946 | 9732 |

TABLE 67-continued

| MHC Restriction of 165-F10G | | | | | | |
|---|---|---|---|---|---|---|
| B-LCL Donor | Allele 1 | Allele 2 | no Ag | SD | GMA | SD |
| 5 | DRβ1*01 | DRβ1*11 | 1200 | 60 | 6221 | 2138 |
| 7 | DRβ1*1501 | DRβ1*03 | 7709 | 336 | 151115 | 6439 |

Donor 3 T-Cell Line 165-B6C

Donor 3 T-cell line 165-B6C was assayed for proliferation, using mitomycin-treated APC from Donors 3, 5, and 6 that had been incubated in the presence or the absence of 20 μg/mL COP. T-cell line 165-B6C had been restimulated six times (not including the initial stimulation) with antigen before the MHC restriction assay was carried out. The data, shown in Table 68 and FIG. 12A, indicate that 165-E9G is restricted by HLA-DRβ1*11.

TABLE 68

| MHC Restriction of 165-B6C | | | | | | |
|---|---|---|---|---|---|---|
| B-LCL Donor | Allele 1 | Allele 2 | no Ag | SD | GMA | SD |
| 3 (Autologous) | DRβ1*1501 | DRβ1*11 | 224 | 13 | 2237 | 421 |
| 5 | DRβ1*01 | DRβ1*11 | 516 | 63 | 8944 | 1014 |
| 6 | DRβ1*1501 | DRβ1*13 | 250 | 16 | 322 | 20 |

Donor 3 T-Cell Line 165-C7C

Donor 3 T-cell line 165-C7C was assayed for proliferation, using mitomycin-treated APC from Donors 3, 5, and 6 that had been incubated in the presence or the absence of 20 μg/mL COP. T-cell line 165-C7C had been restimulated five times (not including the initial stimulation) with antigen before the MHC restriction assay was carried out. The data, shown in Table 69 and FIG. 12B, indicate that 165-E9G is restricted by HLA-DRβ1*11.

TABLE 69

| MHC Restriction of 165-C7C | | | | | | |
|---|---|---|---|---|---|---|
| B-LCL Donor | Allele 1 | Allele 2 | no Ag | SD | GMA | SD |
| 3 (Autologous) | DRβ1*1501 | DRβ1*11 | 1130 | 18 | 13714 | 509 |
| 5 | DRβ1*01 | DRβ1*11 | 7752 | 1101 | 94535 | 369 |
| 6 | DRβ1*1501 | DRβ1*13 | 767 | 66 | 1189 | 348 |

Donor 3 T-Cell Line 165-D3C

Donor 3 T-cell line 165-D3C was assayed for proliferation, using mitomycin-treated APC from Donors 3, 5, and 7 that had been incubated in the presence or the absence of 20 μg/mL COP. T-cell line 165-D3C had been restimulated six times (not including the initial stimulation) with antigen before the MHC restriction assay was carried out. The data, shown in Table 70 and FIG. 13A, indicate that 165-D3Cis restricted by HLA-DRβ1*1501.

TABLE 70

| MHC Restriction of 165-D3C | | | | | | |
|---|---|---|---|---|---|---|
| B-LCL Donor | Allele 1 | Allele 2 | no Ag | SD | GMA | SD |
| 3 (Autologous) | DRβ1*1501 | DRβ1*11 | 7335 | 83 | 106840 | 7358 |
| 5 | DRβ1*01 | DRβ1*11 | 3181 | 43 | 12173 | 5325 |
| 7 | DRβ1*1501 | DRβ1*03 | 18492 | 642 | 149506 | 2288 |

Donor 3 T-Cell Line 165-F3C

Donor 3 T-cell line 165-F3C was assayed for proliferation, using mitomycin-treated APC from Donors 3, 5, and 7 that had been incubated in the presence or the absence of 20 μg/mL COP. T-cell line 165-F3C had been restimulated eight times (not including the initial stimulation) with antigen before the MHC restriction assay was carried out. The data, shown in Table 71 and FIG. 13B, indicate that 165-F3C is restricted by HLA-DRβ1*11.

TABLE 71

| MHC Restriction of 165-F3C | | | | | | |
|---|---|---|---|---|---|---|
| B-LCL Donor | Allele 1 | Allele 2 | no Ag | Std. Dev | GMA | Std. Dev |
| 3 (Autologous) | DRβ1*1501 | DRβ1*11 | 2346 | 290 | 45559 | 4853 |
| 5 | DRβ1*01 | DRβ1*11 | 3582 | 547 | 39565 | 3654 |
| 6 | DRβ1*1501 | DRβ1*3 | 2885 | 356 | 7869 | 2306 |

Donor 3 T-Cell line 165-F6C

Donor 3 T-cell line 165-F6C was assayed for proliferation, using mitomycin-treated APC from Donors 3, 5, and 6 that had been incubated in the presence or the absence of 20 μg/mL COP. T-cell line 165-F6C had been restimulated eight times (not including the initial stimulation) with antigen before the MHC restriction assay was carried out. The data, shown in Table 72 and FIG. 14A, indicate that 165-F6C is restricted by HLA-DRβ1*1501.

TABLE 72

| MHC Restriction of 165-F6C | | | | | | |
|---|---|---|---|---|---|---|
| B-LCL Donor | Allele 1 | Allele 2 | No Ag | SD | GMA | SD |
| 3 (Autologous) | DRβ1*1501 | DRβ1*11 | 837 | 108 | 12562 | 1236 |
| 5 | DRβ1*01 | DRβ1*11 | 963 | 87 | 3142 | 285 |
| 6 | DRβ1*1501 | DRβ1*13 | 1122 | 62 | 30293 | 3836 |

Donor 4 T-Cell Line 205-1D1

Donor 4 T-cell line 205-1D1 was assayed for proliferation, using autologous B-LCL, and B-LCL from Donors 1, 2, and 6 that had been incubated in the presence or absence of 60 μg/mL COP. T-cell line 205-1D1 was restimulated 5 times (not including the initial stimulation) with antigen before the MHC restriction assay was carried out. The results, shown in Table 73, indicate that 205-1D1 is restricted by HLA-DRβ1*13.

TABLE 73

| MHC Restriction of 205-1D1 | | | | | | |
|---|---|---|---|---|---|---|
| B-LCL Donor | Allele 1 | Allele 2 | No Ag | SD | COP | SD |
| 4 (autologous) | DRβ1* 07 | DRβ1* 13 | 1581.0 | 227.4 | 231113.0 | 3122.5 |
| 2 | DRβ1* 04:01 | DRβ1* 04:04 | 1216.7 | 119.9 | 1203.7 | 546.4 |
| 1 | DRβ1* 04:01 | DRβ1* 07:01 | 2546.3 | 251.2 | 1504.7 | 40.4 |
| 6 | DRβ1* 15:01 | DRβ1* 13 | 13472.0 | 1971.9 | 203780.3 | 21756.6 |

Donor 4 T-Cell Line 205-1H7

Donor 4 T-cell line 205-1H7 was assayed for proliferation, using autologous B-LCL, and B-LCL from Donors 1, 2, and 6 that had been incubated in the presence or absence of 40 μg/mL COP. T-cell line 205-1H7 was restimulated 5 times (not including the initial stimulation) with antigen before the MHC restriction assay was carried out. The results, shown in Table 74 and FIG. 14B, indicate that 205-1H7 is restricted by HLA-DRβ1*13.

TABLE 74

MHC Restriction of 205-1H7

| B-LCL Donor | Allele 1 | Allele 2 | No Ag | SD | COP | SD |
|---|---|---|---|---|---|---|
| 4 (autologous) | DRβ1*07 | DRβ1*13 | 1956 | 464 | 32418 | 2996 |
| 1 | DRβ1*04:01 | DRβ1*07:01 | 2748 | 784 | 8430 | 2540 |
| 6 | DRβ1*15:01 | DRβ1*13 | 2729 | 300 | 30583 | 174 |
| 2 | DRβ1*04:01 | DRβ1*04:04 | 2471 | 217 | 2065 | 250 |

Donor 4 T-Cell Line 205-1F4

Donor 4 T-cell line 205-1F4 and 205-1C4 was assayed for proliferation, using autologous B-LCL, and B-LCL from Donors 1, 2, and 6 that had been incubated in the presence or absence of 40 μg/mL COP. T-cell line 205-1F4 was restimulated 7 times (not including the initial stimulation) with antigen before the MHC restriction assay was carried out. T-cell line 205-1F4 was restimulated 7 times (not including the initial stimulation) with antigen before the MHC restriction assay was carried out. The results, shown in Table 75, indicate that 205-1F4 is restricted by HLA-DRβ1*13.

TABLE 75

MHC Restriction of 205-1F4

| | | | 205-1F4 | |
|---|---|---|---|---|
| APC donor | Donor Alleles | Stimulation | Mean | SD |
| 4 | *07, *13 | no antigen | 36999 | 2980 |
| (autologous) | | COP | 84094 | 5074 |
| 2 | *04:01*04:04 | no antigen | 2412 | 140 |
| | | COP | 1786 | 197 |
| 1 | *04:01, *07 | no antigen | 24850 | 1063 |
| | | COP | 11323 | 1116 |
| 6 | *13, *15 | no antigen | 10542 | 297 |
| | | COP | 113079 | 4646 |

Example IV. Characterization of GA-Specific Human T-Cell Lines Based on Analysis of Surface Marker Expression GA-specific T-cell lines were analyzed for surface expression of CD4 and CD8. A PE-labeled CD8 monoclonal antibody and a FITC-labeled CD4 monoclonal antibody were used for detection. As a nonspecific control, the cells were labeled with a PE-labeled mouse isotype matched control IgG1 monoclonal antibody and a FITC-labeled mouse IgG1 monoclonal antibody.

For immunofluorescent staining, T-cells were suspended in PBS containing 2% fetal calf serum at a cell concentration of 1 to $5\times10^6$ per mL. Cells were distributed in 12×75 mm polystyrene tubes at 100 uL per tube. Isotype matched control monoclonal antibodies were non-specific mouse IgG1 labeled with either fluorescein (FITC) or phycoerythrin (PE). FITC labeled anti CD4 and PE labeled anti CD8 were purchased as a cocktail from eBioscience, Inc. (San Diego, Calif.). Fluorochrome-labeled monoclonal antibodies were added at the manufacturer's recommended volume of 5 uL per tube. Cells were incubated with monoclonal antibodies for 15-30 minutes at 2-8° C. Cells were washed once by adding 2 mL of PBS per tube and centrifuging 5 minutes at 200×g. Buffer was decanted and 0.5 mL of PBS was added to each tube. Staining was evaluated using a FACScan flow cytometer and CellQuest software. Dead cells were excluded from analysis based upon forward and side scatter characteristics.

For GA-specific T-cell line 165-E9G, 99.76% detected cells were observed to be $CD4^+$, and none to be $CD8^+$. For GA-specific T-cell line 165-F5G, 97.46% detected cells were observed to be $CD4^+$, and 1.50% to be $CD8^+$. The control flow plots for 165-E9G and 165-F5G are shown in FIGS. 15A and 16A, respectively, and the CD4/CD8 analyses for 165-E9G and 165-F5G are shown in FIGS. 15B and 16B, respectively. Table 76 summarizes surface marker expression results for GA-reactive human T-cell lines generated.

TABLE 76

GMA and Copaxone Initiated T-Cell Lines-CD4+ and CD8+ Expression

| Cell Line | Donor | Culturing Antigen | % CD4+ | % CD8+ |
|---|---|---|---|---|
| 222-BA11 | 1 | GMA | 99 | 0 |
| 165-B5G | 3 | GMA | 99.1 | 0.7 |
| 165-C4G | 3 | GMA | 99.8 | |
| 165-C5G | 3 | GMA | 99.9 | |
| 165-D8G | 3 | GMA | 97.8 | 1.1 |
| 165-E7G | 3 | GMA | 99.8 | |
| 165-E9G | 3 | GMA | 99.8 | |
| 165-F10G | 3 | GMA | 99.7 | |
| 165-F5G | 3 | GMA | 97.5 | 1.5 |
| 165-F8G | 3 | GMA | 99.6 | |
| 165-H11G | 3 | GMA | 99.9 | |
| 222-2D8 | 1 | COP | 99.8 | |
| 222-2F12 | 1 | COP | 99.2 | |
| 165-B6C | 3 | COP | 99.4 | |
| 165-B10C | 3 | COP | 99.4 | |
| 165-C4C | 3 | COP | 99.5 | |
| 165-C7C | 3 | COP | 98.6 | |
| 165-D3C | 3 | COP | 97.7 | 5.4 |
| 165-D11C | 3 | COP | 99.8 | |
| 165-E3C | 3 | COP | 99.4 | |
| 165-F3C | 3 | COP | 99.4 | |
| 165-F6C | 3 | COP | 97.8 | 0.9 |
| 205-1C4 | 4 | COP | 98 | |
| 205-1F4 | 4 | COP | 97.8 | |
| 205-1H5 | 4 | COP | 95.8 | |
| 205-1H7 | 4 | COP | 98.6 | 0 |
| 205-1H11 | 4 | COP | 96.4 | |

Example V. GA-Specific Human T-Cell Line Panel Assay—Comparison of Nine GA Test Lots to Copaxone Proliferation assays, using the panel of six GA-specific long-term human T-cell lines listed in Table 78, were carried out to compare nine GA test lots, GMA/009/14 (GA Lot 009), GMA/010/14 (GA Lot 010), GMA/011/14 (GA Lot 011), GMA/012/14 (GA Lot 012), GMA/013/14 (GA Lot 013), GMA/014/14 (GA Lot 014), GA Lot 016, GMA/017/14 (GA Lot 017), GMA/018/14 (GA Lot 018), and GMA/070/14 (GA Lot 070), manufactured using standard methods, to a Copaxone reference lot.

TABLE 77

| Assay Panel GA-Specific Human T-Cell Lines | | | | | | | |
|---|---|---|---|---|---|---|---|
| T-Cell Line | Donor MHC Class II | Culturing Antigen | MHC Restriction | CD4/CD8 Expression | GA-Specificity Maintained (Restimulations) | Noncanon. Peptide Reactivity | Noncanon. Peptide Non-Reactivity |
| 222-2D8 | *04:01, *07:01 | COP | DR 4 | $CD4^+/CD8^-$ | ≥8 | | |
| 222-2F12 | *04:01, *07:01 | COP | DR 4 | $CD4^+/CD8^-$ | ≥8 | GL 14 | GLT 631<br>GAT 631<br>GAT 111 |
| 165-F3C | *15,*11 | COP | DR 11 | $CD4^+/CD8^-$ | ≥8 | Peptide 026<br>GL 14<br>LT 11 | GLT 631<br>GAT 631<br>GAT 111<br>GT 11<br>GT 41S<br>GA 64 |
| 165-F6C | *15,*11 | COP | DR 15 | $CD4^+/CD8^-$ | ≥8 | Peptide 026<br>GL 14 | GT 11<br>GLT 631<br>GAT 631<br>GAT 111<br>LT 11<br>GT 11<br>GT 41S<br>GA64 |
| 205-1C4 | *07, *13 | COP | | $CD4^+/CD8^-$ | ≥8 | Peptide 026 | GLT 631<br>GAT 631 |
| 205-1F4 | *07, *13 | COP | DR 13 | $CD4^+/CD8^-$ | ≥8 | LT 11 | GLT 631<br>GAT 631<br>GAT 111<br>GL 14<br>GT 41S<br>GA 64 |

Each T-cell line was restimulated using methods described above, using five concentrations of the reference antigen (0.5, 1, 2, 2.5, and 5 μg/ml Copaxone), the same five concentrations of test antigen (the nine GA test lots), and a no antigen control, in the presence of $5\times10^4$ mitomycin-treated autologous B-LCL. Proliferation was measured by ATP assay after 4 days of incubation with antigen, using methods described previously. The results are shown in Tables 78-87.

The percentages in the last column of each table were calculated as follows:

Proliferation response to test antigen minus proliferation response to control (no antigen)÷proliferation response to reference antigen minus proliferation response to control (no antigen)

TABLE 78

Stimulation of Assay Panel T-Cell Lines with GA Lot 009-ATP Proliferation Assay 222-2D8

| Dose | COP (Reference) | | 009 (Test) | | |
|---|---|---|---|---|---|
| μg/mL | Mean | Std Dev | Mean | Std Dev | 009/COP |
| 0.5 | 5,873 | 928 | 6,520 | 467 | 136.0% |
| 1 | 14,017 | 3,561 | 15,533 | 1,280 | 115.2% |
| 2 | 90,328 | 20,393 | 104,628 | 7,566 | 116.6% |
| 2.5 | 129,878 | 3,893 | 142,861 | 6,649 | 110.3% |
| 5 | 171,116 | 12,003 | 174,692 | 5,624 | 102.1% |

Background (No Antigen) value: 4,017 +/− 441

TABLE 78-continued

Stimulation of Assay Panel T-Cell Lines with GA Lot 009-ATP Proliferation Assay 222-2F12

| | COP (Reference) | | 009 (Test) | | |
|---|---|---|---|---|---|
| μg/mL | Mean | Std Dev | Mean | Std Dev | 009/COP |
| 0.5 | 10,879 | 171 | 13,129 | 576 | 162.8% |
| 1 | 27,042 | 508 | 24,268 | 2,645 | 86.0% |
| 2 | 105,024 | 1,834 | 113,978 | 4,261 | 109.2% |
| 2.5 | 115,241 | 1,764 | 115,441 | 7,433 | 100.2% |
| 5 | 129,291 | 1,465 | 132,528 | 3,596 | 102.7% |

Background (No Antigen) value: 7,297 +/− 910

165-F3C

| Dose | COP (Reference) | | 009 (Test) | | |
|---|---|---|---|---|---|
| μg/mL | Mean | Std Dev | Mean | Std Dev | 009/COP |
| 0.5 | 4,783 | 773 | 4,673 | 1,336 | 95.1% |
| 1 | 22,290 | 2,463 | 16,447 | 3,682 | 70.4% |
| 2 | 53,771 | 5,010 | 49,404 | 2,335 | 91.5% |
| 2.5 | 54,539 | 2,237 | 51,336 | 1,503 | 93.8% |
| 5 | 58,110 | 3,484 | 52,941 | 4,149 | 90.7% |

Background (No Antigen) value: 2,555 +/− 186

165-F6C

| | COP (Reference) | | 009 (Test) | | |
|---|---|---|---|---|---|
| μg/mL | Mean | Std Dev | Mean | Std Dev | 009/COP |
| 0.5 | 3,328 | 321 | 3,251 | 181 | 39.3% |
| 1 | 4,620 | 594 | 4,618 | 455 | 99.8% |
| 2 | 13,255 | 4,631 | 9,672 | 963 | 64.4% |

TABLE 78-continued

Stimulation of Assay Panel T-Cell Lines with GA Lot 009-ATP Proliferation Assay

| | | | | | |
|---|---|---|---|---|---|
| 2.5 | 18,726 | 6,563 | 16,212 | 4,933 | 83.8% |
| 5 | 38,653 | 4,745 | 35,066 | 4,305 | 89.9% |
| Background (No Antigen) value: 3,202 +/- 327 | | | | | |

205-1C4

| Dose | COP (Reference) | | 009 (Test) | | |
|---|---|---|---|---|---|
| μg/mL | Mean | Std Dev | Mean | Std Dev | 009/COP |
| 0.5 | 932 | 357 | 825 | 49 | 33.7% |
| 1 | 2,481 | 146 | 1,829 | 335 | 61.9% |
| 2 | 9,432 | 657 | 6,614 | 1,422 | 67.5% |
| 2.5 | 13,744 | 1,733 | 12,582 | 4,369 | 91.0% |
| 5 | 45,451 | 3,658 | 39,117 | 7,455 | 85.8% |
| Background (No Antigen) value: 770 +/- 62 | | | | | |

205-1F4

| | COP (Reference) | | 009 (Test) | | |
|---|---|---|---|---|---|
| μg/mL | Mean | Std Dev | Mean | Std Dev | 009/COP |
| 0.5 | 548 | 91 | 479 | 66 | 46.7% |
| 1 | 1,906 | 653 | 1,815 | 712 | 93.9% |
| 2 | 9,959 | 1,393 | 9,129 | 1,261 | 91.3% |
| 2.5 | 13,589 | 1,245 | 12,785 | 1,362 | 93.9% |
| 5 | 18,491 | 3,267 | 18,752 | 1,679 | 101.4% |
| Background (No Antigen) value: 419 +/- 4 | | | | | |

The dose response curves for GA Lot 009 are shown in FIGS. 17A, 17B, 18A, 18B, 19A, and 19B. Therefore, using a variety of T cell lines with different characteristics, COP and GMA009 elicited comparable responses and thus were considered to be immunologically identical.

TABLE 79

Stimulation of Assay Panel T-Cell Lines with GA Lot 010-ATP Proliferation Assay 222-2D8

| Dose | COP (Reference) | | 009 (Test) | | |
|---|---|---|---|---|---|
| μg/mL | Mean | Std Dev | Mean | Std Dev | 009/COP |
| 0.5 | 4,255 | 505 | 5,049 | 722 | 190.4% |
| 1 | 10,314 | 1,870 | 10,915 | 2,583 | 108.7% |
| 2 | 78,457 | 15,207 | 78,823 | 6,965 | 100.5% |
| 2.5 | 97,873 | 6,379 | 122,230 | 10,886 | 125.8% |
| 5 | 144,399 | 8,605 | 149,682 | 16,251 | 103.7% |
| Background (No Antigen) value: 3,378 +/- 153 | | | | | |

222-2F12

| | COP (Reference) | | 009 (Test) | | |
|---|---|---|---|---|---|
| μg/mL | Mean | Std Dev | Mean | Std Dev | 009/COP |
| 0.5 | 12,703 | 501 | 12,673 | 497 | 99.3% |
| 1 | 23,391 | 2,618 | 21,487 | 1,792 | 87.3% |
| 2 | 112,115 | 7,484 | 109,769 | 12,264 | 97.7% |
| 2.5 | 120,306 | 5,905 | 124,373 | 1,295 | 103.6% |
| 5 | 124,636 | 4,818 | 124,165 | 3,982 | 99.6% |
| Background (No Antigen) value: 8,395 +/- 464 | | | | | |

TABLE 79-continued

Stimulation of Assay Panel T-Cell Lines with GA Lot 010-ATP Proliferation Assay

165-F3C

| Dose | COP (Reference) | | 009 (Test) | | |
|---|---|---|---|---|---|
| μg/mL | Mean | Std Dev | Mean | Std Dev | 009/COP |
| 0.5 | 4,463 | 1,250 | 3,972 | 568 | 75.1% |
| 1 | 21,816 | 6,712 | 17,145 | 2,862 | 75.8% |
| 2 | 49,532 | 5,529 | 45,626 | 4,664 | 91.7% |
| 2.5 | 49,651 | 1,323 | 52,096 | 4,000 | 105.2% |
| 5 | 49,174 | 3,503 | 53,439 | 3,483 | 109.1% |
| Background (No Antigen) value: 2,493 +/- 192 | | | | | |

165-F6C

| | COP (Reference) | | 009 (Test) | | |
|---|---|---|---|---|---|
| μg/mL | Mean | Std Dev | Mean | Std Dev | 009/COP |
| 0.5 | 3,280 | 222 | 3,339 | 344 | 122.6% |
| 1 | 3,964 | 745 | 3,496 | 400 | 50.6% |
| 2 | 11,309 | 3,969 | 7,475 | 1,069 | 53.8% |
| 2.5 | 17,679 | 3,758 | 10,730 | 2,294 | 52.6% |
| 5 | 44,855 | 2,714 | 38,352 | 5,451 | 84.5% |
| Background (No Antigen) value: 3,018 +/- 159 | | | | | |

205-1C4

| Dose | COP (Reference) | | 009 (Test) | | |
|---|---|---|---|---|---|
| μg/mL | Mean | Std Dev | Mean | Std Dev | 009/COP |
| 0.5 | 1,161 | 172 | 978 | 121 | 29.5% |
| 1 | 2,900 | 683 | 1,868 | 339 | 48.4% |
| 2 | 11,911 | 1,293 | 6,957 | 1,479 | 55.0% |
| 2.5 | 22,329 | 3,810 | 11,920 | 4,092 | 51.4% |
| 5 | 44,721 | 3,924 | 40,858 | 2,367 | 91.2% |
| Background (No Antigen) value: 902 +/- 83 | | | | | |

205-1F4

| | COP (Reference) | | 009 (Test) | | |
|---|---|---|---|---|---|
| μg/mL | Mean | Std Dev | Mean | Std Dev | 009/COP |
| 0.5 | 798 | 73 | 862 | 84 | 151.0% |
| 1 | 5,066 | 1,752 | 3,707 | 1,629 | 69.1% |
| 2 | 18,121 | 3,930 | 13,446 | 2,549 | 73.2% |
| 2.5 | 21,921 | 2,364 | 18,853 | 1,841 | 85.6% |
| 5 | 29,173 | 1,524 | 23,905 | 854 | 81.5% |
| Background (No Antigen) value: 672 +/- 68 | | | | | |

TABLE 80

Stimulation of Assay Panel T-Cell Lines with GA Lot 011-ATP Proliferation Assay 222-2D8

| Dose | COP (Reference) | | 009 (Test) | | |
|---|---|---|---|---|---|
| μg/mL | Mean | Std Dev | Mean | Std Dev | 009/COP |
| 0.5 | 1,557 | 456 | 1,512 | 286 | 95.9% |
| 1 | 8,703 | 1,362 | 8,397 | 1,693 | 96.3% |
| 2 | 32,940 | 3,445 | 34,123 | 3,955 | 103.6% |
| 2.5 | 48,525 | 8,931 | 51,422 | 5,676 | 106.0% |
| 5 | 71,567 | 8,205 | 75,757 | 4,512 | 105.9% |
| Background (No Antigen) value: 461 +/- 76 | | | | | |

TABLE 80-continued

Stimulation of Assay Panel T-Cell Lines with GA Lot 011-ATP Proliferation Assay 222-2F12

| | COP (Reference) | | 009 (Test) | | |
|---|---|---|---|---|---|
| µg/mL | Mean | Std Dev | Mean | Std Dev | 009/COP |
| 0.5 | 2,110 | 681 | 1,618 | 225 | 55.2% |
| 1 | 10,990 | 1,608 | 8,548 | 999 | 75.5% |
| 2 | 57,764 | 3,942 | 40,708 | 7,498 | 69.9% |
| 2.5 | 65,033 | 4,308 | 59,306 | 3,142 | 91.1% |
| 5 | 73,060 | 2,058 | 74,006 | 2,646 | 101.3% |

Background (No Antigen) value: 1,012 +/− 168

165-F3C

| Dose | COP (Reference) | | 009 (Test) | | |
|---|---|---|---|---|---|
| µg/mL | Mean | Std Dev | Mean | Std Dev | 009/COP |
| 0.5 | 20,493 | 3,108 | 15,553 | 2,464 | 68.0% |
| 1 | 68,598 | 5,356 | 70,805 | 5,415 | 103.5% |
| 2 | 100,809 | 9,587 | 110,379 | 7,763 | 110.0% |
| 2.5 | 105,322 | 4,191 | 114,694 | 2,804 | 109.3% |
| 5 | 102,499 | 3,416 | 110,289 | 5,200 | 108.0% |

Background (No Antigen) value: 5,034 +/− 307

165-F6C

| | COP (Reference) | | 009 (Test) | | |
|---|---|---|---|---|---|
| µg/mL | Mean | Std Dev | Mean | Std Dev | 009/COP |
| 0.5 | 5,357 | 351 | 5,685 | 469 | 154.7% |
| 1 | 6,511 | 874 | 6,820 | 283 | 117.6% |
| 2 | 7,708 | 541 | 8,527 | 414 | 127.8% |
| 2.5 | 11,862 | 2,882 | 11,399 | 1,492 | 93.5% |
| 5 | 35,725 | 5,659 | 36,869 | 3,807 | 103.7% |

Background (No Antigen) value: 4,787 +/− 482

205-1C4

| Dose | COP (Reference) | | 009 (Test) | | |
|---|---|---|---|---|---|
| µg/mL | Mean | Std Dev | Mean | Std Dev | 009/COP |
| 0.5 | 5,075 | 1,021 | 4,842 | 200 | 74.6% |
| 1 | 17,052 | 4,570 | 10,681 | 3,096 | 50.6% |
| 2 | 68,021 | 4,447 | 58,057 | 6,966 | 84.4% |
| 2.5 | 78,633 | 4,450 | 79,010 | 4,431 | 100.5% |
| 5 | 81,137 | 5,758 | 81,325 | 7,340 | 100.2% |

Background (No Antigen) value: 4,161 +/− 347

205-1F4

| | COP (Reference) | | 009 (Test) | | |
|---|---|---|---|---|---|
| µg/mL | Mean | Std Dev | Mean | Std Dev | 009/COP |
| 0.5 | 3,568 | 598 | 4,342 | 690 | 162.7% |
| 1 | 69,032 | 22,687 | 69,419 | 12,433 | 100.6% |
| 2 | 149,921 | 7,505 | 152,894 | 10,185 | 102.0% |
| 2.5 | 163,087 | 9,462 | 168,342 | 4,837 | 103.3% |
| 5 | 152,755 | 6,433 | 157,571 | 3,542 | 103.2% |

Background (No Antigen) value: 2,334 +/− 162

TABLE 81

Stimulation of Assay Panel T-Cell Lines with GA Lot 012-ATP Proliferation Assay 222-2D8

| Dose | COP (Reference) | | 009 (Test) | | |
|---|---|---|---|---|---|
| µg/mL | Mean | Std Dev | Mean | Std Dev | 009/COP |
| 0.5 | 1,067 | 60 | 1,101 | 122 | 105.4% |
| 1 | 8,354 | 2,087 | 6,193 | 733 | 72.7% |
| 2 | 36,821 | 4,297 | 31,068 | 6,184 | 84.2% |
| 2.5 | 53,029 | 5,449 | 50,894 | 2,421 | 95.9% |
| 5 | 81,271 | 5,745 | 82,775 | 4,069 | 101.9% |

Background (No Antigen) value: 430 +/− 34

222-2F12

| | COP (Reference) | | 009 (Test) | | |
|---|---|---|---|---|---|
| µg/mL | Mean | Std Dev | Mean | Std Dev | 009/COP |
| 0.5 | 1,893 | 188 | 1,469 | 216 | 55.1% |
| 1 | 10,225 | 2,333 | 7,538 | 1,448 | 71.0% |
| 2 | 40,220 | 1,419 | 32,024 | 3,241 | 79.1% |
| 2.5 | 57,292 | 3,144 | 53,168 | 5,176 | 92.7% |
| 5 | 68,039 | 1,978 | 69,258 | 1,701 | 101.8% |

Background (No Antigen) value: 950 +/− 100

165-F3C

| Dose | COP (Reference) | | 009 (Test) | | |
|---|---|---|---|---|---|
| µg/mL | Mean | Std Dev | Mean | Std Dev | 009/COP |
| 0.5 | 15,194 | 1,152 | 14,737 | 4,629 | 95.8% |
| 1 | 67,378 | 4,756 | 58,886 | 6,743 | 86.5% |
| 2 | 102,921 | 5,040 | 106,309 | 2,930 | 103.4% |
| 2.5 | 110,400 | 4,921 | 114,473 | 6,296 | 103.8% |
| 5 | 104,688 | 5,035 | 105,772 | 5,365 | 101.1% |

Background (No Antigen) value: 4,283 +/− 251

165-F6C

| | COP (Reference) | | 009 (Test) | | |
|---|---|---|---|---|---|
| µg/mL | Mean | Std Dev | Mean | Std Dev | 009/COP |
| 0.5 | 4,003 | 479 | 3,890 | 381 | 80.8% |
| 1 | 4,700 | 323 | 4,462 | 400 | 81.5% |
| 2 | 5,888 | 499 | 5,200 | 290 | 72.2% |
| 2.5 | 6,324 | 849 | 5,967 | 1,013 | 87.7% |
| 5 | 13,607 | 3,286 | 13,687 | 3,965 | 100.8% |

Background (No Antigen) value: 3,414 +/− 278

205-1C4

| Dose | COP (Reference) | | 009 (Test) | | |
|---|---|---|---|---|---|
| µg/mL | Mean | Std Dev | Mean | Std Dev | 009/COP |
| 0.5 | 6,392 | 771 | 5,887 | 803 | 79.7% |
| 1 | 19,042 | 4,648 | 11,232 | 3,081 | 48.4% |
| 2 | 82,263 | 9,522 | 78,506 | 8,350 | 95.2% |
| 2.5 | 95,299 | 6,137 | 94,727 | 2,832 | 99.4% |
| 5 | 93,952 | 5,481 | 98,785 | 4,142 | 105.4% |

Background (No Antigen) value: 3,901 +/− 250

205-1F4

| | COP (Reference) | | 009 (Test) | | |
|---|---|---|---|---|---|
| µg/mL | Mean | Std Dev | Mean | Std Dev | 009/COP |
| 0.5 | 3,257 | 321 | 3,945 | 628 | 166.8% |
| 1 | 68,785 | 10,930 | 44,032 | 14,509 | 62.8% |
| 2 | 139,390 | 7,392 | 146,170 | 3,179 | 104.9% |

TABLE 81-continued

| Stimulation of Assay Panel T-Cell Lines with GA Lot 012-ATP Proliferation Assay | | | | | |
|---|---|---|---|---|---|
| 2.5 | 160,581 | 5,164 | 155,997 | 7,765 | 97.1% |
| 5 | 155,605 | 6,639 | 150,329 | 6,076 | 96.6% |
| Background (No Antigen) value: 2,227 +/− 157 | | | | | |

TABLE 82

Stimulation of Assay Panel T-Cell Lines with GA Lot 013-ATP Proliferation Assay 222-2D8

| Dose | COP (Reference) | | 009 (Test) | | |
|---|---|---|---|---|---|
| μg/mL | Mean | Std Dev | Mean | Std Dev | 009/COP |
| 0.5 | 25,365 | 4,220 | 27,316 | 1,982 | 112.4% |
| 1 | 77,981 | 4,058 | 99,345 | 4,984 | 131.2% |
| 2 | 153,313 | 3,143 | 161,150 | 1,648 | 105.5% |
| 2.5 | 168,388 | 4,098 | 170,296 | 5,988 | 101.2% |
| 5 | 147,783 | 5,013 | 158,207 | 5,260 | 107.5% |

Background (No Antigen) value: 9,575 +/− 465

222-2F12

| | COP (Reference) | | 009 (Test) | | |
|---|---|---|---|---|---|
| μg/mL | Mean | Std Dev | Mean | Std Dev | 009/COP |
| 0.5 | 24,901 | 2,351 | 23,156 | 1,553 | 84.6% |
| 1 | 55,453 | 7,018 | 66,725 | 4,436 | 126.9% |
| 2 | 103,212 | 3,256 | 110,099 | 1,828 | 107.7% |
| 2.5 | 108,843 | 4,486 | 111,414 | 3,588 | 102.7% |
| 5 | 106,365 | 4,274 | 109,397 | 2,414 | 103.3% |

Background (No Antigen) value: 13,595 +/− 616

165-F3C

| Dose | COP (Reference) | | 009 (Test) | | |
|---|---|---|---|---|---|
| μg/mL | Mean | Std Dev | Mean | Std Dev | 009/COP |
| 0.5 | 20,375 | 4,140 | 17,678 | 2,582 | 76.4% |
| 1 | 54,977 | 6,036 | 48,036 | 9,773 | 84.9% |
| 2 | 75,772 | 3,879 | 76,003 | 5,773 | 100.3% |
| 2.5 | 71,148 | 8,060 | 76,871 | 5,841 | 109.2% |
| 5 | 63,195 | 4,782 | 68,854 | 4,797 | 110.4% |

Background (No Antigen) value: 8,941 +/− 494

165-F6C

| | COP (Reference) | | 009 (Test) | | |
|---|---|---|---|---|---|
| μg/mL | Mean | Std Dev | Mean | Std Dev | 009/COP |
| 0.5 | 44,939 | 5,060 | 38,142 | 4,681 | 81.8% |
| 1 | 66,323 | 6,482 | 58,969 | 7,116 | 87.5% |
| 2 | 79,579 | 14,622 | 82,653 | 12,578 | 104.3% |
| 2.5 | 76,333 | 11,683 | 81,175 | 6,255 | 107.1% |
| 5 | 59,919 | 2,411 | 70,322 | 3,375 | 119.9% |

Background (No Antigen) value: 7,671 +/− 612

205-1C4

| Dose | COP (Reference) | | 009 (Test) | | |
|---|---|---|---|---|---|
| μg/mL | Mean | Std Dev | Mean | Std Dev | 009/COP |
| 0.5 | 3,847 | 615 | 3,415 | 336 | 42.3% |
| 1 | 7,480 | 929 | 6,177 | 430 | 70.3% |
| 2 | 21,751 | 6,694 | 17,669 | 3,423 | 78.1% |
| 2.5 | 24,737 | 3,120 | 29,260 | 3,679 | 120.9% |
| 5 | 45,039 | 3,496 | 46,083 | 2,233 | 102.5% |

Background (No Antigen) value: 3,098 +/− 267

TABLE 82-continued

Stimulation of Assay Panel T-Cell Lines with GA Lot 013-ATP Proliferation Assay 205-1F4

| | COP (Reference) | | 009 (Test) | | |
|---|---|---|---|---|---|
| μg/mL | Mean | Std Dev | Mean | Std Dev | 009/COP |
| 0.5 | 2,220 | 198 | 2,196 | 168 | 84.5% |
| 1 | 11,015 | 1,628 | 9,630 | 1,309 | 84.5% |
| 2 | 39,375 | 2,106 | 38,187 | 5,098 | 96.8% |
| 2.5 | 42,534 | 1,314 | 37,818 | 2,326 | 88.3% |
| 5 | 38,810 | 1,569 | 39,028 | 2,977 | 100.6% |

Background (No Antigen) value: 2,063 +/− 134

TABLE 83

Stimulation of Assay Panel T-Cell Lines with GA Lot 014-ATP Proliferation Assay 222-2D8

| Dose | COP (Reference) | | 009 (Test) | | |
|---|---|---|---|---|---|
| μg/mL | Mean | Std Dev | Mean | Std Dev | 009/COP |
| 0.5 | 17,943 | 2,305 | 18,146 | 1,407 | 102.1% |
| 1 | 49,878 | 1,107 | 75,336 | 10,941 | 161.0% |
| 2 | 138,669 | 4,438 | 137,785 | 2,730 | 99.3% |
| 2.5 | 148,889 | 5,061 | 145,978 | 4,334 | 97.9% |
| 5 | 141,114 | 4,171 | 149,762 | 2,305 | 106.5% |

Background (No Antigen) value: 8,118 +/− 377

222-2F12

| | COP (Reference) | | 009 (Test) | | |
|---|---|---|---|---|---|
| μg/mL | Mean | Std Dev | Mean | Std Dev | 009/COP |
| 0.5 | 25,481 | 2,172 | 20,573 | 940 | 58.9% |
| 1 | 58,460 | 4,482 | 70,075 | 5,596 | 125.9% |
| 2 | 106,340 | 2,628 | 106,563 | 2,741 | 100.2% |
| 2.5 | 109,948 | 1,984 | 112,155 | 2,215 | 102.3% |
| 5 | 104,449 | 3,162 | 108,272 | 4,634 | 104.2% |

Background (No Antigen) value: 13,533 +/− 630

165-F3C

| Dose | COP (Reference) | | 009 (Test) | | |
|---|---|---|---|---|---|
| μg/mL | Mean | Std Dev | Mean | Std Dev | 009/COP |
| 0.5 | 21,955 | 4,311 | 19,689 | 3,711 | 83.1% |
| 1 | 56,707 | 4,625 | 54,835 | 10,988 | 96.1% |
| 2 | 78,456 | 6,403 | 82,864 | 4,558 | 106.3% |
| 2.5 | 76,247 | 7,609 | 83,752 | 4,254 | 111.1% |
| 5 | 76,428 | 6,804 | 83,080 | 5,529 | 109.8% |

Background (No Antigen) value: 8,584 +/− 523

165-F6C

| | COP (Reference) | | 009 (Test) | | |
|---|---|---|---|---|---|
| μg/mL | Mean | Std Dev | Mean | Std Dev | 009/COP |
| 0.5 | 43,850 | 3,708 | 41,448 | 3,670 | 93.3% |
| 1 | 70,054 | 7,287 | 64,182 | 5,576 | 90.5% |
| 2 | 87,633 | 9,863 | 88,354 | 5,734 | 100.9% |
| 2.5 | 86,427 | 4,647 | 87,136 | 9,302 | 100.9% |
| 5 | 71,493 | 8,356 | 75,027 | 3,629 | 105.6% |

Background (No Antigen) value: 8,054 +/− 426

TABLE 83-continued

Stimulation of Assay Panel T-Cell Lines with GA Lot 014-ATP Proliferation Assay 205-1C4

| Dose | COP (Reference) | | 009 (Test) | | |
|---|---|---|---|---|---|
| μg/mL | Mean | Std Dev | Mean | Std Dev | 009/COP |
| 0.5 | 2,414 | 259 | 2,054 | 112 | −3.5% |
| 1 | 4,570 | 831 | 4,101 | 901 | 81.3% |
| 2 | 11,006 | 253 | 9,628 | 1,032 | 84.6% |
| 2.5 | 15,584 | 1,789 | 14,199 | 1,978 | 89.8% |
| 5 | 32,966 | 2,194 | 30,063 | 3,957 | 90.6% |

Background (No Antigen) value: 2,067 +/− 117

205-1F4

| | COP (Reference) | | 009 (Test) | | |
|---|---|---|---|---|---|
| μg/mL | Mean | Std Dev | Mean | Std Dev | 009/COP |
| 0.5 | 1,164 | 67 | 1,250 | 138 | 45.6% |
| 1 | 4,500 | 976 | 6,012 | 1,120 | 147.6% |
| 2 | 16,304 | 1,271 | 15,354 | 1,092 | 93.7% |
| 2.5 | 20,256 | 1,947 | 20,671 | 2,045 | 102.2% |
| 5 | 21,762 | 2,639 | 19,090 | 1,673 | 86.9% |

Background (No Antigen) value: 1,323 +/− 95

TABLE 84

Stimulation of Assay Panel T-Cell Lines with GA Lot 016-ATP Proliferation Assay 222-2D8

| Dose | COP (Reference) | | 009 (Test) | | |
|---|---|---|---|---|---|
| μg/mL | Mean | Std Dev | Mean | Std Dev | 009/COP |
| 0.5 | 31,023 | 5,756 | 31,816 | 10,004 | 102.8% |
| 1 | 95,723 | 17,899 | 96,463 | 10,112 | 100.8% |
| 2 | 115,013 | 22,227 | 117,909 | 23,892 | 102.6% |
| 2.5 | 104,841 | 15,044 | 108,050 | 15,244 | 103.1% |
| 5 | 87,827 | 5,622 | 91,643 | 5,449 | 104.5% |

Background (No Antigen) value: 4,044 +/− 280

222-2F12

| | COP (Reference) | | 009 (Test) | | |
|---|---|---|---|---|---|
| μg/mL | Mean | Std Dev | Mean | Std Dev | 009/COP |
| 0.5 | 41,489 | 10,690 | 37,371 | 4,627 | 88.8% |
| 1 | 83,701 | 11,958 | 79,918 | 13,963 | 95.2% |
| 2 | 92,174 | 9,955 | 92,618 | 12,040 | 100.5% |
| 2.5 | 86,569 | 9,297 | 85,640 | 13,917 | 98.9% |
| 5 | 71,287 | 5,525 | 70,707 | 2,740 | 99.1% |

Background (No Antigen) value: 4,810 +/− 497

165-F3C

| Dose | COP (Reference) | | 009 (Test) | | |
|---|---|---|---|---|---|
| μg/mL | Mean | Std Dev | Mean | Std Dev | 009/COP |
| 0.5 | 78,891 | 4,035 | 80,754 | 4,671 | 102.5% |
| 1 | 89,826 | 6,773 | 90,449 | 5,890 | 100.7% |
| 2 | 84,724 | 6,869 | 86,489 | 4,049 | 102.2% |
| 2.5 | 87,108 | 4,468 | 87,222 | 4,785 | 100.1% |
| 5 | 72,178 | 2,119 | 74,019 | 1,948 | 102.8% |

Background (No Antigen) value: 5,663 +/− 452

TABLE 84-continued

Stimulation of Assay Panel T-Cell Lines with GA Lot 016-ATP Proliferation Assay

165-F6C

| | COP (Reference) | | 009 (Test) | | |
|---|---|---|---|---|---|
| μg/mL | Mean | Std Dev | Mean | Std Dev | 009/COP |
| 0.5 | 6,258 | 781 | 6,729 | 616 | 115.5% |
| 1 | 13,893 | 2,128 | 13,854 | 2,672 | 99.6% |
| 2 | 20,516 | 1,860 | 19,304 | 3,305 | 93.0% |
| 2.5 | 22,094 | 3,625 | 24,113 | 2,613 | 110.7% |
| 5 | 20,991 | 2,302 | 21,941 | 1,849 | 105.3% |

Background (No Antigen) value: 3,218 +/− 368

205-1C4

| Dose | COP (Reference) | | 009 (Test) | | |
|---|---|---|---|---|---|
| μg/mL | Mean | Std Dev | Mean | Std Dev | 009/COP |
| 0.5 | 12,176 | 1,890 | 9,295 | 377 | 51.8% |
| 1 | 30,953 | 3,200 | 21,346 | 1,865 | 61.2% |
| 2 | 64,477 | 3,039 | 57,946 | 3,563 | 88.8% |
| 2.5 | 62,634 | 2,931 | 63,316 | 1,320 | 101.2% |
| 5 | 63,770 | 2,019 | 66,859 | 4,931 | 105.4% |

Background (No Antigen) value: 6,197 +/− 373

205-1F4

| | COP (Reference) | | 009 (Test) | | |
|---|---|---|---|---|---|
| μg/mL | Mean | Std Dev | Mean | Std Dev | 009/COP |
| 0.5 | 10,197 | 1,212 | 9,640 | 1,510 | 90.9% |
| 1 | 43,418 | 2,404 | 40,835 | 5,758 | 93.4% |
| 2 | 61,785 | 4,871 | 61,704 | 2,824 | 99.9% |
| 2.5 | 60,599 | 2,929 | 64,556 | 6,341 | 107.0% |
| 5 | 50,562 | 2,481 | 51,692 | 3,820 | 102.4% |

Background (No Antigen) value: 4044 +/− 280

TABLE 85

Stimulation of Assay Panel T-Cell Lines with GA Lot 017-ATP Proliferation Assay 222-2D8

| Dose | COP (Reference) | | 009 (Test) | | |
|---|---|---|---|---|---|
| μg/mL | Mean | Std Dev | Mean | Std Dev | 009/COP |
| 0.5 | 28,793 | 4,832 | 30,374 | 6,186 | 106.0% |
| 1 | 95,026 | 17,365 | 98,267 | 9,070 | 103.5% |
| 2 | 111,486 | 22,040 | 114,291 | 18,273 | 102.6% |
| 2.5 | 100,939 | 19,984 | 109,576 | 13,575 | 108.8% |
| 5 | 88,131 | 7,657 | 94,293 | 8,005 | 107.2% |

Background (No Antigen) value: 2,514 +/− 261

222-2F12

| | COP (Reference) | | 009 (Test) | | |
|---|---|---|---|---|---|
| μg/mL | Mean | Std Dev | Mean | Std Dev | 009/COP |
| 0.5 | 35,563 | 3,834 | 32,747 | 9,281 | 90.5% |
| 1 | 88,820 | 7,709 | 85,453 | 7,026 | 95.9% |
| 2 | 96,806 | 11,199 | 97,289 | 10,505 | 100.5% |
| 2.5 | 89,833 | 8,398 | 93,615 | 9,801 | 104.5% |
| 5 | 80,896 | 7,523 | 80,191 | 6,788 | 99.1% |

Background (No Antigen) value: 5,780 +/− 790

TABLE 85-continued

Stimulation of Assay Panel T-Cell Lines with GA Lot 017-ATP Proliferation Assay

165-F3C

| Dose | COP (Reference) | | 009 (Test) | | |
|---|---|---|---|---|---|
| μg/mL | Mean | Std Dev | Mean | Std Dev | 009/COP |
| 0.5 | 82,850 | 5,942 | 79,417 | 4,445 | 95.5% |
| 1 | 90,234 | 9,300 | 88,309 | 7,755 | 97.7% |
| 2 | 89,229 | 8,897 | 89,200 | 6,741 | 100.0% |
| 2.5 | 88,674 | 4,502 | 88,597 | 6,532 | 99.9% |
| 5 | 76,581 | 2,992 | 77,791 | 2,298 | 101.7% |

Background (No Antigen) value: 5,797 +/− 342

165-F6C

| | COP (Reference) | | 009 (Test) | | |
|---|---|---|---|---|---|
| μg/mL | Mean | Std Dev | Mean | Std Dev | 009/COP |
| 0.5 | 5,612 | 741 | 5,862 | 681 | 109.7% |
| 1 | 13,330 | 826 | 13,964 | 2,477 | 106.2% |
| 2 | 18,159 | 3,332 | 20,619 | 3,110 | 116.3% |
| 2.5 | 25,240 | 5,226 | 23,195 | 3,489 | 90.8% |
| 5 | 22,362 | 2,114 | 25,175 | 2,992 | 114.6% |

Background (No Antigen) value: 3,036 +/− 293

205-1C4

| Dose | COP (Reference) | | 009 (Test) | | |
|---|---|---|---|---|---|
| μg/mL | Mean | Std Dev | Mean | Std Dev | 009/COP |
| 0.5 | 11,301 | 1,328 | 9,729 | 875 | 64.3% |
| 1 | 37,118 | 3,918 | 21,686 | 3,554 | 48.9% |
| 2 | 60,447 | 3,187 | 50,742 | 3,003 | 81.9% |
| 2.5 | 62,925 | 2,714 | 59,712 | 3,709 | 94.3% |
| 5 | 61,292 | 2,550 | 57,744 | 3,702 | 93.5% |

Background (No Antigen) value: 6,903 +/− 247

205-1F4

| | COP (Reference) | | 009 (Test) | | |
|---|---|---|---|---|---|
| μg/mL | Mean | Std Dev | Mean | Std Dev | 009/COP |
| 0.5 | 13,053 | 396 | 8,506 | 687 | 46.4% |
| 1 | 50,782 | 4,550 | 44,749 | 3,160 | 86.9% |
| 2 | 66,285 | 2,472 | 66,789 | 2,684 | 100.8% |
| 2.5 | 63,369 | 3,794 | 64,778 | 1,527 | 102.4% |
| 5 | 49,594 | 1,977 | 53,923 | 2,566 | 109.6% |

Background (No Antigen) value: 4,569 +/− 255

TABLE 86

Stimulation of Assay Panel T-Cell Lines with GA Lot 018-ATP Proliferation Assay 222-2D8

| Dose | COP (Reference) | | 009 (Test) | | |
|---|---|---|---|---|---|
| μg/mL | Mean | Std Dev | Mean | Std Dev | 009/COP |
| 0.5 | 14,204 | 2,736 | 11,322 | 1,737 | 76.8% |
| 1 | 67,434 | 14,868 | 64,839 | 8,011 | 96.0% |
| 2 | 107,488 | 16,353 | 104,372 | 18,590 | 97.1% |
| 2.5 | 112,971 | 13,658 | 107,559 | 10,793 | 95.1% |
| 5 | 99,766 | 3,400 | 90,302 | 10,854 | 90.3% |

Background (No Antigen) value: 1,783 +/− 137

TABLE 86-continued

Stimulation of Assay Panel T-Cell Lines with GA Lot 018-ATP Proliferation Assay 222-2F12

| | COP (Reference) | | 009 (Test) | | |
|---|---|---|---|---|---|
| μg/mL | Mean | Std Dev | Mean | Std Dev | 009/COP |
| 0.5 | 25,388 | 2,983 | 16,736 | 2,458 | 60.6% |
| 1 | 87,334 | 7,524 | 82,511 | 4,558 | 94.3% |
| 2 | 97,914 | 7,734 | 100,294 | 7,977 | 102.5% |
| 2.5 | 104,480 | 4,494 | 99,857 | 6,994 | 95.4% |
| 5 | 91,459 | 1,768 | 91,294 | 4,298 | 99.8% |

Background (No Antigen) value: 3,407 +/− 606

165-F3C

| Dose | COP (Reference) | | 009 (Test) | | |
|---|---|---|---|---|---|
| μg/mL | Mean | Std Dev | Mean | Std Dev | 009/COP |
| 0.5 | 64,525 | 4,267 | 66,703 | 4,081 | 103.6% |
| 1 | 73,751 | 6,341 | 74,075 | 5,365 | 100.5% |
| 2 | 67,506 | 5,930 | 69,322 | 3,309 | 102.9% |
| 2.5 | 71,144 | 4,118 | 71,388 | 4,041 | 100.4% |
| 5 | 58,956 | 2,151 | 60,672 | 2,182 | 103.2% |

Background (No Antigen) value: 4,528 +/− 363

165-F6C

| | COP (Reference) | | 009 (Test) | | |
|---|---|---|---|---|---|
| μg/mL | Mean | Std Dev | Mean | Std Dev | 009/COP |
| 0.5 | 10,706 | 1,170 | 11,538 | 1,050 | 115.4% |
| 1 | 23,394 | 3,828 | 23,349 | 5,054 | 99.8% |
| 2 | 33,747 | 2,967 | 32,298 | 6,088 | 94.9% |
| 2.5 | 37,094 | 6,123 | 38,969 | 1,913 | 105.9% |
| 5 | 34,012 | 3,756 | 35,774 | 4,039 | 106.1% |

Background (No Antigen) value: 5,292 +/− 646

205-1C4

| Dose | COP (Reference) | | 009 (Test) | | |
|---|---|---|---|---|---|
| μg/mL | Mean | Std Dev | Mean | Std Dev | 009/COP |
| 0.5 | 9,318 | 1,557 | 7,944 | 1,226 | 71.4% |
| 1 | 15,538 | 872 | 16,767 | 1,979 | 111.1% |
| 2 | 32,955 | 5,076 | 33,706 | 6,896 | 102.6% |
| 2.5 | 38,475 | 2,726 | 31,322 | 5,682 | 78.9% |
| 5 | 37,495 | 4,063 | 34,474 | 3,594 | 90.8% |

Background (No Antigen) value: 4,516 +/− 285

205-1F4

| | COP (Reference) | | 009 (Test) | | |
|---|---|---|---|---|---|
| μg/mL | Mean | Std Dev | Mean | Std Dev | 009/COP |
| 0.5 | 97,968 | 8,249 | 97,744 | 5,919 | 99.8% |
| 1 | 127,580 | 16,207 | 123,254 | 12,623 | 96.5% |
| 2 | 132,098 | 14,469 | 129,142 | 16,175 | 97.7% |
| 2.5 | 120,168 | 5,213 | 116,750 | 17,156 | 97.1% |
| 5 | 80,689 | 3,329 | 75,277 | 2,801 | 92.9% |

Background (No Antigen) value: 4,300 +/− 438

TABLE 87

Stimulation of Assay Panel T-Cell Lines with GA Lot 070-ATP Proliferation Assay 222-2D8

| Dose | COP (Reference) | | 009 (Test) | | |
|---|---|---|---|---|---|
| μg/mL | Mean | Std Dev | Mean | Std Dev | 009/COP |
| 0.5 | 11,842 | 1,576 | 8,720 | 1,175 | 68.8% |
| 1 | 69,696 | 7,696 | 54,975 | 6,608 | 78.3% |
| 2 | 109,375 | 10,010 | 107,963 | 12,438 | 98.7% |
| 2.5 | 113,924 | 10,927 | 107,193 | 11,487 | 94.0% |
| 5 | 110,672 | 4,065 | 100,564 | 7,354 | 90.7% |

Background (No Antigen) value: 1,846 +/− 262

222-2F12

| | COP (Reference) | | 009 (Test) | | |
|---|---|---|---|---|---|
| μg/mL | Mean | Std Dev | Mean | Std Dev | 009/COP |
| 0.5 | 25,260 | 7,567 | 13,483 | 512 | 42.8% |
| 1 | 87,397 | 7,948 | 74,532 | 8,208 | 84.4% |
| 2 | 101,740 | 13,208 | 98,756 | 12,703 | 96.9% |
| 2.5 | 98,368 | 6,874 | 96,695 | 6,339 | 98.2% |
| 5 | 85,490 | 2,250 | 84,329 | 3,489 | 98.6% |

Background (No Antigen) value: 4,680 +/− 322

165-F3C

| Dose | COP (Reference) | | 009 (Test) | | |
|---|---|---|---|---|---|
| μg/mL | Mean | Std Dev | Mean | Std Dev | 009/COP |
| 0.5 | 69,624 | 5,387 | 67,045 | 3,968 | 96.0% |
| 1 | 74,498 | 8,247 | 73,087 | 6,776 | 98.0% |
| 2 | 75,820 | 8,024 | 75,066 | 6,222 | 98.9% |
| 2.5 | 75,347 | 4,056 | 75,150 | 6,037 | 99.7% |
| 5 | 62,262 | 2,789 | 62,866 | 2,399 | 101.1% |

Background (No Antigen) value: 4,684 +/− 274

165-F6C

| | COP (Reference) | | 009 (Test) | | |
|---|---|---|---|---|---|
| μg/mL | Mean | Std Dev | Mean | Std Dev | 009/COP |
| 0.5 | 9,191 | 1,241 | 9,584 | 1,087 | 109.8% |
| 1 | 21,591 | 1,344 | 24,186 | 2,552 | 115.8% |
| 2 | 31,427 | 4,009 | 35,297 | 2,101 | 114.8% |
| 2.5 | 43,097 | 4,356 | 38,878 | 4,273 | 88.9% |
| 5 | 34,995 | 3,786 | 39,286 | 4,699 | 114.4% |

Background (No Antigen) value: 5,198 +/− 497

205-1C4

| Dose | COP (Reference) | | 009 (Test) | | |
|---|---|---|---|---|---|
| μg/mL | Mean | Std Dev | Mean | Std Dev | 009/COP |
| 0.5 | 11,016 | 748 | 10,031 | 362 | 84.6% |
| 1 | 15,555 | 1,750 | 17,283 | 1,782 | 115.8% |
| 2 | 31,330 | 5,756 | 34,642 | 2,703 | 112.4% |
| 2.5 | 37,734 | 7,687 | 37,583 | 6,091 | 99.5% |
| 5 | 35,506 | 2,472 | 37,185 | 3,205 | 105.4% |

Background (No Antigen) value: 4,643 +/− 294

205-1F4

| | COP (Reference) | | 009 (Test) | | |
|---|---|---|---|---|---|
| μg/mL | Mean | Std Dev | Mean | Std Dev | 009/COP |
| 0.5 | 92,174 | 13,223 | 90,344 | 9,200 | 97.9% |
| 1 | 118,103 | 11,828 | 122,053 | 13,761 | 103.5% |
| 2 | 124,021 | 12,956 | 123,294 | 15,746 | 99.4% |
| 2.5 | 114,498 | 12,591 | 111,085 | 15,009 | 96.9% |
| 5 | 79,373 | 5,584 | 79,935 | 7,122 | 100.7% |

Background (No Antigen) value: 3,664 +/− 330

Example VI. GA-Specific Human T-Cell Line Panel Assay—Comparison of Altered GA Lots to Copaxone The panel of six GA-specific human T-cell lines listed in Table 78 above was used to test the immunological identity of altered GA lots to Copaxone.

Manufacture of Altered GA Lots

Each of nine altered GA lots was manufactured using an altered mole fraction of one or more N-carboxy anhydrides (NCAs) used to charge the polymerization, and with an altered concentration of DEA (ranging from 0.01% to 0.1%) used to initiate the polymerization reaction. In other respects, all the lots were prepared using standard processes. A summary of the conditions used to prepare these lots is provided in Table 88.

TABLE 88

Altered Initiator Concentration/N-Carboxy Anhydride (NCA) Mole Fraction Negative Control Lots; Summary of Manufacturing Process Conditions

| | Stage 1 | | | | | | | | |
|---|---|---|---|---|---|---|---|---|---|
| | NCA Moles Added in Charge | | | | DEA | NCA Mole Fraction in Cage | | | |
| Sample | A | E | K | Y | Conc | A | E | K | Y |
| NC-1 (056F) | Per control process | | | | 0.05 | 0.449 | 0.137 | 0.321 | 0.093 |
| NC-2 (051F) | + | + | − | + | 0.1 | 0.403 | 0.185 | 0.288 | 0.125 |
| NC-3 (053F) | + | + | + | + | 0.1 | 0.449 | 0.137 | 0.321 | 0.093 |
| NC-4 (054F) | + | + | − | − | 0.01 | 0.464 | 0.142 | 0.331 | 0.064 |
| NC-5 (055F) | + | − | − | + | 0.01 | 0.530 | 0.108 | 0.252 | 0.109 |
| NC-6 (057F) | − | + | − | − | 0.01 | 0.420 | 0.193 | 0.300 | 0.087 |
| NC-7 (058F) | − | − | + | + | 0.01 | 0.372 | 0.114 | 0.399 | 0.115 |
| NC-8 (059F) | + | − | − | − | 0.1 | 0.550 | 0.112 | 0.262 | 0.076 |
| NC-9 (060F) | − | − | + | − | 0.1 | 0.387 | 0.118 | 0.414 | 0.080 |

(+) Denotes NCA moles increased by 20% relative to control;

(−) Denotes NCA moles decreased by 20% relative to control.

Molecular weight and amino acid ratios for the negative control lots and the specification ranges for each parameter, are shown in Table 89. The shaded cells containing bold text indicate values outside of GA specification ranges, shown at the top of each column.

TABLE 90

Altered Initiator Concentration/NCA Mole Fraction Negative Control Lots; Molecular Weight and Amino Acid Composition Data

| | Molecular Weight | | | | Amino Acid Composition | | | |
|---|---|---|---|---|---|---|---|---|
| Sample | Mn (4700-7500) | Mw (7000-10300) | Mp (5000-9000 | PDI (1.1-1.7) | E (0.127-0.155) | A (0.385-0.471) | Y (0.080-0.106) | K (0.303-0.371) |
| NC-1 (056F) | 7311 | 9435 | 8214 | 1.29 | 0.133 | 0.439 | 0.098 | 0.330 |
| NC-2 (051F) | 7055 | 9073 | 7703 | 1.29 | 0.139 | 0.433 | 0.097 | 0.331 |
| NC-3 (053F) | 7226 | 9310 | 8434 | 1.29 | 0.139 | 0.429 | 0.097 | 0.335 |
| NC-4 (054F) | **8034** | 10037 | 8951 | 1.25 | 0.147 | 0.444 | **0.068** | 0.341 |
| NC-5 (055F) | 6630 | 9383 | 7211 | 1.42 | **0.104** | **0.513** | **0.118** | **0.265** |
| NC-6 (057F) | 7207 | 9026 | 7709 | 1.25 | **0.193** | 0.406 | 0.091 | 0.309 |
| NC-7 (058F) | **8621** | **11834** | **9956** | 1.37 | **0.109** | **0.359** | **0.122** | **0.411** |
| NC-8 (059F) | 6735 | 8826 | 7563 | 1.31 | **0.117** | **0.535** | 0.081 | **0.278** |
| NC-9 (060F) | **10381** | **13333** | **12228** | 1.28 | **0.113** | **0.376** | 0.086 | **0.426** |

Initiator concentration and NCA mole fraction conditions can affect the initiation of polymerization and chain propagation. Significant differences between the negative lots and control were shown by total DEA analysis, DEA/COOH analysis, adduct analysis, peptide mapping, NTS (Edman), and intact HPLC (data not shown).

Comparison of Copaxone and Negative GA Lots Using a Panel of GA-Specific T-Cell Lines Proliferation assays using the panel of six GA-specific T-cell lines (Table 77) were carried out, to compare negative GA lots 051F, 054F, 055F, 057F, 058F, 059F, and 060F (test lots), to Copaxone (reference lot). Each cell line was restimulated using 5 concentrations of reference antigen (Copaxone) and test antigen (the negative GA lots), including a no antigen control (in the presence of $5\times10^4$ mitomycin-treated autologous B-LCL). Proliferation was measured by ATP assay after 4 days of incubation with antigen, using methods described previously. The results are shown in Tables 90-96.

The percentages in the last column of each table were calculated as follows:

Proliferation response to test antigen minus proliferation response to control (no antigen)÷proliferation response to reference antigen minus proliferation response to control (no antigen).

TABLE 90

Proliferation of Assay Panel T-Cell Lines Stimulated with Altered GA Lot NC-2 (051F)

| GA conc. | COP (Reference) | | 051F (Test) | | |
|---|---|---|---|---|---|
| μg/mL | Mean | Std Dev | Mean | Std Dev | 051F/COP |
| 222-2D8 | | | | | |
| 0 | 555 | 78 | 555 | 78 | |
| 0.5 | 2,523 | 717 | 2,455 | 398 | 97% |
| 1 | 11,178 | 1,463 | 8,192 | 1,850 | 72% |
| 2 | 45,028 | 4,147 | 38,828 | 5,943 | 86% |
| 2.5 | 66,202 | 9,918 | 60,869 | 5,492 | 92% |
| 5 | 117,638 | 11,070 | 114,522 | 2,997 | 97% |

TABLE 90-continued

Proliferation of Assay Panel T-Cell Lines Stimulated with Altered GA Lot NC-2 (051F)

| GA conc. | COP (Reference) | | 051F (Test) | | |
|---|---|---|---|---|---|
| μg/mL | Mean | Std Dev | Mean | Std Dev | 051F/COP |
| 222-2F12 | | | | | |
| 0 | 1,712 | 263 | 1,712 | 263 | |
| 0.5 | 4,396 | 844 | 2,958 | 553 | 46% |
| 1 | 11,426 | 1,126 | 7,692 | 1,354 | 62% |
| 2 | 75,298 | 9,861 | 20,827 | 3,809 | 26% |
| 2.5 | 142,360 | 19,820 | 62,617 | 6,424 | 43% |
| 5 | 189,730 | 12,428 | 186,767 | 21,203 | 98% |
| 165-F3 C | | | | | |
| 0 | 2,475 | 162 | 2,475 | 162 | |
| 0.5 | 4,299 | 483 | 3,459 | 75 | 54% |
| 1 | 7,765 | 1,004 | 5,386 | 312 | 55% |
| 2 | 27,428 | 2,286 | 16,581 | 1,247 | 57% |
| 2.5 | 33,740 | 5,955 | 26,095 | 3,248 | 76% |
| 5 | 38,127 | 4,705 | 37,496 | 2,126 | 98% |
| 165-F6C | | | | | |
| 0 | 2,578 | 274 | 2,578 | 274 | |
| 0.5 | 3,678 | 360 | 3,359 | 253 | 71% |
| 1 | 8,745 | 1,126 | 6,068 | 702 | 57% |
| 2 | 36,485 | 5,750 | 16,976 | 2,047 | 42% |
| 2.5 | 53,250 | 4,188 | 34,572 | 4,212 | 63% |
| 5 | 56,466 | 4,402 | 67,326 | 4,561 | 120% |
| 205-1C4 | | | | | |
| 0 | 5,935 | 390 | 5,935 | 390 | |
| 0.5 | 12,962 | 2,258 | 13,252 | 647 | 104% |
| 1 | 67,399 | 14,359 | 48,834 | 12,622 | 70% |
| 2 | 120,159 | 4,117 | 133,578 | 4,943 | 112% |
| 2.5 | 121,868 | 5,875 | 145,780 | 6,121 | 121% |
| 5 | 107,018 | 3,031 | 122,986 | 1,879 | 116% |
| 205-1F4 | | | | | |
| 0 | 2,707 | 176 | 2,707 | 176 | |
| 0.5 | 2,328 | 209 | 2,425 | 127 | 74% |
| 1 | 4,969 | 750 | 2,890 | 188 | 8% |
| 2 | 18,430 | 2,806 | 13,696 | 1,643 | 70% |
| 2.5 | 20,113 | 3,771 | 21,850 | 823 | 110% |
| 5 | 24,016 | 1,692 | 29,856 | 4,451 | 127% |

TABLE 91

Proliferation of Assay Panel T-Cell Lines Stimulated with Altered GA Lot NC-4 (054F)

| GA conc. | COP (Reference) | | 054F (Test) | | |
|---|---|---|---|---|---|
| μg/mL | Mean | Std Dev | Mean | Std Dev | 054F/COP |
| 222-2D8 | | | | | |
| 0 | 238 | 37 | 238 | 37 | |
| 0.5 | 275 | 79 | 287 | 71 | 133% |
| 1 | 1,244 | 191 | 1,346 | 160 | 110% |
| 2 | 10,074 | 1,282 | 6,498 | 1,612 | 64% |
| 2.5 | 16,451 | 3,700 | 18,859 | 3,729 | 115% |
| 5 | 37,005 | 6,547 | 37,433 | 5,442 | 101% |
| 222-2F12 | | | | | |
| 0 | 312 | 59 | 312 | 59 | |
| 0.5 | 239 | 27 | 225 | 63 | 119.9% |
| 1 | 780 | 232 | 412 | 34 | 21.3% |
| 2 | 10,284 | 2,467 | 9,652 | 1,065 | 93.7% |
| 2.5 | 28,607 | 5,246 | 32,495 | 10,353 | 113.7% |
| 5 | 71,541 | 2,085 | 74,514 | 4,545 | 104.2% |
| 165-F3C | | | | | |
| 0 | 2,402 | 236 | 2,402 | 236 | |
| 0.5 | 5,684 | 295 | 4,020 | 666 | 49% |
| 1 | 10,841 | 1,105 | 7,003 | 1,072 | 55% |
| 2 | 29,175 | 3,938 | 21,460 | 3,935 | 71% |
| 2.5 | 33,073 | 1,602 | 32,409 | 3,192 | 98% |
| 5 | 34,862 | 3,362 | 33,339 | 1,875 | 95% |
| 165-F6C | | | | | |
| 0 | 2,358 | 140 | 2,358 | 140 | |
| 0.5 | 3,499 | 200 | 2,783 | 282 | 37% |
| 1 | 7,910 | 1,486 | 5,242 | 603 | 52% |
| 2 | 30,602 | 3,805 | 16,776 | 1,344 | 51% |
| 2.5 | 41,112 | 4,609 | 30,869 | 3,046 | 74% |
| 5 | 56,465 | 4,233 | 43,141 | 2,771 | 75% |
| 205-1C4 | | | | | |
| 0 | 5,764 | 385 | 5,764 | 385 | |
| 0.5 | 12,143 | 1,393 | 6,552 | 304 | 12% |
| 1 | 65,518 | 13,711 | 10,840 | 744 | 8% |
| 2 | 119,307 | 6,285 | 45,562 | 5,558 | 35% |
| 2.5 | 120,551 | 2,673 | 76,503 | 10,228 | 62% |
| 5 | 109,154 | 5,613 | 96,264 | 3,687 | 88% |
| 205-1F4 | | | | | |
| 0 | 2,708 | 137 | 2,708 | 137 | 47% |
| 0.5 | 2,535 | 171 | 2,626 | 151 | −3% |
| 1 | 3,922 | 508 | 2,677 | 102 | 36% |
| 2 | 14,322 | 1,834 | 6,927 | 1,231 | 42% |
| 2.5 | 20,059 | 1,764 | 9,949 | 2,560 | 68% |
| 5 | 20,471 | 1,465 | 14,846 | 2,149 | 47% |

TABLE 92

Proliferation of Assay Panel T-Cell Lines Stimulated with Altered GA Lot NC-5 (055F)

| GA conc. | COP (Reference) | | 055F (Test) | | |
|---|---|---|---|---|---|
| μg/mL | Mean | Std Dev | Mean | Std Dev | 055F/COP |
| 222-2D8 | | | | | |
| 0 | 477 | 36 | 477 | 36 | |
| 0.5 | 715 | 56 | 811 | 120 | 140% |
| 1 | 3,526 | 887 | 2,898 | 567 | 79% |
| 2 | 34,786 | 4,545 | 27,832 | 5,823 | 80% |
| 2.5 | 46,255 | 3,991 | 44,882 | 3,616 | 97% |
| 5 | 70,248 | 3,206 | 68,952 | 7,184 | 98% |
| 222-2F12 | | | | | |
| 0 | 546 | 71 | 546 | 71 | |
| 0.5 | 468 | 81 | 514 | 75 | 40% |

TABLE 92-continued

Proliferation of Assay Panel T-Cell Lines Stimulated with Altered GA Lot NC-5 (055F)

| GA conc. | COP (Reference) | | 055F (Test) | | |
|---|---|---|---|---|---|
| μg/mL | Mean | Std Dev | Mean | Std Dev | 055F/COP |
| 1 | 1,847 | 261 | 1,324 | 156 | 60% |
| 2 | 19,966 | 5,933 | 12,673 | 1,900 | 62% |
| 2.5 | 41,329 | 7,049 | 36,730 | 5,904 | 89% |
| 5 | 76,781 | 6,073 | 81,376 | 2,755 | 106% |
| 165-F3C | | | | | |
| 0 | 3,135 | 247 | 3,135 | 247 | |
| 0.5 | 8,095 | 3,117 | 7,582 | 1,085 | 90% |
| 1 | 22,164 | 3,232 | 26,044 | 7,638 | 120% |
| 2 | 86,801 | 11,964 | 83,923 | 7,426 | 97% |
| 2.5 | 94,830 | 7,778 | 91,725 | 7,214 | 97% |
| 5 | 97,824 | 8,015 | 94,559 | 6,454 | 97% |
| 165-F6C | | | | | |
| 0 | 2,820 | 418 | 2,820 | 418 | |
| 0.5 | 2,706 | 333 | 2,936 | 422 | −101% |
| 1 | 4,067 | 516 | 3,838 | 381 | 82% |
| 2 | 12,513 | 1,539 | 8,417 | 1,280 | 58% |
| 2.5 | 21,520 | 4,146 | 19,798 | 4,538 | 91% |
| 5 | 42,493 | 4,988 | 43,546 | 2,744 | 103% |
| 205-1C4 | | | | | |
| 0 | 1,333 | 175 | 1,333 | 175 | |
| 0.5 | 1,904 | 302 | 3,108 | 731 | 311% |
| 1 | 6,495 | 1,747 | 7,415 | 1,243 | 118% |
| 2 | 31,541 | 7,693 | 63,584 | 4,740 | 206% |
| 2.5 | 50,442 | 4,147 | 73,823 | 1,646 | 148% |
| 5 | 52,458 | 1,923 | 68,206 | 3,022 | 131% |
| 205-1F4 | | | | | |
| 0 | 570 | 38 | 570 | 38 | |
| 0.5 | 598 | 96 | 778 | 154 | 725% |
| 1 | 3,332 | 2,411 | 2,753 | 433 | 79% |
| 2 | 22,705 | 4,347 | 23,727 | 5,988 | 105% |
| 2.5 | 30,794 | 2,666 | 33,707 | 6,660 | 110% |
| 5 | 37,796 | 3,159 | 47,090 | 4,703 | 125% |

TABLE 93

Proliferation of Assay Panel T-Cell Lines Stimulated with Altered GA Lot NC-6 (057F)

| GA conc. | COP (Reference) | | 057F (Test) | | |
|---|---|---|---|---|---|
| μg/mL | Mean | Std Dev | Mean | Std Dev | 057F/COP |
| 222-2D8 | | | | | |
| 0 | 549 | 72 | 549 | 72 | |
| 0.5 | 926 | 165 | 602 | 129 | 14% |
| 1 | 7,205 | 1,741 | 1,727 | 224 | 18% |
| 2 | 34,638 | 2,838 | 17,730 | 4,240 | 50% |
| 2.5 | 41,414 | 3,718 | 35,392 | 4,651 | 85% |
| 5 | 63,294 | 7,114 | 60,764 | 3,004 | 96% |
| 222-2F12 | | | | | |
| 0 | 532 | 104 | 532 | 104 | |
| 0.5 | 607 | 90 | 455 | 51 | −103% |
| 1 | 2,975 | 604 | 612 | 112 | 3% |
| 2 | 36,232 | 6,852 | 5,370 | 558 | 14% |
| 2.5 | 60,048 | 10,334 | 13,749 | 2,566 | 22% |
| 5 | 86,151 | 1,958 | 70,458 | 6,145 | 82% |
| 165-F3C | | | | | |
| 0 | 2,935 | 205 | 2,935 | 205 | |
| 0.5 | 6,874 | 617 | 4,929 | 362 | 51% |
| 1 | 18,867 | 2,046 | 8,433 | 2,404 | 35% |
| 2 | 80,910 | 8,861 | 15,686 | 2,071 | 16% |
| 2.5 | 90,295 | 6,532 | 29,419 | 3,540 | 30% |
| 5 | 88,856 | 2,768 | 69,152 | 7,060 | 77% |

TABLE 93-continued

Proliferation of Assay Panel T-Cell Lines Stimulated with Altered GA Lot NC-6 (057F)

| GA conc. | COP (Reference) | | 057F (Test) | | |
|---|---|---|---|---|---|
| μg/mL | Mean | Std Dev | Mean | Std Dev | 057F/COP |
| 165-F6C | | | | | |
| 0 | 2,215 | 179 | 2,215 | 179 | |
| 0.5 | 2,827 | 402 | 2,898 | 148 | 112% |
| 1 | 4,119 | 484 | 3,129 | 269 | 48% |
| 2 | 20,236 | 4,873 | 5,078 | 204 | 16% |
| 2.5 | 33,695 | 5,758 | 5,511 | 661 | 10% |
| 5 | 41,233 | 4,060 | 18,802 | 3,139 | 43% |
| 205-1C4 | | | | | |
| 0 | 1,283 | 186 | 1,283 | 186 | |
| 0.5 | 2,397 | 324 | 1,400 | 161 | 10% |
| 1 | 7,118 | 1,772 | 2,105 | 224 | 14% |
| 2 | 35,803 | 11,537 | 6,863 | 821 | 16% |
| 2.5 | 47,782 | 9,663 | 17,453 | 6,703 | 35% |
| 5 | 55,213 | 3,152 | 45,214 | 7,441 | 81% |
| 205-1F4 | | | | | |
| 0 | 404 | 78 | 404 | 78 | |
| 0.5 | 444 | 76 | 436 | 37 | 80% |
| 1 | 2,060 | 761 | 424 | 24 | 1% |
| 2 | 13,054 | 3,462 | 3,625 | 1,460 | 25% |
| 2.5 | 15,008 | 3,523 | 11,620 | 5,543 | 77% |
| 5 | 26,457 | 3,990 | 22,288 | 7,335 | 84% |

TABLE 94

Proliferation of Assay Panel T-Cell Lines Stimulated with Altered GA Lot NC-7 (058F)

| GA conc. | COP (Reference) | | 058F (Test) | | |
|---|---|---|---|---|---|
| μg/mL | Mean | Std Dev | Mean | Std Dev | 058F/COP |
| 222-2D8 | | | | | |
| 0 | 1,609 | 201 | 1,609 | 201 | |
| 0.5 | 27,735 | 6,744 | 11,584 | 3,964 | 38% |
| 1 | 95,926 | 17,011 | 77,810 | 15,598 | 81% |
| 2 | 125,126 | 12,315 | 115,411 | 15,617 | 92% |
| 2.5 | 148,061 | 15,380 | 117,194 | 3,794 | 79% |
| 5 | 152,649 | 3,418 | 121,044 | 16,413 | 79% |
| 222-2F12 | | | | | |
| 0 | 1,952 | 208 | 1,952 | 208 | |
| 0.5 | 7,427 | 1,218 | 6,124 | 645 | 118% |
| 1 | 50,426 | 5,994 | 46,619 | 9,555 | 99% |
| 2 | 138,876 | 8,988 | 133,258 | 8,184 | 115% |
| 2.5 | 138,757 | 3,210 | 141,639 | 2,482 | 104% |
| 5 | 154,068 | 6,261 | 142,470 | 5,726 | 105% |
| 165-F3C | | | | | |
| 0 | 1,292 | 112 | 1,292 | 112 | |
| 0.5 | 3,169 | 486 | 4,223 | 264 | 156% |
| 1 | 8,378 | 955 | 8,805 | 1,027 | 106% |
| 2 | 31,536 | 8,165 | 26,984 | 3,809 | 85% |
| 2.5 | 33,777 | 3,717 | 30,925 | 5,419 | 91% |
| 5 | 38,783 | 3,851 | 34,122 | 1,373 | 88% |
| 165-F6C | | | | | |
| 0 | 803 | 803 | 154 | 154 | |
| 0.5 | 1,035 | 2,504 | 153 | 533 | 733% |
| 1 | 2,825 | 12,943 | 457 | 3,070 | 600% |
| 2 | 14,164 | 40,675 | 2,959 | 11,470 | 298% |
| 2.5 | 26,862 | 54,895 | 2,679 | 5,730 | 208% |
| 5 | 36,303 | 47,985 | 4,022 | 4,391 | 133% |
| 205-1C4 | | | | | |
| 0 | 8,068 | 328 | 8,068 | 328 | |
| 0.5 | 14,583 | 1,835 | 17,074 | 3,008 | 138% |

TABLE 94-continued

Proliferation of Assay Panel T-Cell Lines Stimulated with Altered GA Lot NC-7 (058F)

| GA conc. | COP (Reference) | | 058F (Test) | | |
|---|---|---|---|---|---|
| μg/mL | Mean | Std Dev | Mean | Std Dev | 058F/COP |
| 1 | 26,878 | 4,458 | 42,746 | 7,114 | 184% |
| 2 | 148,531 | 16,218 | 158,272 | 9,359 | 107% |
| 2.5 | 156,331 | 23,982 | 151,305 | 11,863 | 97% |
| 5 | 148,116 | 12,905 | 123,960 | 9,327 | 83% |
| 205-1F4 | | | | | |
| 0 | 5,347 | 519 | 5,347 | 519 | |
| 0.5 | 7,657 | 837 | 7,569 | 928 | 96% |
| 1 | 17,074 | 2,403 | 17,741 | 2,509 | 106% |
| 2 | 55,155 | 5,678 | 54,330 | 13,960 | 98% |
| 2.5 | 64,071 | 11,199 | 67,967 | 14,024 | 107% |
| 5 | 69,484 | 6,674 | 64,750 | 5,589 | 93% |

TABLE 95

Proliferation of Assay Panel T-Cell Lines Stimulated with Altered GA Lot NC-8 (059F)

| GA conc. | COP (Reference) | | 059F (Test) | | |
|---|---|---|---|---|---|
| μg/mL | Mean | Std Dev | Mean | Std Dev | 059F/COP |
| 222-2D8 | | | | | |
| 0 | 1,443 | 91 | 1,443 | 91 | |
| 0.5 | 13,958 | 4,236 | 24,260 | 3,408 | 182% |
| 1 | 87,807 | 9,513 | 96,343 | 8,132 | 110% |
| 2 | 142,231 | 12,632 | 154,705 | 6,717 | 109% |
| 2.5 | 140,804 | 12,189 | 149,503 | 10,927 | 106% |
| 5 | 147,182 | 15,768 | 145,847 | 9,712 | 99% |
| 222-2F12 | | | | | |
| 0 | 1,353 | 191 | 1,353 | 191 | |
| 0.5 | 3,580 | 562 | 3,990 | 604 | 118% |
| 1 | 42,304 | 6,772 | 42,076 | 2,732 | 99% |
| 2 | 108,046 | 9,855 | 123,646 | 4,582 | 115% |
| 2.5 | 115,182 | 6,255 | 119,534 | 5,610 | 104% |
| 5 | 123,169 | 9,352 | 129,351 | 8,023 | 105% |
| 165-F3C | | | | | |
| 0 | 1,248 | 199 | 1,248 | 199 | |
| 0.5 | 3,154 | 233 | 3,241 | 662 | 105% |
| 1 | 9,050 | 1,350 | 7,412 | 2,107 | 79% |
| 2 | 27,693 | 1,889 | 25,320 | 8,018 | 91% |
| 2.5 | 28,018 | 5,559 | 26,608 | 4,862 | 95% |
| 5 | 32,151 | 1,963 | 33,907 | 1,902 | 106% |
| 165-F6C | | | | | |
| 0 | 658 | 78 | 658 | 78 | |
| 0.5 | 863 | 126 | 808 | 185 | 73% |
| 1 | 1,838 | 209 | 1,088 | 258 | 36% |
| 2 | 8,163 | 1,400 | 2,593 | 916 | 26% |
| 2.5 | 11,665 | 830 | 6,961 | 1,236 | 57% |
| 5 | 30,422 | 3,878 | 19,251 | 4,424 | 62% |
| 205-1C4 | | | | | |
| 0 | 7,851 | 404 | 7,851 | 404 | |
| 0.5 | 13,267 | 865 | 10,922 | 619 | 57% |
| 1 | 26,848 | 4,312 | 16,622 | 2,503 | 46% |
| 2 | 142,528 | 17,311 | 65,015 | 15,448 | 42% |
| 2.5 | 159,785 | 11,573 | 120,442 | 31,287 | 74% |
| 5 | 171,452 | 6,507 | 167,530 | 2,995 | 98% |
| 205-1F4 | | | | | |
| 0 | 5,118 | 384 | 5,118 | 384 | |
| 0.5 | 6,984 | 357 | 6,442 | 644 | 71% |
| 1 | 15,174 | 2,862 | 11,253 | 1,455 | 61% |
| 2 | 46,598 | 6,377 | 32,522 | 6,841 | 66% |

TABLE 95-continued

Proliferation of Assay Panel T-Cell Lines Stimulated with Altered GA Lot NC-8 (059F)

| GA conc. | COP (Reference) | | 059F (Test) | | |
|---|---|---|---|---|---|
| μg/mL | Mean | Std Dev | Mean | Std Dev | 059F/COP |
| 2.5 | 51,372 | 8,818 | 46,936 | 6,968 | 90% |
| 5 | 61,252 | 3,086 | 62,607 | 8,096 | 102% |

TABLE 96

Proliferation of Assay Panel T-Cell Lines Stimulated with Altered GA Lot NC-9 (060F)

| GA conc. | COP (Reference) | | 060F (Test) | | |
|---|---|---|---|---|---|
| μg/mL | Mean | Std Dev | Mean | Std Dev | 060F/COP |
| 222-2D8 | | | | | |
| 0 | 1,470 | 126 | 1,470 | 126 | |
| 0.5 | 2,785 | 401 | 1,838 | 251 | 28% |
| 1 | 28,970 | 2,992 | 6,093 | 1,608 | 17% |
| 2 | 76,089 | 9,113 | 52,562 | 7,512 | 68% |
| 2.5 | 90,666 | 4,198 | 82,771 | 6,024 | 91% |
| 5 | 99,491 | 7,485 | 91,463 | 4,473 | 92% |
| 222-2F12 | | | | | |
| 0 | 1,616 | 1,616 | 160 | 160 | |
| 0.5 | 2,404 | 2,707 | 541 | 326 | 139% |
| 1 | 11,359 | 8,807 | 4,259 | 1,616 | 74% |
| 2 | 78,880 | 70,354 | 6,266 | 8,423 | 89% |
| 2.5 | 95,825 | 104,397 | 4,400 | 8,044 | 109% |
| 5 | 107,930 | 104,946 | 4,915 | 6,586 | 97% |
| 165-F3C | | | | | |
| 0 | 1,428 | 129 | 1,428 | 129 | |
| 0.5 | 2,577 | 212 | 2,174 | 223 | 65% |
| 1 | 5,743 | 178 | 5,188 | 379 | 87% |
| 2 | 16,415 | 1,314 | 15,903 | 1,645 | 97% |
| 2.5 | 20,446 | 1,413 | 24,511 | 3,124 | 121% |
| 5 | 32,600 | 2,124 | 33,905 | 3,546 | 104% |
| 165-F6C | | | | | |
| 0 | 1,831 | 149 | 1,831 | 149 | |
| 0.5 | 2,228 | 389 | 2,449 | 219 | 155% |
| 1 | 4,270 | 486 | 5,413 | 717 | 147% |
| 2 | 15,430 | 2,875 | 26,433 | 4,456 | 181% |
| 2.5 | 28,942 | 3,101 | 46,334 | 3,480 | 164% |
| 5 | 45,836 | 2,157 | 47,301 | 2,765 | 103% |
| 205-1C4 | | | | | |
| 0 | 8,028 | 680 | 8,028 | 680 | |
| 0.5 | 11,790 | 1,061 | 10,768 | 629 | 73% |
| 1 | 26,004 | 2,141 | 15,367 | 1,352 | 41% |
| 2 | 102,672 | 11,452 | 65,511 | 8,168 | 61% |
| 2.5 | 124,300 | 17,322 | 110,976 | 4,372 | 89% |
| 5 | 129,908 | 3,973 | 117,103 | 9,212 | 89% |
| 205-1F4 | | | | | |
| 0 | 6,912 | 628 | 6,912 | 628 | |
| 0.5 | 8,158 | 255 | 7,907 | 658 | 80% |
| 1 | 17,491 | 3,649 | 11,531 | 931 | 44% |
| 2 | 51,613 | 9,037 | 49,567 | 6,068 | 95% |
| 2.5 | 60,244 | 3,025 | 51,070 | 5,174 | 83% |
| 5 | 54,345 | 7,884 | 41,670 | 3,255 | 73% |

Example VII. Determination of Immunological Identity Using a Panel of GA-Specific Human T-Cell Lines An assay panel of clonal GA-specific human T-cell lines, representing a range of MHC restrictions and non-canonical peptide reactivities, is selected and used to determine the immunological identity of GA preparations. All cell lines are tested in triplicate samples for reactivity to 1, 3, and 10 μg/mL of each of a test preparation of GA and Copaxone (as a reference standard), including a no antigen control and an MBP control (all in the presence of $2\times10^5$ mitomycin-treated autologous B-LCL/mL) by ATP proliferation assay. For each cell line, the mean RLU at each concentration of the test preparation of GA is calculated and compared with the corresponding mean RLU at each concentration of the GA reference standard using the formula:

(GA-elicited response to test antigen minus the same response to control)÷(GA-elicited response to reference antigen minus response to control)

Immunological identity of the test preparation of GA and the GA reference standard is determined when this formula gives a relative value of 0.80 to 1.20 (80% to 120%) at a given GA concentration. Thus, the test and reference standard GA preparations are determined to be immunologically identical based on a single reference, single dose analysis.

The mean RLU are further plotted by GA concentration to obtain a dose-response curve and the slopes of the GA test and reference standard curves compared. The test preparation of GA and the GA reference standard are confirmed as immunologically identical based on a single-reference lot dose response curve analysis.

Example VIII. Determination of Immunological Identity Using a Panel of GA-Specific Human T-Cell Lines: Multiple Reference Dose-Response Curve Analysis An assay panel of clonal GA-specific human T-cell lines, representing a range of MHC restrictions and non-canonical peptide reactivities, is selected and used to determine the immunological identity of GA preparations. All cell lines are tested in triplicate samples for reactivity to 1, 3, and 10 μg/mL of each of a test preparation of GA and multiple Copaxone lots (as a reference standard), including a no antigen control and an MBP control (all in the presence of $2\times10^5$ mitomycin-treated autologous B-LCL/mL) by ATP proliferation assay. Multiple Copaxone reference lots are included in the assay, to provide multiple datasets, e.g., to account for lot-to-lot variation. For each cell line, the mean RLU at each concentration of the test preparation of GA is calculated and compared with the corresponding mean RLU at each concentration of the GA reference standard.

The mean RLU are plotted by GA concentration to obtain a dose-response curve and the slopes of the curves compared. The data from the multiple reference lots are used to determine acceptable variation from the reference slope.

The test preparation of GA and the GA reference standards are confirmed to be immunologically identical based on a multiple-reference dose-response curve analysis.

Example IX. Determination of Immunological Identity Using a Panel of GA-Specific Human T-Cell Lines: Reference Repeat Dose-Response Curve Analysis An assay panel of clonal GA-specific human T-cell lines, representing a range of MHC restrictions and non-canonical peptide reactivities, is selected and used to determine the immunological identity of GA preparations. All cell lines are tested in triplicate samples for reactivity to 1, 3, and 10 μg/mL of each of a test preparation of GA and a Copaxone lot (as a reference standard), including a no antigen control and an MBP control (all in the presence of $2\times10^5$ mitomycin-treated autologous B-LCL/mL) by ATP proliferation assay. Multiple samples of the same Copaxone reference lot are included in the assay, to provide repeat data, e.g., to account for assay variation. For each cell line, the mean RLU at each concentration of the test preparation of GA is calculated and compared with the corresponding mean RLU at each concentration of the GA reference standard.

The mean RLU are plotted by GA concentration to obtain a dose-response curve and the slopes of the curves compared. The reference lot repeat data are used to determine acceptable variation from the reference slope.

The test preparation of GA and the GA reference standard are confirmed to be immunologically identical based on a repeated reference dose-response curve analysis.

What is claimed is:

1. A process for preparing a drug product or pharmaceutical composition containing glatiramer acetate (GA), comprising:

determining whether a test preparation of GA, produced by reacting protected GA with hydrobromic acid to form trifluoroacetyl GA, and treating said trifluoroacetyl copolymer-1 with aqueous piperidine solution, and a GA reference standard, are immunologically identical, using an assay panel of GA-specific human T-cell lines, wherein each of the GA-specific human T-cell lines is obtained from a GA-naïve donor, by:

1) incubating cells of each GA-specific human T-cell line in the assay panel with appropriate antigen presenting cells (APC), wherein the assay panel comprises at least four different GA-specific human T-cell lines, and wherein the at least four different GA-specific human T-cell lines include:
   a) a first GA-specific human T-cell line, wherein the first GA-specific human T-cell line is not reactive to a first non-canonical GA peptide;
   b) a second GA-specific human T-cell line, wherein the second GA-specific human T-cell line is reactive to the first non-canonical GA peptide;
   c) a third GA-specific human T-cell line, wherein the third GA-specific human T-cell line is not reactive to a second non-canonical GA peptide; and
   d) a fourth GA-specific human T-cell line, wherein the fourth GA-specific human T-cell line is reactive to the second non-canonical GA peptide;
2) stimulating cells in a first set samples, the first set of samples comprising at least four samples of each of the at least four GA-specific human T cell lines, each sample comprising a predetermined number of cells of each of the at least four GA-specific human T-cell lines incubated with APC in step (1), wherein each of the at least four samples of each T cell line is stimulated with a different amount of GA, wherein the GA is the test preparation of GA;
3) separately stimulating cells in a second set of samples, the second set of samples comprising the same number of samples of each of the at least four GA-specific human T cell lines as the first set of samples, each sample in the second set of samples comprising the same predetermined number of cells, of each of the at least four GA-specific human T-cell lines incubated with APC in step (1) as the samples in the first set of samples, wherein each sample in the second set of samples is stimulated with the same amount of GA used to stimulate each corresponding sample in the first set of samples in step (2), wherein the GA is a GA reference standard;
4) measuring at least one GA-elicited response in each sample of the first set of samples stimulated in step (2) and measuring the same at least one GA-elicited response in each sample of the second set of samples stimulated in step (3);
5) comparing each measurement obtained in step (4) for each sample of the first set of samples, with the corresponding measure obtained for the corresponding sample in the second set of samples; and
6) determining the test preparation of GA and the GA reference standard to be immunologically identical when about 80% to about 100% of the comparisons made in step (5) for each set of samples are within acceptable limits, wherein the acceptable limits for the measurement comparison are about 80% to about 120%;

wherein the test preparation of GA is admixed in the drug product or pharmaceutical composition if it is determined to be immunologically identical to the GA reference standard.

2. The process of claim 1, wherein at least one GA-specific human T-cell line is a long-term GA-specific T-cell line.

3. The process of claim 2, wherein at least one long-term GA-specific human T-cell line is a clonal long-term GA-specific T-cell line.

4. The process of claim 2, wherein the at least one long-term GA-specific human T-cell line has been maintained in culture for at least about four weeks prior to its use in determining whether the test preparation of GA and the GA reference standard are immunologically identical.

5. The process of claim 4, wherein the maintenance in culture of the at least one long-term GA-specific human T-cell line incubated in step (1) comprises recurrent restimulation with GA and autologous APC, in the absence of mitogen.

6. The process of claim 2, wherein the at least one long-term GA-specific human T-cell line incubated in step (1) has undergone at least 4 restimulations prior to its use in step (1).

7. The process of claim 6, wherein the at least one long-term GA-specific human T-cell line incubated in step (1) has undergone at least 8 restimulations prior to its use in step (1).

8. The method of claim 1, wherein the assay panel comprises at least one positive or negative control.

9. The method of claim 1, wherein the acceptable limits for the measurement comparison are about 90% to about 110%.

10. The method of claim 1, wherein the at least one measured GA-elicited response is selected from proliferation, production of a response biomarker, expression of a nucleic acid encoding a response biomarker, and a combination thereof.

11. The method of claim 10, wherein the at least one measured GA-elicited response is production of a response biomarker, and wherein the response biomarker is a cytokine, an activation marker, or a chemokine.

12. The method of claim 10, wherein the at least one measured GA-elicited response is expression of a nucleic acid encoding a response biomarker, and wherein the response biomarker encoded by the nucleic acid is a cytokine, an activation marker, or a chemokine.

13. The method of claim 1, wherein each of the at least four samples in the first set of samples of each GA-specific human T cell line is stimulated with one of an escalating series of amounts of the test preparation of GA, and wherein the at least four samples in the second set of samples of each GA-specific human T cell line in step (3) comprises at least three samples, wherein each of the at least three samples is stimulated with one of the same escalating series of amounts of the GA reference standard.

14. The method of claim 1, wherein step (5) further comprises generating dose response curves for the test and reference preparations of GA, and wherein the test preparation of GA and the GA reference standard are determined to be immunologically identical when the slopes in the linear range of the dose response curve are statistically similar.

15. The method of claim 14, wherein the assay panel comprises at least one positive or negative control.

16. The method of claim 14, wherein the acceptable limits are about 90% to about 110%.

17. The process of claim 1, wherein the first non-canonical GA peptide, the second non-canonical GA peptide, or both, consists of the amino acids L-tyrosine (Y), L-glutamic acid (E), L-alanine (A), and L-lysine (K), and wherein the average molar fraction of at least one of the amino acids is selected from:

- (i) L-glutamic acid (E) outside a range of about 0.127 to about 0.155;
- (ii) L-alanine (A) outside a range of about 0.385 to about 0.471;
- (iii) L-tyrosine (Y) outside a range of about 0.080 to about 0.106; and
- (iv) L-lysine (K) outside a range of about 0.303 to about 0.371.

18. The process of claim 1, wherein the first non-canonical GA peptide, the second non-canonical GA peptide, or both, consists of any one, two, or three of the following amino acids: L-tyrosine (Y); L-glutamic acid (E); L-alanine (A); and L-lysine (K).

19. The process of claim 1, wherein the assay panel comprises or further comprises at least one GA-specific human T cell line that has a first known GA response biomarker profile, and comprising or further comprising at least one GA-specific human T cell line that has a second known GA response biomarker profile that is different from the first known GA response biomarker profile.

20. The process of claim 1, comprising or further comprising at least one GA-specific human T cell line that has a first known WIC restriction, and comprising or further comprising at least one GA-specific human T cell line that has a second known MHC restriction that is different from the first known MHC restriction.

21. A method of determining whether a test preparation of glatiramer acetate (GA) and a GA reference standard are immunologically identical using an assay panel of GA-specific human T-cell lines, wherein each of the GA-specific human T-cell lines is obtained from a GA-naïve donor, the method comprising:

1) incubating cells of each GA-specific human T-cell line in the assay panel with appropriate antigen presenting cells (APC), wherein the assay panel comprises at least four different GA-specific human T-cell lines, and wherein the at least four different GA-specific human T-cell lines include:
   - a) a first GA-specific human T-cell line, wherein the first GA-specific human T-cell line is not reactive to a first non-canonical GA peptide;
   - b) a second GA-specific human T-cell line, wherein the second GA-specific human T-cell line is reactive to the first non-canonical GA peptide;
   - c) a third GA-specific human T-cell line, wherein the third GA-specific human T-cell line is not reactive to a second non-canonical GA peptide; and
   - d) a fourth GA-specific human T-cell line, wherein the fourth GA-specific human T-cell line is reactive to the second non-canonical GA peptide;
2) stimulating cells in a first set samples, the first set of samples comprising at least four samples of each of the at least four GA-specific human T cell lines, each sample comprising a predetermined number of cells of each of the at least four GA-specific human T-cell lines incubated with APC in step (1), wherein each of the at least four samples of each T cell line is stimulated with a different amount of GA, wherein the GA is the test preparation of GA;
3) separately stimulating cells in a second set of samples, the second set of samples comprising the same number of samples of each of the at least four GA-specific human T cell lines as the first set of samples, each sample in the second set of samples comprising the same predetermined number of cells, of each of the at least four GA-specific human T-cell lines incubated with APC in step (1) as the samples in the first set of samples, wherein each sample in the second set of samples is stimulated with the same amount of GA used to stimulate each corresponding sample in the first set of samples in step (2), wherein the GA is a GA reference standard;
4) measuring at least one GA-elicited response in each sample of the first set of samples stimulated in step (2) and measuring the same at least one GA-elicited response in each sample of the second set of samples stimulated in step (3);
5) comparing each measurement obtained in step (4) for each sample in the first set of samples with the corresponding measurement for each corresponding sample in the second set of samples; and
6) determining the test preparation of GA and the GA reference standard to be immunologically identical when about 80% to about 100% of the comparisons made in step (5) for each set of samples are within acceptable limits, and wherein the acceptable limits for the measurement comparison are about 80% to about 120%.

22. A method comprising selecting for pharmaceutical use a test preparation of GA having immunologic identity to a GA reference standard, wherein immunologic identity is determined according to the method of claim 21.

23. The method of claim 22, wherein the at least one measured GA-elicited response is selected from proliferation, production of a response biomarker, expression of a nucleic acid encoding a response biomarker, and a combination thereof.

24. The method of claim 23, wherein the at least one measured GA-elicited response is production of a response biomarker, and wherein the response biomarker is a cytokine, an activation marker, or a chemokine.

25. The method of claim 23, wherein the at least one measured GA-elicited response is expression of a nucleic acid encoding a response biomarker, and wherein the response biomarker encoded by the nucleic acid is a cytokine, an activation marker, or a chemokine.

26. The method of claim 21, wherein at least one GA-specific human T-cell line in the assay panel is a long-term T-cell line.

27. The method of claim 26, wherein the at least one long-term GA-specific human T-cell line is a clonal long-term T-cell line.

28. The method of claim 26, wherein the at least one long-term GA-specific human T-cell line has been maintained in culture for at least about four weeks prior to its use in determining whether the test preparation of GA and the GA reference standard are immunologically identical.

29. The method of claim 28, wherein the maintenance in culture of the at least one long-term GA-specific human T-cell line incubated in step (1) comprises recurrent restimulation with GA and autologous APC, in the absence of mitogen.

30. The method of claim 29, wherein the at least one long-term GA-specific human T-cell line incubated in step (1) has undergone at least 4 restimulations prior to its use in step (1).

31. The method of claim 30, wherein the at least one long-term GA-specific human T-cell line incubated in step (1) has undergone at least 8 restimulations prior to its use in step (1).

32. The method of claim 21, wherein each of the at least four samples in the first set of samples of each GA-specific human T cell line is stimulated with one of an escalating series of amounts of the test preparation of GA, and wherein the at least four samples in the second set of samples of each GA-specific human T cell line in step (3) comprises at least three samples, wherein each of the at least three samples is stimulated with one of the same escalating series of amounts of the GA reference standard.

33. The method of claim 32, wherein step (5) further comprises generating dose response curves for the test and reference preparations of GA, and wherein the test preparation of GA and the GA reference standard are determined to be immunologically identical when the slopes in the linear range of the dose response curve are statistically similar.

34. The method of claim 21, wherein the test preparation of GA is admixed in a drug product or pharmaceutical composition if it is determined to be immunologically identical to the GA reference standard.

35. The method of claim 21, wherein the assay panel comprises at least one positive or negative control.

36. The method of claim 21, wherein the acceptable limits for the measurement comparison are about 90% to about 110%.

37. The method of claim 21, wherein the first non-canonical GA peptide, the second non-canonical GA peptide, or both, consists of the amino acids L-tyrosine (Y), L-glutamic acid (E), L-alanine (A), and L-lysine (K), and wherein the average molar fraction of at least one of the amino acids is selected from:

(i) L-glutamic acid (E) outside a range of about 0.127 to about 0.155;

(ii) L-alanine (A) outside a range of about 0.385 to about 0.471;

(iii) L-tyrosine (Y) outside a range of about 0.080 to about 0.106; and (iv) L-lysine (K) outside a range of about 0.303 to about 0.371.

38. The method of claim 21, wherein the first non-canonical GA peptide, the second non-canonical GA peptide, or both, consists of any one, two, or three of the following amino acids: L-tyrosine (Y); L-glutamic acid (E); L-alanine (A); and L-lysine (K).

39. The method of claim 21, wherein the assay panel comprises or further comprises at least one GA-specific human T cell line that has a first known GA response biomarker profile, and comprising or further comprising at least one GA-specific human T cell line that has a second known GA response biomarker profile that is different from the first known GA response biomarker profile.

40. The method of claim 21, comprising or further comprising at least one GA-specific human T cell line that has a first known WIC restriction, and comprising or further comprising at least one GA-specific human T cell line that has a second known MHC restriction that is different from the first known MHC restriction.

* * * * *